United States Patent
Kohli et al.

(10) Patent No.: US 11,634,700 B2
(45) Date of Patent: Apr. 25, 2023

(54) HYPERACTIVE AID/APOBEC AND HMC DOMINANT TET ENZYMES

(71) Applicant: THE TRUSTEES OF THE UNIVERSITY OF PENNSYLVANIA, Philadelphia, PA (US)

(72) Inventors: Rahul Kohli, Penn Valley, PA (US); Emily Schutsky, Philadelphia, PA (US); Monica Yun Liu, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 17/207,101

(22) Filed: Mar. 19, 2021

(65) Prior Publication Data
US 2021/0301278 A1 Sep. 30, 2021

Related U.S. Application Data

(62) Division of application No. 16/025,261, filed on Jul. 2, 2018, now Pat. No. 10,961,525.

(60) Provisional application No. 62/528,808, filed on Jul. 5, 2017.

(51) Int. Cl.
*C12N 9/78* (2006.01)
*C12N 9/02* (2006.01)

(52) U.S. Cl.
CPC ............. *C12N 9/78* (2013.01); *C12N 9/0071* (2013.01)

(58) Field of Classification Search
CPC ...................................................... C12N 9/78
See application file for complete search history.

(56) References Cited

U.S. PATENT DOCUMENTS

2012/0151613 A1 6/2012 Wang et al.

OTHER PUBLICATIONS

Siriwardena. Characterization of the Catalytic Domain of Human APOBEC3B and the Critical Structural Role for a Conserved Methionine J Mol Biol. Sep. 25, 2015; 427(19): 3042-3055.*

Case, David A. et al., "The Amber Biomolecular Simulation Programs," Journal of Computational Chemistry, vol. 26, No. 16, Dec. 2005, pp. 1668-1688.

Fang, Dong et al., "Alternative Pathway for the Reaction Catalyzed by DNA Dealkylase AlkB from Ab Initio QM/MM Calculations," Journal of Chemical Theory and Computation, vol. 10, Sep. 25, 2014, pp. 5136-5148.

Gajula, Kiran S. et al., "High-throughput mutagenesis reveals functional determinants for DNA targeting by activation-induced deaminase," Nucleic Acids Research, vol. 42, No. 15, Jul. 26, 2014, pp. 9964-9975.

(Continued)

*Primary Examiner* — Yong D Pak
(74) *Attorney, Agent, or Firm* — Kathleen D. Rigaut; Howson & Howson LLP

(57) ABSTRACT

The present invention includes mutant AID, APOBEC, and Tet enzymes with improved functions. In one aspect the invention provides APOBEC fusion proteins comprising hyperactive deamination activity. In another aspect, the invention provides AID mutant proteins comprising hyperactive deamination activity. In yet another aspect, the invention provides mutant Tet proteins capable of stalling oxidation at a 5-hydroxymethylcytosine (hmC).

2 Claims, 33 Drawing Sheets

Specification includes a Sequence Listing.

(56) References Cited

OTHER PUBLICATIONS

Hu, Lulu et al., "Crystal Structure of TET2-DNA Complex: Insight into TET-Mediated 5mC Oxidation," Cell, vol. 155, Dec. 19, 2013, pp. 1545-1555.

Kohli, Rahul M. et al., "A Portable Hot Spot Recognition Loop Transfers Sequence Preferences from APOBEC Family Members to Activation-induced Cytidine Deaminase," The Journal of Biological Chemistry, vol. 284, No. 34, Aug. 21, 2009, pp. 22898-22904.

Liu, M. Y. et al., "Quantification of Oxidized 5-Methylcytosine Bases and TET Enzyme Activity," Methods in Enzymology, vol. 573, 2016, pp. 365-385.

MacMillan, Alyssa A. et al., "APOBEC3 Inhibition of Mouse Mammary Tumor Virus Infection: the Role of Cytidine Deamination versus Inhibition of Reverse Transcription," Journal of Virology, vol. 87, No. 9, May 2013 pp. 4808-4817.

Nabel, Christopher S. et al., "Nucleic acid determinants for selective deamination of DNA over RNA by activation-induced deaminase," PNAS, vol. 110, No. 35, Aug. 27, 2013, pp. 14225-14230.

Liu, Monica Yun et al., "Mutations along a TET2 active site scaffold stall oxidation at 5-hydroxymethylcytosine," Nature Chemical Biology, vol. 13, Feb. 2017, pp. 181-190.

Schutsky, Emily K. et al., "APOBEC3A efficiently deaminates methylated, but not TET-oxidized, cytosine bases in DNA," Nucleic Acids Research, vol. 45, No. 13, Jul. 27, 2017, pp. 7655-7665.

Studer, Romain A., "Residue mutations and their impact on protein structure and function: detecting beneficial and pathogenic changes," Biochemical Journal, vol. 449, 2013, pp. 581-594.

Fu, Yang et al., "DNA cytosine and methylcytosine deamination by APOBEC3B: enhancing methylcytosine deamination by engineering APOBEC3B," Biochemical Journal, vol. 471, 2015, pp. 25-35.

Nabel, Christopher S. et al., "AID/APOBEC deaminases disfavor modified cytosines implicated in DNA demethylation," Nature Chemical Biology, vol. 8, No. 9, Sep. 2012, pp. 751-758.

* cited by examiner

|  | 400 nM | | 5mM | |
|---|---|---|---|---|
|  | Raw Percent Conversion | Normalized to U | Raw Percent Conversion | Normalized to U |
| A3A | 0.76 | 0.95 | 0.84 | 1.06 |
| A3B | 0.32 | 0.40 | 0.59 | 0.74 |
| A3Bc | 0.09 | 0.11 | 0.30 | 0.39 |
| A3Bn | 0.00 | 0.00 | 0.00 | 0.00 |
| A3Bc/A3Ac | 0.00 | 0.00 | 0.38 | 0.48 |
| A3Ac/A3Bc | 0.51 | 0.64 | 0.77 | 0.97 |
| C | 0.00 | 0.00 | 0.00 | 0.00 |
| U | 0.81 | 1.00 | 0.79 | 1.00 |

FIG. 4

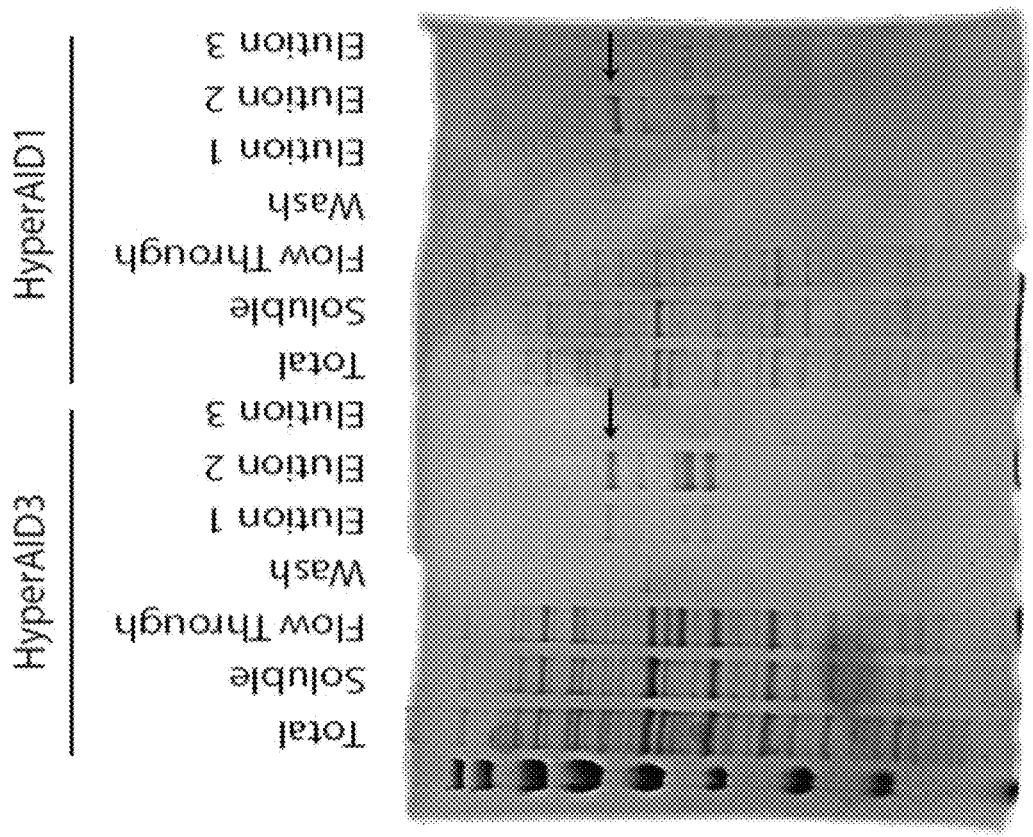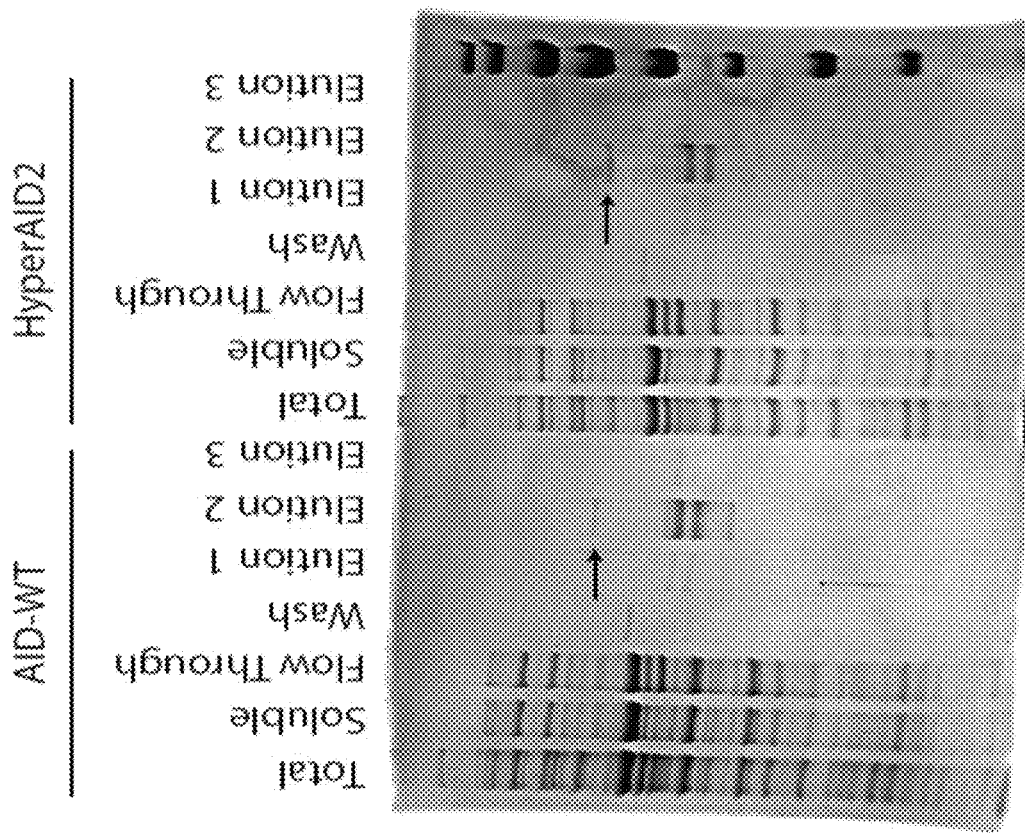
FIG. 9

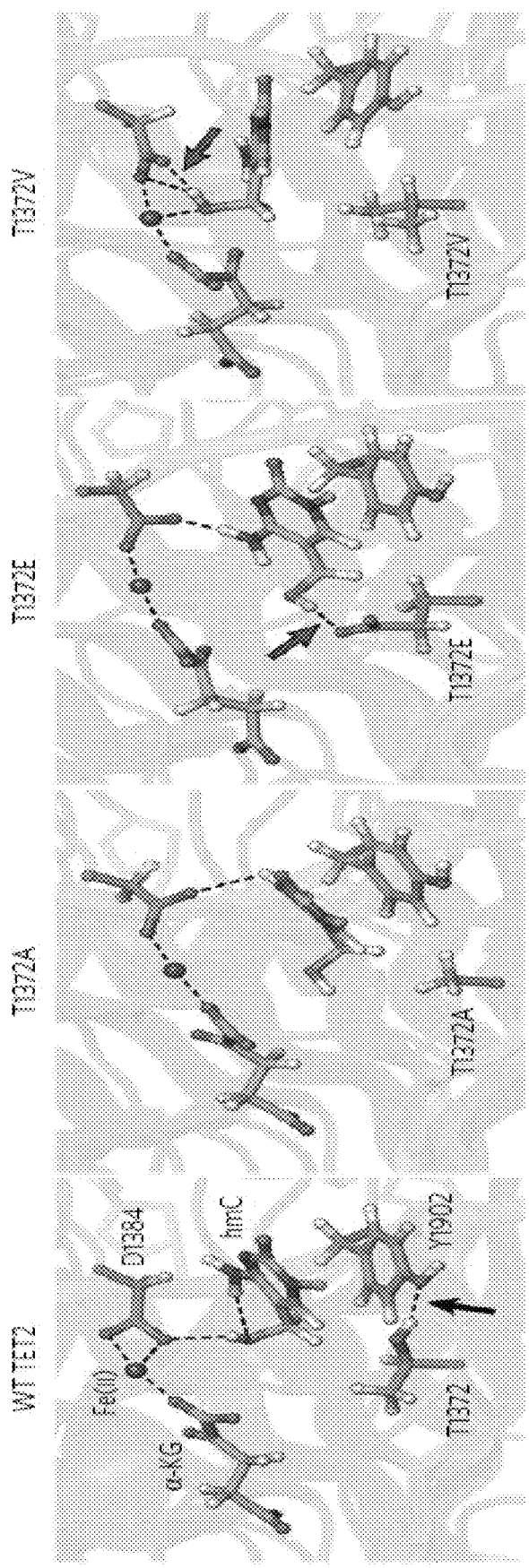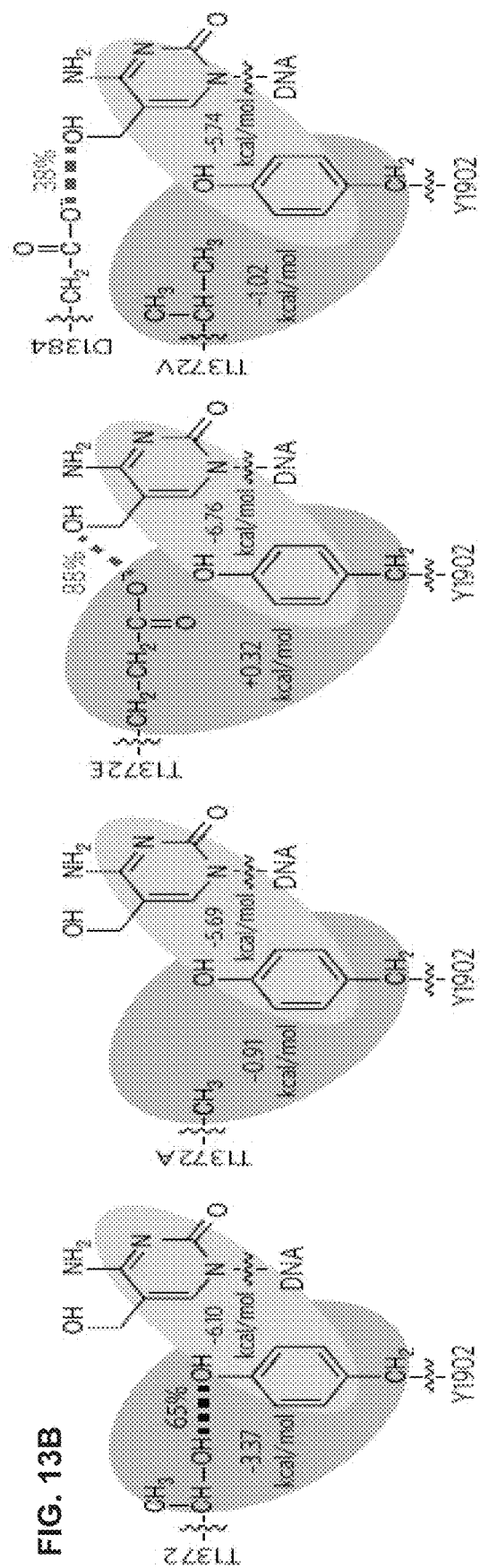
FIG. 13A
FIG. 13B

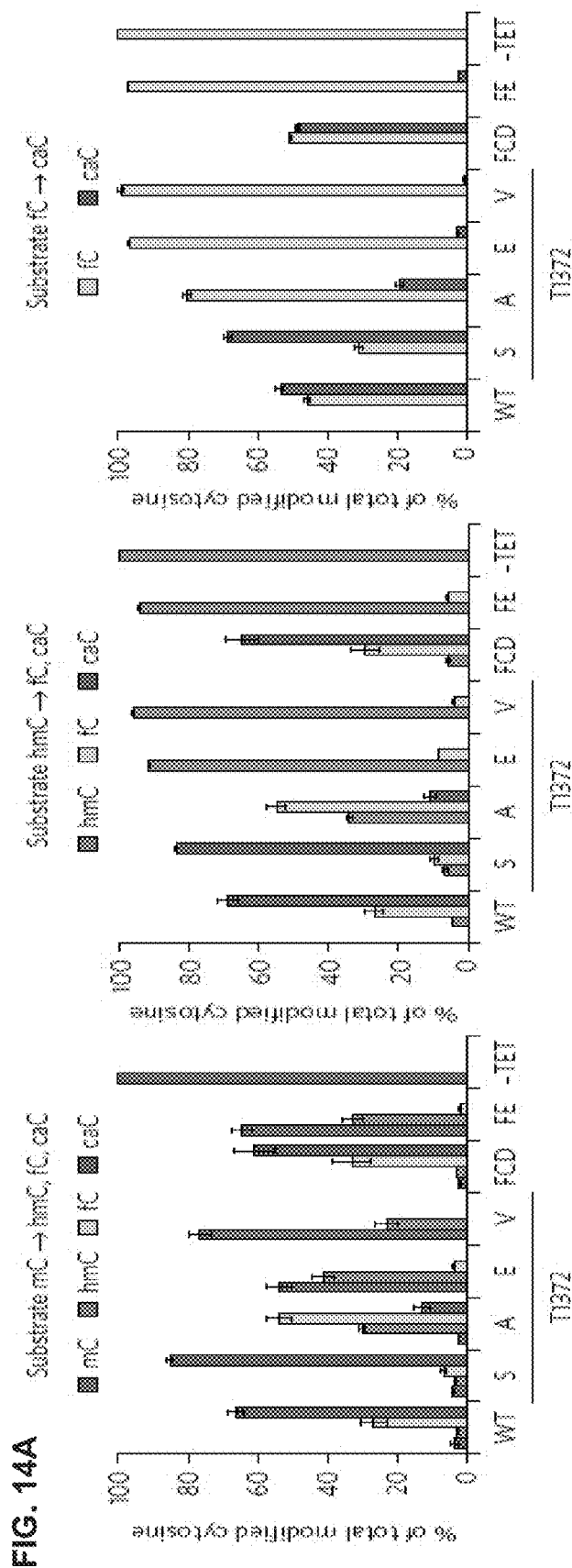
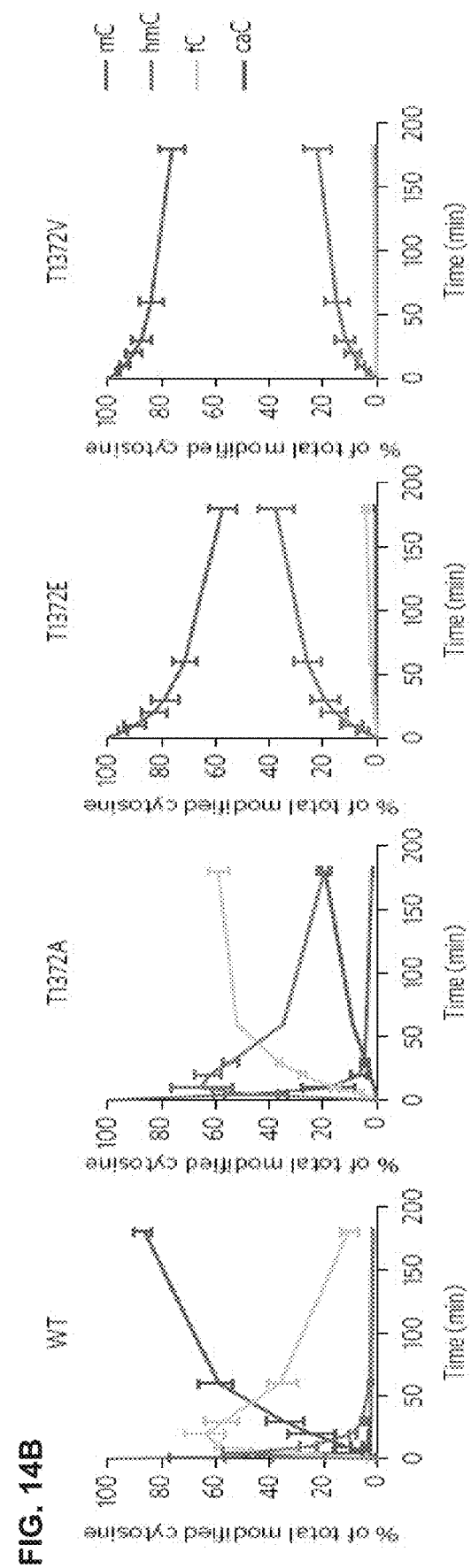
FIG. 14A
FIG. 14B

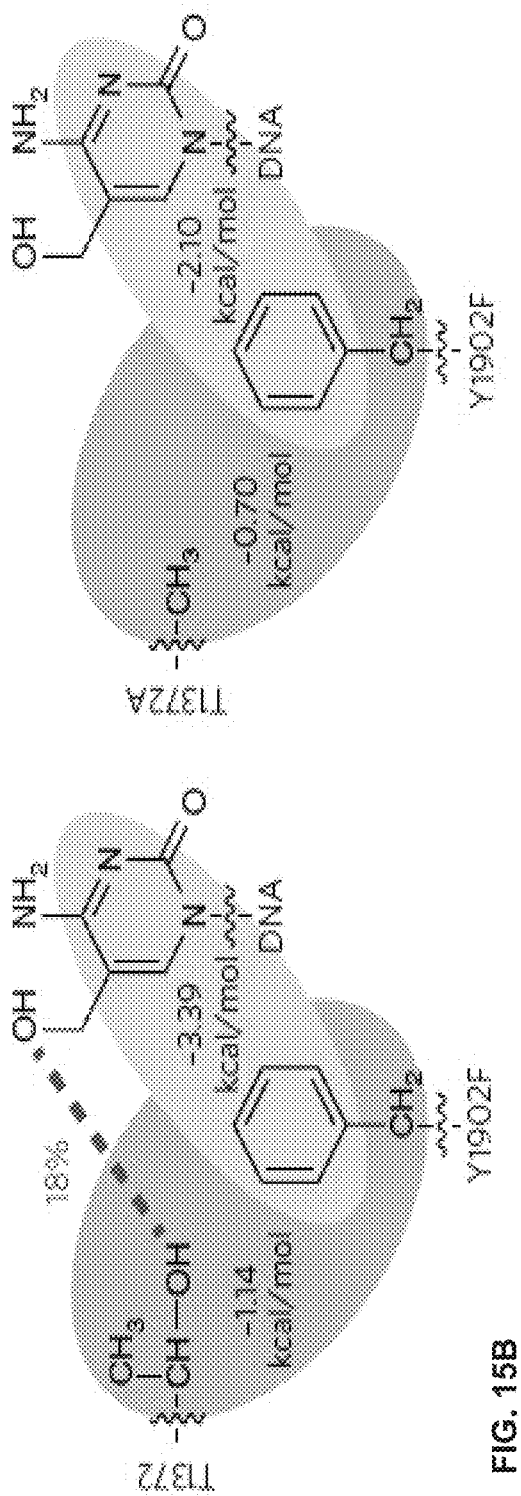
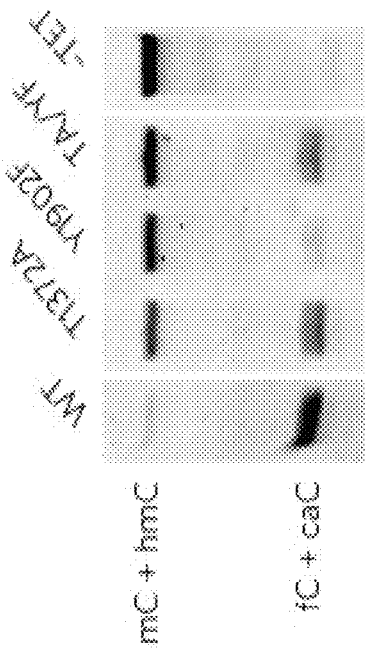
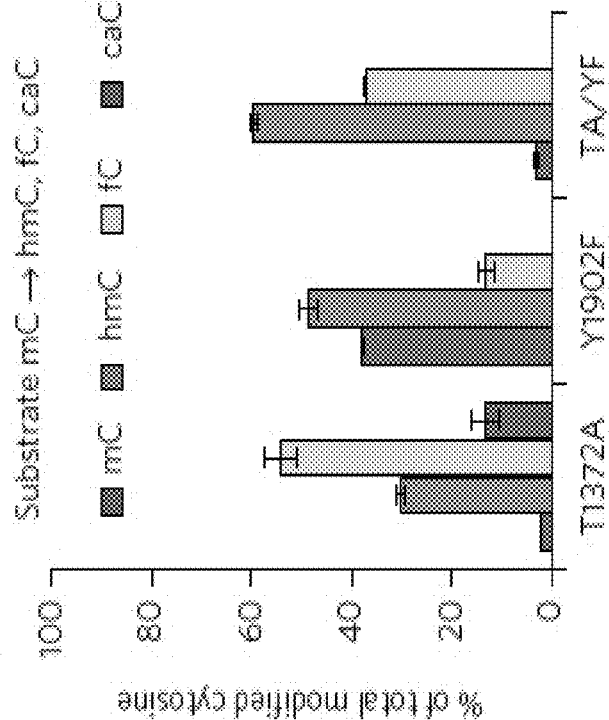
FIG. 15A
FIG. 15B
FIG. 15C

Table 1 | Activity of representative TET2 variants on mC and hmC.

| Substrate consumed (nmol/mg/min) | WT | T372A | T372E | Y1902F | T372A/Y1902F |
|---|---|---|---|---|---|
| mC | 2.9 ± 0.2 | 2.9 ± 0.1 | 0.48 ± 0.02 | 0.29 ± 0.03 | 1.0 ± 0.1 |
| hmC | 1.1 ± 0.1 | 0.51 ± 0.03 | 0.059 ± 0.006 | 0.079 ± 0.025 | 0.20 ± 0.02 |

Values are mean ± s.e.m. from three independent experiments.

FIG. 16

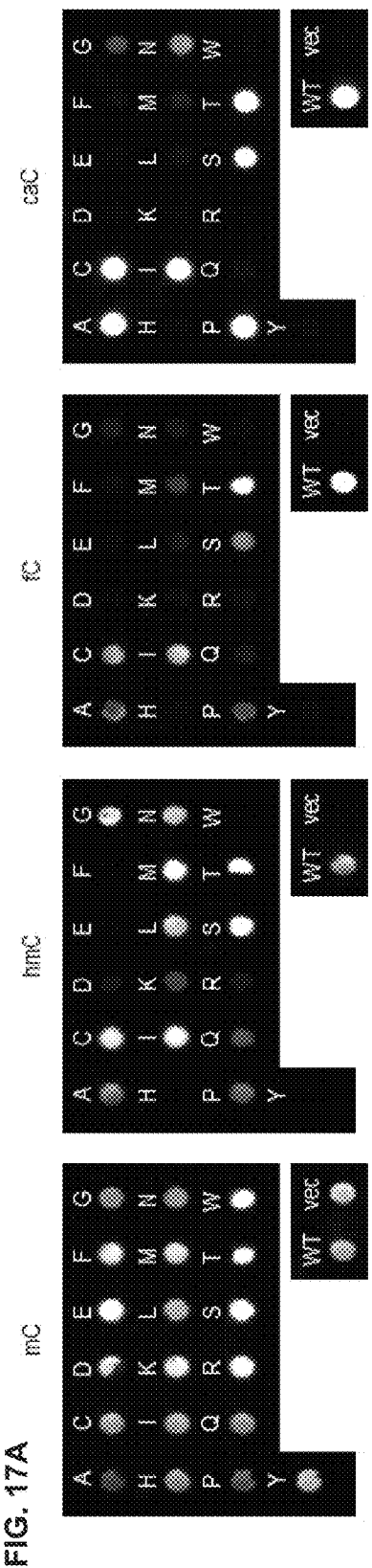
FIG. 17A
FIG. 17B
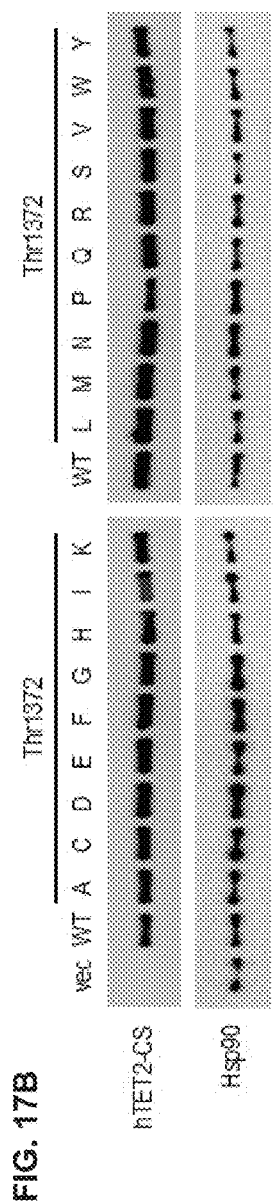
FIG. 17C

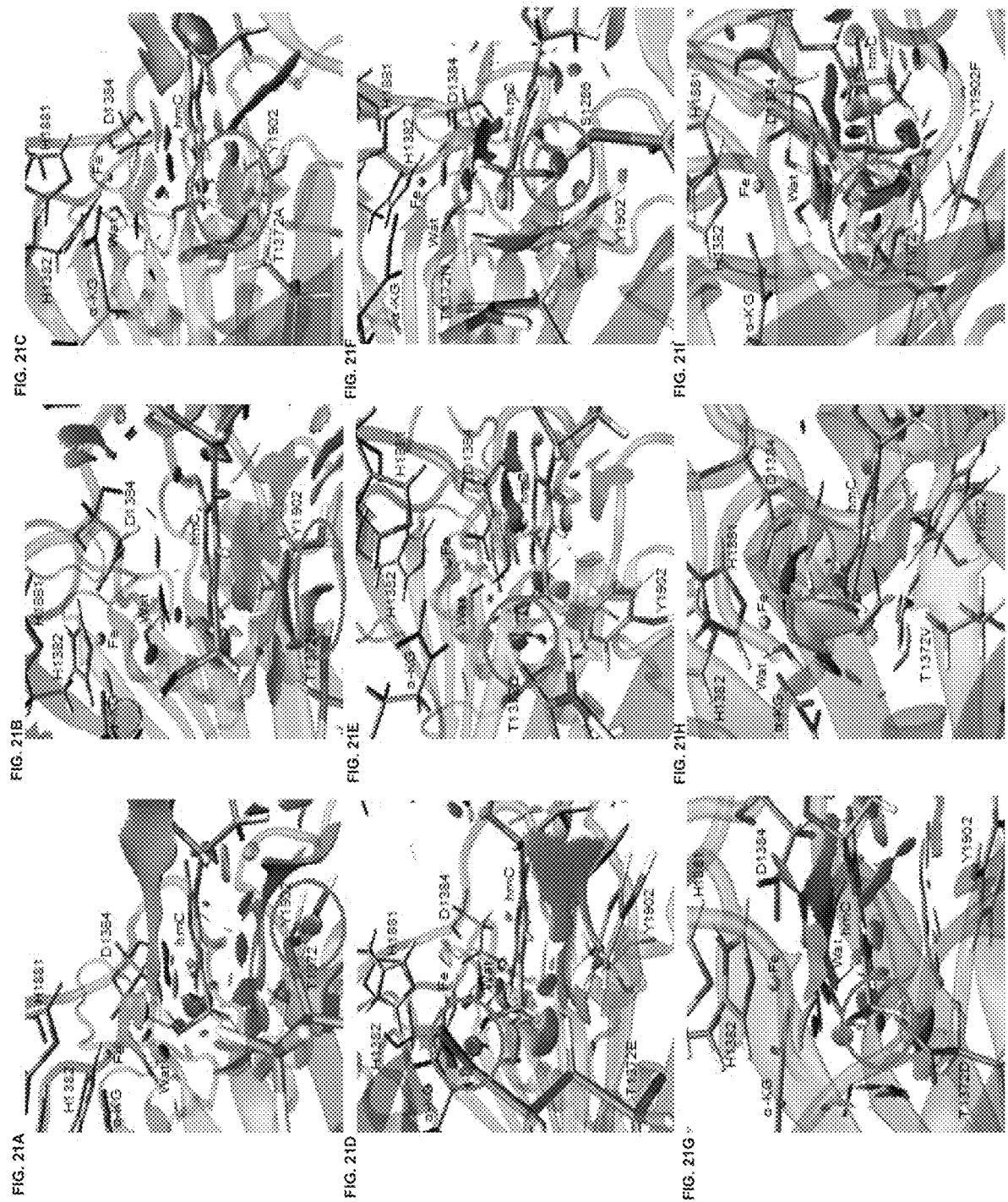

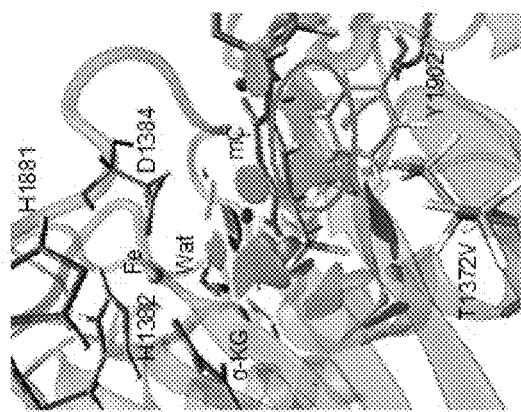
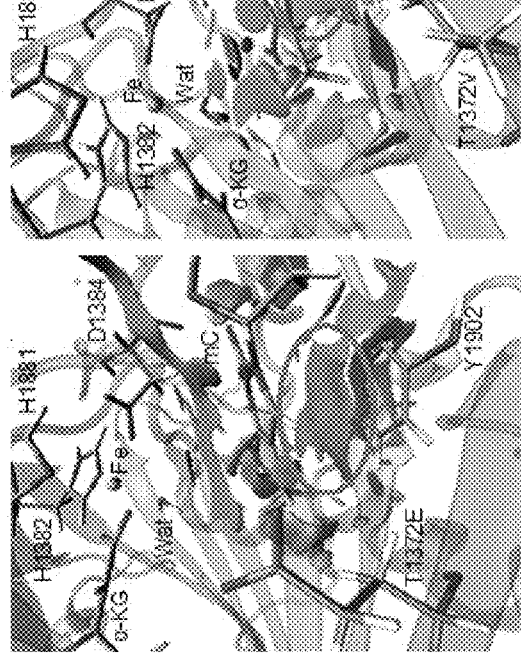
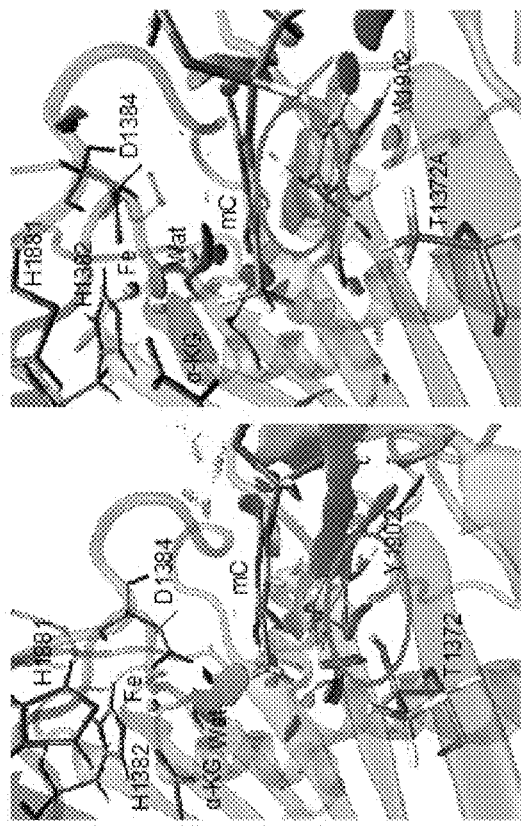
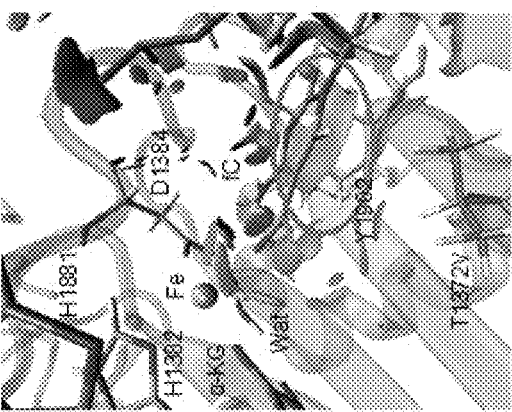
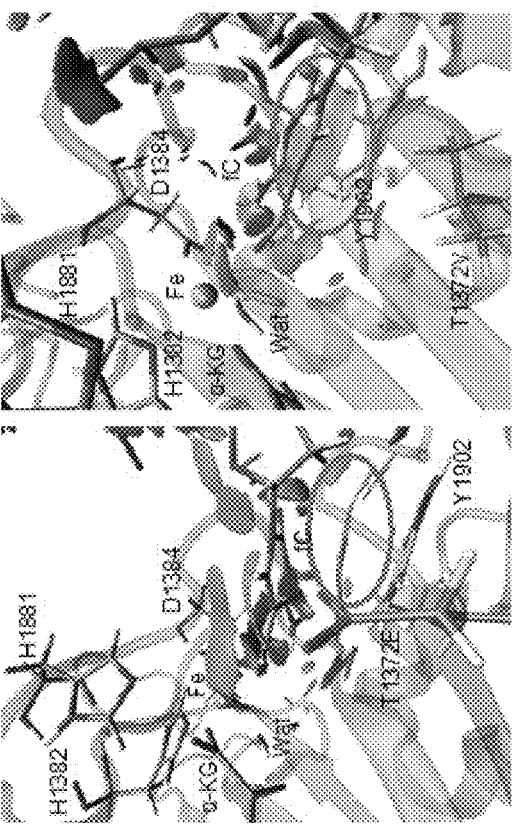
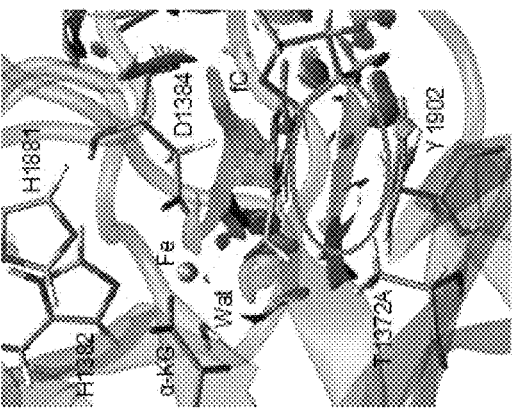
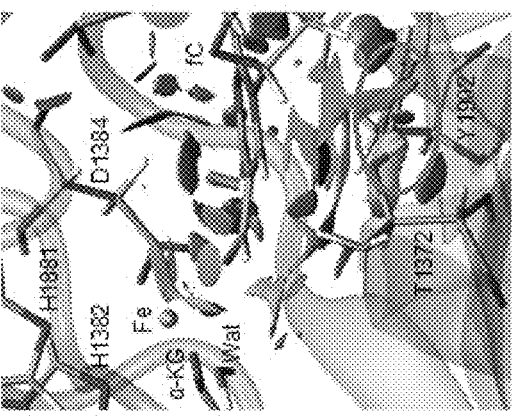
FIG. 22A  FIG. 22B  FIG. 22C  FIG. 22D
FIG. 22E  FIG. 22F  FIG. 22G  FIG. 22H

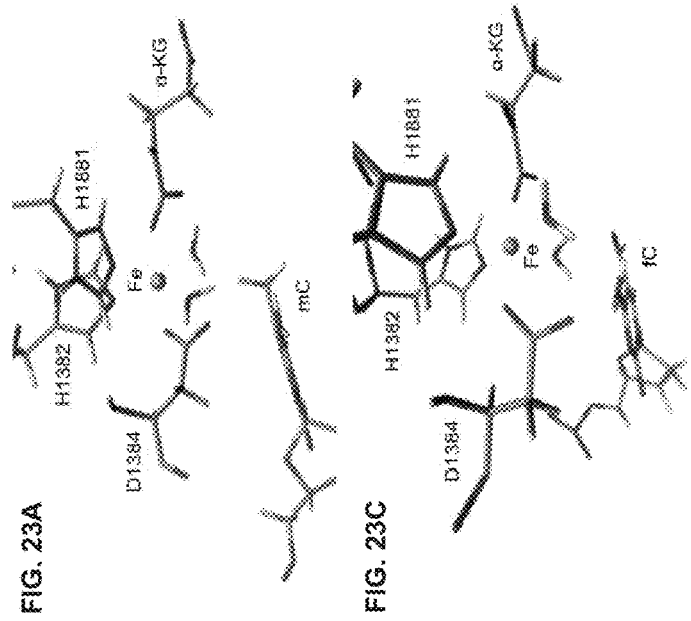
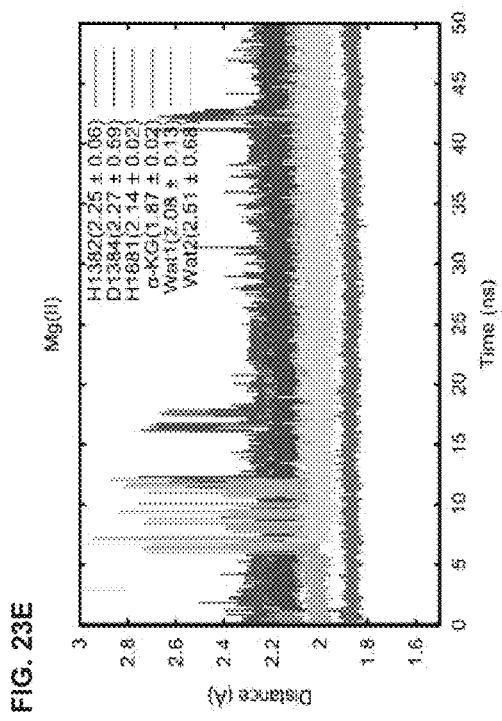
FIG. 23A  FIG. 23B  FIG. 23C  FIG. 23D  FIG. 23E  FIG. 23F

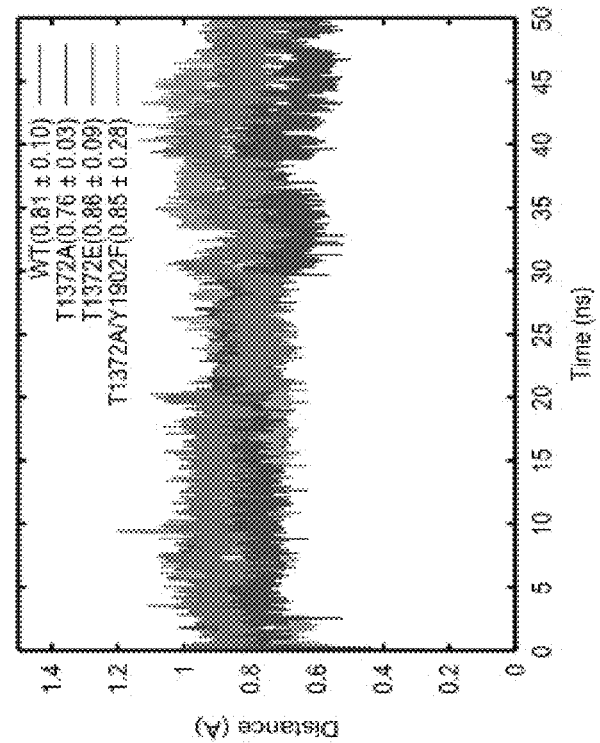
FIG. 24A
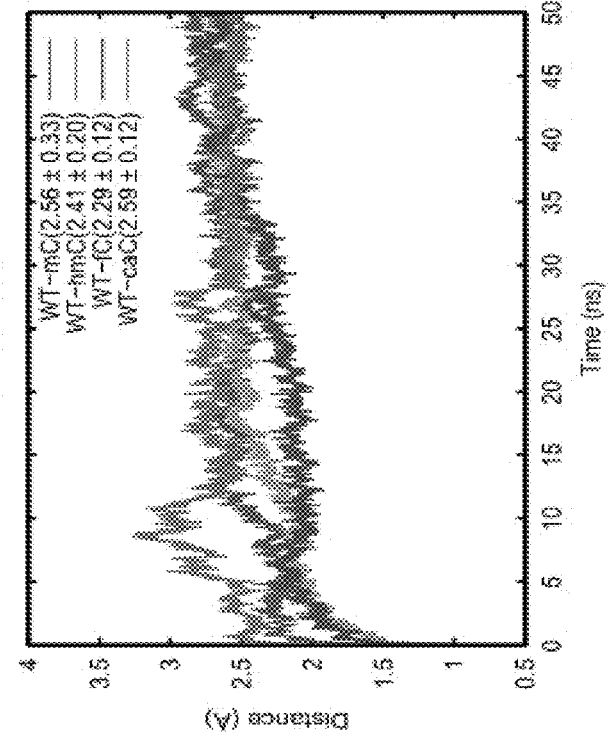
FIG. 24B
FIG. 24C

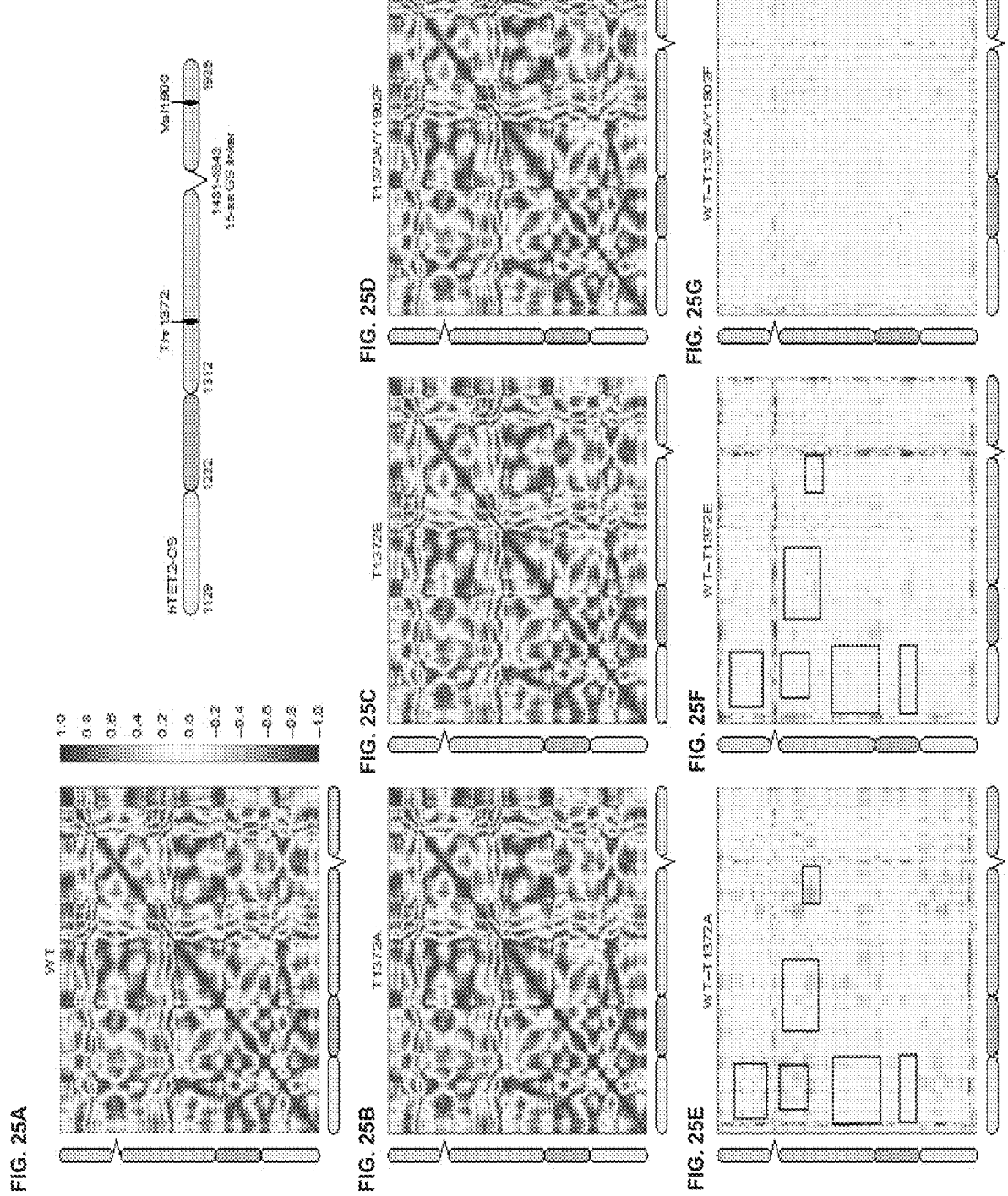

| Name | Sequence (5'-3') |
|---|---|
| T1372A | CTAGGCCTGAAGGAGGGTCGACCCTTCAGCGGGGTGGCCGCCACCCGCTTCTGCGCCTGCCTGCGGGGGAGAGCGCACACC (SEQ ID NO:50) |
| T1372A -r | GTGCGTGGGCGCAGAAGGGTCGACCCTTCAGCGAGGCAGGCGGCCACCCGCGGGGTGTGCGCCACGCACC (SEQ ID NO:51) |
| T1372C | CTAGGCCTGAAGGAGGGTCGACCCTTCAGCGAGAAGTCCAGGCAGGCGCACACCGCTTCTGCGCCTGGACTTCTGAAGGGTCGACCCACGCACACC (SEQ ID NO:52) |
| T1372C -r | GTGCGTGGGCGCAGAAGTCCAGGCAGGCGCACACCCGCTGAAGGGTCGACCCTTCAGCGGTGTGC (SEQ ID NO:53) |
| T1372D | CTAGGCCTGAAGGAGGGTCGACCCTTCAGCGAGGCGCAGGCGTCCACCCGCTGCCTGGACTTCTGCGCCACGCACACC (SEQ ID NO: 54) |
| T1372D -r | GTGCGTGGGCGCAGAAGTCCAGGCAGGCGTCCACCCGCTGAAGGGTCGACCCTTCAGCGGTGCGC (SEQ ID NO: 55) |
| T1372E | CTAGGCCTGAAGGAGGGTCGACCCTTCAGCGAGGCCTCCACCCGCTGCCTGGACTTCTGCGACCCTCTTCAGGC (SEQ ID NO: 56) |
| T1372E -r | GTGCGTGGGCGCAGAAGTCCAGGCAGGCCTCCACCCGCTGAAGGGTCGACCCTCTTCAGGC (SEQ ID NO: 57) |
| T1372F | CTAGGCCTGAAGGGTCGACCCTTCAGCGGGGTGTTCGCCTGCCTGCACGCCACGCACACC (SEQ ID NO: 58) |
| T1372F -r | GTGCGTGGGCGCAGAAGTCGACCCTTCAGCGAACACCCGCTGAAGGGTCGACCCTCTTCAGGC (SEQ ID NO: 59) |
| T1372G | CTAGGCCTGAAGGAGGGTCGACCCTTCAGCGAGGCAGGCGCCCACCCGTCGCGCCTGGACTTCTGCGCCACGCACACC (SEQ ID NO: 60) |
| T1372G -r | GTGCGTGGGCGCAGAAGTCCAGGCAGGCGCCCACCCGCTGAAGGGTCGACCCTCTTCAGGC (SEQ ID NO: 61) |
| T1372H | CTAGGCCTGAAGGAGGGTCGACCCTTCAGCGGGGTGCACGCCACGCGCCCTGGACTTCTGCACGCCACGCACACC (SEQ ID NO: 62) |
| T1372H -r | GTGCGTGGGCGCAGAAGTCGACCCTTCAGCGGCACGCCACCCGCTGAAGGGTCGACCCTCTTCAGGC (SEQ ID NO: 63) |
| T1372I | CTAGGCCTGAAGGAGGGTCGACCCTTCAGCGAGGCGGGTGATCACCCCGCTGCCTGGACTTCTGCGCCACGCACACC (SEQ ID NO: 64) |
| T1372I -r | GTGCGTGGGCGCAGAAGTCCAGGCAGGCGGGTGATCACCCCGCTGAAGGGTCGACCCTCTTCAGGC (SEQ ID NO: 65) |
| T1372K | CTAGGCCTGAAGGAGGGTCGACCCTTCAGCGAGGCGGGGTGAAGGCCTGCCTGGACTTCTGCGCCACGCACACC (SEQ ID NO: 66) |
| T1372K -r | GTGCGTGGGCGCAGAAGGCCTTCACCCCGCTGAAGGGTCGACCCTCTTCAGGC (SEQ ID NO: 67) |
| T1372L | CTAGGCCTGAAGGAGGGTCGACCCTTCAGCGAGGCAGGCGTCTGCGGGGTGTCCACCCGCTGCCTGGACTTCTGCGCCACGCACACC (SEQ ID NO: 68) |
| T1372L -r | GTGCGTGGGCGCAGAAGTCCAGGCAGGCGGGGTGATGCCACGCGCTGAAGGGTCGACCCTCTTCAGGC (SEQ ID NO: 69) |
| T1372M | CTAGGCCTGAAGGAGGGTCGACCCTTCAGCGAGGCAGGCGGGGTGATGCCACGCCTGCCTGGACTTCTGCGCCACGCACACC (SEQ ID NO: 70) |
| T1372M -r | GTGCGTGGGCGCAGAAGTCCAGGCAGGCGGGGTGCATGACCCCGCTGAAGGGTCGACCCTCTTCAGGC (SEQ ID NO: 71) |
| T1372N | CTAGGCCTGAAGGAGGGTCGACCCTTCAGCGAGGCGGGGTGAACGCCGTCACCCCGCTGCCTGGACTTCTGCGCCACGCACACC (SEQ ID NO: 72) |
| T1372N -r | GTGCGTGGGCGCAGAAGTCCAGGCAGGCGGGGTGACGGCGTTCACCCGCTGAAGGGTCGACCCTCTTCAGGC (SEQ ID NO: 73) |
| T1372P | CTAGGCCTGAAGGAGGGTCGACCCTTCAGCGAGGCGGGGTGCCGGCACCCGCCTGCCTGGACTTCTGCACGCCACGCACACC (SEQ ID NO: 74) |
| T1372P -r | GTGCGTGGGCGCAGAAGGGTCGACCCTTCAGCGGGTGCCGGCACCCCGCTGAAGGGTCGACCCTCTTCAGGC (SEQ ID NO: 75) |
| T1372Q | CTAGGCCTGAAGGGTCGACCCTTCAGCGAGGCGGGGTGCAGGCACCCGCCTGCCTGGACTTCTGCGCCACGCACACC (SEQ ID NO: 76) |
| T1372Q -r | GTGCGTGGGCGCAGAAGTCCAGGCAGGCTGCACCCCGCTGAAGGGTCGACCCTCTTCAGGC (SEQ ID NO: 77) |

FIG. 27A

| | | |
|---|---|---|
| T1372Q | CTAGGCCTGAAGGAGGGTCGACCCTTCAGCGGGGTCGCAGGCCTGCCTGGACTTCTGCGCCACGCACACC | (SEQ ID NO: 78) |
| T1372Q -r | GTGCGTGGCGCAGAAGTCCAGGCAGGCCTGCACCCCGCTGAAGGGTCGACCCTCCTTCAGGC | (SEQ ID NO: 79) |
| T1372R | CTAGGCCTGAAGGAGGGTCGACCCTTCAGCGGGGTGAGGCCTGCGCCACCGCACACC | (SEQ ID NO: 80) |
| T1372R -r | GTGCGTGGCGCAGGAGGAGCCTCAGAAGTCCAGGCCTCACCCGCTGAAGGGTCGACCCTCCTTCAGGC | (SEQ ID NO: 81) |
| T1372S | CTAGGCCTGAAGGAGGGTCGACCCTTCAGCGCGGGTGAGCGGCTGCCTGGACTTCTGCGCCACGCACACC | (SEQ ID NO: 82) |
| T1372S -r | GTGCGTGGCGCAGAAGTCCAGGCAGCCGCTCACCCGCTGAAGGGTCGACCCTCCTTCAGGC | (SEQ ID NO: 83) |
| T1372V | CTAGGCCTGAAGGAGGGTCGACCCTTCAGCGGGTGGTGTCGCAGGCCACCACCGCTGAAGGGTCGACCCTCTTCAGGC | (SEQ ID NO: 84) |
| T1372V -r | GTGCGTGGCGCAGAAGTCCAGGCAGGCCACCACCCGCTGAAGGGTCGACCCTCCTTCAGGC | (SEQ ID NO: 85) |
| T1372W | CTAGGCCTGAAGGAGGGTCGACCCTTCAGCGGGGTGTGGGCCTGCGCCACCGCACACC | (SEQ ID NO: 86) |
| T1372W -r | GTGCGTGGCGCAGGAGGAGCCTCAGCAGGCCTGCACCCGCTGAAGGGTCGACCCTCCTTCAGGC | (SEQ ID NO: 87) |
| T1372Y | CTAGGCCTGAAGGAGGGTCGACCCTTCAGCGCGTGTACGCCTGGACTTCTGCGCCACGCACACC | (SEQ ID NO: 88) |
| T1372Y -r | GTGCGTGGCGCAGAAGTCCAGGCGTACACGCTGAAGGGTCGACCCTCCTTCAGGC | (SEQ ID NO: 89) |
| V1900A | CGCGTATAAGCTTGGCCCTTCTACCAGCAGCACAA GAGCATGAACGAGCCTAAACACGGG | (SEQ ID NO: 90) |
| V1900A -r | CGCGTATAAGCTTGTTGTGCTGCTGGTAGAAGGGCCAAGCTTATA | (SEQ ID NO: 91) |
| V1900C | CGCGTATAAGCTTGTGTTAGCTCGTTCTACCAGCAGCATGAACGAGCCTAAACACGGG | (SEQ ID NO: 92) |
| V1900C -r | CGCGTATAAGCTTGTGTTAGCTCGTTCATGCTGCTGGTAGAACGAGCTAAACACAAGCTTATA | (SEQ ID NO: 93) |
| V1900D | CGCGTATAAGCTTGGACTTCTACCAGCAGCATGAACGAGCCTAAACACGGG | (SEQ ID NO: 94) |
| V1900D -r | CGCGTATAAGCTTGTGTTAGCTCGTTCATGCTGCTGGTAGAAGTCCAAGCTTATA | (SEQ ID NO: 95) |
| V1900E | CGCGTATAAGCTTGGAGTTCTACCAGCAGCATGAACGAGCCTAAACACGGG | (SEQ ID NO: 96) |
| V1900E -r | CGCGTATAAGCTTGTGTTAGCTCGTTCATGCTGCTGGTAGAACTCCAAGCTTATA | (SEQ ID NO: 97) |
| V1900F | CGCGTATAAGCTTGTTCTTCTACCAGCAGCATGAACGAGCCTAAACACGGG | (SEQ ID NO: 98) |
| V1900F -r | CGCGTATAAGCTTGTGTTAGCTCGTTCATGCTGCTGGTAGAAGAACAAGCTTATA | (SEQ ID NO: 99) |
| V1900G | CGCGTATAAGCTTGGGTTCTACCAGCAGCATGAACGAGCCTAAACACGGG | (SEQ ID NO: 100) |
| V1900G -r | CGCGTATAAGCTTGTGTTAGCTCGTTCATGCTGCTGGTAGAACCCAAGCTTATA | (SEQ ID NO: 101) |
| V1900H | CGCGTATAAGCTTGCACTTCTACCAGCAGCATGAACGAGCCTAAACACGGG | (SEQ ID NO: 102) |
| V1900H -r | CGCGTATAAGCTTGTGTTAGCTCGTTCATGCTGCTGGTAGAAGTGCAAGCTTATA | (SEQ ID NO: 103) |
| V1900I | CGCGTATAAGCTTGATCTTCTACCAGCAGCATGAACGAGCCTAAACACGGG | (SEQ ID NO: 104) |
| V1900I -r | CGCGTATAAGCTTGTGTTAGCTCGTTCATGCTGCTGGTAGAAGATCAAGCTTATA | (SEQ ID NO: 105) |
| V1900K | CGCGTATAAGCTTGAAGTTCTACCAGCAGCATGAACGAGCCTAAACACGGG | (SEQ ID NO: 106) |

FIG. 27B

| | |
|---|---|
| V1900K-r | CTAGCCCGTGTTAGGCTCGTTCATGCTCTTGTGCTGGTAGAACTTCAAGCTTATA (SEQ ID NO: 107) |
| V1900L | CGCGTATAAGCTTGCTGTTCTACCAGCACAAGAGCATGAACGAGCCTAAACACGGG (SEQ ID NO: 108) |
| V1900L-r | CTAGCCCGTGTTTAGGCTCGTTCATGCTCTTGTGCTGGTAGAACAGCAAGCTTATA (SEQ ID NO: 109) |
| V1900M | CGCGTATAAGCTTGATGTTCTACCAGCACAAGAGCATGAACGAGCCTAAACACGGG (SEQ ID NO: 110) |
| V1900M-r | CTAGCCCGTGTTTAGGCTCGTTCATGCTCTTGTGCTGGTAGAACATCAAGCTTATA (SEQ ID NO: 111) |
| V1900N | CGCGTATAAGCTTGAACTTCTACCAGCACAAGAGCATGAACGAGCCTAAACACGGG (SEQ ID NO: 112) |
| V1900N-r | CTAGCCCGTGTTTAGGCTCGTTCATGCTCTTGTGCTGGTAGAAGTTCAAGCTTATA (SEQ ID NO: 113) |
| V1900P | CGCGTATAAGCTTGCCCTTCTACCAGCACAAGAGCATGAACGAGCCTAAACACGGG (SEQ ID NO: 114) |
| V1900P-r | CTAGCCCGTGTTTAGGCTCGTTCATGCTCTTGTGCTGGTAGAAGGGCAAGCTTATA (SEQ ID NO: 115) |
| V1900Q | CGCGTATAAGCTTGCAGTTCTACCAGCACAAGAGCATGAACGAGCCTAAACACGGG (SEQ ID NO: 116) |
| V1900Q-r | CTAGCCCGTGTTTAGGCTCGTTCATGCTCTTGTGCTGGTAGAACTGCAAGCTTATA (SEQ ID NO: 117) |
| V1900R | CGCGTATAAGCTTGAGGTTCTACCAGCACAAGAGCATGAACGAGCCTAAACACGGG (SEQ ID NO: 118) |
| V1900R-r | CTAGCCCGTGTTTAGGCTCGTTCATGCTCTTGTGCTGGTAGAACCTCAAGCTTATA (SEQ ID NO: 119) |
| V1900S | CGCGTATAAGCTTGAGCTTCTACCAGCACAAGAGCATGAACGAGCCTAAACACGGG (SEQ ID NO: 120) |
| V1900S-r | CTAGCCCGTGTTTAGGCTCGTTCATGCTCTTGTGCTGGTAGAAGCTCAAGCTTATA (SEQ ID NO: 121) |
| V1900T | CGCGTATAAGCTTGACCTTCTACCAGCACAAGAGCATGAACGAGCCTAAACACGGG (SEQ ID NO: 122) |
| V1900T-r | CTAGCCCGTGTTTAGGCTCGTTCATGCTCTTGTGCTGGTAGAAGGTCAAGCTTATA (SEQ ID NO: 123) |
| V1900W | CGCGTATAAGCTTGTGGTTCTACCAGCACAAGAGCATGAACGAGCCTAAACACGGG (SEQ ID NO: 124) |
| V1900W-r | CTAGCCCGTGTTTAGGCTCGTTCATGCTCTTGTGCTGGTAGAACCACAAGCTTATA (SEQ ID NO: 125) |
| V1900Y | CGCGTATAAGCTTGTACTTCTACCAGCACAAGAGCATGAACGAGCCTAAACACGGG (SEQ ID NO: 126) |
| V1900Y-r | CTAGCCCGTGTTTAGGCTCGTTCATGCTCTTGTGCTGGTAGAAGTACAAGCTTATA (SEQ ID NO: 127) |
| Y1902F | CGCGTATAAGCTTGGTGTTCTCCAGCACAAGAGCATGAACGAGCCTAAACACGGG (SEQ ID NO: 128) |
| Y1902F-r | CTAGCCCGTGTTTAGGCTCGTTCATGCTCTTGTGCTGGAAGAACACCAAGCTTATA (SEQ ID NO: 129) |

FIG. 27C

```
                              SEQUENCE LISTING

<160> NUMBER OF SEQ ID NOS: 145

<210> SEQ ID NO 1
<211> LENGTH: 387
<212> TYPE: PRT
<213> ORGANISM: Homo sapiens

<400> SEQUENCE: 1

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Asp Val Ala Ala Thr Gly Asp Gly Pro Asp Ile Ile Phe Trp Ala
    50                  55                  60

His Asp Arg Phe Gly Gly Tyr Ala Asp Ser Gly Leu Leu Ala Glu Ile
65                  70                  75                  80

Thr Pro Asp Lys Ala Phe Asp Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Asp Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220
```

```
Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Asp Pro Ser
            245                 250                 255

Lys Pro Phe Val Gly Val Leu Ser Ala Gly Ile Asn Ala Ala Ser Pro
        260                 265                 270

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Asp Lys Gly Glu Ile Met Pro Asn Ile Pro Asp
                325                 330                 335

Met Ser Ala Phe Trp Tyr Ala Val Arg Thr Ala Val Ile Asn Ala Ala
                340                 345                 350

Ser Gly Arg Asp Thr Val Asp Glu Ala Leu Lys Asp Ala Asp Thr Asn
            355                 360                 365

Ser Ser Ser Asn Asn Asn Asn Asn Asn Asn Asn Asn Leu Gly Ile
370                 375                 380

Glu Gly Arg
385

<210> SEQ ID NO 2
<211> LENGTH: 199
<212> TYPE: PRT
<213> ORGANISM: Homo sapiens

<400> SEQUENCE: 2

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 3
<211> LENGTH: 382
<212> TYPE: PRT
<213> ORGANISM: Homo sapiens

<400> SEQUENCE: 3

```
Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Glu Pro Gln
    50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
    210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
        275                 280                 285

Cys Ala Gly Glu Val Arg Ala Phe Leu Gln Glu Asn Thr His Val Arg
    290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335

Thr Tyr Asp Glu Phe Glu Tyr Cys Trp Asp Thr Phe Val Tyr Arg Gln
            340                 345                 350

Gly Cys Pro Phe Gln Pro Trp Asp Gly Leu Glu Glu His Ser Gln Ala
        355                 360                 365

Leu Ser Gly Arg Leu Arg Ala Ile Leu Gln Asn Gln Gly Asn
```

```
                 370                 375                 380

<210> SEQ ID NO 4
<211> LENGTH: 192
<212> TYPE: PRT
<213> ORGANISM: Homo sapiens

<400> SEQUENCE: 4

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Glu Pro Gln
    50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

<210> SEQ ID NO 5
<211> LENGTH: 190
<212> TYPE: PRT
<213> ORGANISM: Homo sapiens

<400> SEQUENCE: 5

Met Asp Pro Asp Thr Phe Thr Phe Asn Phe Asn Asn Asp Pro Leu Val
1               5                   10                  15

Leu Arg Arg Arg Gln Thr Tyr Leu Cys Tyr Glu Val Glu Arg Leu Asp
            20                  25                  30

Asn Gly Thr Trp Val Leu Met Asp Gln His Met Gly Phe Leu Cys Asn
        35                  40                  45

Glu Ala Lys Asn Leu Leu Cys Gly Phe Tyr Gly Arg His Ala Glu Leu
    50                  55                  60

Arg Phe Leu Asp Leu Val Pro Ser Leu Gln Leu Asp Pro Ala Gln Ile
65                  70                  75                  80

Tyr Arg Val Thr Trp Phe Ile Ser Trp Ser Pro Cys Phe Ser Trp Gly
                85                  90                  95

Cys Ala Gly Glu Val Arg Ala Phe Leu Gln Glu Asn Thr His Val Arg
            100                 105                 110

Leu Arg Ile Phe Ala Ala Arg Ile Tyr Asp Tyr Asp Pro Leu Tyr Lys
        115                 120                 125

Glu Ala Leu Gln Met Leu Arg Asp Ala Gly Ala Gln Val Ser Ile Met
```

```
                    130                 135                 140
Thr Tyr Asp Glu Phe Glu Tyr Cys Trp Asp Thr Phe Val Tyr Arg Gln
145                 150                 155                 160

Gly Cys Pro Phe Gln Pro Trp Asp Gly Leu Glu His Ser Gln Ala
                    165                 170                 175

Leu Ser Gly Arg Leu Arg Ala Ile Leu Gln Asn Gln Gly Asn
                180                 185                 190

<210> SEQ ID NO 6
<211> LENGTH: 187
<212> TYPE: PRT
<213> ORGANISM: Homo sapiens

<400> SEQUENCE: 6

Met Asp Pro His Ile Phe Thr Ser Asn Phe Asn Asn Gly Ile Gly Arg
1               5                   10                  15

His Lys Thr Tyr Leu Cys Tyr Glu Val Glu Arg Leu Asp Asn Gly Thr
                20                  25                  30

Ser Val Lys Met Asp Gln His Arg Gly Phe Leu His Asn Gln Ala Lys
            35                  40                  45

Asn Leu Leu Cys Gly Phe Tyr Gly Arg His Ala Glu Leu Arg Phe Leu
50                  55                  60

Asp Leu Val Pro Ser Leu Gln Leu Asp Pro Ala Gln Ile Tyr Arg Val
65                  70                  75                  80

Thr Trp Phe Ile Ser Trp Ser Pro Cys Phe Ser Trp Gly Cys Ala Gly
                85                  90                  95

Glu Val Arg Ala Phe Leu Gln Glu Asn Thr His Val Arg Leu Arg Ile
            100                 105                 110

Phe Ala Ala Arg Ile Tyr Asp Tyr Asp Pro Leu Tyr Lys Glu Ala Leu
        115                 120                 125

Gln Met Leu Arg Asp Ala Gly Ala Gln Val Ser Ile Met Thr Tyr Asp
130                 135                 140

Glu Phe Lys His Cys Trp Asp Thr Phe Val Asp His Gln Gly Cys Pro
145                 150                 155                 160

Phe Gln Pro Trp Asp Gly Leu Asp Glu His Ser Gln Ala Leu Ser Gly
                165                 170                 175

Arg Leu Arg Ala Ile Leu Gln Asn Gln Gly Asn
            180                 185

<210> SEQ ID NO 7
<211> LENGTH: 379
<212> TYPE: PRT
<213> ORGANISM: Homo sapiens

<400> SEQUENCE: 7

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Gln Val Tyr Phe Glu Pro Gln
        50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
```

```
                    85                  90                  95
Cys Pro Asp Cys Val Ala Lys Leu Ala Glu Phe Leu Ser Glu His Pro
                100                 105                 110

Asn Val Thr Leu Thr Ile Ser Ala Ala Arg Leu Tyr Tyr Tyr Trp Glu
                115                 120                 125

Arg Asp Tyr Arg Arg Ala Leu Cys Arg Leu Ser Gln Ala Gly Ala Arg
            130                 135                 140

Val Lys Ile Met Asp Tyr Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
                180                 185                 190

Met Asp Pro His Ile Phe Thr Ser Asn Phe Asn Asn Gly Ile Gly Arg
                195                 200                 205

His Lys Thr Tyr Leu Cys Tyr Glu Val Glu Arg Leu Asp Asn Gly Thr
            210                 215                 220

Ser Val Lys Met Asp Gln His Arg Gly Phe Leu His Asn Gln Ala Lys
225                 230                 235                 240

Asn Leu Leu Cys Gly Phe Tyr Gly Arg His Ala Glu Leu Arg Phe Leu
                245                 250                 255

Asp Leu Val Pro Ser Leu Gln Leu Asp Pro Ala Gln Ile Tyr Arg Val
                260                 265                 270

Thr Trp Phe Ile Ser Trp Ser Pro Cys Phe Ser Trp Gly Cys Ala Gly
            275                 280                 285

Glu Val Arg Ala Phe Leu Gln Glu Asn Thr His Val Arg Leu Arg Ile
290                 295                 300

Phe Ala Ala Arg Ile Tyr Asp Tyr Asp Pro Leu Tyr Lys Glu Ala Leu
305                 310                 315                 320

Gln Met Leu Arg Asp Ala Gly Ala Gln Val Ser Ile Met Thr Tyr Asp
                325                 330                 335

Glu Phe Lys His Cys Trp Asp Thr Phe Val Asp His Gln Gly Cys Pro
                340                 345                 350

Phe Gln Pro Trp Asp Gly Leu Asp Glu His Ser Gln Ala Leu Ser Gly
            355                 360                 365

Arg Leu Arg Ala Ile Leu Gln Asn Gln Gly Asn
            370                 375

<210> SEQ ID NO 8
<211> LENGTH: 391
<212> TYPE: PRT
<213> ORGANISM: Homo sapiens

<400> SEQUENCE: 8

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Gln Val Tyr Phe Glu Pro Gln
        50                  55                  60

Tyr His Ala Glu Met Cys Phe Leu Ser Trp Phe Cys Gly Asn Gln Leu
65                  70                  75                  80
```

-continued

```
Pro Ala Tyr Lys Cys Phe Gln Ile Thr Trp Phe Val Ser Trp Thr Pro
             85                  90                  95

Cys Pro Asp Cys Val Ala Lys Leu Ala Glu Phe Leu Ser Glu His Pro
        100                 105                 110

Asn Val Thr Leu Thr Ile Ser Ala Ala Arg Leu Tyr Tyr Tyr Trp Glu
    115                 120                 125

Arg Asp Tyr Arg Arg Ala Leu Cys Arg Leu Ser Gln Ala Gly Ala Arg
130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Glu Ala Ser Pro Ala Ser Gly Pro Arg His Leu Met Asp Pro His
        195                 200                 205

Ile Phe Thr Ser Asn Phe Asn Asn Gly Ile Gly Arg His Lys Thr Tyr
    210                 215                 220

Leu Cys Tyr Glu Val Glu Arg Leu Asp Asn Gly Thr Ser Val Lys Met
225                 230                 235                 240

Asp Gln His Arg Gly Phe Leu His Asn Gln Ala Lys Asn Leu Leu Cys
                245                 250                 255

Gly Phe Tyr Gly Arg His Ala Glu Leu Arg Phe Leu Asp Leu Val Pro
            260                 265                 270

Ser Leu Gln Leu Asp Pro Ala Gln Ile Tyr Arg Val Thr Trp Phe Ile
        275                 280                 285

Ser Trp Ser Pro Cys Phe Ser Trp Gly Cys Ala Gly Glu Val Arg Ala
    290                 295                 300

Phe Leu Gln Glu Asn Thr His Val Arg Leu Arg Ile Phe Ala Ala Arg
305                 310                 315                 320

Ile Tyr Asp Tyr Asp Pro Leu Tyr Lys Glu Ala Leu Gln Met Leu Arg
                325                 330                 335

Asp Ala Gly Ala Gln Val Ser Ile Met Thr Tyr Asp Glu Phe Lys His
            340                 345                 350

Cys Trp Asp Thr Phe Val Asp His Gln Gly Cys Pro Phe Gln Pro Trp
        355                 360                 365

Asp Gly Leu Asp Glu His Ser Gln Ala Leu Ser Gly Arg Leu Arg Ala
    370                 375                 380

Ile Leu Gln Asn Gln Gly Asn
385                 390

<210> SEQ ID NO 9
<211> LENGTH: 190
<212> TYPE: PRT
<213> ORGANISM: Homo sapiens

<400> SEQUENCE: 9

Met Asp Pro Asp Thr Phe Thr Phe Asn Phe Asn Asn Asp Pro Leu Val
1               5                   10                  15

Leu Arg Arg Arg Gln Thr Tyr Leu Cys Tyr Glu Val Glu Arg Leu Asp
            20                  25                  30

Asn Gly Thr Trp Val Leu Met Asp Gln His Met Gly Phe Leu Cys Asn
        35                  40                  45

Glu Ala Lys Asn Leu Leu Cys Gly Phe Tyr Gly Arg His Ala Glu Leu
    50                  55                  60
```

Arg Phe Leu Asp Leu Val Pro Ser Leu Gln Leu Asp Pro Ala Gln Ile
65                  70                  75                  80

Tyr Arg Val Thr Trp Phe Ile Ser Trp Ser Pro Cys Phe Ser Trp Gly
                85                  90                  95

Cys Ala Gly Glu Val Arg Ala Phe Leu Gln Glu Asn Thr His Val Arg
            100                 105                 110

Leu Arg Ile Phe Ala Ala Arg Ile Tyr Asp Tyr Asp Pro Leu Tyr Lys
            115                 120                 125

Glu Ala Leu Gln Met Leu Arg Asp Ala Gly Ala Gln Val Ser Ile Met
130                 135                 140

Thr Tyr Asp Glu Phe Lys His Cys Trp Asp Thr Phe Val Asp His Gln
145                 150                 155                 160

Gly Cys Pro Phe Gln Pro Trp Asp Gly Leu Asp Glu His Ser Gln Ala
                165                 170                 175

Leu Ser Gly Arg Leu Arg Ala Ile Leu Gln Asn Gln Gly Asn
            180                 185                 190

<210> SEQ ID NO 10
<211> LENGTH: 187
<212> TYPE: PRT
<213> ORGANISM: Homo sapiens

<400> SEQUENCE: 10

Met Asp Pro His Ile Phe Thr Ser Asn Phe Asn Asn Gly Ile Gly Arg
1               5                   10                  15

His Lys Thr Tyr Leu Cys Tyr Glu Val Glu Arg Leu Asp Asn Gly Thr
            20                  25                  30

Ser Val Lys Met Asp Gln His Arg Gly Phe Leu His Asn Gln Ala Lys
        35                  40                  45

Asn Leu Leu Cys Gly Phe Tyr Gly Arg His Ala Glu Leu Arg Phe Leu
    50                  55                  60

Asp Leu Val Pro Ser Leu Gln Leu Asp Pro Ala Gln Ile Tyr Arg Val
65                  70                  75                  80

Thr Trp Phe Ile Ser Trp Ser Pro Cys Phe Ser Trp Gly Cys Ala Gly
                85                  90                  95

Glu Val Arg Ala Phe Leu Gln Glu Asn Thr His Val Arg Leu Arg Ile
            100                 105                 110

Phe Ala Ala Arg Ile Tyr Asp Tyr Asp Pro Leu Tyr Lys Glu Ala Leu
        115                 120                 125

Gln Met Leu Arg Asp Ala Gly Ala Gln Val Ser Ile Met Thr Tyr Asp
    130                 135                 140

Glu Phe Glu Tyr Cys Trp Asp Thr Phe Val Tyr Arg Gln Gly Cys Pro
145                 150                 155                 160

Phe Gln Pro Trp Asp Gly Leu Glu Glu His Ser Gln Ala Leu Ser Gly
                165                 170                 175

Arg Leu Arg Ala Ile Leu Gln Asn Gln Gly Asn
            180                 185

<210> SEQ ID NO 11
<211> LENGTH: 379
<212> TYPE: PRT
<213> ORGANISM: Homo sapiens

<400> SEQUENCE: 11

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Glu Pro Gln
 50                  55                  60

Tyr His Ala Glu Met Cys Phe Leu Ser Trp Phe Cys Gly Asn Gln Leu
65                   70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
            115                 120                 125

Arg Asp Tyr Arg Arg Ala Leu Cys Arg Leu Ser Gln Ala Gly Ala Arg
130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro His Ile Phe Thr Ser Asn Phe Asn Asn Gly Ile Gly Arg
            195                 200                 205

His Lys Thr Tyr Leu Cys Tyr Glu Val Glu Arg Leu Asp Asn Gly Thr
210                 215                 220

Ser Val Lys Met Asp Gln His Arg Gly Phe Leu His Asn Gln Ala Lys
225                 230                 235                 240

Asn Leu Leu Cys Gly Phe Tyr Gly Arg His Ala Glu Leu Arg Phe Leu
                245                 250                 255

Asp Leu Val Pro Ser Leu Gln Leu Asp Pro Ala Gln Ile Tyr Arg Val
            260                 265                 270

Thr Trp Phe Ile Ser Trp Ser Pro Cys Phe Ser Trp Gly Cys Ala Gly
            275                 280                 285

Glu Val Arg Ala Phe Leu Gln Glu Asn Thr His Val Arg Leu Arg Ile
290                 295                 300

Phe Ala Ala Arg Ile Tyr Asp Tyr Asp Pro Leu Tyr Lys Glu Ala Leu
305                 310                 315                 320

Gln Met Leu Arg Asp Ala Gly Ala Gln Val Ser Ile Met Thr Tyr Asp
                325                 330                 335

Glu Phe Glu Tyr Cys Trp Asp Thr Phe Val Tyr Arg Gln Gly Cys Pro
            340                 345                 350

Phe Gln Pro Trp Asp Gly Leu Glu Glu His Ser Gln Ala Leu Ser Gly
            355                 360                 365

Arg Leu Arg Ala Ile Leu Gln Asn Gln Gly Asn
370                 375

<210> SEQ ID NO 12
<211> LENGTH: 382
<212> TYPE: PRT
<213> ORGANISM: Homo sapiens

<400> SEQUENCE: 12

Met Asn Pro Gln Ile Arg Asn Pro Met Glu Arg Met Tyr Arg Asp Thr

```
1               5                    10                   15
Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
                35                  40                  45

Leu Trp Asp Thr Gly Val Phe Arg Gly Gln Val Tyr Phe Glu Pro Gln
            50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
                100                 105                 110

Asn Val Thr Leu Thr Ile Ser Ala Ala Arg Leu Tyr Tyr Tyr Trp Glu
            115                 120                 125

Arg Asp Tyr Arg Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
    210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
        275                 280                 285

Cys Ala Gly Glu Val Arg Ala Phe Leu Gln Glu Asn Thr His Val Arg
            290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335

Thr Tyr Asp Glu Phe Lys His Cys Trp Asp Thr Phe Val Asp His Gln
            340                 345                 350

Gly Cys Pro Phe Gln Pro Trp Asp Gly Leu Asp Glu His Ser Gln Ala
        355                 360                 365

Leu Ser Gly Arg Leu Arg Ala Ile Leu Gln Asn Gln Gly Asn
    370                 375                 380

<210> SEQ ID NO 13
<211> LENGTH: 199
<212> TYPE: PRT
<213> ORGANISM: Homo sapiens

<400> SEQUENCE: 13
```

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Ala Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 14
<211> LENGTH: 391
<212> TYPE: PRT
<213> ORGANISM: Homo sapiens

<400> SEQUENCE: 14

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Gln Val Tyr Phe Glu Pro Gln
        50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
                100                 105                 110

Asn Val Thr Leu Thr Ile Ser Ala Ala Arg Leu Tyr Tyr Tyr Trp Glu
            115                 120                 125

Arg Asp Tyr Arg Arg Ala Leu Cys Arg Leu Ser Gln Ala Gly Ala Arg
        130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

```
Asn Tyr Ala Phe Leu His Arg Thr Leu Lys Glu Ile Leu Arg Tyr Leu
            180                 185                 190

Met Glu Ala Ser Pro Ala Ser Gly Pro Arg His Leu Met Asp Pro His
        195                 200                 205

Ile Phe Thr Ser Asn Phe Asn Asn Gly Ile Gly Arg His Lys Thr Tyr
    210                 215                 220

Leu Cys Tyr Glu Val Glu Arg Leu Asp Asn Gly Thr Ser Val Lys Met
225                 230                 235                 240

Asp Gln His Arg Gly Phe Leu His Asn Gln Ala Lys Asn Leu Leu Cys
                245                 250                 255

Gly Phe Tyr Gly Arg His Ala Ala Leu Arg Phe Leu Asp Leu Val Pro
            260                 265                 270

Ser Leu Gln Leu Asp Pro Ala Gln Ile Tyr Arg Val Thr Trp Phe Ile
        275                 280                 285

Ser Trp Ser Pro Cys Phe Ser Trp Gly Cys Ala Gly Glu Val Arg Ala
    290                 295                 300

Phe Leu Gln Glu Asn Thr His Val Arg Leu Arg Ile Phe Ala Ala Arg
305                 310                 315                 320

Ile Tyr Asp Tyr Asp Pro Leu Tyr Lys Glu Ala Leu Gln Met Leu Arg
                325                 330                 335

Asp Ala Gly Ala Gln Val Ser Ile Met Thr Tyr Asp Glu Phe Lys His
            340                 345                 350

Cys Trp Asp Thr Phe Val Asp His Gln Gly Cys Pro Phe Gln Pro Trp
        355                 360                 365

Asp Gly Leu Asp Glu His Ser Gln Ala Leu Ser Gly Arg Leu Arg Ala
    370                 375                 380

Ile Leu Gln Asn Gln Gly Asn
385                 390

<210> SEQ ID NO 15
<211> LENGTH: 198
<212> TYPE: PRT
<213> ORGANISM: Homo sapiens

<400> SEQUENCE: 15

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
```

```
145                 150                 155                 160
Ala Trp Glu Gly Leu His Glu Asn Ser Val Arg Leu Ser Arg Gln Leu
                165                 170                 175
Arg Arg Ile Leu Leu Pro Leu Tyr Glu Val Asp Asp Leu Arg Asp Ala
            180                 185                 190
Phe Arg Thr Leu Gly Leu
            195

<210> SEQ ID NO 16
<211> LENGTH: 181
<212> TYPE: PRT
<213> ORGANISM: Homo sapiens

<400> SEQUENCE: 16

Met Asp Ser Leu Leu Met Asn Arg Arg Glu Phe Leu Tyr Gln Phe Lys
1               5                   10                  15
Asn Val Arg Trp Ala Lys Gly Arg Arg Glu Thr Tyr Leu Cys Tyr Val
                20                  25                  30
Val Lys Arg Arg Asp Ser Ala Thr Ser Phe Ser Leu Asp Phe Gly Tyr
            35                  40                  45
Leu Arg Asn Lys Asn Gly Cys His Val Glu Leu Leu Phe Leu Arg Tyr
    50                  55                  60
Ile Ser Asp Trp Asp Leu Asp Pro Gly Arg Cys Tyr Arg Val Thr Trp
65                  70                  75                  80
Phe Ile Ser Trp Ser Pro Cys Tyr Asp Cys Ala Arg His Val Ala Asp
                85                  90                  95
Phe Leu Arg Gly Asn Pro Asn Leu Ser Leu Arg Ile Phe Thr Ala Arg
            100                 105                 110
Leu Tyr Phe Cys Glu Ala Gly Arg Arg Glu Pro Glu Gly Leu Arg Arg
        115                 120                 125
Leu His Arg Ala Gly Val Gln Ile Ala Ile Met Thr Phe Lys Asp Tyr
    130                 135                 140
Phe Tyr Cys Trp Asn Thr Phe Val Glu Asn His Gly Arg Thr Phe Lys
145                 150                 155                 160
Ala Trp Glu Gly Leu His Glu Asn Ser Val Arg Leu Ser Arg Gln Leu
                165                 170                 175
Arg Arg Ile Leu Leu
            180

<210> SEQ ID NO 17
<211> LENGTH: 198
<212> TYPE: PRT
<213> ORGANISM: Homo sapiens

<400> SEQUENCE: 17

Met Asp Ser Leu Leu Met Asn Arg Arg Glu Phe Leu Tyr Gln Phe Lys
1               5                   10                  15
Asn Val Arg Trp Ala Lys Gly Arg Arg Glu Thr Tyr Leu Cys Tyr Val
                20                  25                  30
Val Lys Arg Arg Asp Ser Ala Thr Ser Phe Ser Leu Asp Phe Gly Tyr
            35                  40                  45
Leu Arg Asn Lys Asn Gly Cys His Val Glu Leu Leu Phe Leu Arg Tyr
    50                  55                  60
Ile Ser Asp Trp Asp Leu Asp Pro Gly Arg Cys Tyr Arg Val Thr Trp
65                  70                  75                  80
Phe Ile Ser Trp Ser Pro Cys Tyr Asp Cys Ala Arg His Val Ala Asp
```

```
                         85                  90                  95

Phe Leu Arg Gly Asn Pro Asn Leu Ser Leu Arg Ile Phe Thr Ala Arg
                100                 105                 110

Leu Tyr Phe Cys Glu Ala Gly Arg Arg Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
                180                 185                 190

Phe Arg Thr Leu Gly Leu
                195

<210> SEQ ID NO 18
<211> LENGTH: 181
<212> TYPE: PRT
<213> ORGANISM: Homo sapiens

<400> SEQUENCE: 18

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Ala Gly Arg Arg Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu
            180

<210> SEQ ID NO 19
<211> LENGTH: 181
<212> TYPE: PRT
<213> ORGANISM: Homo sapiens

<400> SEQUENCE: 19

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
```

```
                    20                  25                  30
Val Lys Arg Arg Asp Ser Ala Thr Ser Phe Ser Leu Asp Phe Gly Tyr
            35                  40                  45
Leu Arg Asn Lys Asn Gly Cys His Val Glu Leu Leu Phe Leu Arg Tyr
        50                  55                  60
Ile Ser Asp Trp Asp Leu Asp Pro Gly Arg Cys Tyr Arg Val Thr Trp
65                  70                  75                  80
Phe Ile Ser Trp Ser Pro Cys Tyr Asp Cys Ala Arg His Val Ala Asp
                85                  90                  95
Phe Leu Arg Gly Asn Pro Asn Leu Ser Leu Arg Ile Phe Thr Ala Arg
            100                 105                 110
Leu Tyr Phe Cys Glu Asp Gly Lys Ala Glu Pro Glu Gly Leu Arg Arg
        115                 120                 125
Leu His Arg Ala Gly Val Gln Ile Ala Ile Met Thr Phe Lys Asp Tyr
    130                 135                 140
Phe Tyr Cys Trp Asn Thr Phe Val Glu Asn His Gly Arg Thr Phe Lys
145                 150                 155                 160
Ala Trp Glu Gly Leu His Glu Asn Ser Val Arg Leu Ser Arg Gln Leu
                165                 170                 175
Arg Arg Ile Leu Leu
            180

<210> SEQ ID NO 20
<211> LENGTH: 198
<212> TYPE: PRT
<213> ORGANISM: Homo sapiens

<400> SEQUENCE: 20

Met Asp Ser Leu Leu Met Asn Arg Arg Glu Phe Leu Tyr Gln Phe Lys
1               5                   10                  15
Asn Val Arg Trp Ala Lys Gly Arg Arg Glu Thr Tyr Leu Cys Tyr Val
            20                  25                  30
Val Lys Arg Arg Asp Ser Ala Thr Ser Glu Ser Leu Asp Phe Gly Tyr
        35                  40                  45
Leu Arg Asn Lys Asn Gly Cys His Val Glu Leu Leu Phe Leu Arg Tyr
    50                  55                  60
Ile Ser Asp Trp Asp Leu Asp Pro Gly Arg Cys Tyr Arg Val Thr Trp
65                  70                  75                  80
Phe Ile Ser Trp Ser Pro Cys Tyr Asp Cys Ala Arg His Val Ala Asp
                85                  90                  95
Phe Leu Arg Gly Asn Pro Asn Leu Ser Leu Arg Ile Phe Thr Ala Arg
            100                 105                 110
Leu Tyr Phe Cys Glu Ala Gly Arg Arg Glu Pro Glu Gly Leu Arg Arg
        115                 120                 125
Leu Ala Glu Ala Gly Val Gln Ile Ala Ile Met Thr Tyr Lys Asp Tyr
    130                 135                 140
Glu Tyr Cys Trp Asn Thr Phe Val Glu Asn His Gly Arg Thr Phe Lys
145                 150                 155                 160
Ala Trp Glu Gly Leu His Glu Asn Ser Val Arg Leu Ser Arg Gln Leu
                165                 170                 175
Arg Arg Ile Leu Leu Pro Leu Tyr Glu Val Asp Asp Leu Arg Asp Ala
            180                 185                 190
Phe Arg Thr Leu Gly Leu
        195
```

<210> SEQ ID NO 21
<211> LENGTH: 474
<212> TYPE: PRT
<213> ORGANISM: Homo sapiens

<400> SEQUENCE: 21

Met Asp Tyr Lys Asp Asp Asp Lys His Met Gly Gly Ser Asp Phe
1               5                   10                  15

Pro Ser Cys Arg Cys Val Glu Gln Ile Ile Glu Lys Asp Glu Gly Pro
            20                  25                  30

Phe Tyr Thr His Leu Gly Ala Gly Pro Asn Val Ala Ala Ile Arg Glu
                35                  40                  45

Ile Met Glu Glu Arg Phe Gly Gln Lys Gly Lys Ala Ile Arg Ile Glu
    50                  55                  60

Arg Val Ile Tyr Thr Gly Lys Glu Gly Lys Ser Ser Gln Gly Cys Pro
65                  70                  75                  80

Ile Ala Lys Trp Val Val Arg Arg Ser Ser Glu Glu Lys Leu Leu
                85                  90                  95

Cys Leu Val Arg Glu Arg Ala Gly His Thr Cys Glu Ala Ala Val Ile
            100                 105                 110

Val Ile Leu Ile Leu Val Trp Glu Gly Ile Pro Leu Ser Leu Ala Asp
        115                 120                 125

Lys Leu Tyr Ser Glu Leu Thr Glu Thr Leu Arg Lys Tyr Gly Thr Leu
    130                 135                 140

Thr Asn Arg Arg Cys Ala Leu Asn Glu Glu Arg Thr Cys Ala Cys Gln
145                 150                 155                 160

Gly Leu Asp Pro Glu Thr Cys Gly Ala Ser Phe Ser Phe Gly Cys Ser
                165                 170                 175

Trp Ser Met Tyr Tyr Asn Gly Cys Lys Phe Ala Arg Ser Lys Ile Pro
                180                 185                 190

Arg Lys Phe Lys Leu Leu Gly Asp Asp Pro Lys Glu Glu Lys Leu
            195                 200                 205

Glu Ser His Leu Gln Asn Leu Ser Thr Leu Met Ala Pro Thr Tyr Lys
    210                 215                 220

Lys Leu Ala Pro Asp Ala Tyr Asn Asn Gln Ile Glu Tyr Glu His Arg
225                 230                 235                 240

Ala Pro Glu Cys Arg Leu Gly Leu Lys Glu Gly Arg Pro Phe Ser Gly
                245                 250                 255

Val Thr Ala Cys Leu Asp Phe Cys Ala His Ala His Arg Asp Leu His
            260                 265                 270

Asn Met Gln Asn Gly Ser Thr Leu Val Cys Thr Leu Thr Arg Glu Asp
    275                 280                 285

Asn Arg Glu Phe Gly Gly Lys Pro Glu Asp Glu Gln Leu His Val Leu
    290                 295                 300

Pro Leu Tyr Lys Val Ser Asp Val Asp Glu Phe Gly Ser Val Glu Ala
305                 310                 315                 320

Gln Glu Glu Lys Lys Arg Ser Gly Ala Ile Gln Val Leu Ser Ser Phe
                325                 330                 335

Arg Arg Lys Val Arg Met Leu Ala Glu Pro Val Lys Thr Cys Arg Gln
            340                 345                 350

Arg Lys Leu Glu Ala Lys Lys Ala Ala Ala Glu Lys Leu Ser Gly Gly
        355                 360                 365

Gly Gly Ser Gly Gly Gly Gly Ser Gly Gly Gly Gly Ser Asp Glu Val
    370                 375                 380

Trp Ser Asp Ser Glu Gln Ser Phe Leu Asp Pro Asp Ile Gly Gly Val
385                 390                 395                 400

Ala Val Ala Pro Thr His Gly Ser Ile Leu Ile Glu Cys Ala Lys Arg
            405                 410                 415

Glu Leu His Ala Thr Thr Pro Leu Lys Asn Pro Asn Arg Asn His Pro
        420                 425                 430

Thr Arg Ile Ser Leu Val Phe Tyr Gln His Lys Ser Met Asn Glu Pro
            435                 440                 445

Lys His Gly Leu Ala Leu Trp Glu Ala Lys Met Ala Glu Lys Ala Arg
        450                 455                 460

Glu Lys Glu Glu Glu Cys Glu Lys Tyr Gly
465                 470

<210> SEQ ID NO 22
<211> LENGTH: 878
<212> TYPE: PRT
<213> ORGANISM: Homo sapiens

<400> SEQUENCE: 22

Met Gly Gly Ser Asp Phe Pro Ser Cys Arg Cys Val Glu Gln Ile Ile
1               5                   10                  15

Glu Lys Asp Glu Gly Pro Phe Tyr Thr His Leu Gly Ala Gly Pro Asn
            20                  25                  30

Val Ala Ala Ile Arg Glu Ile Met Glu Glu Arg Phe Gly Gln Lys Gly
        35                  40                  45

Lys Ala Ile Arg Ile Glu Arg Val Ile Tyr Thr Gly Lys Glu Gly Lys
    50                  55                  60

Ser Ser Gln Gly Cys Pro Ile Ala Lys Trp Val Arg Arg Ser Ser
65                  70                  75                  80

Ser Glu Glu Lys Leu Leu Cys Leu Val Arg Glu Arg Ala Gly His Thr
                85                  90                  95

Cys Glu Ala Ala Val Ile Val Ile Leu Ile Leu Val Trp Glu Gly Ile
            100                 105                 110

Pro Leu Ser Leu Ala Asp Lys Leu Tyr Ser Glu Leu Thr Glu Thr Leu
        115                 120                 125

Arg Lys Tyr Gly Thr Leu Thr Asn Arg Arg Cys Ala Leu Asn Glu Glu
    130                 135                 140

Arg Thr Cys Ala Cys Gln Gly Leu Asp Pro Glu Thr Cys Gly Ala Ser
145                 150                 155                 160

Phe Ser Phe Gly Cys Ser Trp Ser Met Tyr Tyr Asn Gly Cys Lys Phe
                165                 170                 175

Ala Arg Ser Lys Ile Pro Arg Lys Phe Lys Leu Leu Gly Asp Asp Pro
            180                 185                 190

Lys Glu Glu Glu Lys Leu Glu Ser His Leu Gln Asn Leu Ser Thr Leu
        195                 200                 205

Met Ala Pro Thr Tyr Lys Lys Leu Ala Pro Asp Ala Tyr Asn Asn Gln
    210                 215                 220

Ile Glu Tyr Glu His Arg Ala Pro Glu Cys Arg Leu Gly Leu Lys Glu
225                 230                 235                 240

Gly Arg Pro Phe Ser Gly Val Thr Ala Cys Leu Asp Phe Cys Ala His
                245                 250                 255

Ala His Arg Asp Leu His Asn Met Gln Asn Gly Ser Thr Leu Val Cys
            260                 265                 270

Thr Leu Thr Arg Glu Asp Asn Arg Glu Phe Gly Gly Lys Pro Glu Asp

```
            275                 280                 285
Glu Gln Leu His Val Leu Pro Leu Tyr Lys Val Ser Asp Val Asp Glu
    290                 295                 300

Phe Gly Ser Val Glu Ala Gln Glu Glu Lys Lys Arg Ser Gly Ala Ile
305                 310                 315                 320

Gln Val Leu Ser Ser Phe Arg Arg Lys Val Arg Met Leu Ala Glu Pro
                325                 330                 335

Val Lys Thr Cys Arg Gln Arg Lys Leu Glu Ala Lys Lys Ala Ala Ala
                340                 345                 350

Glu Lys Leu Ser Ser Leu Glu Asn Ser Ser Asn Lys Asn Glu Lys Glu
                355                 360                 365

Lys Ser Ala Pro Ser Arg Thr Lys Gln Thr Glu Asn Ala Ser Gln Ala
    370                 375                 380

Lys Gln Leu Ala Glu Leu Leu Arg Leu Ser Gly Pro Val Met Gln Gln
385                 390                 395                 400

Ser Gln Gln Pro Gln Pro Leu Gln Lys Gln Pro Pro Gln Pro Gln Gln
                405                 410                 415

Gln Gln Arg Pro Gln Gln Gln Pro His Pro Gln Thr Glu Ser
                420                 425                 430     Ser

Val Asn Ser Tyr Ser Ala Ser Gly Ser Thr Asn Pro Tyr Met Arg Arg
    435                 440                 445

Pro Asn Pro Val Ser Pro Tyr Pro Asn Ser Ser His Thr Ser Asp Ile
450                 455                 460

Tyr Gly Ser Thr Ser Pro Met Asn Phe Tyr Ser Thr Ser Ser Gln Ala
465                 470                 475                 480

Ala Gly Ser Tyr Leu Asn Ser Ser Asn Pro Met Asn Pro Tyr Pro Gly
                485                 490                 495

Leu Leu Asn Gln Asn Thr Gln Tyr Pro Ser Tyr Gln Cys Asn Gly Asn
                500                 505                 510

Leu Ser Val Asp Asn Cys Ser Pro Tyr Leu Gly Ser Tyr Ser Pro Gln
                515                 520                 525

Ser Gln Pro Met Asp Leu Tyr Arg Tyr Pro Ser Gln Asp Pro Leu Ser
    530                 535                 540

Lys Leu Ser Leu Pro Pro Ile His Thr Leu Tyr Gln Pro Arg Phe Gly
545                 550                 555                 560

Asn Ser Gln Ser Phe Thr Ser Lys Tyr Leu Gly Tyr Gly Asn Gln Asn
                565                 570                 575

Met Gln Gly Asp Gly Phe Ser Ser Cys Thr Ile Arg Pro Asn Val His
                580                 585                 590

His Val Gly Lys Leu Pro Pro Tyr Pro Thr His Glu Met Asp Gly His
                595                 600                 605

Phe Met Gly Ala Thr Ser Arg Leu Pro Pro Asn Leu Ser Asn Pro Asn
    610                 615                 620

Met Asp Tyr Lys Asn Gly Glu His His Ser Pro Ser His Ile Ile His
625                 630                 635                 640

Asn Tyr Ser Ala Ala Pro Gly Met Phe Asn Ser Ser Leu His Ala Leu
                645                 650                 655

His Leu Gln Asn Lys Glu Asn Asp Met Leu Ser His Thr Ala Asn Gly
                660                 665                 670

Leu Ser Lys Met Leu Pro Ala Leu Asn His Asp Arg Thr Ala Cys Val
                675                 680                 685

Gln Gly Gly Leu His Lys Leu Ser Asp Ala Asn Gly Gln Glu Lys Gln
    690                 695                 700
```

```
Pro Leu Ala Leu Val Gln Gly Val Ala Ser Gly Ala Glu Asp Asn Asp
705                 710                 715                 720

Glu Val Trp Ser Asp Ser Glu Gln Ser Phe Leu Asp Pro Asp Ile Gly
            725                 730                 735

Gly Val Ala Val Ala Pro Thr His Gly Ser Ile Leu Ile Glu Cys Ala
        740                 745                 750

Lys Arg Glu Leu His Ala Thr Thr Pro Leu Lys Asn Pro Asn Arg Asn
            755                 760                 765

His Pro Thr Arg Ile Ser Leu Val Phe Tyr Gln His Lys Ser Met Asn
    770                 775                 780

Glu Pro Lys His Gly Leu Ala Leu Trp Glu Ala Lys Met Ala Glu Lys
785                 790                 795                 800

Ala Arg Glu Lys Glu Glu Cys Glu Lys Tyr Gly Pro Asp Tyr Val
                805                 810                 815

Pro Gln Lys Ser His Gly Lys Lys Val Lys Arg Glu Pro Ala Glu Pro
            820                 825                 830

His Glu Thr Ser Glu Pro Thr Tyr Leu Arg Phe Ile Lys Ser Leu Ala
            835                 840                 845

Glu Arg Thr Met Ser Val Thr Thr Asp Ser Thr Val Thr Thr Ser Pro
850                 855                 860

Tyr Ala Phe Thr Arg Val Thr Gly Pro Tyr Asn Arg Tyr Ile
865                 870                 875

<210> SEQ ID NO 23
<211> LENGTH: 474
<212> TYPE: PRT
<213> ORGANISM: Homo sapiens

<400> SEQUENCE: 23

Met Asp Tyr Lys Asp Asp Asp Asp Lys His Met Gly Gly Ser Asp Phe
1               5                   10                  15

Pro Ser Cys Arg Cys Val Glu Gln Ile Ile Glu Lys Asp Glu Gly Pro
            20                  25                  30

Phe Tyr Thr His Leu Gly Ala Gly Pro Asn Val Ala Ala Ile Arg Glu
        35                  40                  45

Ile Met Glu Glu Arg Phe Gly Gln Lys Gly Lys Ala Ile Arg Ile Glu
    50                  55                  60

Arg Val Ile Tyr Thr Gly Lys Glu Gly Lys Ser Ser Gln Gly Cys Pro
65                  70                  75                  80

Ile Ala Lys Trp Val Val Arg Arg Ser Ser Glu Glu Lys Leu Leu
                85                  90                  95

Cys Leu Val Arg Glu Arg Ala Gly His Thr Cys Glu Ala Ala Val Ile
                100                 105                 110

Val Ile Leu Ile Leu Val Trp Glu Gly Ile Pro Leu Ser Leu Ala Asp
            115                 120                 125

Lys Leu Tyr Ser Glu Leu Thr Glu Thr Leu Arg Lys Tyr Gly Thr Leu
    130                 135                 140

Thr Asn Arg Arg Cys Ala Leu Asn Glu Glu Arg Thr Cys Ala Cys Gln
145                 150                 155                 160

Gly Leu Asp Pro Glu Thr Cys Gly Ala Ser Phe Ser Phe Gly Cys Ser
                165                 170                 175

Trp Ser Met Tyr Tyr Asn Gly Cys Lys Phe Ala Arg Ser Lys Ile Pro
            180                 185                 190

Arg Lys Phe Lys Leu Leu Gly Asp Asp Pro Lys Glu Glu Glu Lys Leu
```

```
            195                 200                 205
Glu Ser His Leu Gln Asn Leu Ser Thr Leu Met Ala Pro Thr Tyr Lys
    210                 215                 220

Lys Leu Ala Pro Asp Ala Tyr Asn Asn Gln Ile Glu Tyr Glu His Arg
225                 230                 235                 240

Ala Pro Glu Cys Arg Leu Gly Leu Lys Glu Gly Arg Pro Phe Ser Gly
                245                 250                 255

Val Glu Ala Cys Leu Asp Phe Cys Ala His Ala His Arg Asp Leu His
            260                 265                 270

Asn Met Gln Asn Gly Ser Thr Leu Val Cys Thr Leu Thr Arg Glu Asp
        275                 280                 285

Asn Arg Glu Phe Gly Gly Lys Pro Glu Asp Glu Gln Leu His Val Leu
    290                 295                 300

Pro Leu Tyr Lys Val Ser Asp Val Asp Glu Phe Gly Ser Val Glu Ala
305                 310                 315                 320

Gln Glu Glu Lys Lys Arg Ser Gly Ala Ile Gln Val Leu Ser Ser Phe
                325                 330                 335

Arg Arg Lys Val Arg Met Leu Ala Glu Pro Val Lys Thr Cys Arg Gln
            340                 345                 350

Arg Lys Leu Glu Ala Lys Ala Ala Ala Glu Lys Leu Ser Gly Gly
        355                 360                 365

Gly Gly Ser Gly Gly Gly Ser Gly Gly Gly Ser Asp Glu Val
    370                 375                 380

Trp Ser Asp Ser Glu Gln Ser Phe Leu Asp Pro Asp Ile Gly Gly Val
385                 390                 395                 400

Ala Val Ala Pro Thr His Gly Ser Ile Leu Ile Glu Cys Ala Lys Arg
                405                 410                 415

Glu Leu His Ala Thr Thr Pro Leu Lys Asn Pro Asn Arg Asn His Pro
            420                 425                 430

Thr Arg Ile Ser Leu Val Phe Tyr Gln His Lys Ser Met Asn Glu Pro
        435                 440                 445

Lys His Gly Leu Ala Leu Trp Glu Ala Lys Met Ala Glu Lys Ala Arg
    450                 455                 460

Glu Lys Glu Glu Glu Cys Glu Lys Tyr Gly
465                 470

<210> SEQ ID NO 24
<211> LENGTH: 878
<212> TYPE: PRT
<213> ORGANISM: Homo sapiens

<400> SEQUENCE: 24

Met Gly Gly Ser Asp Phe Pro Ser Cys Arg Cys Val Glu Gln Ile Ile
1               5                   10                  15

Glu Lys Asp Glu Gly Pro Phe Tyr Thr His Leu Gly Ala Gly Pro Asn
            20                  25                  30

Val Ala Ala Ile Arg Glu Ile Met Glu Glu Arg Phe Gly Gln Lys Gly
        35                  40                  45

Lys Ala Ile Arg Ile Glu Arg Val Ile Tyr Thr Gly Lys Glu Gly Lys
    50                  55                  60

Ser Ser Gln Gly Cys Pro Ile Ala Lys Trp Val Val Arg Arg Ser Ser
65                  70                  75                  80

Ser Glu Glu Lys Leu Leu Cys Leu Val Arg Glu Arg Ala Gly His Thr
                85                  90                  95
```

```
Cys Glu Ala Ala Val Ile Val Ile Leu Ile Leu Val Trp Glu Gly Ile
                100                 105                 110

Pro Leu Ser Leu Ala Asp Lys Leu Tyr Ser Glu Leu Thr Glu Thr Leu
            115                 120                 125

Arg Lys Tyr Gly Thr Leu Thr Asn Arg Arg Cys Ala Leu Asn Glu Glu
        130                 135                 140

Arg Thr Cys Ala Cys Gln Gly Leu Asp Pro Glu Thr Cys Gly Ala Ser
145                 150                 155                 160

Phe Ser Phe Gly Cys Ser Trp Ser Met Tyr Tyr Asn Gly Cys Lys Phe
                165                 170                 175

Ala Arg Ser Lys Ile Pro Arg Lys Phe Lys Leu Leu Gly Asp Asp Pro
            180                 185                 190

Lys Glu Glu Glu Lys Leu Glu Ser His Leu Gln Asn Leu Ser Thr Leu
        195                 200                 205

Met Ala Pro Thr Tyr Lys Lys Leu Ala Pro Asp Ala Tyr Asn Asn Gln
210                 215                 220

Ile Glu Tyr Glu His Arg Ala Pro Glu Cys Arg Leu Gly Leu Lys Glu
225                 230                 235                 240

Gly Arg Pro Phe Ser Gly Val Glu Ala Cys Leu Asp Phe Cys Ala His
                245                 250                 255

Ala His Arg Asp Leu His Asn Met Gln Asn Gly Ser Thr Leu Val Cys
            260                 265                 270

Thr Leu Thr Arg Glu Asp Asn Arg Glu Phe Gly Gly Lys Pro Glu Asp
        275                 280                 285

Glu Gln Leu His Val Leu Pro Leu Tyr Lys Val Ser Asp Val Asp Glu
290                 295                 300

Phe Gly Ser Val Glu Ala Gln Glu Glu Lys Lys Arg Ser Gly Ala Ile
305                 310                 315                 320

Gln Val Leu Ser Ser Phe Arg Arg Lys Val Arg Met Leu Ala Glu Pro
                325                 330                 335

Val Lys Thr Cys Arg Gln Arg Lys Leu Glu Ala Lys Lys Ala Ala Ala
            340                 345                 350

Glu Lys Leu Ser Ser Leu Glu Asn Ser Ser Asn Lys Asn Glu Lys Glu
        355                 360                 365

Lys Ser Ala Pro Ser Arg Thr Lys Gln Thr Glu Asn Ala Ser Gln Ala
370                 375                 380

Lys Gln Leu Ala Glu Leu Leu Arg Leu Ser Gly Pro Val Met Gln Gln
385                 390                 395                 400

Ser Gln Gln Pro Gln Pro Leu Gln Lys Gln Pro Pro Gln Pro Gln Gln
                405                 410                 415

Gln Gln Arg Pro Gln Gln Gln Pro His His Pro Gln Thr Glu Ser
            420                 425                 430

Val Asn Ser Tyr Ser Ala Ser Gly Ser Thr Asn Pro Tyr Met Arg Arg
        435                 440                 445

Pro Asn Pro Val Ser Pro Tyr Pro Asn Ser Ser His Thr Ser Asp Ile
450                 455                 460

Tyr Gly Ser Thr Ser Pro Met Asn Phe Tyr Ser Thr Ser Ser Gln Ala
465                 470                 475                 480

Ala Gly Ser Tyr Leu Asn Ser Ser Asn Pro Met Asn Pro Tyr Pro Gly
                485                 490                 495

Leu Leu Asn Gln Asn Thr Gln Tyr Pro Ser Tyr Gln Cys Asn Gly Asn
            500                 505                 510

Leu Ser Val Asp Asn Cys Ser Pro Tyr Leu Gly Ser Tyr Ser Pro Gln
```

```
              515                 520                 525
Ser Gln Pro Met Asp Leu Tyr Arg Tyr Pro Ser Gln Asp Pro Leu Ser
530                 535                 540

Lys Leu Ser Leu Pro Pro Ile His Thr Leu Tyr Gln Pro Arg Phe Gly
545                 550                 555                 560

Asn Ser Gln Ser Phe Thr Ser Lys Tyr Leu Gly Tyr Gly Asn Gln Asn
                565                 570                 575

Met Gln Gly Asp Gly Phe Ser Ser Cys Thr Ile Arg Pro Asn Val His
            580                 585                 590

His Val Gly Lys Leu Pro Pro Tyr Pro Thr His Glu Met Asp Gly His
        595                 600                 605

Phe Met Gly Ala Thr Ser Arg Leu Pro Pro Asn Leu Ser Asn Pro Asn
610                 615                 620

Met Asp Tyr Lys Asn Gly Glu His His Ser Pro Ser His Ile Ile His
625                 630                 635                 640

Asn Tyr Ser Ala Ala Pro Gly Met Phe Asn Ser Ser Leu His Ala Leu
                645                 650                 655

His Leu Gln Asn Lys Glu Asn Asp Met Leu Ser His Thr Ala Asn Gly
            660                 665                 670

Leu Ser Lys Met Leu Pro Ala Leu Asn His Asp Arg Thr Ala Cys Val
        675                 680                 685

Gln Gly Gly Leu His Lys Leu Ser Asp Ala Asn Gly Gln Glu Lys Gln
690                 695                 700

Pro Leu Ala Leu Val Gln Gly Val Ala Ser Gly Ala Glu Asp Asn Asp
705                 710                 715                 720

Glu Val Trp Ser Asp Ser Glu Gln Ser Phe Leu Asp Pro Asp Ile Gly
                725                 730                 735

Gly Val Ala Val Ala Pro Thr His Gly Ser Ile Leu Ile Glu Cys Ala
            740                 745                 750

Lys Arg Glu Leu His Ala Thr Thr Pro Leu Lys Asn Pro Asn Arg Asn
        755                 760                 765

His Pro Thr Arg Ile Ser Leu Val Phe Tyr Gln His Lys Ser Met Asn
770                 775                 780

Glu Pro Lys His Gly Leu Ala Leu Trp Glu Ala Lys Met Ala Glu Lys
785                 790                 795                 800

Ala Arg Glu Lys Glu Glu Cys Glu Lys Tyr Gly Pro Asp Tyr Val
                805                 810                 815

Pro Gln Lys Ser His Gly Lys Val Lys Arg Glu Pro Ala Glu Pro
            820                 825                 830

His Glu Thr Ser Glu Pro Thr Tyr Leu Arg Phe Ile Lys Ser Leu Ala
        835                 840                 845

Glu Arg Thr Met Ser Val Thr Thr Asp Ser Thr Val Thr Thr Ser Pro
850                 855                 860

Tyr Ala Phe Thr Arg Val Thr Gly Pro Tyr Asn Arg Tyr Ile
865                 870                 875

<210> SEQ ID NO 25
<211> LENGTH: 1161
<212> TYPE: DNA
<213> ORGANISM: Homo sapiens

<400> SEQUENCE: 25
atgaaaatcg aagaaggtaa actggtaatc tggattaacg gcgataaagg ctataacggt     60
ctcgctgaag tcggtaagaa attcgagaaa gataccggaa ttaaagtcac cgttgagcat    120
```

```
ccggataaac tggaagagaa attcccacag gttgcggcaa ctggcgatgg ccctgacatt      180
atcttctggg cacacgaccg ctttggtggc tacgctcaat ctggcctgtt ggctgaaatc      240
accccggaca aagcgttcca ggacaagctg tatccgttta cctgggatgc cgtacgttac      300
aacggcaagc tgattgctta cccgatcgct gttgaagcgt tatcgctgat ttataacaaa      360
gatctgctgc cgaacccgcc aaaaacctgg aagagatcc cggcgctgga taagaactg       420 aaagcgaaag gtaagagcgc gctgatgttc aacctgcaag aaccgtactt cacctggccg      480
ctgattgctg ctgacggggg ttatgcgttc aagtatgaaa acggcaagta cgacattaaa      540
gacgtgggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacggcccg tgggcatggt ccaacatcga caccagcaaa      720
gtgaattatg gtgtaacggt actgccgacc ttcaagggtc aaccatccaa accgttcgtt      780
ggcgtgctga cgcagggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggcga agatccacg tattgccgcc       960 actatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa     1080 gccctgaaag acgcgcagac taattcgagc tcgaacaaca caacaataa caataacaac     1140 aacctcggga tcgagggaag g                                               1161

<210> SEQ ID NO 26
<211> LENGTH: 597
<212> TYPE: DNA
<213> ORGANISM: Homo sapiens

<400> SEQUENCE: 26
atggaagcca gcccagcatc cgggcccaga cacttgatgg atccacacat attcacttcc       60
aactttaaca atggcattgg aaggcataag acctacctgt gctacgaagt ggagcgcctg      120
gacaatggca cctcggtcaa gatggaccag cacaggggct tctacacaa ccaggctaag       180 aatcttctct gtggcttta cggccgccat gcggagctgc gcttcttgga cctggttcct      240
tctttgcagt tggaccccgc ccagatctac agggtcactt ggttcatctc ctggagcccc      300
tgcttctcct ggggctgtgc cggggaagtg cgtgcgttcc ttcaggagaa cacacacgtg      360
agactgcgta tcttcgctgc ccgcatctat gattacgacc ccctatataa ggaggcactg      420
caaatgctgc gggatgctgg ggcccaagtc tccatcatga cctacgatga atttaagcac      480
tgctgggaca ccttttgtgga ccaccaggga tgtcccttcc agccctggga tggactagat      540
gagcacagcc aagccctgag tgggaggctg cgggccattc tccagaatca gggaaac       597

<210> SEQ ID NO 27
<211> LENGTH: 1146
<212> TYPE: DNA
<213> ORGANISM: Homo sapiens

<400> SEQUENCE: 27
atgaatccac agattcgtaa ccccatggag cgcatgtatc gcgacacctt ttacgataac       60
tttgagaacg aaccgatttt atatggccgc agctatactt ggctgtgtta cgaagtgaag      120
atcaaacgcg gccgcagcaa tttactgtgg gatactggag tgtttcgtgg gcaggtgtat      180
```

```
ttcgaacccc agtaccacgc ggaaatgtgt ttcttgtctt ggttttgcgg caaccaactt    240
cctgcataca aatgtttcca gattacctgg tttgtttcct ggactccgtg cccggactgt    300
gtggcgaaac tggccgaatt tttgtccgaa caccccaacg tgacgcttac gatcagtgcc    360
gcgcgcctgt attattattg ggaacgtgac tatcgccgtg ccctctgccg cctcagccag    420
gcgggcgcac gtgttaagat tatggattat gaagaattcg catactgttg ggaaaacttc    480
gtgtacaatg aagggcaaca atttatgccc tggtataaat tcgatgaaaa ttatgctttt    540
ctgcatcgca ctttgaagga aatcttgcgc tatctgatgg acccagatac gtttacgttc    600
aattttaata cgatccgtt ggttctgcga cgtcgccaga cctacctgtg ttatgaagtg    660
gaacgcttgg acaacggtac gtgggtgctg atggaccaac atatgggatt tctgtgcaat    720
gaagcgaaga tctgcttttg tggcttctac ggccgccatg cagaactgcg ttttttggat    780
ttggtcccgt cattgcaatt ggatccggcc cagatctatc gcgtgacttg gttcatttcc    840
tggagtccgt gttttagctg gggctgcgcc ggcgaggtgc gtgccttcct gcaagaaaac    900
actcatgttc gccttcgcat ctttgcggct cgtatttacg attatgaccc gttgtataaa    960
gaggccttac agatgcttcg cgatgccggc gcacaggtaa gtatcatgac gtacgatgaa   1020
tttgaatatt gctgggacac gtttgtctat cgtcaagggt gtccttttcca gccatgggac   1080 ggcttggaag aacactcaca ggccctgagc ggccgtctgc gtgcaattct gcagaaccag   1140
ggaaat                                                              1146
```

<210> SEQ ID NO 28
<211> LENGTH: 576
<212> TYPE: DNA
<213> ORGANISM: Homo sapiens

<400> SEQUENCE: 28

```
atgaatccac agattcgtaa ccccatggag cgcatgtatc gcgacacctt ttacgataac     60
tttgagaacg aaccgatttt atatggccgc agctatactt ggctgtgtta cgaagtgaag    120
atcaaacgcg gccgcagcaa tttactgtgg gatactggag tgtttcgtgg gcaggtgtat    180
ttcgaacccc agtaccacgc ggaaatgtgt ttcttgtctt ggttttgcgg caaccaactt    240
cctgcataca aatgtttcca gattacctgg tttgtttcct ggactccgtg cccggactgt    300
gtggcgaaac tggccgaatt tttgtccgaa caccccaacg tgacgcttac gatcagtgcc    360
gcgcgcctgt attattattg ggaacgtgac tatcgccgtg ccctctgccg cctcagccag    420
gcgggcgcac gtgttaagat tatggattat gaagaattcg catactgttg ggaaaacttc    480
gtgtacaatg aagggcaaca atttatgccc tggtataaat tcgatgaaaa ttatgctttt    540
ctgcatcgca ctttgaagga aatcttgcgc tatctg                              576
```

<210> SEQ ID NO 29
<211> LENGTH: 570
<212> TYPE: DNA
<213> ORGANISM: Homo sapiens

<400> SEQUENCE: 29

```
atggacccag atacgtttac gttcaatttt aataacgatc cgttggttct gcgacgtcgc     60
cagacctacc tgtgttatga agtggaacgc ttggacaacg gtacgtgggt gctgatggac    120
caacatatgg gatttctgtg caatgaagcg aagaatctgc tttgtggctt ctacggccgc    180 catgcagaaac tgcgtttttt ggatttggtc ccgtcattgc aattggatcc ggcccagatc    240
tatcgcgtga cttggttcat ttcctggagt ccgtgtttta gctggggctg cgccggcgag    300
```

```
gtgcgtgcct tcctgcaaga aaacactcat gttcgccttc gcatctttgc ggctcgtatt    360
tacgattatg acccgttgta taagaggcc ttacagatgc ttcgcgatgc cggcgcacag    420
gtaagtatca tgacgtacga tgaatttgaa tattgctggg acacgtttgt ctatcgtcaa    480
gggtgtcctt tccagccatg ggacggcttg gaagaacact cacaggccct gagcggccgt    540
ctgcgtgcaa ttctgcagaa ccagggaaat                                    570

<210> SEQ ID NO 30
<211> LENGTH: 561
<212> TYPE: DNA
<213> ORGANISM: Homo sapiens

<400> SEQUENCE: 30
atggatccac acatattcac ttccaacttt aacaatggca ttggaaggca taagacctac     60
ctgtgctacg aagtggagcg cctggacaat ggcacctcgg tcaagatgga ccagcacagg    120
ggctttctac acaaccaggc taagaatctt ctctgtggct tttacggccg ccatgcggag    180
ctgcgcttct tggacctggt tccttctttg cagttggacc cggcccagat ctacagggtc    240
acttggttca tctcctggag cccctgcttc tcctggggct gtgccgggga agtgcgtgcg    300
ttccttcagg agaacacaca cgtgagactg cgtatcttcg ctgcccgcat ctatgattac    360
gaccccctat ataaggaggc actgcaaatg ctgcgggatg ctggggccca agtctccatc    420
atgacctacg atgaatttaa gcactgctgg gacaccttg tggaccacca gggatgtccc    480
ttccagccct gggatggact agatgagcac agccaagccc tgagtgggag gctgcgggcc    540
attctccaga atcagggaaa c                                             561

<210> SEQ ID NO 31
<211> LENGTH: 1137
<212> TYPE: DNA
<213> ORGANISM: Homo sapiens

<400> SEQUENCE: 31
atgaatccac agattcgtaa ccccatggag cgcatgtatc gcgacacctt ttacgataac     60
tttgagaacg aaccgatttt atatggccgc agctatactt ggctgtgtta cgaagtgaag    120
atcaaacgcg gccgcagcaa tttactgtgg gatactggag tgtttcgtgg caggtgtat    180 ttcgaacccc agtaccacgc ggaaatgtgt ttcttgtctt ggttttgcgg caaccaactt    240
cctgcataca aatgtttcca gattacctgg tttgtttcct ggactccgtg cccggactgt    300
gtggcgaaac tggccgaatt tttgtccgaa caccccaacg tgacgcttac gatcagtgcc    360
gcgcgcctgt attattattg ggaacgtgac tatcgccgtg ccctctgccg cctcagccag    420
gcgggcgcac gtgttaagat tatggattat aagaaattcg catactgttg ggaaaacttc    480
gtgtacaatg aagggcaaca atttatgccc tggtataaat tcgatgaaaa ttatgctttt    540
ctgcatcgca ctttgaagga atcttgcgc tatctgatgg atccacacat attcacttcc    600
aactttaaca atggcattgg aaggcataag acctacctgt gctacgaagt ggagcgcctg    660
gacaatggca cctcggtcaa gatgaccag cacaggggct ttctacacaa ccaggctaag    720
aatcttctct gtggctttta cggccgccat gcggagctgc gcttcttgga cctggttcct    780
tctttgcagt tggacccggc ccagatctac agggtcactt ggttcatctc ctggagcccc    840
tgcttctcct ggggctgtgc cggggaagtg cgtgcgttcc ttcaggagaa cacacacgtg    900
agactgcgta tcttcgctgc ccgcatctat gattacgacc cctatataa ggaggcactg    960
```

| | |
|---|---:|
| caaatgctgc gggatgctgg ggcccaagtc tccatcatga cctacgatga atttaagcac | 1020 |
| tgctgggaca cctttgtgga ccaccaggga tgtcccttcc agccctggga tggactagat | 1080 |
| gagcacagcc aagccctgag tgggaggctg cgggccattc tccagaatca gggaaac | 1137 |

<210> SEQ ID NO 32
<211> LENGTH: 1173
<212> TYPE: DNA
<213> ORGANISM: Homo sapiens

<400> SEQUENCE: 32

| | |
|---|---:|
| atgaatccac agattcgtaa ccccatggag cgcatgtatc gcgacacctt ttacgataac | 60 |
| tttgagaacg aaccgatttt atatggccgc agctatactt ggctgtgtta cgaagtgaag | 120 |
| atcaaacgcg ccgcagcaa tttactgtgg gatactggag tgtttcgtgg caggtgtat | 180 |
| ttcgaacccc agtaccacgc ggaaatgtgt ttcttgtctt ggttttgcgg caaccaactt | 240 |
| cctgcataca aatgtttcca gattacctgg tttgtttcct ggactccgtg cccggactgt | 300 |
| gtggcgaaac tggccgaatt tttgtccgaa cacccaacg tgacgcttac gatcagtgcc | 360 |
| gcgcgcctgt attattattg gaacgtgac tatcgccgtg ccctctgccg cctcagccag | 420 |
| gcgggcgcac gtgttaagat tatggattat gaagaattcg catactgttg gaaaacttc | 480 |
| gtgtacaatg aagggcaaca atttatgccc tggtataaat tcgatgaaaa ttatgctttt | 540 |
| ctgcatcgca ctttgaagga aatcttgcgc tatctgatgg aagccagccc agcatccggg | 600 |
| cccagacact tgatggatcc acacatattc acttccaact ttaacaatgg cattggaagg | 660 |
| cataagacct acctgtgcta cgaagtggag cgcctggaca tggcacctc ggtcaagatg | 720 |
| gaccagcaca ggggctttct acacaaccag gctaagaatc ttctctgtgg cttttacggc | 780 |
| cgccatgcgg agctgcgctt cttggacctg gttccttctt tgcagttgga cccggcccag | 840 |
| atctacaggg tcacttggtt catctcctgg agccctgct tctcctgggg ctgtgccggg | 900 |
| gaagtgcgtg cgttccttca ggagaacaca cacgtgagac tgcgtatctt cgctgcccgc | 960 |
| atctatgatt acgacccct atataaggag gcactgcaaa tgctgcggga tgctggggcc | 1020 |
| caagtctcca tcatgaccta cgatgaattt aagcactgct gggacacctt tgtgaccac | 1080 |
| cagggatgtc ccttccagcc ctgggatgga ctagatgagc acagccaagc cctgagtggg | 1140 |
| aggctgcggg ccattctcca gaatcaggga aac | 1173 |

<210> SEQ ID NO 33
<211> LENGTH: 570
<212> TYPE: DNA
<213> ORGANISM: Homo sapiens

<400> SEQUENCE: 33

| | |
|---|---:|
| atggacccag atacgtttac gttcaatttt aataacgatc cgttggttct gcgacgtcgc | 60 |
| cagacctacc tgtgttatga agtggaacgc ttggacaacg gtacgtgggt gctgatggac | 120 |
| caacatatgg gatttctgtg caatgaagcg aagaatctgc tttgtggctt ctacggccgc | 180 |
| catgcagaac tgcgtttttt ggatttggtc ccgtcattgc aattggatcc ggcccagatc | 240 |
| tatcgcgtga cttggttcat ttcctggagt ccgtgtttta ctggggctg cgccggcgag | 300 |
| gtgcgtgcgt tccttcagga gaacacacac gtgagactgc gtatcttcgc tgcccgcatc | 360 |
| tatgattacg acccctata taaggaggca ctgcaaatgc tgcgggatgc tggggcccaa | 420 |
| gtctccatca tgacctacga tgaatttaag cactgctggg acacctttgt ggaccaccag | 480 |
| ggatgtccct tccagccctg ggatggacta gatgagcaca gccaagccct gagtggagg | 540 |

```
ctgcgggcca ttctccagaa tcagggaaac                                      570
```

```
<210> SEQ ID NO 34
<211> LENGTH: 561
<212> TYPE: DNA
<213> ORGANISM: Homo sapiens

<400> SEQUENCE: 34
atggatccac acatattcac ttccaacttt aacaatggca ttggaaggca taagacctac      60
ctgtgctacg aagtggagcg cctggacaat ggcacctcgg tcaagatgga ccagcacagg     120
ggctttctac acaaccaggc taagaatctt ctctgtggct tttacggccg ccatgcggag     180
ctgcgcttct tggacctggt tccttctttg cagttggacc cggcccagat ctacagggtc     240
acttggttca tctcctggag ccctgcttc tcctggggct gtgccgggga agtgcgtgcc      300
ttcctgcaag aaaacactca tgttcgcctt cgcatctttg cggctcgtat ttacgattat     360
gacccgttgt ataagaggc cttacagatg cttcgcgatg ccggcgcaca ggtaagtatc      420
atgacgtacg atgaatttga atattgctgg gacacgtttg tctatcgtca agggtgtcct     480
ttccagccat gggacggctt ggaagaacac tcacaggccc tgagcggccg tctgcgtgca     540
attctgcaga accagggaaa t                                              561
```

```
<210> SEQ ID NO 35
<211> LENGTH: 1137
<212> TYPE: DNA
<213> ORGANISM: Homo sapiens

<400> SEQUENCE: 35
atgaatccac agattcgtaa ccccatggag cgcatgtatc gcgacacctt ttacgataac      60
tttgagaacg aaccgatttt atatggccgc agctatactt ggctgtgtta cgaagtgaag     120
atcaaacgcg ccgcagcaa tttactgtgg gatactggag tgtttcgtgg caggtgtat      180
ttcgaacccc agtaccacgc ggaaatgtgt ttcttgtctt ggttttgcgg caaccaactt     240
cctgcataca aatgtttcca gattacctgg tttgtttcct ggactccgtg cccggactgt     300
gtggcgaaac tggccgaatt tttgtccgaa caccccaacg tgacgcttac gatcagtgcc     360
gcgcgcctgt attattattg gaacgtgac tatcgccgtg ccctctgccg cctcagccag      420
gcgggcgcac gtgttaagat tatggattat gaagaattcg catactgttg gaaaacttc      480
gtgtacaatg aagggcaaca atttatgccc tggtataaat tcgatgaaaa ttatgctttt     540
ctgcatcgca ctttgaagga atcttgcgc tatctgatgg atccacacat attcacttcc      600
aactttaaca atggcattgg aaggcataag acctacctgt gctacgaagt ggagcgcctg     660
gacaatggca cctcggtcaa gatggaccag cacaggggct tctacacaa ccaggctaag      720
aatcttctct gtggctttta cggccgccat gcggagctgc gcttcttgga cctggttcct     780
tctttgcagt tggacccggc ccagatctac agggtcactt ggttcatctc ctggagcccc     840
tgcttctcct ggggctgtgc cggggaagtg cgtgccttcc tgcaagaaaa cactcatgtt     900
cgccttcgca tctttgcggc tcgtatttac gattatgacc cgttgtataa agaggcctta     960
cagatgcttc gcgatgccgg cgcacaggta agtatcatga cgtacgatga atttgaatat    1020
tgctgggaca cgtttgtcta tcgtcaaggg tgtcctttcc agccatggga cggcttggaa    1080
gaacactcac aggccctgag cggccgtctg cgtgcaattc tgcagaacca gggaaat      1137
```

```
<210> SEQ ID NO 36
```

<211> LENGTH: 1146
<212> TYPE: DNA
<213> ORGANISM: Homo sapiens

<400> SEQUENCE: 36

```
atgaatccac agattcgtaa ccccatggag cgcatgtatc gcgacacctt ttacgataac      60
tttgagaacg aaccgatttt atatggccgc agctatactt ggctgtgtta cgaagtgaag     120
atcaaacgcg gccgcagcaa tttactgtgg gatactggag tgtttcgtgg caggtgtat     180
ttcgaacccc agtaccacgc ggaaatgtgt ttcttgtctt ggttttgcgg caaccaactt     240
cctgcataca aatgtttcca gattacctgg tttgtttcct ggactccgtg cccggactgt     300
gtggcgaaac tggccgaatt tttgtccgaa cacccccaacg tgacgcttac gatcagtgcc     360
gcgcgcctgt attattattg gaacgtgac tatcgccgtg ccctctgccg cctcagccag     420
gcgggcgcac gtgttaagat tatggattat gaagaattcg catactgttg ggaaaacttc     480
gtgtacaatg aagggcaaca atttatgccc tggtataaat tcgatgaaaa ttatgctttt     540
ctgcatcgca ctttgaagga atcttgcgc tatctgatgg acccagatac gtttacgttc     600
aattttaata cgatccgtt ggttctgcga cgtcgccaga cctacctgtg ttatgaagtg     660
gaacgcttgg acaacggtac gtgggtgctg atggaccaac atatgggatt tctgtgcaat     720
gaagcgaaga tctgcttttg tggcttctac ggccgccatg cagaactgcg ttttttggat     780
ttggtcccgt cattgcaatt ggatccggcc cagatctatc gcgtgacttg gttcatttcc     840
tggagtccgt gttttagctg gggctgcgcc ggcgaggtgc gtgcgttcct tcaggagaac     900
acacacgtga gactgcgtat cttcgctgcc cgcatctatg attacgaccc cctatataag     960
gaggcactgc aaatgctgcg ggatgctggg gcccaagtct ccatcatgac ctacgatgaa    1020
tttaagcact gctgggacac ctttgtggac caccagggat gtcccttcca gccctgggat    1080
ggactagatg agcacagcca agccctgagt gggaggctgc gggccattct ccagaatcag    1140
ggaaac                                                               1146
```

<210> SEQ ID NO 37
<211> LENGTH: 597
<212> TYPE: DNA
<213> ORGANISM: Homo sapiens

<400> SEQUENCE: 37

```
atggaagcca gcccagcatc cgggcccaga cacttgatgg atccacacat attcacttcc      60
aactttaaca atggcattgg aaggcataag acctacctgt gctacgaagt ggagcgcctg     120
gacaatggca cctcggtcaa gatggaccag cacaggggct tctacacaa ccaggctaag     180
aatcttctct gtggctttta cggccgccat gcggcgctgc gcttcttgga cctggttcct     240
tctttgcagt tggacccggc ccagatctac agggtcactt ggttcatctc ctggagcccc     300
tgcttctcct ggggctgtgc cggggaagtg cgtgcgttcc ttcaggagaa cacacacgtg     360
agactgcgta tcttcgctgc ccgcatctat gattacgacc cctatataa ggaggcactg     420
caaatgctgc gggatgctgg ggcccaagtc tccatcatga cctacgatga atttaagcac     480
tgctgggaca cctttgtgga ccaccaggga tgtcccttcc agccctggga tggactagat     540
gagcacagcc aagccctgag tgggaggctg cgggccattc tccagaatca gggaaac       597
```

<210> SEQ ID NO 38
<211> LENGTH: 1173
<212> TYPE: DNA
<213> ORGANISM: Homo sapiens

<400> SEQUENCE: 38

```
atgaatccac agattcgtaa ccccatggag cgcatgtatc gcgacacctt ttacgataac      60
tttgagaacg aaccgatttt atatggccgc agctatactt ggctgtgtta cgaagtgaag     120
atcaaacgcg gccgcagcaa tttactgtgg gatactggag tgtttcgtgg gcaggtgtat     180
ttcgaacccc agtaccacgc ggaaatgtgt tccttgtctt ggttttgcgg caaccaactt     240
cctgcataca aatgtttcca gattacctgg tttgtttcct ggactccgtg cccggactgt     300
gtggcgaaac tggccgaatt tttgtccgaa cacccccaacg tgacgcttac gatcagtgcc    360
gcgcgcctgt attattattg gaacgtgac tatcgccgtg ccctctgccg cctcagccag      420
gcgggcgcac gtgttaagat tatggattat gaagaattcg catactgttg gaaaacttc      480
gtgtacaatg aagggcaaca atttatgccc tggtataaat tcgatgaaaa ttatgctttt     540
ctgcatcgca ctttgaagga atcttgcgc tatctgatgg aagccagccc agcatccggg      600
cccagacact tgatggatcc acacatattc acttccaact ttaacaatgg cattggaagg     660
cataagacct acctgtgcta cgaagtggag cgcctggaca atggcacctc ggtcaagatg     720
gaccagcaca ggggctttct acacaaccag gctaagaatc ttctctgtgg cttttacggc     780
cgccatgcgg cgctgcgctt cttggacctg gttccttctt tgcagttgga cccggcccag     840
atctacaggg tcacttggtt catctcctgg agccoctgct tctcctgggg ctgtgccggg     900
gaagtgcgtg cgttccttca ggagaacaca cacgtgagac tgcgtatctt cgctgcccgc    960
atctatgatt acgacccccct atataaggag gcactgcaaa tgctgcggga tgctggggcc   1020
caagtctcca tcatgaccta cgatgaattt aagcactgct gggacacctt tgtggaccac   1080
cagggatgtc ccttccagcc ctgggatgga ctagatgagc acagccaagc cctgagtggg   1140
aggctgcggg ccattctcca gaatcaggga aac                                 1173
```

<210> SEQ ID NO 39
<211> LENGTH: 597
<212> TYPE: DNA
<213> ORGANISM: Homo sapiens

<400> SEQUENCE: 39

```
atggatagcc tgctgatgaa ccgtcgtaaa tttctgtatc agtttaaaaa cgtgcgttgg      60
gcgaaaggcc gtcgtgaaac ctatctgtgc tatgtggtga acgtcgtga tagcgcgacc      120
agctttagcc tggattttgg ctatctgcgt aacaaaaacg ctgccatgt ggaactgctg       180
tttctgcgtt atattagcga ttgggatctg gatccgggcc gttgctatcg tgtgacctgg      240
tttaccagct ggagcccgtg ctatgattgc gcgcgtcatg tggcggattt ctgcgtggc      300
aacccgaacc tgagcctgcg tattttttacc gcgcgtctgt attttgcga agatcgtaaa    360
gcggaaccgg aaggcctgcg tcgtctgcat cgtgcgggcg tgcagattgc gattatgacc      420
tttaaagatt attttatttg ctggaacacc tttgtggaaa accatgaacg tacctttaaa      480
gcgtgggaag gcctgcatga aaacagcgtg cgtctgagcc gtcagctgcg tcgtattctg      540
ctgccgctgt atgaagtgga tgatctgcgt gatgcgtttc gtaccctggg cctgtag         597
```

<210> SEQ ID NO 40
<211> LENGTH: 546
<212> TYPE: DNA
<213> ORGANISM: Homo sapiens

<400> SEQUENCE: 40

```
atggatagcc tgctgatgaa ccgtcgtgaa tttctgtatc agtttaaaaa cgtgcgttgg    60
gcgaaaggcc gtcgtgaaac ctatctgtgc tatgtggtga aacgtcgtga tagcgcgacc   120
agctttagcc tggattttgg ctatctgcgt aacaaaaacg gctgccatgt ggaactgctg   180
tttctgcgtt atattagcga ttgggatctg gatccgggcc gttgctatcg tgtgacctgg   240
tttatcagct ggagcccgtg ctatgattgc gcgcgtcatg tggcggattt tctgcgtggc   300
aacccgaacc tgagcctgcg tatttttacc gcgcgtctgt attttgcga agccggcagg    360 cgtgaaccgg aaggcctgcg tcgtctgcat cgtgcgggcg tgcagattgc gattatgacc   420
tttaaagatt attttattg ctggaacacc tttgtggaaa accatggacg tacctttaaa    480
gcgtgggaag gcctgcatga aacagcgtg cgtctgagcc gtcagctgcg tcgtattctg     540
ctgtag                                                              546
```

<210> SEQ ID NO 41
<211> LENGTH: 597
<212> TYPE: DNA
<213> ORGANISM: Homo sapiens

<400> SEQUENCE: 41

```
atggatagcc tgctgatgaa ccgtcgtgaa tttctgtatc agtttaaaaa cgtgcgttgg    60
gcgaaaggcc gtcgtgaaac ctatctgtgc tatgtggtga aacgtcgtga tagcgcgacc   120
agctttagcc tggattttgg ctatctgcgt aacaaaaacg gctgccatgt ggaactgctg   180
tttctgcgtt atattagcga ttgggatctg gatccgggcc gttgctatcg tgtgacctgg   240
tttatcagct ggagcccgtg ctatgattgc gcgcgtcatg tggcggattt tctgcgtggc   300
aacccgaacc tgagcctgcg tatttttacc gcgcgtctgt attttgcga agccggcagg    360 cgtgaaccgg aaggcctgcg tcgtctgcat cgtgcgggcg tgcagattgc gattatgacc   420
tttaaagatt attttattg ctggaacacc tttgtggaaa accatggacg tacctttaaa    480
gcgtgggaag gcctgcatga aacagcgtg cgtctgagcc gtcagctgcg tcgtattctg     540
ctgccgctgt atgaagtgga tgatctgcgt gatgcgtttc gtaccctggg cctgtag      597
```

<210> SEQ ID NO 42
<211> LENGTH: 546
<212> TYPE: DNA
<213> ORGANISM: Homo sapiens

<400> SEQUENCE: 42

```
atggatagcc tgctgatgaa ccgtcgtaaa tttctgtatc agtttaaaaa cgtgcgttgg    60
gcgaaaggcc gtcgtgaaac ctatctgtgc tatgtggtga aacgtcgtga tagcgcgacc   120
agctttagcc tggattttgg ctatctgcgt aacaaaaacg gctgccatgt ggaactgctg   180
tttctgcgtt atattagcga ttgggatctg gatccgggcc gttgctatcg tgtgacctgg   240
tttaccagct ggagcccgtg ctatgattgc gcgcgtcatg tggcggattt tctgcgtggc   300
aacccgaacc tgagcctgcg tatttttacc gcgcgtctgt attttgcga agccggcagg    360 cgtgaaccgg aaggcctgcg tcgtctgcat cgtgcgggcg tgcagattgc gattatgacc   420
tttaaagatt attttattg ctggaacacc tttgtggaaa accatgaacg tacctttaaa    480
gcgtgggaag gcctgcatga aacagcgtg cgtctgagcc gtcagctgcg tcgtattctg     540
ctgtag                                                              546
```

<210> SEQ ID NO 43
<211> LENGTH: 546

<212> TYPE: DNA
<213> ORGANISM: Homo sapiens

<400> SEQUENCE: 43

| | |
|---|---|
| atggatagcc tgctgatgaa ccgtcgtgaa tttctgtatc agtttaaaaa cgtgcgttgg | 60 |
| gcgaaaggcc gtcgtgaaac ctatctgtgc tatgtggtga acgtcgtga tagcgcgacc | 120 |
| agctttagcc tggattttgg ctatctgcgt aacaaaaacg ctgccatgt ggaactgctg | 180 |
| tttctgcgtt atattagcga ttgggatctg gatccgggcc gttgctatcg tgtgacctgg | 240 |
| tttatcagct ggagcccgtg ctatgattgc gcgcgtcatg tggcggattt tctgcgtggc | 300 |
| aacccgaacc tgagcctgcg tattttacc gcgcgtctgt attttgcga agatggcaaa | 360 |
| gcggaaccgg aaggcctgcg tcgtctgcat cgtgcgggcg tgcagattgc gattatgacc | 420 |
| tttaaagatt attttattg ctggaacacc tttgtgaaaa accatggacg tacctttaaa | 480 |
| gcgtgggaag gcctgcatga aaacagcgtg cgtctgagcc gtcagctgcg tcgtattctg | 540 |
| ctgtag | 546 |

<210> SEQ ID NO 44
<211> LENGTH: 597
<212> TYPE: DNA
<213> ORGANISM: Homo sapiens

<400> SEQUENCE: 44

| | |
|---|---|
| atggatagcc tgctgatgaa ccgtcgtgaa tttctgtatc agtttaaaaa cgtgcgttgg | 60 |
| gcgaaaggcc gtcgtgaaac ctatctgtgc tatgtggtga acgtcgtga tagcgcgacc | 120 |
| agcgaaagcc tggattttgg ctatctgcgt aacaaaaacg ctgccatgt ggaactgctg | 180 |
| tttctgcgtt atattagcga ttgggatctg gatccgggcc gttgctatcg tgtgacctgg | 240 |
| tttatcagct ggagcccgtg ctatgattgc gcgcgtcatg tggcggattt tctgcgtggc | 300 |
| aacccgaacc tgagcctgcg tattttacc gcgcgtctgt attttgcga agccggcagg | 360 |
| cgtgaaccgg aaggcctgcg tcgtctggcg gaagcgggcg tgcagattgc gattatgacc | 420 |
| tataaagatt atgaatattg ctggaacacc tttgtgaaaa accatggacg tacctttaaa | 480 |
| gcgtgggaag gcctgcatga aaacagcgtg cgtctgagcc gtcagctgcg tcgtattctg | 540 |
| ctgccgctgt atgaagtgga tgatctgcgt gatgcgtttc gtaccctggg cctgtag | 597 |

<210> SEQ ID NO 45
<211> LENGTH: 1386
<212> TYPE: DNA
<213> ORGANISM: Homo sapiens

<400> SEQUENCE: 45

| | |
|---|---|
| atggacttcc ccagctgcag gtgcgtggag cagatcatcg agaaggacga gggccccttc | 60 |
| tacacccacc tgggcgccgg ccccaacgtg gccgccatca gggagatcat ggaggagagg | 120 |
| ttcggccaga gggcaaggc catcaggatc gagagggtga tctacaccgg caaggagggc | 180 |
| aagagcagcc agggctgccc catcgccaag tgggtggtga ggaggagcag cagcgaggag | 240 |
| aagctgctgt gcctggtgag ggagagggca ggccacacct gcgaggccgc cgtgatcgtg | 300 |
| atcctgatcc tggtgtggga gggcatcccc ctgtccctgg ccgacaagct gtacagcgag | 360 |
| ctgaccgaga ccctgaggaa gtacggcacc ctgaccaaca ggaggtgcgc cctgaacgag | 420 |
| gagagaacct gcgcctgcca gggcctggac cccgagacct gcggcgccag cttcagcttc | 480 |
| ggctgcagct ggagcatgta ctacaacggc tgcaagttcg ccaggagcaa gatccccagg | 540 |

| | |
|---|---:|
| aagttcaagc tgctgggcga cgaccccaag gaggaggaga agctggagag ccacctgcag | 600 |
| aacctgtcca ccctgatggc ccccacctac aagaagctgg ccccgacgc ctacaacaac | 660 |
| cagatcgagt acgagcacag gccccgag tgccgcctag gcctgaagga gggccggccc | 720 |
| ttcagcgggg tgaccgcctg cctggacttc tgcgcccacg cacaccgtga cctgcacaac | 780 |
| atgcagaacg atccaccct ggtgtgcacc ctgaccaggg aggacaacag ggagttcggc | 840 |
| ggcaagcccg aggacgagca gctgcacgtg ctgcccctgt acaaggtgag cgacgtggac | 900 |
| gagttcggca gcgtggaggc ccaggaggag aagaagagga gcggcgccat ccaggtgctg | 960 |
| agcagcttca ggaggaaggt gaggatgctg gccgagcccg tgaagacctg caggcagagg | 1020 |
| aagctggagg ccaagaaggc cgcagccgag aagctgagcg gcggaggcgg aagcggcgga | 1080 |
| ggaggcagcg gcggaggcgg aagcgacgag gtgtggagcg acagcgagca gagcttcctg | 1140 |
| gaccccgaca tcggcggcgt ggccgtggcc cccacccacg gcagcatcct gatcgagtgc | 1200 |
| gccaagaggg agctgcacgc caccaccccc cttaagaacc caacaggaa ccaccccacg | 1260 |
| cgtatcagcc tggtgttcta ccagcacaag agcatgaacg agcctaagca cgggctagcc | 1320 |
| ctgtgggagg ccaagatggc cgagaaggcc agggagaagg aggaggagtg cgagaagtac | 1380 |
| ggctga | 1386 |

<210> SEQ ID NO 46
<211> LENGTH: 2628
<212> TYPE: DNA
<213> ORGANISM: Homo sapiens

<400> SEQUENCE: 46

| | |
|---|---:|
| atggacttcc ccagctgcag gtgcgtggag cagatcatcg agaaggacga gggccccttc | 60 |
| tacacccacc tgggcgccgg ccccaacgtg gccgccatca gggagatcat ggaggagagg | 120 |
| ttcggccaga agggcaaggc catcaggatc gagagggtga tctacaccgg caaggagggc | 180 |
| aagagcagcc agggctgccc catcgccaag tgggtggtga ggaggagcag cagcgaggag | 240 |
| aagctgctgt gcctggtgag ggagagggca ggccacacct gcgaggccgc cgtgatcgtg | 300 |
| atcctgatcc tggtgtggga gggcatcccc ctgtccctgg ccgacaagct gtacagcgag | 360 |
| ctgaccgaga ccctgaggaa gtacggcacc ctgaccaaca ggaggtgcgc cctgaacgag | 420 |
| gagagaacct cgcgcctgcca gggctgac cccgagacct cgcggcgcag cttcagcttc | 480 |
| ggctgcagct ggagcatgta ctacaacggc tgcaagttcg ccaggagcaa gatccccagg | 540 |
| aagttcaagc tgctgggcga cgaccccaag gaggaggaga agctggagag ccacctgcag | 600 |
| aacctgtcca ccctgatggc ccccacctac aagaagctgg ccccgacgc ctacaacaac | 660 |
| cagatcgagt acgagcacag gccccgag tgccgcctag gcctgaagga gggccggccc | 720 |
| ttcagcgggg tgaccgcctg cctggacttc tgcgcccacg cacaccgtga cctgcacaac | 780 |
| atgcagaacg atccaccct ggtgtgcacc ctgaccaggg aggacaacag ggagttcggc | 840 |
| ggcaagcccg aggacgagca gctgcacgtg ctgcccctgt acaaggtgag cgacgtggac | 900 |
| gagttcggca gcgtggaggc ccaggaggag aagaagagga gcggcgccat ccaggtgctg | 960 |
| agcagcttca ggaggaaggt gaggatgctg gccgagcccg tgaagacctg caggcaaagg | 1020 |
| aaactggaag ccaagaaagc tgccgctgag aagctctctt cactggagaa ctcaagcaat | 1080 |
| aagaatgaga aggagaagag tgcaccctcc agaacgaaac agactgaaaa cgcatcccag | 1140 |
| gcgaaacagc tggctgagct gctgcgcctc tctggaccag tgatgcaaca gagccagcag | 1200 |
| cctcaacccc tgcagaaaca acccccacag ccccaacagc aacaacgccc acagcagcag | 1260 |

```
caacccatc atcctcagac ggaatctgtc aactcataca gcgcatccgg ttctacgaat    1320
ccgtatatgc gaagacctaa tcctgtctca ccctatccca attccagcca tacatccgac    1380
atctacggca gcacgtcccc tatgaacttt tacagtacaa gctcccaggc tgccggatca    1440
tacctcaatt catctaaccc catgaacccc tacccagggc tgcttaacca aaacactcag    1500
tacccttcat atcaatgtaa cggcaatttg agcgttgata actgtagtcc ctatctgggt    1560
tcctattcac cgcagagcca gccgatggac ctgtaccgat atccctccca ggaccctctg    1620
tccaagctca gtctgcctcc cattcacaca ctttaccagc cccgctttgg caacagtcag    1680
tcatttacta gcaaatacct tggctacggg aatcagaaca tgcagggcga cgggttctct    1740
tcttgcacca ttcgcccgaa tgtacatcac gtggggaagc tcccccccta tcctacacac    1800
gagatggatg ggcattttat gggcgcgact tctcggcttc ctcccaacct tagtaaccct    1860
aacatggact acaagaatgg cgaacaccat agtccctcac acattattca taactactcc    1920
gccgcacccg gaatgtttaa ctcttccctg cacgctctgc acctgcaaaa caaagagaat    1980
gatatgttga gtcataccgc caacggcctg tccaagatgc tccccgctct taaccacgat    2040
agaaccgcct gtgtccaggg aggtcttcac aaattgagcg atgctaatgg ccaggagaag    2100
cagccactgg ccttggtgca gggggtggca tccggggcag aggacaatga tgaagtgtgg    2160
tctgactctg agcaatcctt cctggacccc gacatcggcg gggtagcagt ggctcctacc    2220
cacggctcta tcttgattga gtcgccaaaa agagagctgc acgctactac cccacttaag    2280
aaccccaaca ggaaccaccc cacgcgtatc agcctggtgt ctaccagca caagagcatg    2340 aacgagccta agcacgggct agctctgtgg gaggccaaaa tggcagagaa agctcgggaa    2400
aaagaagagg aatgtgagaa atacggacca gattatgtgc cgcagaaatc tcatggaaaa    2460
aaagtgaaac gggaacctgc agaacccat gagaccagtg agcccactta cctgaggttt    2520
atcaagtccc tcgccgaacg aaccatgtca gtgacgaccg atagcaccgt tactaccagt    2580
ccttacgctt tcacccgggt tactggcccc tacaatcgat atatatga    2628
```

<210> SEQ ID NO 47
<211> LENGTH: 1386
<212> TYPE: DNA
<213> ORGANISM: Homo sapiens

<400> SEQUENCE: 47

```
atggacttcc ccagctgcag gtgcgtggag cagatcatcg agaaggacga gggccccttc     60
tacacccacc tgggcgccgg ccccaacgtg gccgccatca gggagatcat ggaggagagg    120
ttcggccaga agggcaaggc catcaggatc gagagggtga tctacaccgg caaggagggc    180
aagagcagcc agggctgccc catcgccaag tgggtggtga ggaggagcag cagcgaggag    240
aagctgctgt gcctggtgag ggagagggca ggccacacct gcgaggccgc cgtgatcgtg    300
atcctgatcc tggtgtggga gggcatcccc tgtccctgg ccgacaagct gtacagcgag    360
ctgaccgaga ccctgaggaa gtacggcacc ctgaccaaca ggaggtgcgc cctgaacgag    420
gagagaacct cgccctgcca gggcctggac cccgagacct cggcgccag cttcagcttc    480 ggctgcagct ggagcatgta ctacaacggc tgcaagttcg ccaggagcaa gatccccagg    540
aagttcaagc tgctgggcga cgaccccaag gaggaggaga agctggagag ccacctgcag    600
aacctgtcca ccctgatggc ccccacctac aagaagctgg cccccgacgc ctacaacaac    660
cagatcgagt acgagcacag ggccccgag tgccgcctag gcctgaagga gggtcgaccc    720
```

| | |
|---|---|
| ttcagcgggg tggaggcctg cctggacttc tgcgcccacg cacaccgtga cctgcacaac | 780 |
| atgcagaacg gatccaccct ggtgtgcacc ctgaccaggg aggacaacag ggagttcggc | 840 |
| ggcaagcccg aggacgagca gctgcacgtg ctgcccctgt acaaggtgag cgacgtggac | 900 |
| gagttcggca gcgtggaggc ccaggaggag aagaagagga gcggcgccat ccaggtgctg | 960 |
| agcagcttca ggaggaaggt gaggatgctg gccgagcccg tgaagacctg caggcagagg | 1020 |
| aagctggagg ccaagaaggc cgcagccgag aagctgagcg gcggaggcgg aagcggcgga | 1080 |
| ggaggcagcg gcggaggcgg aagcgacgag gtgtggagcg acagcgagca gagcttcctg | 1140 |
| gaccccgaca tcggcggcgt ggccgtggcc cccacccacg gcagcatcct gatcgagtgc | 1200 |
| gccaagaggg agctgcacgc caccaccccc cttaagaacc ccaacaggaa ccaccccacg | 1260 |
| cgtatcagcc tggtgttcta ccagcacaag agcatgaacg agcctaagca cgggctagcc | 1320 |
| ctgtgggagg ccaagatggc cgagaaggcc agggagaagg aggaggagtg cgagaagtac | 1380 |
| ggctga | 1386 |

<210> SEQ ID NO 48
<211> LENGTH: 2628
<212> TYPE: DNA
<213> ORGANISM: Homo sapiens

<400> SEQUENCE: 48

| | |
|---|---|
| atggacttcc ccagctgcag gtgcgtggag cagatcatcg agaaggacga gggcccctcc | 60 |
| tacacccacc tgggcgccgg ccccaacgtg gccgccatca gggagatcat ggaggagagg | 120 |
| ttcggccaga agggcaaggc catcaggatc gagagggtga tctacaccgg caaggagggc | 180 |
| aagagcagcc agggctgccc catcgccaag tgggtggtga ggaggagcag cagcgaggag | 240 |
| aagctgctgt gcctggtgag ggagagggca ggccacacct gcgaggccgc cgtgatcgtg | 300 |
| atcctgatcc tggtgtggga gggcatcccc ctgtccctgg ccgacaagct gtacagcgag | 360 |
| ctgaccgaga ccctgaggaa gtacggcacc ctgaccaaca ggaggtgcgc cctgaacgag | 420 |
| gagagaacct gcgcctgcca gggcctggac ccgagacct gcggcgccag cttcagcttc | 480 |
| ggctgcagct ggagcatgta ctacaacggc tgcaagttcg ccaggagcaa gatccccagg | 540 |
| aagttcaagc tgctgggcga cgaccccaag gaggaggaga agctggagag ccacctgcag | 600 |
| aacctgtcca ccctgatggc ccccacctac aagaagctgg ccccgacgc ctacaacaac | 660 |
| cagatcgagt acgagcacag ggccccgag tgccgcctag gcctgaagga gggtcgaccc | 720 |
| ttcagcgggg tggaggcctg cctggacttc tgcgcccacg cacaccgtga cctgcacaac | 780 |
| atgcagaacg gatccaccct ggtgtgcacc ctgaccaggg aggacaacag ggagttcggc | 840 |
| ggcaagcccg aggacgagca gctgcacgtg ctgcccctgt acaaggtgag cgacgtggac | 900 |
| gagttcggca gcgtggaggc ccaggaggag aagaagagga gcggcgccat ccaggtgctg | 960 |
| agcagcttca ggaggaaggt gaggatgctg gccgagcccg tgaagacctg caggcaaagg | 1020 |
| aaactggaag ccaagaaagc tgccgctgag aagctctctt cactggagaa ctcaagcaat | 1080 |
| aagaatgaga aggagaagag tgcaccctcc agaacgaaac agactgaaaa cgcatcccag | 1140 |
| gcgaaacagc tggctgagct gctgcgcctc tctggaccag tgatgcaaca gagccagcag | 1200 |
| cctcaacccc tgcagaaaca accccacag ccccaacagc aacaacgccc acagcagcag | 1260 |
| caaccccatc atcctcagac ggaatctgtc aactcataca gcgcatccgg ttctacgaat | 1320 |
| ccgtatatgc gaagacctaa tcctgtctca ccctatccca attccagcca tacatccgac | 1380 |
| atctacggca gcacgtcccc tatgaacttt tacagtacaa gctcccaggc tgccggatca | 1440 |

```
tacctcaatt catctaaccc catgaacccc tacccagggc tgcttaacca aaacactcag    1500 taccctcat atcaatgtaa cggcaatttg agcgttgata actgtagtcc ctatctgggt    1560
tcctattcac cgcagagcca gccgatggac ctgtaccgat atccctccca ggaccctctg    1620
tccaagctca gtctgcctcc cattcacaca ctttaccagc cccgctttgg caacagtcag    1680
tcatttacta gcaaatacct tggctacggg aatcagaaca tgcagggcga cgggttctct    1740
tcttgcacca ttcgcccgaa tgtacatcac gtggggaagc tccccccta tcctacacac     1800 gagatggatg gcattttat gggcgcgact tctcggcttc ctcccaacct tagtaaccct     1860
aacatggact acaagaatgg cgaacaccat agtccctcac acattattca taactactcc    1920
gccgcacccg aatgtttaa ctcttccctg cacgctctgc acctgcaaaa caagagaat      1980 gatatgttga gtcataccgc aacggcctg tccaagatgc tccccgctct taaccacgat     2040
agaaccgcct gtgtccaggg aggtcttcac aaattgagcg atgctaatgg ccaggagaag    2100
cagccactgg ccttggtgca gggggtggca tccggggcag aggacaatga tgaagtgtgg    2160
tctgactctg agcaatcctt cctggacccc gacatcggcg gggtagcagt ggctcctacc    2220
cacggctcta tcttgattga gtgcgccaaa agagagctgc acgctactac cccacttaag    2280
aaccccaaca ggaaccaccc cacgcgtatc agcctggtgt ctaccagca caagagcatg     2340 aacgagccta gcacgggct agctctgtgg gaggccaaaa tggcagagaa agctcgggaa    2400
aaagaagagg aatgtgagaa atacggacca gattatgtgc cgcagaaatc tcatggaaaa    2460
aaagtgaaac gggaacctgc agaaccccat gagaccagtg agcccactta cctgaggttt    2520
atcaagtccc tcgccgaacg aaccatgtca gtgacgaccg atagcaccgt tactaccagt    2580
ccttacgctt tcacccgggt tactggcccc tacaatcgat atatatga                 2628

<210> SEQ ID NO 49
<211> LENGTH: 35
<212> TYPE: DNA
<213> ORGANISM: Artificial Sequence
<220> FEATURE:
<223> OTHER INFORMATION: Artificially generated sequence

<400> SEQUENCE: 49
tgaggaatga agttgattca aatgtgatga ggtga                               35

<210> SEQ ID NO 50
<211> LENGTH: 70
<212> TYPE: DNA
<213> ORGANISM: Artificial Sequence
<220> FEATURE:
<223> OTHER INFORMATION: Oligonucleotide

<400> SEQUENCE: 50
ctaggcctga aggagggtcg acccttcagc ggggtggccg cctgcctgga cttctgcgcc    60
cacgcacacc                                                            70

<210> SEQ ID NO 51
<211> LENGTH: 63
<212> TYPE: DNA
<213> ORGANISM: Artificial Sequence
<220> FEATURE:
<223> OTHER INFORMATION: Oligonucleotide

<400> SEQUENCE: 51
gtgcgtgggc gcagaagtcc aggcaggcgg ccaccccgct gaagggtcga ccctccttca    60
```

```
                                                                        ggc                                                                63
```

<210> SEQ ID NO 52
<211> LENGTH: 70
<212> TYPE: DNA
<213> ORGANISM: Artificial Sequence
<220> FEATURE:
<223> OTHER INFORMATION: Oligonucleotide

<400> SEQUENCE: 52

```
ctaggcctga aggagggtcg acccttcagc ggggtgtgcg cctgcctgga cttctgcgcc      60
cacgcacacc                                                            70
```

<210> SEQ ID NO 53
<211> LENGTH: 63
<212> TYPE: DNA
<213> ORGANISM: Artificial Sequence
<220> FEATURE:
<223> OTHER INFORMATION: Oligonucleotide

<400> SEQUENCE: 53

```
gtgcgtgggc gcagaagtcc aggcaggcgc acaccccgct gaagggtcga ccctccttca      60
ggc                                                                   63
```

<210> SEQ ID NO 54
<211> LENGTH: 70
<212> TYPE: DNA
<213> ORGANISM: Artificial Sequence
<220> FEATURE:
<223> OTHER INFORMATION: Oligonucleotide

<400> SEQUENCE: 54

```
ctaggcctga aggagggtcg acccttcagc ggggtggacg cctgcctgga cttctgcgcc      60
cacgcacacc                                                            70
```

<210> SEQ ID NO 55
<211> LENGTH: 63
<212> TYPE: DNA
<213> ORGANISM: Artificial Sequence
<220> FEATURE:
<223> OTHER INFORMATION: Oligonucleotide

<400> SEQUENCE: 55

```
gtgcgtgggc gcagaagtcc aggcaggcgt ccaccccgct gaagggtcga ccctccttca      60
ggc                                                                   63
```

<210> SEQ ID NO 56
<211> LENGTH: 70
<212> TYPE: DNA
<213> ORGANISM: Artificial Sequence
<220> FEATURE:
<223> OTHER INFORMATION: Oligonucleotide

<400> SEQUENCE: 56

```
ctaggcctga aggagggtcg acccttcagc ggggtggagg cctgcctgga cttctgcgcc      60
cacgcacacc                                                            70
```

<210> SEQ ID NO 57
<211> LENGTH: 63
<212> TYPE: DNA
<213> ORGANISM: Artificial Sequence
<220> FEATURE:
<223> OTHER INFORMATION: Oligonucleotide

<400> SEQUENCE: 57
gtgcgtgggc gcagaagtcc aggcaggcct ccaccccgct gaagggtcga ccctccttca      60
ggc                                                                    63

<210> SEQ ID NO 58
<211> LENGTH: 70
<212> TYPE: DNA
<213> ORGANISM: Artificial Sequence
<220> FEATURE:
<223> OTHER INFORMATION: Oligonucleotide

<400> SEQUENCE: 58
ctaggcctga aggagggtcg acccttcagc ggggtgttcg cctgcctgga cttctgcgcc      60
cacgcacacc                                                             70

<210> SEQ ID NO 59
<211> LENGTH: 63
<212> TYPE: DNA
<213> ORGANISM: Artificial Sequence
<220> FEATURE:
<223> OTHER INFORMATION: Oligonucleotide

<400> SEQUENCE: 59
gtgcgtgggc gcagaagtcc aggcaggcga acaccccgct gaagggtcga ccctccttca      60
ggc                                                                    63

<210> SEQ ID NO 60
<211> LENGTH: 70
<212> TYPE: DNA
<213> ORGANISM: Artificial Sequence
<220> FEATURE:
<223> OTHER INFORMATION: Oligonucleotide

<400> SEQUENCE: 60
ctaggcctga aggagggtcg acccttcagc ggggtgggcg cctgcctgga cttctgcgcc      60
cacgcacacc                                                             70

<210> SEQ ID NO 61
<211> LENGTH: 63
<212> TYPE: DNA
<213> ORGANISM: Artificial Sequence
<220> FEATURE:
<223> OTHER INFORMATION: Oligonucleotide

<400> SEQUENCE: 61
gtgcgtgggc gcagaagtcc aggcaggcgc ccaccccgct gaagggtcga ccctccttca      60
ggc                                                                    63

<210> SEQ ID NO 62
<211> LENGTH: 70
<212> TYPE: DNA
<213> ORGANISM: Artificial Sequence
<220> FEATURE:
<223> OTHER INFORMATION: Oligonucleotide

<400> SEQUENCE: 62
ctaggcctga aggagggtcg acccttcagc ggggtgcacg cctgcctgga cttctgcgcc      60
cacgcacacc                                                             70

<210> SEQ ID NO 63

<211> LENGTH: 63
<212> TYPE: DNA
<213> ORGANISM: Artificial Sequence
<220> FEATURE:
<223> OTHER INFORMATION: Oligonucleotide

<400> SEQUENCE: 63
gtgcgtgggc gcagaagtcc aggcaggcgt gcaccccgct gaagggtcga ccctccttca    60
ggc    63

<210> SEQ ID NO 64
<211> LENGTH: 70
<212> TYPE: DNA
<213> ORGANISM: Artificial Sequence
<220> FEATURE:
<223> OTHER INFORMATION: Oligonucleotide

<400> SEQUENCE: 64
ctaggcctga aggagggtcg acccttcagc ggggtgatcg cctgcctgga cttctgcgcc    60
cacgcacacc    70

<210> SEQ ID NO 65
<211> LENGTH: 63
<212> TYPE: DNA
<213> ORGANISM: Artificial Sequence
<220> FEATURE:
<223> OTHER INFORMATION: Oligonucleotide

<400> SEQUENCE: 65
gtgcgtgggc gcagaagtcc aggcaggcga tcaccccgct gaagggtcga ccctccttca    60
ggc    63

<210> SEQ ID NO 66
<211> LENGTH: 70
<212> TYPE: DNA
<213> ORGANISM: Artificial Sequence
<220> FEATURE:
<223> OTHER INFORMATION: Oligonucleotide

<400> SEQUENCE: 66
ctaggcctga aggagggtcg acccttcagc ggggtgaagg cctgcctgga cttctgcgcc    60
cacgcacacc    70

<210> SEQ ID NO 67
<211> LENGTH: 63
<212> TYPE: DNA
<213> ORGANISM: Artificial Sequence
<220> FEATURE:
<223> OTHER INFORMATION: Oligonucleotide

<400> SEQUENCE: 67
gtgcgtgggc gcagaagtcc aggcaggcct tcaccccgct gaagggtcga ccctccttca    60
ggc    63

<210> SEQ ID NO 68
<211> LENGTH: 70
<212> TYPE: DNA
<213> ORGANISM: Artificial Sequence
<220> FEATURE:
<223> OTHER INFORMATION: Oligonucleotide

<400> SEQUENCE: 68
ctaggcctga aggagggtcg acccttcagc ggggtgctgg cctgcctgga cttctgcgcc    60

```
cacgcacacc                                                              70

<210> SEQ ID NO 69
<211> LENGTH: 63
<212> TYPE: DNA
<213> ORGANISM: Artificial Sequence
<220> FEATURE:
<223> OTHER INFORMATION: Oligonucleotide

<400> SEQUENCE: 69
gtgcgtgggc gcagaagtcc aggcaggcca gcaccccgct gaagggtcga ccctccttca      60
ggc                                                                    63

<210> SEQ ID NO 70
<211> LENGTH: 70
<212> TYPE: DNA
<213> ORGANISM: Artificial Sequence
<220> FEATURE:
<223> OTHER INFORMATION: Oligonucleotide

<400> SEQUENCE: 70
ctaggcctga aggagggtcg acccttcagc ggggtgatgg cctgcctgga cttctgcgcc      60
cacgcacacc                                                             70

<210> SEQ ID NO 71
<211> LENGTH: 63
<212> TYPE: DNA
<213> ORGANISM: Artificial Sequence
<220> FEATURE:
<223> OTHER INFORMATION: Oligonucleotide

<400> SEQUENCE: 71
gtgcgtgggc gcagaagtcc aggcaggcca tcaccccgct gaagggtcga ccctccttca      60
ggc                                                                    63

<210> SEQ ID NO 72
<211> LENGTH: 70
<212> TYPE: DNA
<213> ORGANISM: Artificial Sequence
<220> FEATURE:
<223> OTHER INFORMATION: Oligonucleotide

<400> SEQUENCE: 72
ctaggcctga aggagggtcg acccttcagc ggggtgaacg cctgcctgga cttctgcgcc      60
cacgcacacc                                                             70

<210> SEQ ID NO 73
<211> LENGTH: 63
<212> TYPE: DNA
<213> ORGANISM: Artificial Sequence
<220> FEATURE:
<223> OTHER INFORMATION: Oligonucleotide

<400> SEQUENCE: 73
gtgcgtgggc gcagaagtcc aggcaggcgt tcaccccgct gaagggtcga ccctccttca      60
ggc                                                                    63

<210> SEQ ID NO 74
<211> LENGTH: 70
<212> TYPE: DNA
<213> ORGANISM: Artificial Sequence
<220> FEATURE:
```

```
<223> OTHER INFORMATION: Oligonucleotide

<400> SEQUENCE: 74
ctaggcctga aggagggtcg acccttcagc ggggtgcccg cctgcctgga cttctgcgcc      60
cacgcacacc                                                            70

<210> SEQ ID NO 75
<211> LENGTH: 63
<212> TYPE: DNA
<213> ORGANISM: Artificial Sequence
<220> FEATURE:
<223> OTHER INFORMATION: Oligonucleotide

<400> SEQUENCE: 75
gtgcgtgggc gcagaagtcc aggcaggcgg gcacccngct gaagggtcga ccctccttca      60
ggc                                                                   63

<210> SEQ ID NO 76
<211> LENGTH: 70
<212> TYPE: DNA
<213> ORGANISM: Artificial Sequence
<220> FEATURE:
<223> OTHER INFORMATION: T1372Q

<400> SEQUENCE: 76
ctaggcctga aggagggtcg acccttcagc ggggtgcagg cctgcctgga cttctgcgcc      60
cacgcacacc                                                            70

<210> SEQ ID NO 77
<211> LENGTH: 63
<212> TYPE: DNA
<213> ORGANISM: Artificial Sequence
<220> FEATURE:
<223> OTHER INFORMATION: Oligonucleotide

<400> SEQUENCE: 77
gtgcgtgggc gcagaagtcc aggcaggcct gcacccngct gaagggtcga ccctccttca      60
ggc                                                                   63

<210> SEQ ID NO 78
<211> LENGTH: 70
<212> TYPE: DNA
<213> ORGANISM: Artificial Sequence
<220> FEATURE:
<223> OTHER INFORMATION: Oligonucleotide

<400> SEQUENCE: 78
ctaggcctga aggagggtcg acccttcagc ggggtgcagg cctgcctgga cttctgcgcc      60
cacgcacacc                                                            70

<210> SEQ ID NO 79
<211> LENGTH: 63
<212> TYPE: DNA
<213> ORGANISM: Artificial Sequence
<220> FEATURE:
<223> OTHER INFORMATION: Oligonucleotide

<400> SEQUENCE: 79
gtgcgtgggc gcagaagtcc aggcaggcct gcacccngct gaagggtcga ccctccttca      60
ggc                                                                   63
```

<210> SEQ ID NO 80
<211> LENGTH: 70
<212> TYPE: DNA
<213> ORGANISM: Artificial Sequence
<220> FEATURE:
<223> OTHER INFORMATION: Oligonucleotide

<400> SEQUENCE: 80
ctaggcctga aggagggtcg acccttcagc ggggtgaggg cctgcctgga cttctgcgcc     60
cacgcacacc                                                            70

<210> SEQ ID NO 81
<211> LENGTH: 63
<212> TYPE: DNA
<213> ORGANISM: Artificial Sequence
<220> FEATURE:
<223> OTHER INFORMATION: Oligonucleotide

<400> SEQUENCE: 81
gtgcgtgggc gcagaagtcc aggcaggccc tcaccccgct gaagggtcga ccctccttca     60
ggc                                                                   63

<210> SEQ ID NO 82
<211> LENGTH: 70
<212> TYPE: DNA
<213> ORGANISM: Artificial Sequence
<220> FEATURE:
<223> OTHER INFORMATION: T1372S

<400> SEQUENCE: 82
ctaggcctga aggagggtcg acccttcagc ggggtgagcg cctgcctgga cttctgcgcc     60
cacgcacacc                                                            70

<210> SEQ ID NO 83
<211> LENGTH: 63
<212> TYPE: DNA
<213> ORGANISM: Artificial Sequence
<220> FEATURE:
<223> OTHER INFORMATION: Oligonucleotide

<400> SEQUENCE: 83
gtgcgtgggc gcagaagtcc aggcaggcgc tcaccccgct gaagggtcga ccctccttca     60
ggc                                                                   63

<210> SEQ ID NO 84
<211> LENGTH: 70
<212> TYPE: DNA
<213> ORGANISM: Artificial Sequence
<220> FEATURE:
<223> OTHER INFORMATION: T1372V

<400> SEQUENCE: 84
ctaggcctga aggagggtcg acccttcagc ggggtggtgg cctgcctgga cttctgcgcc     60
cacgcacacc                                                            70

<210> SEQ ID NO 85
<211> LENGTH: 63
<212> TYPE: DNA
<213> ORGANISM: Artificial Sequence
<220> FEATURE:
<223> OTHER INFORMATION: Oligonucleotide

<400> SEQUENCE: 85

```
gtgcgtgggc gcagaagtcc aggcaggcca ccaccccgct gaagggtcga ccctccttca    60
ggc                                                                  63
```

<210> SEQ ID NO 86
<211> LENGTH: 70
<212> TYPE: DNA
<213> ORGANISM: Artificial Sequence
<220> FEATURE:
<223> OTHER INFORMATION: Oligonucleotide

<400> SEQUENCE: 86

```
ctaggcctga aggagggtcg acccttcagc ggggtgtggg cctgcctgga cttctgcgcc    60
cacgcacacc                                                           70
```

<210> SEQ ID NO 87
<211> LENGTH: 63
<212> TYPE: DNA
<213> ORGANISM: Artificial sequence
<220> FEATURE:
<223> OTHER INFORMATION: Oligonucleotide

<400> SEQUENCE: 87

```
gtgcgtgggc gcagaagtcc aggcaggccc acaccccgct gaagggtcga ccctccttca    60
ggc                                                                  63
```

<210> SEQ ID NO 88
<211> LENGTH: 70
<212> TYPE: DNA
<213> ORGANISM: Artificial Sequence
<220> FEATURE:
<223> OTHER INFORMATION: Oligonucleotide

<400> SEQUENCE: 88

```
ctaggcctga aggagggtcg acccttcagc ggggtgtacg cctgcctgga cttctgcgcc    60
cacgcacacc                                                           70
```

<210> SEQ ID NO 89
<211> LENGTH: 63
<212> TYPE: DNA
<213> ORGANISM: Artificial sequence
<220> FEATURE:
<223> OTHER INFORMATION: Oligonucleotide

<400> SEQUENCE: 89

```
gtgcgtgggc gcagaagtcc aggcaggcgt acaccccgct gaagggtcga ccctccttca    60
ggc                                                                  63
```

<210> SEQ ID NO 90
<211> LENGTH: 56
<212> TYPE: DNA
<213> ORGANISM: Artificial Sequence
<220> FEATURE:
<223> OTHER INFORMATION: Oligonucleotide

<400> SEQUENCE: 90

```
cgcgtataag cttggccttc taccagcaca agagcatgaa cgagcctaaa cacggg        56
```

<210> SEQ ID NO 91
<211> LENGTH: 56
<212> TYPE: DNA
<213> ORGANISM: Artificial Sequence
<220> FEATURE:
<223> OTHER INFORMATION: Oligonucleotide

```
<400> SEQUENCE: 91
ctagcccgtg tttaggctcg ttcatgctct tgtgctggta gaaggccaag cttata        56

<210> SEQ ID NO 92
<211> LENGTH: 56
<212> TYPE: DNA
<213> ORGANISM: Artificial Sequence
<220> FEATURE:
<223> OTHER INFORMATION: Oligonucleotide

<400> SEQUENCE: 92
cgcgtataag cttgtgcttc taccagcaca agagcatgaa cgagcctaaa cacggg        56

<210> SEQ ID NO 93
<211> LENGTH: 56
<212> TYPE: DNA
<213> ORGANISM: Artificial Sequence
<220> FEATURE:
<223> OTHER INFORMATION: Oligonucleotide

<400> SEQUENCE: 93
ctagcccgtg tttaggctcg ttcatgctct tgtgctggta gaagcacaag cttata        56

<210> SEQ ID NO 94
<211> LENGTH: 56
<212> TYPE: DNA
<213> ORGANISM: Artificial Sequence
<220> FEATURE:
<223> OTHER INFORMATION: Oligonucleotide

<400> SEQUENCE: 94
cgcgtataag cttggacttc taccagcaca agagcatgaa cgagcctaaa cacggg        56

<210> SEQ ID NO 95
<211> LENGTH: 56
<212> TYPE: DNA
<213> ORGANISM: Artificial Sequence
<220> FEATURE:
<223> OTHER INFORMATION: Oligonucleotide

<400> SEQUENCE: 95
ctagcccgtg tttaggctcg ttcatgctct tgtgctggta gaagtccaag cttata        56

<210> SEQ ID NO 96
<211> LENGTH: 56
<212> TYPE: DNA
<213> ORGANISM: Artificial sequence
<220> FEATURE:
<223> OTHER INFORMATION: Oligonucleotide

<400> SEQUENCE: 96
cgcgtataag cttggagttc taccagcaca agagcatgaa cgagcctaaa cacggg        56

<210> SEQ ID NO 97
<211> LENGTH: 56
<212> TYPE: DNA
<213> ORGANISM: Artificial sequence
<220> FEATURE:
<223> OTHER INFORMATION: Oligonucleotide

<400> SEQUENCE: 97
ctagcccgtg tttaggctcg ttcatgctct tgtgctggta gaactccaag cttata        56

<210> SEQ ID NO 98
```

```
<211> LENGTH: 56
<212> TYPE: DNA
<213> ORGANISM: Artificial sequence
<220> FEATURE:
<223> OTHER INFORMATION: Oligonucleotide

<400> SEQUENCE: 98
cgcgtataag cttgttcttc taccagcaca agagcatgaa cgagcctaaa cacggg        56

<210> SEQ ID NO 99
<211> LENGTH: 56
<212> TYPE: DNA
<213> ORGANISM: Artificial sequence
<220> FEATURE:
<223> OTHER INFORMATION: Oligonucleotide

<400> SEQUENCE: 99
ctagcccgtg tttaggctcg ttcatgctct tgtgctggta gaagaacaag cttata        56

<210> SEQ ID NO 100
<211> LENGTH: 56
<212> TYPE: DNA
<213> ORGANISM: Artificial sequence
<220> FEATURE:
<223> OTHER INFORMATION: Oligonucleotide

<400> SEQUENCE: 100
cgcgtataag cttgggcttc taccagcaca agagcatgaa cgagcctaaa cacggg        56

<210> SEQ ID NO 101
<211> LENGTH: 56
<212> TYPE: DNA
<213> ORGANISM: Artificial sequence
<220> FEATURE:
<223> OTHER INFORMATION: Oligonucleotide

<400> SEQUENCE: 101
ctagcccgtg tttaggctcg ttcatgctct tgtgctggta gaagcccaag cttata        56

<210> SEQ ID NO 102
<211> LENGTH: 56
<212> TYPE: DNA
<213> ORGANISM: Artificial sequence
<220> FEATURE:
<223> OTHER INFORMATION: Oligonucleotide

<400> SEQUENCE: 102
cgcgtataag cttgcacttc taccagcaca agagcatgaa cgagcctaaa cacggg        56

<210> SEQ ID NO 103
<211> LENGTH: 56
<212> TYPE: DNA
<213> ORGANISM: Artificial sequence
<220> FEATURE:
<223> OTHER INFORMATION: Oligonucleotide

<400> SEQUENCE: 103
ctagcccgtg tttaggctcg ttcatgctct tgtgctggta gaagtgcaag cttata        56

<210> SEQ ID NO 104
<211> LENGTH: 56
<212> TYPE: DNA
<213> ORGANISM: Artificial sequence
<220> FEATURE:
<223> OTHER INFORMATION: Oligonucleotide

<400> SEQUENCE: 104
```
cgcgtataag cttgatcttc taccagcaca agagcatgaa cgagcctaaa cacggg       56

<210> SEQ ID NO 105
<211> LENGTH: 56
<212> TYPE: DNA
<213> ORGANISM: Artificial sequence
<220> FEATURE:
<223> OTHER INFORMATION: Oligonucleotide

<400> SEQUENCE: 105
ctagcccgtg tttaggctcg ttcatgctct tgtgctggta gaagatcaag cttata       56

<210> SEQ ID NO 106
<211> LENGTH: 56
<212> TYPE: DNA
<213> ORGANISM: Artificial sequence
<220> FEATURE:
<223> OTHER INFORMATION: Oligonucleotide

<400> SEQUENCE: 106
cgcgtataag cttgaagttc taccagcaca agagcatgaa cgagcctaaa cacggg       56

<210> SEQ ID NO 107
<211> LENGTH: 56
<212> TYPE: DNA
<213> ORGANISM: Artificial sequence
<220> FEATURE:
<223> OTHER INFORMATION: Oligonucleotide

<400> SEQUENCE: 107
ctagcccgtg tttaggctcg ttcatgctct tgtgctggta gaacttcaag cttata       56

<210> SEQ ID NO 108
<211> LENGTH: 56
<212> TYPE: DNA
<213> ORGANISM: Artificial sequence
<220> FEATURE:
<223> OTHER INFORMATION: Oligonucleotide

<400> SEQUENCE: 108
cgcgtataag cttgctgttc taccagcaca agagcatgaa cgagcctaaa cacggg       56

<210> SEQ ID NO 109
<211> LENGTH: 56
<212> TYPE: DNA
<213> ORGANISM: Artificial sequence
<220> FEATURE:
<223> OTHER INFORMATION: Oligonucleotide

<400> SEQUENCE: 109
ctagcccgtg tttaggctcg ttcatgctct tgtgctggta gaacagcaag cttata       56

<210> SEQ ID NO 110
<211> LENGTH: 56
<212> TYPE: DNA
<213> ORGANISM: Artificial sequence
<220> FEATURE:
<223> OTHER INFORMATION: Oligonucleotide

<400> SEQUENCE: 110
cgcgtataag cttgatgttc taccagcaca agagcatgaa cgagcctaaa cacggg       56

<210> SEQ ID NO 111
<211> LENGTH: 56
<212> TYPE: DNA

```
<213> ORGANISM: Artificial sequence
<220> FEATURE:
<223> OTHER INFORMATION: Oligonucleotide

<400> SEQUENCE: 111
ctagcccgtg tttaggctcg ttcatgctct tgtgctggta gaacatcaag cttata        56

<210> SEQ ID NO 112
<211> LENGTH: 56
<212> TYPE: DNA
<213> ORGANISM: Artificial sequence
<220> FEATURE:
<223> OTHER INFORMATION: Oligonucleotide

<400> SEQUENCE: 112
cgcgtataag cttgaacttc taccagcaca agagcatgaa cgagcctaaa cacggg        56

<210> SEQ ID NO 113
<211> LENGTH: 56
<212> TYPE: DNA
<213> ORGANISM: Artificial sequence
<220> FEATURE:
<223> OTHER INFORMATION: Oligonucleotide

<400> SEQUENCE: 113
ctagcccgtg tttaggctcg ttcatgctct tgtgctggta gaagttcaag cttata        56

<210> SEQ ID NO 114
<211> LENGTH: 56
<212> TYPE: DNA
<213> ORGANISM: Artificial sequence
<220> FEATURE:
<223> OTHER INFORMATION: Oligonucleotide

<400> SEQUENCE: 114
cgcgtataag cttgcccttc taccagcaca agagcatgaa cgagcctaaa cacggg        56

<210> SEQ ID NO 115
<211> LENGTH: 56
<212> TYPE: DNA
<213> ORGANISM: Artificial sequence
<220> FEATURE:
<223> OTHER INFORMATION: Oligonucleotide

<400> SEQUENCE: 115
ctagcccgtg tttaggctcg ttcatgctct tgtgctggta gaagggcaag cttata        56

<210> SEQ ID NO 116
<211> LENGTH: 56
<212> TYPE: DNA
<213> ORGANISM: Artificial sequence
<220> FEATURE:
<223> OTHER INFORMATION: Oligonucleotide

<400> SEQUENCE: 116
cgcgtataag cttgcagttc taccagcaca agagcatgaa cgagcctaaa cacggg        56

<210> SEQ ID NO 117
<211> LENGTH: 56
<212> TYPE: DNA
<213> ORGANISM: Artificial sequence
<220> FEATURE:
<223> OTHER INFORMATION: Oligonucleotide

<400> SEQUENCE: 117
ctagcccgtg tttaggctcg ttcatgctct tgtgctggta gaactgcaag cttata        56
```

<210> SEQ ID NO 118
<211> LENGTH: 56
<212> TYPE: DNA
<213> ORGANISM: Artificial sequence
<220> FEATURE:
<223> OTHER INFORMATION: Oligonucleotide

<400> SEQUENCE: 118
cgcgtataag cttgaggttc taccagcaca agagcatgaa cgagcctaaa cacggg        56

<210> SEQ ID NO 119
<211> LENGTH: 56
<212> TYPE: DNA
<213> ORGANISM: Artificial sequence
<220> FEATURE:
<223> OTHER INFORMATION: Oligonucleotide

<400> SEQUENCE: 119
ctagcccgtg tttaggctcg ttcatgctct tgtgctggta gaacctcaag cttata        56

<210> SEQ ID NO 120
<211> LENGTH: 56
<212> TYPE: DNA
<213> ORGANISM: Artificial sequence
<220> FEATURE:
<223> OTHER INFORMATION: Oligonucleotide

<400> SEQUENCE: 120
cgcgtataag cttgagcttc taccagcaca agagcatgaa cgagcctaaa cacggg        56

<210> SEQ ID NO 121
<211> LENGTH: 56
<212> TYPE: DNA
<213> ORGANISM: Artificial sequence
<220> FEATURE:
<223> OTHER INFORMATION: Oligonucleotide

<400> SEQUENCE: 121
ctagcccgtg tttaggctcg ttcatgctct tgtgctggta gaagctcaag cttata        56

<210> SEQ ID NO 122
<211> LENGTH: 56
<212> TYPE: DNA
<213> ORGANISM: Artificial sequence
<220> FEATURE:
<223> OTHER INFORMATION: Oligonucleotide

<400> SEQUENCE: 122
cgcgtataag cttgaccttc taccagcaca agagcatgaa cgagcctaaa cacggg        56

<210> SEQ ID NO 123
<211> LENGTH: 56
<212> TYPE: DNA
<213> ORGANISM: Artificial sequence
<220> FEATURE:
<223> OTHER INFORMATION: Oligonucleotide

<400> SEQUENCE: 123
ctagcccgtg tttaggctcg ttcatgctct tgtgctggta gaaggtcaag cttata        56

<210> SEQ ID NO 124
<211> LENGTH: 56
<212> TYPE: DNA
<213> ORGANISM: Artificial sequence
<220> FEATURE:

<223> OTHER INFORMATION: Oligonucleotide

<400> SEQUENCE: 124
cgcgtataag cttgtggttc taccagcaca agagcatgaa cgagcctaaa cacggg      56

<210> SEQ ID NO 125
<211> LENGTH: 56
<212> TYPE: DNA
<213> ORGANISM: Artificial sequence
<220> FEATURE:
<223> OTHER INFORMATION: Oligonucleotide

<400> SEQUENCE: 125
ctagcccgtg tttaggctcg ttcatgctct tgtgctggta gaaccacaag cttata      56

<210> SEQ ID NO 126
<211> LENGTH: 56
<212> TYPE: DNA
<213> ORGANISM: Artificial sequence
<220> FEATURE:
<223> OTHER INFORMATION: Oligonucleotide

<400> SEQUENCE: 126
cgcgtataag cttgtacttc taccagcaca agagcatgaa cgagcctaaa cacggg      56

<210> SEQ ID NO 127
<211> LENGTH: 56
<212> TYPE: DNA
<213> ORGANISM: Artificial sequence
<220> FEATURE:
<223> OTHER INFORMATION: Oligonucleotide

<400> SEQUENCE: 127
ctagcccgtg tttaggctcg ttcatgctct tgtgctggta gaagtacaag cttata      56

<210> SEQ ID NO 128
<211> LENGTH: 56
<212> TYPE: DNA
<213> ORGANISM: Artificial sequence
<220> FEATURE:
<223> OTHER INFORMATION: Oligonucleotide

<400> SEQUENCE: 128
cgcgtataag cttggtgttc ttccagcaca agagcatgaa cgagcctaaa cacggg      56

<210> SEQ ID NO 129
<211> LENGTH: 56
<212> TYPE: DNA
<213> ORGANISM: Artificial sequence
<220> FEATURE:
<223> OTHER INFORMATION: Oligonucleotide

<400> SEQUENCE: 129
ctagcccgtg tttaggctcg ttcatgctct tgtgctggaa gaacaccaag cttata      56

<210> SEQ ID NO 130
<211> LENGTH: 34
<212> TYPE: PRT
<213> ORGANISM: Homo sapiens

<400> SEQUENCE: 130

Pro Phe Ser Gly Val Thr Ala Cys Leu Asp Phe Cys Ala His Pro His
1               5                   10                  15

Arg Asp Ile His Asn Arg Leu Ser Leu Val Phe Tyr Gln His Lys Asn
            20                  25                  30

Leu Asn

<210> SEQ ID NO 131
<211> LENGTH: 34
<212> TYPE: PRT
<213> ORGANISM: Mus musculus

<400> SEQUENCE: 131

Pro Phe Ser Gly Val Thr Cys Cys Met Asp Phe Cys Ala His Ser His
1               5                   10                  15

Lys Asp Ile His Asn Arg Val Ser Leu Val Phe Tyr Gln His Lys Ser
            20                  25                  30

Leu Asn

<210> SEQ ID NO 132
<211> LENGTH: 34
<212> TYPE: PRT
<213> ORGANISM: Homo sapiens

<400> SEQUENCE: 132

Pro Phe Ser Gly Val Thr Ala Cys Leu Asp Phe Cys Ala His Ala His
1               5                   10                  15

Arg Asp Leu His Asn Arg Ile Ser Leu Val Phe Tyr Gln His Lys Ser
            20                  25                  30

Met Asn

<210> SEQ ID NO 133
<211> LENGTH: 34
<212> TYPE: PRT
<213> ORGANISM: Mus musculus

<400> SEQUENCE: 133

Pro Phe Ser Gly Val Thr Ala Cys Leu Asp Phe Ser Ala His Ser His
1               5                   10                  15

Arg Asp Gln Gln Asn Arg Ile Ser Leu Val Leu Tyr Arg His Lys Asn
            20                  25                  30

Leu Phe

<210> SEQ ID NO 134
<211> LENGTH: 34
<212> TYPE: PRT
<213> ORGANISM: Homo sapiens

<400> SEQUENCE: 134

Pro Phe Ala Gly Val Thr Ala Cys Met Asp Phe Cys Ala His Ala His
1               5                   10                  15

Lys Asp Gln His Asn Arg Ile Ser Leu Val Phe Tyr Gln His Lys Asn
            20                  25                  30

Leu Asn

<210> SEQ ID NO 135
<211> LENGTH: 34
<212> TYPE: PRT
<213> ORGANISM: Mus musculus

<400> SEQUENCE: 135

Pro Phe Ser Gly Val Thr Ala Cys Met Asp Phe Cys Ala His Ala His
1               5                   10                  15

Lys Asp Gln His Asn Arg Ile Ser Leu Val Phe Tyr Gln His Lys Asn

```
                    20                  25                  30

Leu Asn

<210> SEQ ID NO 136
<211> LENGTH: 53
<212> TYPE: PRT
<213> ORGANISM: Homo sapiens

<400> SEQUENCE: 136

Glu Cys Arg Leu Gly Ser Lys Glu Gly Arg Pro Phe Ser Gly Val Thr
1               5                   10                  15

Ala Cys Leu Asp Phe Cys Ala His Pro His Arg Asp Ile His Asn Met
            20                  25                  30

Asn Asn Gly Arg Asn His Pro Thr Arg Leu Ser Leu Val Phe Tyr Gln
        35                  40                  45

His Lys Asn Leu Asn
    50

<210> SEQ ID NO 137
<211> LENGTH: 53
<212> TYPE: PRT
<213> ORGANISM: Mus musculus

<400> SEQUENCE: 137

Asp Cys Arg Leu Gly Asn Glu Glu Gly Arg Pro Phe Ser Gly Val Thr
1               5                   10                  15

Cys Cys Met Asp Phe Cys Ala His Ser His Lys Asp Ile His Asn Met
            20                  25                  30

His Asn Gly Arg Gly Val Pro Phe Arg Val Ser Leu Val Phe Tyr Gln
        35                  40                  45

His Lys Ser Leu Asn
    50

<210> SEQ ID NO 138
<211> LENGTH: 53
<212> TYPE: PRT
<213> ORGANISM: Homo sapiens

<400> SEQUENCE: 138

Glu Cys Arg Leu Gly Leu Lys Glu Gly Arg Pro Phe Ser Gly Val Thr
1               5                   10                  15

Ala Cys Leu Asp Phe Cys Ala His Ala His Arg Asp Leu His Asn Met
            20                  25                  30

Gln Asn Gly Arg Asn His Pro Thr Arg Ile Ser Leu Val Phe Tyr Gln
        35                  40                  45

His Lys Ser Met Asn
    50

<210> SEQ ID NO 139
<211> LENGTH: 53
<212> TYPE: PRT
<213> ORGANISM: Mus musculus

<400> SEQUENCE: 139

Asp Cys Cys Leu Gly Leu Lys Glu Gly Arg Pro Phe Ser Gly Val Thr
1               5                   10                  15

Ala Cys Leu Asp Phe Ser Ala His Ser His Arg Asp Gln Gln Asn Met
            20                  25                  30

Pro Asn Gly Arg Asn His Pro Thr Arg Ile Ser Leu Val Leu Tyr Arg
```

His Lys Asn Leu Phe
    50

<210> SEQ ID NO 140
<211> LENGTH: 53
<212> TYPE: PRT
<213> ORGANISM: Homo sapiens

<400> SEQUENCE: 140

Asp Cys Arg Leu Gly Leu Lys Glu Gly Arg Pro Phe Ala Gly Val Thr
1               5                   10                  15

Ala Cys Met Asp Phe Cys Ala His Ala His Lys Asp Gln His Asn Leu
            20                  25                  30

Tyr Asn Gly Arg Cys His Pro Thr Arg Ile Ser Leu Val Phe Tyr Gln
        35                  40                  45

His Lys Asn Leu Asn
    50

<210> SEQ ID NO 141
<211> LENGTH: 53
<212> TYPE: PRT
<213> ORGANISM: Mus musculus

<400> SEQUENCE: 141

Asp Cys Arg Leu Gly Leu Lys Glu Gly Arg Pro Phe Ser Gly Val Thr
1               5                   10                  15

Ala Cys Met Asp Phe Cys Ala His Ala His Lys Asp Gln His Asn Leu
            20                  25                  30

Tyr Asn Gly Arg Cys His Pro Thr Arg Ile Ser Leu Val Phe Tyr Gln
        35                  40                  45

His Lys Asn Leu Asn
    50

<210> SEQ ID NO 142
<211> LENGTH: 47
<212> TYPE: PRT
<213> ORGANISM: Trypanosoma brucei

<400> SEQUENCE: 142

Val Val Arg Ile His Gly Ser Pro Phe Ser Thr Leu Thr Val Asn Glu
1               5                   10                  15

Arg Phe Arg Thr Ala Ser His Thr Asp Asn Gly Asp Phe Asp Asn Gly
            20                  25                  30

Asn Ala Thr Trp Asn Arg Leu Ser Cys Val Phe Tyr Tyr Arg Ala
        35                  40                  45

<210> SEQ ID NO 143
<211> LENGTH: 50
<212> TYPE: PRT
<213> ORGANISM: Trypanosoma brucei

<400> SEQUENCE: 143

Glu Tyr Met Leu Phe Asn Thr Val Phe Ser Thr Val Ser Val Asn Lys
1               5                   10                  15

Asn Phe Arg Thr Ala Val His Arg Asp Lys Gly Asp Phe Arg Gly Gly
            20                  25                  30

Glu Gly Ser Trp Arg Arg Ile Ser Ile Val Cys Tyr Leu Arg Cys Gly
        35                  40                  45

```
<210> SEQ ID NO 144
<211> LENGTH: 51
<212> TYPE: PRT
<213> ORGANISM: Naegleria gruberi

<400> SEQUENCE: 144

Tyr Ala Leu Asn Asn Cys Leu Tyr Pro Ser Thr Ala Phe Asn Ser Leu
1               5                   10                  15

Lys Pro Ser Asn Asp Gly His Arg Ile Arg Lys Pro His Lys Asp Asn
            20                  25                  30

Leu Asp Ile Thr Gly Trp Arg Ile Gly Leu Val Tyr Phe Ala His Lys
        35                  40                  45

Gly Ser Lys
    50

<210> SEQ ID NO 145
<211> LENGTH: 45
<212> TYPE: PRT
<213> ORGANISM: Escherichia coli

<400> SEQUENCE: 145

Gln Pro Asp Ala Cys Leu Ile Asn Arg Tyr Ala Pro Gly Ala Lys Leu
1               5                   10                  15

Cys Leu His Gln Asp Lys Asp Glu Pro Asp Leu Arg Ala Leu Thr Ile
            20                  25                  30

Asp Cys Arg Tyr Asn Leu Thr Phe Arg Gln Ala Gly Lys
        35                  40                  45
```

HYPERACTIVE AID/APOBEC AND HMC DOMINANT TET ENZYMES

CROSS-REFERENCE TO RELATED APPLICATIONS

This application is a divisional application of U.S. patent application Ser. No. 16/025,261, filed Jul. 2, 2018, which claims the benefit of priority under 35 U.S.C. § 119(e) to U.S. Provisional Patent Application No. 62/528,808, filed Jul. 5, 2017, the contents of each being incorporated by reference herein in their entirety.

STATEMENT REGARDING FEDERALLY SPONSORED RESEARCH OR DEVELOPMENT

This invention was made with government support under K08 AI089242 and R01 GM118501 awarded by the National Institutes of Health. The government has certain rights in the invention.

BACKGROUND OF THE INVENTION

In mammalian genomes, cytosine modifying enzymes provide an added layer of diversity to the genome. Cytosine can be modified by deamination, oxidation and methylation, with each of these modifications leading to different outcomes. In nature, these transformations are catalyzed by several enzymes, and the reactions play an important role in multiple processes including immunity and epigenetics.

One family of these cytosine modifying enzymes are the AID/APOBEC (apolipoprotein B editing complex) family. These enzymes deaminate cytidine to uridine, leading to nucleotide changes in RNA and DNA that can alter function. In mammals, the larger family of APOBECs include four subfamilies (APOBEC1-4) and the well characterized, activation-induced deaminase, AID. While evolution has tuned the specific functions of the individual AID/APOBECs in cells, as deaminases, they all share key structural features necessary for catalytic function. Within this larger family AID and APOBEC3 enzymes are known to preferentially deaminate cytosine bases in singe stranded DNA (ssDNA) contexts.

AID is a deaminase that is essential for adaptive immunity, and can be found as far back in evolution as jawless vertebrae, suggesting an important and conserved role in immunity. AID acts by introducing targeted uracil lesions within the immunoglobulin genes. Mutations introduced into the regions of antibody genes that recognize antigen drive increased affinity and an improved ability to recognize targets in a process known as somatic hypermutation. AID also acts in the "switch" regions of immunoglobulin genes, where double stranded DNA breaks introduced by the targeted introduction of uracil in neighboring strands leads to class switch recombination and a change from IgG to alternative isotypes IgM, IgA, IgE, which can alter the effector function of antibodies.

The APOBEC3 family has more recently evolved and is best known for its function in specific targeting of retroviral and transposable elements that threaten genomic integrity. As a result of selective pressures, the APOBEC3 (A3) locus in primates has undergone numerous duplication events to give rise to seven genes on chromosome 22 that encode for deaminases. These seven genes are commonly abbreviated A3A-A3H. Most A3s also have been shown to restrict retroviruses and retrotransposons; however, they differ in their tissue and subcellular localization. While the structure and sequences of the catalytic regions of A3s are largely conserved, there are some important structural and sequence differences between members of the A3 subfamily of deaminases. For example, A3A, A3C, and A3H are all single domain deaminase proteins, similar to APOBEC1, APOBEC2, and APOBEC4. On the other hand, A3B, A3DE, and A3G are all double domain deaminases.

A second key class of modifications that can occur to cytosine bases are catalyzed by the Ten-eleven translocation (TET) enzymes. TET enzymes catalyze the oxidation of 5-methylcytosine (mC), the mainstay of the epigenome, into three additional bases: 5-hydroxymethylcytosine (hmC), 5-formylcytosine (fC), and 5-carboxyl cytosine (caC). Mounting evidence suggests that these oxidized mC (ox-mC) bases stably populate mammalian genomes, are integral intermediates in DNA demethylation, and potentially encode unique epigenetic information. However, the functions of each individual base and the mechanisms governing their formation are currently unknown.

The overall catalytic mechanism of TET enzymes (TET1, TET2, and TET3 in mammals) has been largely inferred from related proteins in the Fe(II)/$\alpha$-ketoglutarate ($\alpha$-KG)-dependent family of dioxygenases, such as AlkB. Enzymes in this family couple decarboxylation of $\alpha$-KG with substrate oxidation via a transient Fe(IV)-oxo intermediate, with succinate and $CO_2$ as byproducts. TET enzymes apply this general mechanism to not one but three stepwise reactions. It is currently unknown whether these enzymes are specialized for one particular step of oxidation or for three-step oxidation as a whole. Moreover, stepwise oxidation obscures the function of individual ox-mCs, creating a need to break the linkage between steps in order to study each base in isolation.

A need exists for novel AID, APOBEC, and TET enzymes with modified and tailored functions. The present invention satisfies this need.

SUMMARY OF THE INVENTION

The present invention provides a fusion protein comprising hyperactive deamination activity having a first domain with an apolipoprotein B editing complex (APOBEC) 3B (A3B) domain, and having an APOBEC3A (A3A) catalytic domain a second domain. In some embodiments, the fusion protein comprises the amino acid sequence of SEQ ID NO: 8.

In some embodiments, the present invention provides a mutant A3B protein having the following amino acid mutations: D196H, T197I, Delta(206-210), Ins(206)GIG, R212H Q213K, W228S I230K, M235R, C239H, E241Q, E342K, Y343H, Y350D, R351H, and E363D. The mutant A3B protein displays hyperactive deamination activity.

In some embodiments, the present invention provides an isolated nucleic acid encoding a fusion protein comprising hyperactive deamination activity with a first domain having an A3B domain and a second domain having an A3A catalytic domain.

In some embodiments, the present invention provides an activation-induced cytidine deaminase (AID) mutant protein comprising hyperactive deamination activity with an amino acid sequence corresponding to SEQ ID NO:16.

In some embodiments, the present invention provides an AID mutant protein having hyperactive deamination activity and with an amino acid sequence corresponding to SEQ ID NO:17.

In some embodiments, the present invention provides an AID mutant protein having hyperactive deamination activity with an amino acid sequence corresponding to SEQ ID NO:18.

In some embodiments, the present invention provides an AID mutant protein having hyperactive deamination activity and having the amino acid sequence corresponding to SEQ ID NO:19.

In some embodiments, the present invention provides an AID mutant protein with hyperactive deamination activity having an amino acid sequence corresponding to SEQ ID NO:20.

In some embodiments, the present invention provides a mutant Ten-Eleven Translocation (TET) enzyme capable of stalling oxidation at a 5-hydroxymethylcytosine (hmC). In some embodiments, the mutant TET enzyme is derived from a human. In some embodiments, the mutant TET enzyme is derived from a mouse. In some embodiments, the mutant TET enzyme is derived from the family of TET proteins selected from the group consisting of TET1, TET2, and TET3. In some embodiments, the mutant TET enzyme includes mutant TET enzymes wherein residue 1372 of any one of SEQ ID NOs: 21-22 has been mutated. In some embodiments, the mutant TET enzyme includes mutant TET enzymes wherein the threonine (T) residue at position 1372 is changed to a glutamine (Q) residue. In some embodiments, the threonine (T) residue at position 1372 is changed to an asparagine (N) residue. In some embodiments, the threonine (T) residue at position 1372 is changed to an aspartic acid (D) residue. In some embodiments, the threonine (T) residue at position 1372 is changed to a glutamic acid (E) residue. In some embodiments, the mutant TET enzyme further comprises an additional mutation at position 1902 of any one of SEQ ID NOs: 21-22. In some embodiments, the tyrosine (Y) residue at position 1902 is changed to a phenylalanine (F) residue. In some embodiments, the mutant TET enzyme includes the amino acid sequence corresponding to SEQ ID NO: 23. In some embodiments, the mutant TET enzyme includes the amino acid sequence corresponding to SEQ ID NO: 24.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 4 is a table illustrating quantification of UDG activity.

FIG. 5A shows 500 nM of FAM-labeled oligonucleotide substrate containing one single cytosine in the preferred context for AID was incubated with the stated amount of each AID construct, and co-incubated with uracil DNA glycosylase. After 1 hour at 37° C. the reactions were quenched with formamide buffer containing NaOH and heated to cleave abasic sites generated by UDG acting on newly generated uracil bases. FIG. 5B illustrates the quantified product formation showing the marked enhancement in activity with purified hyperactive AIDs.

FIG. 6A is a schematic depicting the SwaI assay used herein. FIG. 6B shows results from the SwaI assay. 400 nm protein was used, reactions were incubated overnight.

FIG. 9 is a set of images illustrating hyperAID preps and activity of hyperactive AIDs. HyperAID preps: AID-WT or hyperactive variant were expressed from pET41 expression plasmids as MBP fusion proteins and purified using Amylose resin. Shown are the total and soluble fractions, along with the flow through after binding to amylose resin, wash fractions and three elution fractions. The full length MBP-AID constructs are denoted with an arrow.

FIG. 11A is a schematic of the hTET2-CS construct (drawn to scale, adapted from Hu et al. (2013) Cell 155, 1545-1555). The two cysteine-rich domains are shown in pink and purple, and the double-stranded (β-helix (DSBH) domain is in green; residues are numbered as in the complete hTET2 protein. Both Thr1372 and Val1900 are conserved across mouse and human TET proteins. SEQ ID NOS: 130-135 are shown in descending order. FIG. 11B shows the structure of the hTET2-CS active site (PDB 4NM6) highlighting the targets for mutagenesis, Thr1372 and Val1900. The mC base flips into the active site pocket, pointing toward Fe(II) and the α-KG analog N-oxalylglycine. Shown are the nearest distances between the residues and the 5-methyl carbon.

FIG. 12A shows dot blots for mC, hmC, fC, and caC in 400 ng of genomic DNA isolated from transfected HEK293T cells. DNA from cells transfected with WT hTET2-CS or empty vector (vec) was spotted first, followed by the Thr1372 mutants in alphabetical order (uncropped image in FIG. 26A). Further analysis of mutant phenotypes focused on variants that were capable of oxidation at least to hmC. FIG. 12B shows genomic levels of mC, hmC, fC, and caC modifications produced by catalytically active Thr1372 mutants, quantified by LC-MS/MS as the percent of total C modifications. Mutants are approximately presented in decreasing order of activity, from WT-like T1372S, to A/C/G that form highly oxidized bases at reduced levels, to E/Q/N/D/V that largely stall at hmC. Shown are the mean and s.d. from independent experiments (WT, n=7; vec, n=6; mutants, n=3; T1372I, n=2).

FIGS. 13A-13B are a series of images illustrating molecular dynamics modeling reveals a critical Thr1372-Tyr1902 scaffold that is disrupted in the low-efficiency and hmC-dominant mutants. FIG. 13A shows selected snapshots from MD simulations highlighting key active site components and hydrogen bonds. In WT enzyme (and T1372S), Thr1372 forms a hydrogen bond (black arrow) with Tyr1902, which orients Tyr1902 for optimal non-bonded interactions with the substrate. Low efficiency mutants such as T1372A disrupt this scaffold, while hmC-dominant mutants such as T1372E and T1372V not only disrupt the scaffold but also elicit new hydrogen bonds (red arrows) with the 5-hydroxymethyl group of hmC. FIG. 13B shows a simplified scheme of interactions between key residues and hmC, as determined by MD. Hydrogen bonds (dashed lines) are quantified as percentage of simulation time observed. The values are an average over 2-5 simulation runs of 50 ns. Non-bonded interactions are indicated in gray, and total energies of interaction are given in kcal/mol.

FIGS. 14A-14B are a series of plots illustrating biochemical characterization of purified hTET2 mutants. FIG. 14A shows TET2 variants (30 µg/ml) were reacted with 20 nM double-stranded DNA substrates containing mC, hmC, or fC for 30 min. The reaction products were purified, degraded to nucleosides, and quantified by LC-MS/MS. WT and T1372E were also generated in the full catalytic domain of TET2 (FCD and FE, respectively) to confirm that the phenotypes are the same as in the hTET2-CS constructs. Mean values are plotted (n=2), and error bars represent the range. FIG. 14B shows time courses for reactions of 30 µg/ml purified TET2 on 25 nM mC substrates. Mean values are plotted (WT, n=3; mutants, n=2), and error bars represent the range.

FIGS. 15A-15C are a series of plots and images illustrating T1372A/Y1902F double mutant rescues the hmC-dominant phenotype by configuring active site interactions. FIG. 15A shows that modeling predicts that in the Y1902F single mutant, Thr1372 would hydrogen bond instead with hmC, producing an hmC-dominant phenotype. Addition of a T1372A mutation to Y1902F would remove hydrogen bonding, which is predicted to restore activity. The values shown are an average over 2-3 simulation runs of 50 ns each. FIG. 15B shows reaction of 30 µg/ml purified mutants on 20 nM mC substrate, analyzed by LC-MS/MS. Mean values are plotted (n=2), and error bars represent the range. As predicted by the model, Y1902F mimics hmC-dominant mutants, with relatively low activity on mC and little fC formed. The double mutant (TA/YF) restores activity to resemble the T1372A single mutant. FIG. 15C shows that to highlight fC and caC in the reaction products, the purified oligonucleotides (oligos) were treated with recombinant TDG. After alkaline-mediated cleavage at the resulting abasic sites, denaturing PAGE was used to separate intact oligos containing mC and hmC from cleaved oligos that contained fC and caC (uncropped image in FIG. 26B).

FIG. 16 is a table showing activity of representative TET2 variants on mC and hmC.

FIGS. 17A-17C are a series of images illustrating saturation mutagenesis along the conserved active site scaffold. FIG. 17A shows dot blots for mC, hmC, fC, and caC in 400 ng of genomic DNA isolated from HEK293T cells transfected with Val1900 mutants. Mutants are in alphabetical order, followed by WT and vector-transfected samples. To maintain consistency, all results shown here and in FIG. 12A are cropped from the same representative blots (uncropped dot blots in FIG. 26A). FIG. 17B shows Western blots using anti-FLAG antibody to detect hTET2-CS mutants in lysates of transfected HEK293T cells. Hsp90α/β served as a loading control. WT and Thr1372 mutants are shown in alphabetical order, along with an empty vector-transfected control. FIG. 17C shows multiple sequence alignment of human and mouse TET isoforms, the trypanosomal JBP1/2 thymidine hydroxylases, the *Naegleria* Tet-like protein NgTet1, and AlkB of *E. coli*. All these homologues, except AlkB, have been shown to be capable of multistep oxidation on their natural substrates. The residues of interest, Thr1372 and Val1900 in TET2, are highlighted (green), along with the key scaffold residue, Tyr1902 (blue), and HxD motif (red) characteristic of the Fe(II)/α-KG-dependent family of dioxygenases. Alignments were done using the PROMALS3D algorithm, based on the crystal structures of hTET2 (PDB 4NM6), NgTet1 (PDB 4LT5), and AlkB (PDB 3BIE). SEQ ID NOS: 136 to 145 are shown in descending order.

FIG. 18A shows representative standard curves for mC, hmC, fC, and caC nucleosides. So that all data were weighted equally, the slopes were calculated by scaling the data points to 1 nM and taking the average. FIG. 18B shows representative LC-MS/MS spectrum of gDNA from HEK293T cells expressing WT hTET2-CS. Using the slopes of the standard curves, the peak areas were converted into concentrations of each modified cytosine in the gDNA sample. These were then expressed as the percent of total cytosine modifications.

FIG. 19A shows SDS-PAGE of TET2 variants purified from 519 insect cells: WT hTET2-FCD and T1372E-FCD, plus WT hTET2-CS and T1372S/A/E/V, Y1902F, and T1372A/Y1902F mutants. FIGS. 19B-19C show reactions of 30 µg/mL TET2 with 20 nM dsDNA substrates containing (FIG. 19B) mC or (FIG. 19C) hmC. The reaction products were purified and subjected to both LC-MS/MS (FIG. 14A) and chemoenzymatic assays, as described herein. Control mC, hmC, fC, and caC substrates without TET were used to illustrate the cleavage patterns in each assay. These orthogonal, complementary assays corroborate the quantitative LC-MS/MS results. FIG. 19D shows the total oxidation events over the 3-h time course (FIG. 14B), counting hmC once, fC twice, and caC three times to reflect the number of oxidation steps required to generate each base from mC substrate: Total oxidation events (arbitrary units)=1×(% hmC)+2×(% fC)+3×(% caC). The results further illustrate the distinct WT, low-efficiency, and hmC-dominant phenotypes. Mean values are plotted (WT n=3, mutants n=2), and error bars represent the range.

FIGS. 21A-21I are a series of images illustrating non-covalent interaction (NCI) analysis on a representative snapshot for WT hTET2-CS and mutants in the presence of hmC. (FIG. 21A) WT (FIG. 21B) T1372S (FIG. 21C) T1372A (FIG. 21D) T1372E (FIG. 21E) T1372Q (FIG. 21F) T1372N (FIG. 21G) T1372D (FIG. 21H) T1372V (FIG. 21I) Y1902F. Green surfaces denote weak interactions (e.g. van der Waals), blue surfaces are strong attractive interactions (e.g. hydrogen bonds), and red surfaces are strong repulsive interactions. Key interactions are circled. The coordinating water occupying the sixth (equatorial) position is omitted for clarity. The WT Thr1372-Tyr1902 active site scaffold is preserved in T1372S. T1372A removes the hydrogen bonding partner, leaving weakened non-covalent interactions in the active site. The hmC-dominant mutants T1372E/Q/N/D/V elicit a new hydrogen bond directly with the 5-hydroxymethyl moiety; for E/Q/D, the hydrogen bond involves the mutated residue itself, while for N/V the hydrogen bond involves nearby residue(s). The iso value for NCI is 0.3 au, and $-0.2$ au$<\text{sign}(\lambda_2)\rho<0.2$ au.

FIGS. 22A-22H are a series of images illustrating NCI analysis on a representative snapshot for WT and T1372A, E, and V mutants in the presence of mC and fC. (FIG. 22A) WT with mC (FIG. 22B) T1372A with mC (FIG. 22C) T1372E with mC (FIG. 22D) T1372V with mC (FIG. 22E) WT with fC (FIG. 22F) T1372A with fC (FIG. 22G) T1372E with fC (FIG. 22H) T1372V with fC. Green surfaces denote weak interactions (e.g. van der Waals), blue surfaces are strong attractive interactions (e.g. hydrogen bonds), and red surfaces are strong repulsive interactions. Key interactions are circled. The coordinating water occupying the sixth (equatorial) position is omitted for clarity. The WT Thr1372-Tyr1902 active site scaffold is present in mC and fC models, as well as hmC (FIG. 21A), but the aberrant new hydrogen bonding in hmC-dominant mutants is specific to hmC and is not observed with mC or fC. The isovalue for NCI is 0.3 au, and $-0.2$ au$<\text{sign}(\lambda_2)\rho<0.2$ au.

FIGS. 23A-23F are a series of images illustrating coordination sphere in WT simulations for (FIG. 23A) mC, (FIG. 23B) hmC, (FIG. 23C) fC, and (FIG. 23D) caC. The Fe(II) surrogate (denoted Fe) was simulated by a Mg(II) and is hexa-coordinated in all systems. Note that in the crystal structure and our initial structure for MD simulations, α-KG is coordinated to iron in a bidentate fashion via O2' and O1. However, over the course of the simulation, as shown here, α-KG loses one of its coordination interactions to become a monodentate ligand (via only O1). The sixth (equatorial) position is occupied by a water molecule. This is consistent with our previous QM/MM studies of the reaction mechanism of AlkB, which is used as a prototype to understand TET enzymes. To validate the appropriateness of the surrogate, test simulations were performed for WT with hmC using Mg(II) and Fe(II). FIGS. 23E-23F show the distance of all the ligands in the first coordination shell of the metal, Mg(II) and Fe(II) respectively, for the duration of the trajectory. These results validate our point-charge force field used for modeling. Note that Water 2 comes into the active site and coordinates to the metal cation after α-KG becomes a monodentate ligand (after 7 ns and 2 ns in Mg(II) and Fe(II) simulations, respectively). The mean RMSDs for Wat2 in Mg(II) and Fe(II) simulations decrease to 2.01±0.02 and 2.06±0.01, respectively, after excluding the distances before coordinating to metal. The values in parentheses are mean±s.d. The numbers in square brackets are the third significant figure for values <0.005.

FIGS. 24A-24C are a set of plots and a table illustrating root mean square deviation (RMSD) analysis with respect to the crystal structure (PDB 4NM6). FIG. 24A depicts RMSD plots for protein backbone in a representative simulation of WT TET2 with mC/hmC/fC/caC showing stability across the 50 ns simulation. FIG. 24B depicts RMSD plots for the hmC base (all atoms) in WT, T1372A, T1372E, and T1372A/Y1902F showing small conformational changes for the cytosine base throughout the simulations. FIG. 24C depicts RMSD values for protein backbone in WT and mutants with hmC-containing DNA. The mean±s.d in FIGS. 24A-24C are calculated based on the mean value from each replicate simulation. No errors are provided with T1372S and T1372C since those simulations were only performed once.

FIGS. 25A-25G are a series of correlation plots for (FIG. 25A) WT, (FIG. 25B) T1372A, (FIG. 25C) T1372E, and (FIG. 25D) T1372A/Y1902F. Correlation analysis by residue was carried out using the cpptraj module of Amber14, across the entire simulations. Residue pairs with correlated motions are shown in blue, while anti-correlated motions are shown in red. The correlation difference plots for (FIG. 25E) T1372A, (FIG. 25F) T1372E and (FIG. 25G) T1372A/Y1902F compare the mutant correlation plot to that of the WT and were calculated using an in-house python script. The range in difference plots was narrowed to −0.3 to 0.3 to highlight areas that appear different. Illustrative, regional changes in the single mutants are marked with boxes. For instance, residues 1425-1480 and 1400-1425 in T1372E are correlated but in T1372A are anti-correlated. The double mutant shows a pattern more consistent with the WT, suggesting that protein dynamics could be an added mechanism contributing to the differential reactivity of the variants.

FIG. 26A shows dot blots of mC and hmC (left panel) and fC and caC (right panel) used for FIG. 12A and FIG. 17A. FIG. 26B shows for FIG. 15C, 13 purified TET variants were reacted with oligonucleotides containing mC, and the reaction products were purified and treated with TDG to yield cleavage products at sites of fC and caC formation. These products were analyzed by DNA polyacrylamide gel electrophoresis. Relevant lanes are labeled; the four lanes at right are mC, hmC, fC, and caC oligo controls illustrating the specificity of TDG in this assay.

FIGS. 27A-27C are a series of tables showing oligonucleotides used for cassette mutagenesis.

FIG. 28A illustrates a structural model of AID bound to ssDNA (Gajula et al., NAR (2014) 42(14):9964-9975) overlaid with three clusters of residues where mutations have been independently shown to confer hyperactivity. FIG. 28B depicts a modified fluctuation analysis approach used to analyze and quantify deamination efficiency. Combining mutational clusters results in significant AID hyperactivation. AID-E58A, inactive mutant. FIG. 28C shows cells expressing AID-WT and the AIDC123* variant plated under rifampin selection, demonstrating the increase in mutagenesis with variant expression.

DETAILED DESCRIPTION

Definitions

Figure 1:
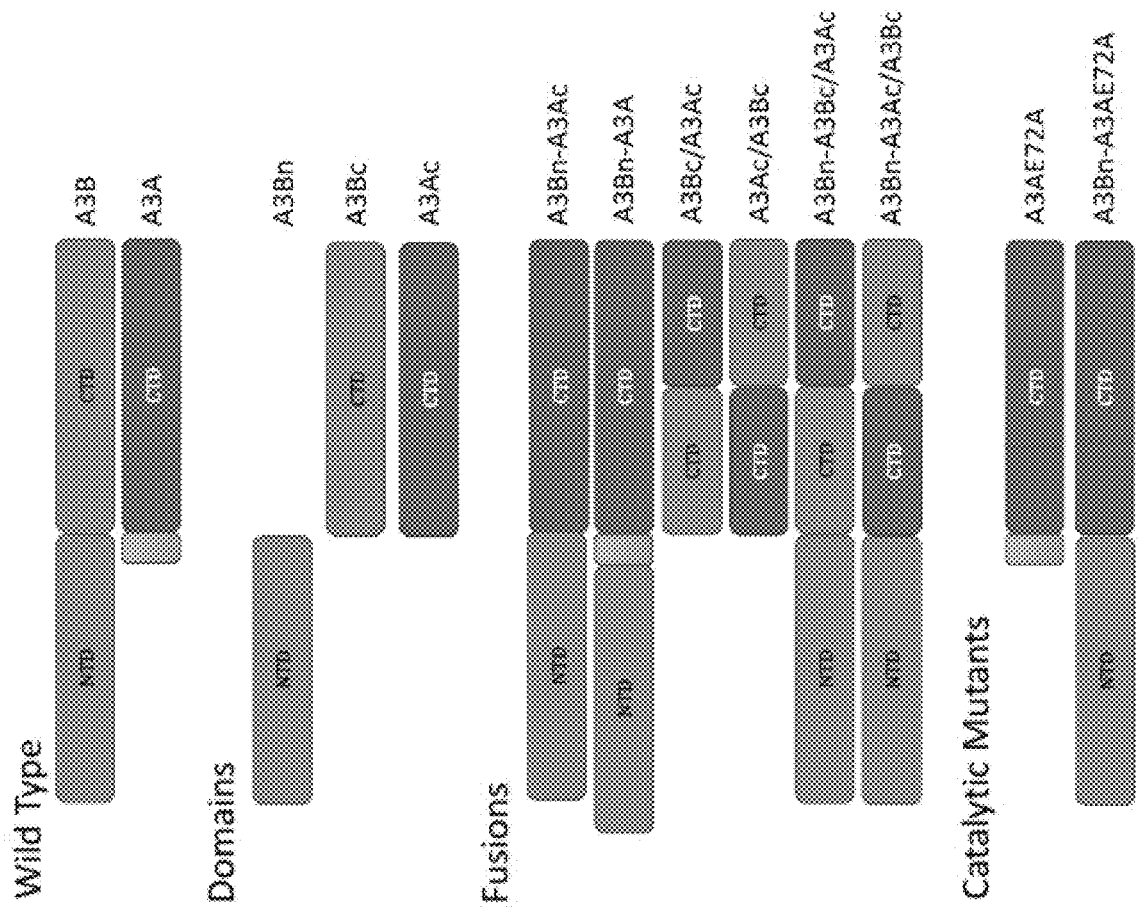
FIG. 1 is a schematic of the APOBEC constructs described herein.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue, or system.

As used herein, the term "exogenous" refers to any material introduced from or produced outside an organism, cell, tissue, or system.

The term "expression" as used herein is defined as the transcription and/or translation of a particular nucleotide sequence driven by its promoter.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modified" as used herein, is meant a changed state or structure of a molecule or cell of the invention. Molecules may be modified in many ways, including chemically, structurally, and functionally. Cells may be modified through the introduction of nucleic acids.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides mutant AID, APOBEC, and Tet enzymes with improved functions. In one aspect the invention provides APOBEC fusion proteins comprising hyperactive deamination activity. In another aspect, the invention provides AID mutant proteins comprising hyperactive deamination activity. In yet another aspect, the invention provides mutant Tet proteins capable of stalling oxidation at a 5-hydroxymethylcytosine (hmC). These AID and APOBEC mutant enzymes are useful for creating mutations in a genome or synthetic DNA substrate at an increased rate compared to wild-type enzymes. Tet mutant enzymes are useful for stalling oxidation at the hmC stage and/or introducing hmC modifications into a genome or synthetic DNA substrate.

AID/APOBEC Enzymes

The AID/APOBEC (apolipoprotein B editing complex) family of enzymes deaminates cytidine to uridine, leading to mutations in RNA and DNA. APOBECs have many physiological functions within the cell ranging from editing pre-mRNA to conferring immunity. However, recently, two members of this family, A3B and A3A, have been implicated as sources of mutations in cancer genomes. The experiments described herein elucidate the biochemical and functional differences between the two in mutating single stranded DNA (ssDNA) in order to elucidate their respective roles in oncogenesis. By testing different constructs that swap between the domains of the two proteins, the following experiments examine the catalytic activity of the two proteins in vitro. A qualitative toxicity E. coli screen was used as a primary assay to assess differential deaminase activity between the constructs. These results were then verified through more quantitative activity assays, which not only confirmed the findings, but also led to insights on the residues in the catalytic domains of each protein that are important for deaminase activity.

Human APOBEC3B (A3B) (SEQ ID NO: 3) is a double-domained deaminase and is closely related to human APOBEC3A (A3A) (SEQ ID NO: 2). A hyperactive A3B (HYPER-A3B-1, also referred to as A3B(N)-A3A) was created herein by making a fusion of domains A3A and A3B. The catalytic domain of wild-type A3B was replaced with that of the closely related A3A, resulting in a hyperactive construct containing a host of mutations relative to the wild-type sequence (D196H, T197I, Delta(206-210), Ins (206)GIG, R212H Q213K, W228S I230K, M235R, C239H, E241Q, E342K, Y343H, Y350D, R351H, E363D) (SEQ ID NO: 8). The combination of these mutations is relevant, as is the contribution of individual mutations. Deamination hyperactivity was also shown with other APOI3EC mutants including: A3Bn-A3Ac (SEQ ID NO: 7), A3Bn-A3Ac/A3Bc (SEQ ID NO: 11), and A3Bn-A3Bc/A3Ac (SEQ ID NO: 12).

In one aspect, the invention includes a fusion protein comprising hyperactive deamination activity comprising a first domain and a second domain, wherein the first domain comprises an apolipoprotein B editing complex (APOBEC) 3B (A3B) domain and the second domain comprises an APOBEC3A (A3A) catalytic domain. In one embodiment, the fusion protein comprises the amino acid sequence of SEQ ID NO: 8.

In another aspect, the invention includes a mutant A3B protein comprising amino acid mutations consisting of: D196H, T197I, Delta(206-210), Ins(206)GIG, R212H Q213K, W228S I230K, M235R, C239H, E241Q, E342K, Y343H, Y350D, R351H, and E363D, wherein the mutant A3B protein displays hyperactive deamination activity.

In yet another aspect, the invention includes an isolated nucleic acid encoding a fusion protein comprising hyperactive deamination activity comprising a first domain and a second domain, wherein the first domain comprises an A3B domain and the second domain comprises an A3A catalytic domain. In one embodiment, the isolated nucleic acid comprises the sequence selected from the group consisting of SEQ ID NOs: 25-38.

The invention also provides activation-induced cytidine deaminase (AID) mutant proteins comprising hyperactive deamination activity. In one embodiment, the AID mutant protein comprises the amino acid sequence of SEQ ID NO:16. In another embodiment, the AID mutant protein comprises the amino acid sequence of SEQ ID NO:17. In another embodiment, the AID mutant protein comprises the amino acid sequence of SEQ ID NO:18. In yet another embodiment, the AID mutant protein comprises the amino acid sequence of SEQ ID NO:19. In still another embodiment, the AID mutant protein comprises the amino acid sequence of SEQ ID NO: 20.

Applications of a hyperactive APOBEC or hyperactive AID proteins include using it in APOBEC-Coupled Epigenetic Sequencing (ACE-Seq) or other epigenetic sequencing, using it to evolve antibodies faster, and using it for gene editing in combination with CRISPR or other tools for targeting. ACE-Seq is a method whereby the deaminases enzymes are used to distinguish cytosine from modified cytosine bases in genomic or synthetic DNA. AID/APOBEC deaminases have also been used to perform targeted gene editing and hyperactive deaminases can overcome the limitations of low editing efficiency.

Ten-Eleven Translocation (TET) Enzymes

Figure 11A:
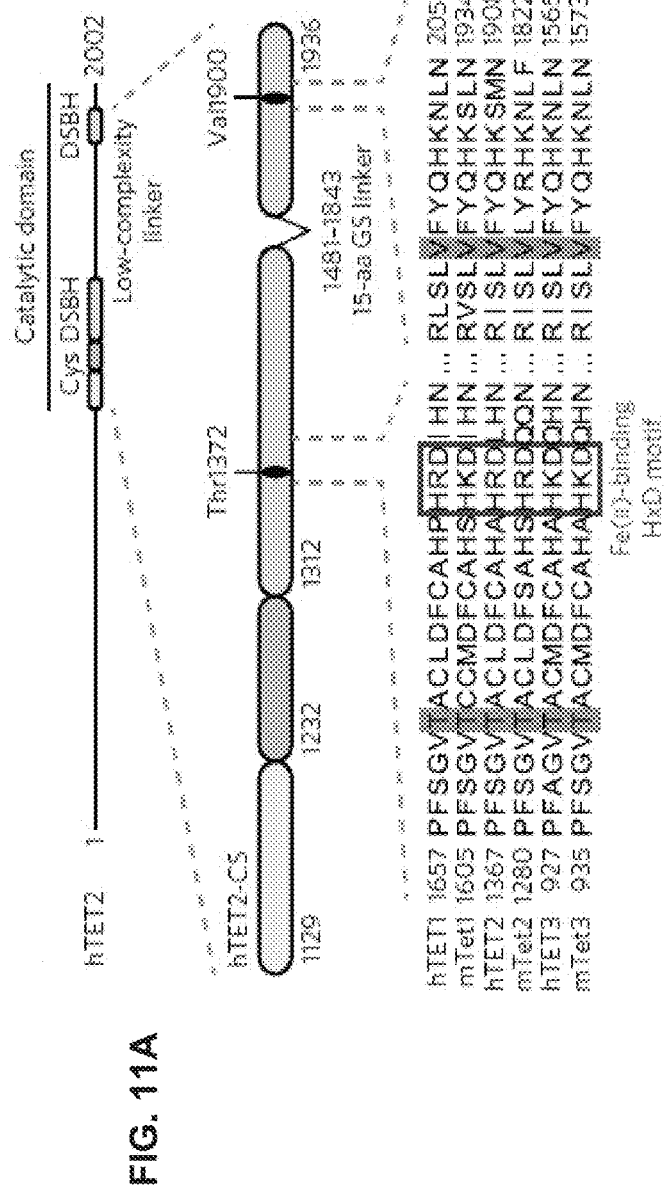
FIGS. 11A-11B are a series of images illustrating Thr1372 and Val1900 were targeted for their potential role in TET2-catalyzed cytosine oxidation.
Figure 11B:
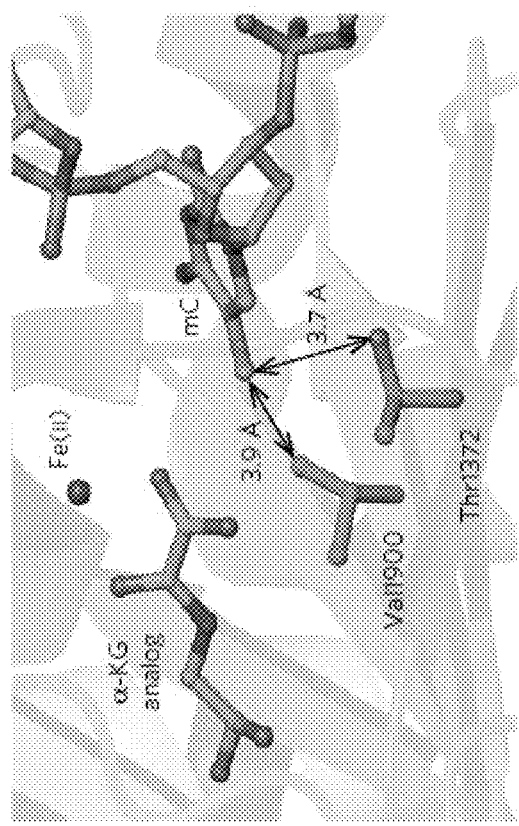

As described herein, the active site of human TET2 was examined for potential structure-function determinants of stepwise oxidation. In the crystal structures of TET2 bound to DNA, the enzyme was truncated to the minimal regions necessary for catalytic activity (hTET2-CS, residues 11291936 A1481-1843) (FIG. 11A). The target nucleobase was everted out of the DNA duplex and occupied a tunnel-like space in the active site, with the 5-modified group pointing toward the α-KG analog and Fe(II) (FIG. 11B). Although the residues that formed this tunnel had no obvious interaction with the 5-modified groups, it was hypothesized that they could impact the progress of stepwise oxidation by hydrogen bonding or steric interactions. Therefore two conserved residues located close to the 5-methyl group were targeted (FIG. 11A-11B). By substituting all 20 amino acids at these positions, notably Thr1372, a relationship between the side chain properties and stepwise oxidation activity was uncovered, including variants that stall oxidation at hmC, with little to no fC or caC formed. Molecular dynamics simulations, coupled with biochemical analyses, revealed that a. conserved Thr1372-Tyr1902 active site scaffold was required for efficient fC and caC formation, providing the first evidence that wild-type (WT) TET2 was specifically shaped to enable higher-order oxidation. lt. was further demonstrated that mutations along this core scaffold could reconfigure active site interactions to stall oxidation at hmC, providing opportunities to test the importance of hmC compared to fC and caC in biological and pathological systems.

The present invention includes mutant TET enzymes. In one embodiment, the mutant TET enzymes stall oxidation at hmC. By stalling oxidation, the TET mutants can introduce hmC at a specific site and/or sites in a genome. This could be useful, for example, in epigenome editing. Epigenome editing with TET mutants can be using in combination with other molecular biology or gene targeting tools such as CRISPR. TET mutants can also be used in conjunction with existing sequencing methods and/or novel epigenetic sequencing methods.

The mutant TET enzymes can be derived from a variety of species including but not limited to mouse, human, fungi, or Trypanosomes. In one embodiment, the mutant TET enzyme is derived from a human. In another embodiment, the mutant TET enzyme is derived from a mouse. The mutant TET enzymes can be derived from any TET family, including but not limited to TET1, TET2, and TET3. In one embodiment, the mutant TET enzyme is derived from human TET2. In another embodiment, the mutant TET enzyme is derived from human TET1. In certain embodiments, the mutant TET enzyme is derived from mouse TET1 or mouse TET2 or mouse TET3.

Certain aspects of the invention include a TET mutant wherein position 1372 of the enzyme (SEQ ID NOs: 21-22) has been mutated. In one embodiment, the threonine (T) residue at position 1372 is changed to a glutamine (Q) (T1372Q). In another embodiment, the threonine (T) residue at position 1372 is changed to an asparagine (N) (T1372N), In yet another embodiment, the Threonine (T) residue at position 1372 is changed to an aspartic acid (D) (T1372D), In still another embodiment, the threonine (T) residue at position 1372 is changed to a glutamic acid (E) (T1372E). In yet another embodiment, the TET mutant comprises the amino acid sequence of SEQ ID NO: 23. In still another embodiment, the TET mutant comprises the amino acid sequence of SEQ 1D NO: 24.

In certain embodiments, the TET mutant can contain an additional mutation of any one of SEQ ID NOs: 21-22 at position 1902. In one embodiment, the Tyrosine (Y) residue at position 1902 is changed to a Phenylalanine (F) residue.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1: APOBEC Hyper-Active Mutants

The materials and methods employed in the experiments of Example 1 are now described.

Sequences of Constructs: The human APOBEC3A (A3A) sequence (SEQ ID NO: 2) and the human APOBEC3B (A3B) (SEQ ID NO: 3) isoform sequences were used as the wildtype sequences. The catalytic mutants have a glutamic acid to alanine mutation at position 72 in the A3A sequence. A schematic of the different constructs created is shown in FIG. 1. The protein sequences for the different APOBEC constructs are shown below (SEQ ID NOs. 2-14). Silent mutations were introduced in the constructs to optimize for cloning. Nucleic acid sequences for the different APOBEC constructs are also shown below (SEQ ID NOs. 26-38).

```
MBP (SEQ ID NO: 1):
MKIEEGKLVI WINGDKGYNGLAEVGKKFEKDTGIKVTVEHPDKLEEKFPQVAATGD

GPDIIFWAHDRFGGYAQSGLLAEITPDKAFQDKLYPFTWDAVRYNGKLIAYPIAVEA

LSLIYNKDLLPNPPKTWEEIPALDKELKAKGKSALMFNLQEPYFTWPLIAADGGYAF

KYENGKYDIKDVGVDNAGAKAGLTFLVDLIKNKHMNADTDYSIAEAAFNKGETAM

TINGP WAWSNIDTSKVNYGVTVLPTFKGQPSKPFVGVLSAGINAASPNKELAKEFLE

NYLLTDEGLEAVNKDKPLGAVALKSYEEELAKDPRIAATMENAQKGEIMPNIPQMS

AF WYAVRTAVINAASGRQTVDEALKDAQTNSS SNNNNNNNNNNLGIEGR
```

Wild-type APOBEC3A (A3A): (GenBank Accession No: NP_663745)(SEQ ID NO: 2):
MEASPASGPRHLMDPHIFTSNFNNGIGRHKTYLCYEVERLDNGTSVKMDQHRGFLH

NQAKNLLCGFYGRHAELRFLDLVPSLQLDPAQIYRVTWFISWSPCFSWGCAGEVRAF

LQENTHVRLRIFAARIYDYDPLYKEALQMLRDAGAQVSIMTYDEFKHCWDTFVDHQ

GCPFQPWDGLDEHSQALSGRLRAILQNGN

Wild-type APOBEC3B (A3B): (GenBank ID: EAW60281.1)(SEQ ID NO: 3):
MNPQIRNPMERMYRDTFYDNFENEPILYGRSYTWLCYEVKIKRGRSNLLWDTGVFR

GQVYFEPQYHAEMCFLSWFCGNQLPAYKCFQITWFVSWTPCPDCVAKLAEFLSEHP

NVTLTISAARLYYYWERDYRRALCRLSQAGARVKIMDYEEFAYCWENFVYNEGQQ

FMPWYKFDENYAFLHRTLKEILRYLMDPDTFTFNFNNDPLVLRRRQTYLCYEVERL

DNGTWVLMDQHMGFLCNEAKNLLCGFYGRHAELRFLDLVPSLQLDPAQIYRVTWFI

SWSPCISWGCAGEVRAFLQENTHVRLRIFAARIYDYDPLYKEALQMIRDAGAQVSI

MTYDEFEYCWDTFVYRQGCPFQPWDGLEEHSQALSGRLRAILQNGN

A3Bn (SEQ ID NO: 4):
MNPQIRNPMERMYRDTFYDNFENEPILYGRSYTWLCYEVKIKRGRSNLLWDTGVFR

GQVYFEPQYHAEMCFLSWFCGNQLPAYKCFQITWFVSWTPCPDCVAKLAEFLSEHP

NVTLTISAARLYYYWERDYRRALCRLSQAGARVKIMDYEEFAYCWENFVYNEGQQ

FMPWYKFDENYAFLHRTLKEILRYL

A3Bc (SEQ ID NO: 5):
MDPDTFTFNFNNDPLVLRRRQTYLCYEVERLDNGTWVLMDQHMGFLCNEAKNLLC

GFYGRHAELRFLDLVPSLQLDPAQIYRVTWFISWSPCFSWGCAGEVRAFLQENTHVR

LRIFAARIYDYDPLYKEALQMLRDAGAQVSIMTYDEFEYCWDTFVYRQGCPFQPWD

GLEEHSQALSGRLRAILQNGN

A3Ac (SEQ ID NO: 6):
MDPHIFTSNFNNGIGRHKTYLCYEVERLDNGTSVKMDQHRGFLHNQAKNLLCGFYG

RHAELRFLDLVPSLQLDPAQIYRVTWFISWSPCFSWGCAGEVRAFLQENTHVRLRIF

AARIYDYDPLYKEALQMLRDAGAQVSIMTYDEFKHCWDTFVDHQGCPFQPWDGLD

EHSQALSGRLRAILQNGN

A3Bn-A3Ac (SEQ ID NO: 7):
MNPQIRNPMERMYRDTFYDNFENEPILYGRSYTWLCYEVKIKRGRSNLLWDTG

VFRGQVYFEPQYHAEMCFLSWFCGNQLPAYKCFQITWFVSWTPCPDCVAKLAE

FLSEHPNVTLTISAARLYYYWERDYRRALCRLSQAGARVKIMDYEEFAYCWEN

FVYNEGQQFMPWYKFDENYAFLHRTLKEILRYLMDPHIFTSNFNNGIGRHKTYLC

YEVERLDNGTSVKMDQHRGILHNQAKNLLCGFYGRHAELRFLDLVPSLQLDPAQIY

RVTWFISWSPCFSWGCAGEVRAFLQENTHVRLRIFAARIYDYDPLYKEALQMLRDA

GAQVSIMTYDEFKHCWDTFVDHQGCPFQPWDGLDEHSQALSGRLRAILQNGN

A3Bn-A3A (HYPER-A3B-1)(SEQ ID NO: 8):
MNPQIRNPMERMYRDTFYDNFENEPILYGRSYTWLCYEVKIKRGRSNLLWDTG

VFRGQVYFEPQYHAEMCFLSWFCGNQLPAYKCFQITWFVSWTPCPDCVAKLAE

FLSEHPNVTLTISAARLYYYWERDYRRALCRLSQAGARVKIMDYEEFAYCWEN

FVYNEGQQFMPWYKFDENYAFLHRTLKEILRYLMEASPASGPRHLMDPHIFTSNF

NNGIGRHKTYLCYEVERLDNGTSVKMDQHRGFLHNQAKNLLCGFYGRHAELRFLD

LVPSLQLDPAQIYRVTWFISWSPCFSWGCAGEVRAFLQENTHVRLRIFAARIYDYDPL

YKEALQMLRDAGAQVSIMTYDEFKHCWDTFVDHQGCPFQPWDGLDEHSQALSGRL

RAILQNQGN

A3Bc/A3Ac (SEQ ID NO: 9):
MDPDTFTFNFNNDPLVLRRRQTYLCYEVERLDNGTWVLMDQHMGFLCNEAKN

LLCGFYGRHAELRFLDLVPSLQLDPAQIYRVTWFISWSPCFSWGCAGEVRAFLQ

ENTHVRLRIFAARIYDYDPLYKEALQMLRDAGAQVSIMTYDEFKHCWDTFVDHQGC

PFQPWDGLDEHSQALSGRLRAILQNQGN

A3Ac/A3Bc (SEQ ID NO: 10):
MDPHIFTSNFNNGIGRHKTYLCYEVERLDNGTSVKMDQHRGFLHNQAKNLLCGFYG

RHAELRFLDLVPSLQLDPAQIYRVTWFISWSPCFSWGCAGEVRAFLQENTHVRLRIF

AARIYDYDPLYKEALQMLRDAGAQVSIMTYDEFEYCWDTFVYRQGCPFQPWD

GLEEHSQALSGRLRAILQNQGN

A3Bn-A3Ac/A3Bc (SEQ ID NO: 11):
MNPQIRNPMERMYRDTFYDNFENEPILYGRSYTWLCYEVKIKRGRSNLLWDTG

VFRGQVYFEPQYHAEMCFLSWFCGNQLPAYKCFQITWFVSWTPCPDCVAKLAE

FLSEHPNVTLTISAARLYYYWERDYRRALCRLSQAGARVKIMDYEEFAYCWEN

FVYNEGQQFMPWYKFDENYAFLHRTLKEILRYLMDPHIFTSNFNNGIGRHKTYLC

YEVERLDNGTSVKMDQHRGFLHNQAKNLLCGFYGRHAELRFLDLVPSLQLDPAQIY

RVTWFISWSPCFSWGCAGEVRAFLQENTHVRLRIFAARIYDYDPLYKEALQMLR

DAGAQVSIMTYDEFEYCWDTFVYRQGCPFQPWDGLEEHSQALSGRLRAILQNQ

GN

A3Bn-A3Bc/A3Ac (SEQ ID NO: 12):
MNPQIRNPMERMYRDTFYDNFENEPILYGRSYTWLCYEVKIKRGRSNLLWDTG

VFRGQVYFEPQYHAEMCFLSWFCGNQLPAYKCFQITWFVSWTPCPDCVAKLAE

FLSEHPNVTLTISAARLYYYWERDYRRALCRLSQAGARVKIMDYEEFAYCWEN

FVYNEGQQFMPWYKFDENYAFLHRTLKEILRYLMDPDTFTFNFNNDPLVLRRR

QTYLCYEVERLDNGTWVLMDQHMGFLCNEAKNLLCGFYGRHAELRFLDLVPS

LQLDPAQIYRVTWFISWSPCFSWGCAGEVRAFLQENTHVRLRIFAARIYDYDPLY

KEALQMLRDAGAQVSIMTYDEFKHCWDTFVDHQGCPFQPWDGLDEHSQALSGRLR

AILQNQGN

A3AE72A (SEQ ID NO: 13):
MEASPASGPRHLMDPHIFTSNFNNGIGRHKTYLCYEVERLDNGTSVKMDQHRGFLH

NQAKNLLCGFYGRHAALRFLDLVPSLQLDPAQIYRVTWFISWSPCFSWGCAGEVRA

FLQENTHVRLRIFAARIYDYDPLYKEALQMLRDAGAQVSIMTYDEFKHCWDTIVDH

QGCPFQPWDGLDEHSQALSGRLRAILQNQGN

A3Bn-A3AE72A (SEQ ID NO: 14):
MNPQIRNPMERMYRDTFYDNFENEPILYGRSYTWLCYEVKIKRGRSNLLWDTG

VFRGQVYFEPQYHAEMCFLSWFCGNQLPAYKCFQITWFVSWTPCPDCVAKLAE

FLSEHPNVTLTISAARLYYYWERDYRRALCRLSQAGARVKIMDYEEFAYCWEN

FVYNEGQQFMPWYKFDENYAFLHRTLKEILRYLMEASPASGPRHLMDPHIFTSNF

NNGIGRHKTYLCYEVERLDNGTSVKMDQHRGFLHNQAKNLLCGFYGRHAALRFLD

LVPSLQLDPAQIYRVTWFISWSPCFSWGCAGEVRAFLQENTHVRLRIFAARIYDYDPL

YKEALQMLRDAGAQVSIMTYDEFKHCWDTFVDHQGCPFQPWDGLDEHSQALSGRL

RAILQNQGN

MBP (SEQ ID NO: 25):

-continued

```
atgaaaatcgaagaaggtaaactggtaatctggattaacggcgataaaggctataacggtctcgctgaagtcggtaagaaattcgaga
aagataccggaattaaagtcaccgttgagcatccggataaactggaagagaaattcccacaggttgcggcaactggcgatggccctg
acattatcttctgggcacacgaccgctttggtggctacgctcaatctggcctgttggctgaaatcaccccggacaaagcgttccaggac
aagctgtatccgtttacctgggatgccgtacgttacaacggcaagctgattgcttacccgatcgctgttgaagcgttatcgctgatttataa
caaagatctgctgccgaacccgccaaaaacctgggaagagatcccggcgctggataaagaactgaaagcgaaggtaagagcgc
gctgatgttcaacctgcaagaaccgtacttcacctggccgctgattgctgctgacggggggttatgcgttcaagtatgaaaacggcaagt
acgacattaaagacgtgggcgtggataacgctggcgcgaaagcgggtctgaccttcctggttgacctgattaaaaacaaacacatgaa
tgcagacaccgattactccatcgcagaagctgcctttaataaaggcgaaacagcgatgaccatcaacggcccgtgggcatggtccaa
catcgacaccagcaaagtgaattatggtgtaacggtactgccgaccttcaagggtcaaccatccaaaccgttcgttggcgtgctgagc
gcaggtattaacgccgccagtccgaacaaagagctggcaaaagagttcctcgaaaactatctgctgactgatgaaggtctggaagcg
gttaataaagacaaaccgctgggtgccgtagcgctgaagtcttacgaggaagagttggcgaaagatccacgtattgccgccactatgg
aaaacgcccagaaaggtgaaatcatgccgaacatcccgcagatgtccgctttctggtatgccgtgcgtactgcggtgatcaacgccgc
cagcggtcgtcagactgtcgatgaagccctgaaagacgcgcagactaattcgagctcgaacaacaacaacaataacaataacaacaa
cctcgggatcgagggaagg
```

Wild-type APOBEC3A (A3A): (GenBank Accession No: NP_663745)(SEQ ID NO: 26):
```
atggaagccagcccagcatccgggcccagacacttgatggatccacacatattcacttccaactttaacaatggcattggaaggcataa
gacctacctgtgctacgaagtggagcgcctggacaatggcacctcggtcaagatggaccagcacaggggctttctacacaaccagg
ctaagaatcttctctgtggcttttacggccgccatgcggagctgcgcttcttggacctggttccttctttgcagttggacccggcccagatc
tacagggtcacttggttcatctcctggagcccctgcttctcctggggctgtgccggggaagtgcgtgcgttccttcaggagaacacaca
cgtgagactgcgtatcttcgctgcccgcatctatgattacgaccccctatataaggaggcactgcaaatgctgcgggatgctggggccc
aagtctccatcatgacctacgatgaatttaagcactgctgggacaccttttgtggaccaccagggatgtcccttccagccctgggatgga
ctagatgagcacagccaagccctgagtgggaggctgcgggccattctccagaatcagggaaac
```

Wild-type APOBEC3B (A3B): (GenBank ID: EAW60281.1)(SEQ ID NO: 27):
```
atgaatccacagattcgtaaccccatggagcgcatgtatcgcgacacctttttacgataaactttgagaacgaaccgattttatatggccgca
gctatacttggctgtgttacgaagtgaagatcaaacgcggccgcagcaatttactgtgggatactggagtgtttcgtgggcaggtgtattt
cgaaccccagtaccacgcggaaatgtgtttcttgtcttggttttgcggcaaccaacttcctgcatacaaatgtttccagattacctggtttgt
ttcctggactccgtgcccggactgtgtggcgaaactggccgaattttttgtccgaacaccccaacgtgacgcttacgatcagtgccgcgc
gcctgtattattattgggaacgtgactatcgccgtgccctctgccgcctcagccaggcgggcgcacgtgttaagattatggattatgaag
aattcgcatactgtttgggaaaacttcgtgtacaatgaagggcaacaatttatgccctggtataaattcgatgaaaattatgcttttctgcatc
gcactttgaaggaaatcttgcgctatctgatggacccagatacgtttacgttcaattttaataacgatccgttggttctgcgacgtcgccag
acctacctgtgttatgaagtggaacgcttggacaacggtacgtgggtgctgatgaccaacatatgggatttctgtgcaatgaagcgaa
gaatctgctttgtggcttctacgccgccatgcagaactgcgttttttggatttggtcccgtcattgcaattggatccgcccagatctatc
gcgtgacttggttcatttcctggagtccgtgttttagctggggctgcgccggcgaggtgcgtgccttcctgcaagaaaacactcatgttc
gccttcgcatctttgcggctcgtatttacgattatgacccgttgtataaagaggccttacagatgcttcgcgatgccggcgcacaggtaag
tatcatgacgtacgatgaatttgaatattgctgggacacgtttgtctatcgtcaagggtgtcctttccagccatgggacggcttggaagaa
cactcacaggccctgagcggccgtctgcgtgcaattctgcagaaccagggaaat
```

A3Bn (SEQ ID NO: 28):
```
atgaatccacagattcgtaaccccatggagcgcatgtatcgcgacacctttttacgataaactttgagaacgaaccgattttatatggccgca
gctatacttggctgtgttacgaagtgaagatcaaacgcggccgcagcaatttactgtgggatactggagtgtttcgtgggcaggtgtattt
cgaaccccagtaccacgcggaaatgtgtttcttgtcttggttttgcggcaaccaacttcctgcatacaaatgtttccagattacctggtttgt
ttcctggactccgtgcccggactgtgtggcgaaactggccgaattttttgtccgaacaccccaacgtgacgcttacgatcagtgccgcgc
gcctgtattattattgggaacgtgactatcgccgtgccctctgccgcctcagccaggcgggcgcacgtgttaagattatggattatgaag
```

-continued aattcgcatactgttgggaaaacttcgtgtacaatgaagggcaacaatttatgccctggtataaattcgatgaaaattatgcttttctgcatc gcactttgaaggaaatcttgcgctatctg A3Bc (SEQ ID NO: 29):
atggacccagatacgtttacgttcaattttaataacgatccgttggttctgcgacgtcgccagacctacctgtgttatgaagtggaacgctt ggacaacggtacgtgggtgctgatggaccaacatatgggattctgtgcaatgaagcgaagaatctgctttgtggcttctacggccgcc atgcagaactgcgttttttggatttggtcccgtcattgcaattggatccggcccagatctatcgcgtgacttggttcatttcctggagtccgt gttttagctggggctgcgccggcgaggtgcgtgccttcctgcaagaaaacactcatgttcgccttcgcatctttgcggctcgtatttacga ttatgacccgttgtataaagaggccttacagatgcttcgcgatgccggcgcacaggtaagtatcatgacgtacgatgaatttgaatattgc tgggacacgtttgtctatcgtcaagggtgtccttccagccatgggacggcttggaagaacactcacaggccctgagcggccgtctgc gtgcaattctgcagaaccagggaaat A3Ac (SEQ ID NO: 30):
atggatccacacatattcacttccaactttaacaatggcattggaaggcataagacctacctgtgctacgaagtggagcgcctggacaat ggcacctcggtcaagatggaccagcacaggggctttctacacaaccaggctaagaatcttctctgtggcttttacggccgccatgcgg agctgcgcttcttggacctggttccttctttgcagttggacccggcccagatctacagggtcacttggttcatctcctggagcccctgcttc tcctggggctgtgccggggaagtgcgtgcgttccttcaggagaacacacacgtgagactgcgtatcttcgctgcccgcatctatgatta cgaccccctatataaggaggcactgcaaatgctgcgggatgctggggcccaagtctccatcatgacctacgatgaatttaagcactgct gggacacctttgtggaccaccagggatgtcccttccagccctgggatggactagatgagcacagccaagccctgagtgggaggctg cgggccattctccagaatcagggaaac A3Bn-A3Ac (SEQ ID NO: 31):
atgaatccacagattcgtaaccccatggagcgcatgtatcgcgacacctttacgataactttgagaacgaaccgattttatatggccgca gctatacttggctgtgttacgaagtgaagatcaaacgcggccgcagcaatttactgtgggatactggagtgtttcgtgggcaggtgtattt cgaaccccagtaccacgcggaaatgtgtttcttgtcttggttttgcggcaaccaacttcctgcatacaaatgtttccagattacctggtttgt ttcctggactccgtgcccgactgtgtggcgaaactggccgaattttttgtccgaacaccccaacgtgacgcttacgatcagtgccgcgc gcctgtattattattgggaacgtgactatcgccgtgccctctgccgcctcagccaggcgggcgcacgtgttaagattatggattatgaag aattcgcatactgttgggaaaacttcgtgtacaatgaagggcaacaatttatgccctggtataaattcgatgaaaattatgcttttctgcatc gcactttgaaggaaatcttgcgctatctgatggatccacacatattcacttccaactttaacaatggcattggaaggcataagacctacct gtgctacgaagtggagcgcctggacaatggcacctcggtcaagatggaccagcacaggggctttctacacaaccaggctaagaatct tctctgtggcttttacggccgccatgcggagctgcgcttcttggacctggttccttctttgcagttggacccggcccagatctacagggtc acttggttcatctcctggagcccctgcttctcctggggctgtgccggggaagtgcgtgcgttccttcaggagaacacacacgtgagact gcgtatcttcgctgcccgcatctatgattacgaccccctatataaggaggcactgcaaatgctgcgggatgctggggcccaagtctcca tcatgacctacgatgaatttaagcactgctgggacacctttgtggaccaccagggatgtcccttccagccctgggatggactagatgag cacagccaagccctgagtgggaggctgcgggccattctccagaatcagggaaac A3Bn-A3A (HYPER-A3B-1)(SEQ ID NO: 32):
atgaatccacagattcgtaaccccatggagcgcatgtatcgcgacacctttacgataactttgagaacgaaccgattttatatggccgca gctatacttggctgtgttacgaagtgaagatcaaacgcggccgcagcaatttactgtgggatactggagtgtttcgtgggcaggtgtattt cgaaccccagtaccacgcggaaatgtgtttcttgtcttggttttgcggcaaccaacttcctgcatacaaatgtttccagattacctggtttgt ttcctggactccgtgcccgactgtgtggcgaaactggccgaattttttgtccgaacaccccaacgtgacgcttacgatcagtgccgcgc gcctgtattattattgggaacgtgactatcgccgtgccctctgccgcctcagccaggcgggcgcacgtgttaagattatggattatgaag aattcgcatactgttgggaaaacttcgtgtacaatgaagggcaacaatttatgccctggtataaattcgatgaaaattatgcttttctgcatc gcactttgaaggaaatcttgcgctatctgatggaagccagcccagcatccgggcccagacttgatggatccacacatattcacttcc aactttaacaatggcattggaaggcataagacctacctgtgctacgaagtggagcgcctggacaatggcacctcggtcaagatggacc agcacaggggctttctacacaaccaggctaagaatcttctctgtggcttttacggccgccatgcggagctgcgcttcttggacctggttc cttctttgcagttggacccggcccagatctacagggtcacttggttcatctcctggagcccctgcttctcctggggctgtgccggggaag -continued tgcgtgcgttccttcaggagaacacacacgtgagactgcgtatcttcgctgcccgcatctatgattacgaccccctatataaggaggca ctgcaaatgctgcgggatgctggggcccaagtctccatcatgacctacgatgaatttaagcactgctgggacacctttgtggaccacca gggatgtcccttccagccctgggatggactagatgagcacagccaagccctgagtgggaggctgcgggccattctccagaatcagg gaaac A3Bc/A3Ac (SEQ ID NO: 33):
atggacccagatacgtttacgttcaattttaataacgatccgttggttctgcgacgtcgccagacctacctgtgttatgaagtggaacgctt ggacaacggtacgtgggtgctgatggaccaacatatgggatttctgtgcaatgaagcgaagaatctgctttgtggcttctacggccgcc atgcagaactgcgtttttggatttggtcccgtcattgcaattgatccggcccagatctatcgcgtgacttggttcatttcctggagtccgt gttttagctggggctgcgccggcgaggtgcgtgcgttccttcaggagaacacacacgtgagactgcgtatcttcgctgcccgcatctat gattacgaccccctatataaggaggcactgcaaatgctgcgggatgctggggcccaagtctccatcatgacctacgatgaatttaagca ctgctgggacacctttgtggaccaccagggatgtcccttccagccctgggatggactagatgagcacagccaagccctgagtgggag gctgcgggccattctccagaatcagggaaac A3Ac/A3Bc (SEQ ID NO: 34):
atggatccacacatattcacttccaactttaacaatggcattggaaggcataagacctacctgtgctacgaagtggagcgcctggacaat ggcacctcggtcaagatggaccagcacaggggctttctacacaaccaggctaagaatcttctctgtggcttttacggccgccatgcgg agctgcgcttcttggacctggttccttctttgcagttggacccggcccagatctacagggtcacttggttcatctcctggagcccctgcttc tcctgggctgtgccggggaagtgcgtgccttcctgcaagaaaacactcatgttcgccttcgcatctttgcggctcgtatttacgattatg acccgttgtataaagaggccttacagatgcttcgcgatgccggcgcacaggtaagtatcatgacgtacgatgaatttgaatattgctggg acacgtttgtctatcgtcaaggggtgtcctttccagccatgggacggcttggaagaacactcacaggccctgagcggccgtctgcgtgc aattctgcagaaccagggaaat A3Bn-A3Ac/A3Bc (SEQ ID NO: 35):
atgaatccacagattcgtaaccccatggagcgcatgtatcgcgacaccttttacgataactttgagaacgaaccgattttatatggccgca gctatacttggctgtgttacgaagtgaagatcaaacgcggccgcagcaatttactgtgggatactggagtgtttcgtgggcaggtgtattt cgaaccccagtaccacgcggaaatgtgtttcttgtcttggttttgcggcaaccaacttcctgcatacaaatgtttccagattacctggtttgt ttcctggactccgtgcccggactgtgtggcgaaactggccgaattttgtccgaacaccccaacgtgacgcttacgatcagtgccgcgc gcctgtattattattgggaacgtgactatcgccgtgccctctgccgcctcagccaggcgggcgcacgtgttaagattatggattatgaag aattcgcatactgttgggaaaacttcgtgtacaatgaagggcaacaatttatgccctggtataaattcgatgaaaattatgcttttctgcatc gcactttgaaggaaatcttgcgctatctgatggatccacacatattcacttccaactttaacaatggcattggaaggcataagacctacct gtgctacgaagtggagcgcctggacaatggcacctcggtcaagatggaccagcacaggggctttctacacaaccaggctaagaatct tctctgtggcttttacggccgccatgcggagctgcgcttcttggacctggttccttctttgcagttggacccggcccagatctacagggtc acttggttcatctcctggagcccctgcttctcctgggctgtgccggggaagtgcgtgccttcctgcaagaaaacactcatgttcgccttc gcatctttgcggctcgtatttacgattatgacccgttgtataaagaggccttacagatgcttcgcgatgccggcgcacaggtaagtatcat gacgtacgatgaatttgaatattgctgggacacgtttgtctatcgtcaaggggtgtcctttccagccatgggacggcttggaagaacactc acaggccctgagcggccgtctgcgtgcaattctgcagaaccagggaaat A3Bn-A3Bc/A3Ac (SEQ ID NO: 36):
atgaatccacagattcgtaaccccatggagcgcatgtatcgcgacaccttttacgataactttgagaacgaaccgattttatatggccgca gctatacttggctgtgttacgaagtgaagatcaaacgcggccgcagcaatttactgtgggatactggagtgtttcgtgggcaggtgtattt cgaaccccagtaccacgcggaaatgtgtttcttgtcttggttttgcggcaaccaacttcctgcatacaaatgtttccagattacctggtttgt ttcctggactccgtgcccggactgtgtggcgaaactggccgaattttgtccgaacaccccaacgtgacgcttacgatcagtgccgcgc gcctgtattattattgggaacgtgactatcgccgtgccctctgccgcctcagccaggcgggcgcacgtgttaagattatggattatgaag aattcgcatactgttgggaaaacttcgtgtacaatgaagggcaacaatttatgccctggtataaattcgatgaaaattatgcttttctgcatc gcactttgaaggaaatcttgcgctatctgatggacccagatacgtttacgttcaattttaataacgatccgttggttctgcgacgtcgccag -continued acctacctgtgttatgaagtggaacgcttggacaacggtacgtgggtgctgatggaccaacatatgggatttctgtgcaatgaagcgaa gaatctgctttgtggcttctacggccgccatgcagaactgcgtttttggatttggtcccgtcattgcaattggatccggcccagatctatc gcgtgacttggttcatttcctggagtccgtgttttagctggggctgcgccggcgaggtgcgtgcgttccttcaggagaacacacacgtg agactgcgtatcttcgctgcccgcatctatgattacgaccccctatataaggaggcactgcaaatgctgcgggatgctggggcccaagt ctccatcatgacctacgatgaatttaagcactgctgggacacctttgtggaccaccagggatgtcccttccagccctgggatggactag atgagcacagccaagcctgagtgggaggctgcgggccattctccagaatcagggaaac A3AE72A (SEQ ID NO: 37):
atggaagccagcccagcatccgggcccagacacttgatggatccacacatattcacttccaactttaacaatggcattggaaggcataa gacctacctgtgctacgaagtggagcgcctggacaatggcacctcggtcaagatggaccagcacaggggctttctacacaaccagg ctaagaatcttctctgtggcttttacggccgccatgcggcgctgcgcttcttggacctggttccttctttgcagttggacccggcccagatc tacagggtcacttggttcatctcctggagccctgcttctcctggggctgtgccggggaagtgcgtgcgttccttcaggagaacacaca cgtgagactgcgtatcttcgctgcccgcatctatgattacgaccccctatataaggaggcactgcaaatgctgcgggatgctggggccc aagtctccatcatgacctacgatgaatttaagcactgctgggacacctttgtggaccaccagggatgtcccttccagccctgggatgga ctagatgagcacagccaagcctgagtgggaggctgcgggccattctccagaatcagggaaac A3Bn-A3AE72A (SEQ ID NO: 38):
atgaatccacagattcgtaacccatggagcgcatgtatcgcgacacctttttacgataactttgagaacgaaccgattttatatggccgca gctatacttggctgtgttacgaagtgaagatcaaacgcggccgcagcaatttactgtgggatactggagtgtttcgtgggcaggtgtattt cgaaccccagtaccacgcggaaatgtgtttcttgtcttggttttgcggcaaccaacttcctgcatacaaatgtttccagattacctggtttgt ttcctggactccgtgcccggactgtgtggcgaaactggccgaattttttgtccgaacaccccaacgtgacgcttacgatcagtgccgcgc gcctgtattattattgggaacgtgactatcgccgtgccctctgccgcctcagccaggcgggcgcacgtgttaagattatggattatgaag aattcgcatactgttgggaaaacttcgtgtacaatgaagggcaacaatttatgccctggtataaattcgatgaaaattatgcttttctgcatc gcactttgaaggaaatcttgcgctatctgatggaagccagcccagcatccgggcccagacacttgatggatccacacatattcacttcc aactttaacaatggcattggaaggcataagacctacctgtgctacgaagtggagcgcctggacaatggcacctcggtcaagatggacc agcacaggggctttctacacaaccaggctaagaatcttctctgtggcttttacggccgccatgcggcgctgcgcttcttggacctggttc cttctttgcagttggacccggcccagatctacagggtcacttggttcatctcctggagccctgcttctcctggggctgtgccggggaag tgcgtgcgttccttcaggagaacacacacgtgagactgcgtatcttcgctgcccgcatctatgattacgaccccctatataaggaggca ctgcaaatgctgcgggatgctggggcccaagtctccatcatgacctacgatgaatttaagcactgctgggacacctttgtggaccacca gggatgtcccttccagccctgggatggactagatgagcacagccaagcctgagtgggaggctgcgggccattctccagaatcagg gaaac Cloning: A3B, A3Bn, A3Bc, A3A, and A3AM13 were cloned into the pET41 vector with a Kanamycin resistance marker. Transcription of pET41 was under the control of a T7 RNA polymerase promoter. All constructs were cloned in between a N-terminal MBP tag and a C-terminal His tag with a TEV-cleavable linker (MBP-tev-protein-tev-His). Maltose Binding Protein (MBP) is a 42.5 kD protein (SEQ ID NO: 1) that increases the solubility and aids in folding AID/APOBEC proteins (Nabel et al, *Nat Chem Bio* Vol 8, September 2012). The His tag consisted of eight repeated histidines (8×H), added for purification of the protein of interest. The TEV-cleavable linker (ENLYFQ) can be cleaved with the addition of the Tobacco etch virus (TEV) protease, thus removing both tags from the construct.

A3Bn-A3AM13, A3Bc/A3Ac, A3Ac/A3Bc, and A3Bn-A3Ac/A3Bc were cloned using overlap extension into the pET41 vector, maintaining the MBP tag, His tag, and Tev-linker. The pET41 vector was prepared for classical ligation by digesting with both SalI (New England Biolabs) and KpnI (New EnglandBiolabs) restriction enzymes at 37° C. This reaction was then run on an agarose gel and appropriate bands were purified using a ThermoFisher Scientific or Zymo Research gel purification kit. Ligations were performed with T4 DNA Ligase (New England Biolabs), using an overnight ligation protocol that cycles between 30° C. and 10° C. in 30 second intervals.

Protein Purification: Protein constructs cloned into pET41 vectors were expressed in BL21(DE3) *E. coli* cells containing a plasmid encoding trigger factor (TF) protein to aid with folding. The cells were then grown up in liquid media (LB Broth, Miller) and induced when at 0.4 to 0.6 OD with 1 mM Isopropyl P-thiogalactopyranoside (IPTG, Sigma). They were then allowed to express protein overnight, shaking at 16° C. The cells were then pelleted and lysed. Smaller preps (less than 50 mL) were lysed with the BugBuster Master Mix without protease inhibitors (Novagen). Larger preps were lysed by sonication. HisPur Cobalt Resin was washed and re-suspended in wash buffer (50 mM Tris, pH 7.5; 150 mM NaCl; 10% Glycerol; 25 mM imidazole). The soluble fraction of the lysed cells mutated in the Cobalt resin for 1-2 hours at 4° C. Resin was washed twice with wash buffer and the protein of interest was then eluted with elution buffer (50 mM Tris, pH 7.5; 150 mM NaCl; 10% Glycerol; 425 mM imidazole). The elution fractions were analyzed on an 8% SDS-PAGE denaturing gel and the elutions that had the purified protein of interest were pooled. The protein was then dialyzed overnight at 4° C. into storage buffer (50 mM Tris, pH 7.5; 50 mM NaCl, 10% Glycerol; 0.5 mM DTT, 0.05% Tween-20).

Concentrations of the proteins were determined by conducting a Bradford Protein Assay using Protein Assay Dye Reagent Concentrate (Bio-Rad).

UDG Activity Assay: The activities of the protein constructs were determined using a Uracil DNA glycosylase (UDG) based assay. UDG is an enzyme that cleaves the glycosidic bond between a uracil base and its deoxyribose sugar. For this assay, two 35-base, FAM-labeled substrates were synthesized with either a single cytosine or single uracil (5'-TGAGGAATGAAGTTGATTCAAATGTGAT-GAGGTGA-3') (SEQ ID NO: 49). The substrate was synthesized to place the C (or U) in the preferred sequence context for A3A (5'-TCA-3'). The purified MBP and His tagged protein constructs were allowed to react with 1 µM of the cytosine substrate in reaction buffer (20 mM Tris, pH 7; 1% Tween-20) at 37° C.

Then, 5 U of UDG was added to the reaction and incubated for 30 minutes at 37° C. The reactions were then treated with base (NaOH). If the cytosine in the DNA substrate was deaminated to a uracil, the addition of NaOH will allow for the cleavage of the DNA strand at abasic site resulting from UDG treatment. The reactions were then run on an DNA-PAGE gel and the fluorescent substrates were imaged using a Typhoon scanner. The bands were then quantified and analyzed using the NIH ImageJ software.

SwaI Activity Assay: The activities of protein constructs on 5-methylcytosines (5mC) was determined using a SwaI restriction enzyme based assay as described in Shutsky et al., (Nucleic Acids Res 2017 gkx345. doi: 10. I093/nar/gkx345).

Library Construction: The plasmid library was created using sequential polymerase chain reactions (PCR) with oligos ordered from Integrated DNA Technologies that have mixed bases strategically incorporated to encode for either the A3A or A3B C-terminal domain (CTD) sequence. To access two amino acid point mutations that were inaccessible by a single mixed base and the insert/deletion, four different pools of the library were created separately. Each pool of the library was ligated into pET41 between an MBP tagged A3Bn and a C-terminal His tag using classical ligation. The ligations were then transformed into electrocompetent NEB Turbo Cells. A fraction of the culture was plated on LB Agar (Invitrogen) with Kanamycin resistance to measure electroporation efficiency. The remainder was diluted into LB Broth (Miller) with Kanamycin resistance and grown overnight at 37° C. The culture was then miniprepped (Qiagen). The individually miniprepped plasmid pools were then pooled together in a 1:1:1:1 ratio. Concentrations of plasmids and PCR products were measured using a Qubit 3.0 Fluorometer (ThermoFisher Scientific).

In vitro protein expression: 1 µg of plasmids expressing Hyper-A3B (SEQ ID NO: 8), A3A (SEQ ID NO: 2), and catalytically inactive Hyper-A3B (SEQ ID NO: 14) were incubated with the NEB PureExpress In Vitro Protein Synthesis Kit as per manufacturer's protocols. After the synthesis reaction, 5 µL of each reaction was run on an SDS-PAGE gel and stained with Coomassie dye. Visible bands were present at the correct size for each protein. After small-scale amylose purification, partially-purified samples were tested for activity using a UDG activity assay as described herein.

The results of the experiments from Example 1 are now described.

1.1 Biochemical Characterization of APOBECs

The biochemical properties that differentiate A3A from A3B were characterized herein. Due to their catalytic similarities, it was hypothesized that the difference in potency between A3A and A3B involves different levels of affinity to their substrate. A potential explanation for this difference was hypothesized to be A3B's N-terminal domain (NTD) and thus, the first set of experiments investigated the role of A3B's NTD in deaminase activity using both a qualitative bacterial screen and more quantitative activity assays.

Previously, an expression system and E. coli cell line expressing A3A and other AID/APOBECs revealed a correlation between activity of the cytosine deaminase and toxicity to the bacteria. Therefore, the phenotypic differences of the E. coli after they have been transformed with plasmids encoding for different cytosine deaminase constructs can be used as a qualitative screen for activity. This screen takes advantage of the basal, "leaky" expression of T7 RNA polymerase (RNAP) in bacterial cell lines, such as BL21(DE3) TF cells, that encode for the T7 RNAP. To utilize this qualitative screen, constructs were cloned into the pET41 vector, a plasmid that places the gene's transcription under the control of a T7 RNAP promoter. Upon transforming those plasmids into BL21(DE3) TF cells, the pre-induction expression of the T7 RNAP led to the basal transcription and translation of the protein constructs. These copies have been shown to access the E. coli genome, causing cytosine to thymine mutations that are toxic to the E. coli bacteria, causing smaller colonies to grow on LB agar plates.

Figure 2A:
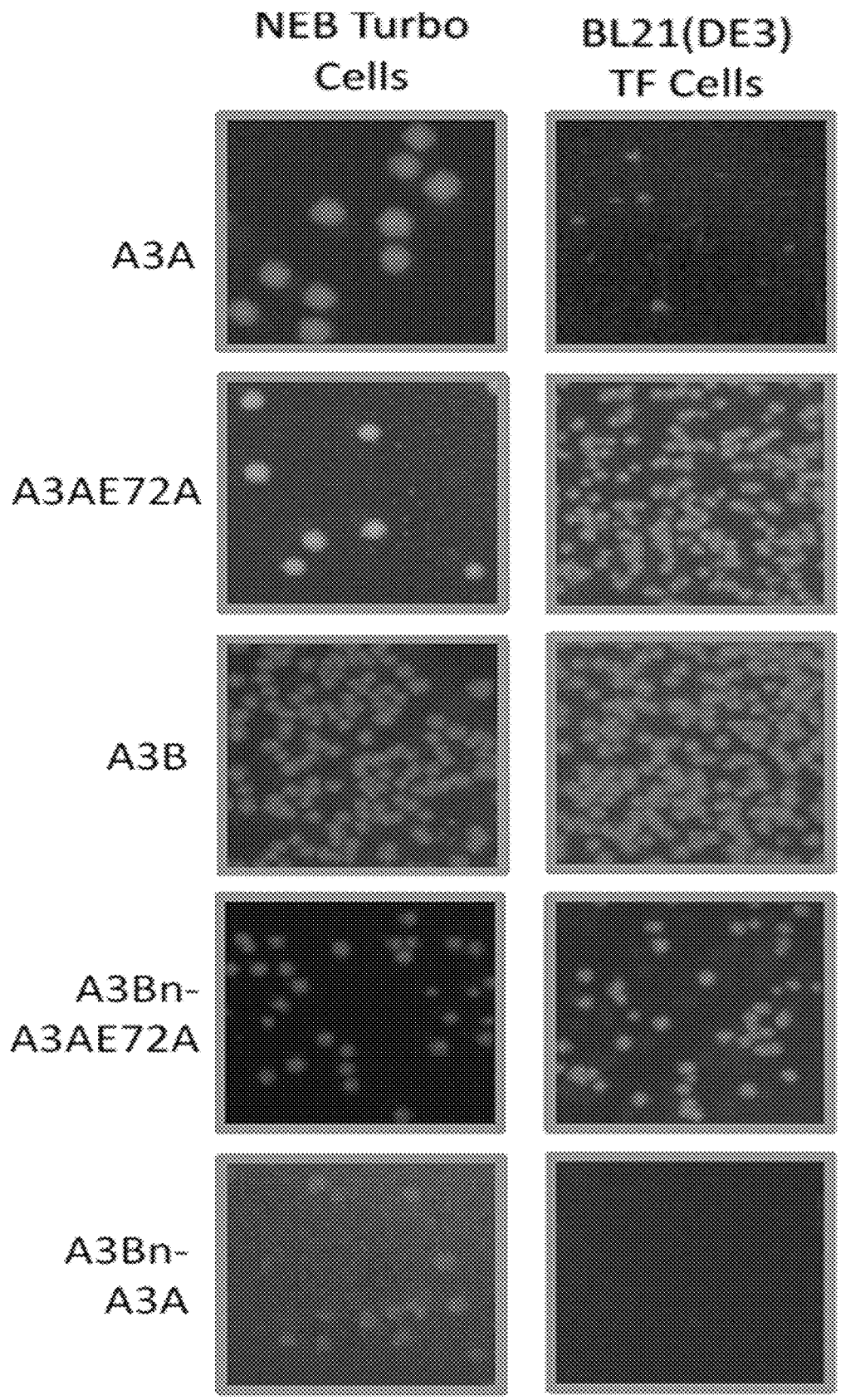
FIG. 2A illustrates APOBEC constructs subcloned into pET41 vectors were transformed in NEB Turbo $E.\ coli$ and BL21(DE3) TF $E.\ coli$ and grown on Kanamycin or Kanamycin/Chloroamphenicol LB Agar plates, respectively, overnight 37° C.

The relative activities of A3A, A3AE72A, A3B, A3Bn-A3A, and A3Bn-A3AE72A were assessed using this screen. FIG. 2A shows a side-by-side comparison of these constructs transformed in a cloning cell line (NEB Turbo E. coli) versus the BL21(DE3) TF expression cell line. The NEB Turbo E. coli were used because they don't encode for the T7 RNAP necessary to transcribe the constructs. Thus, they act as a control that should have homogeneous-sized colonies. This phenotypic readout was compared to the same constructs transformed into BL21(DE3) TF E. coli.

The sizes of the colonies were compared between the two different cell lines transformed with the same construct (FIG. 2A). When all of the constructs tested were transformed into NEB Turbo cells, homogenous, medium-sized colonies grew (FIG. 2A first column). This control indicated that the plasmid encoding for the construct was successfully internalized by the bacteria, but that there was no leaky expression of the protein that could be causing toxicity. Those results were then compared to the observed phenotypes of the same constructs in the BL21(DE3) TF cells. BL21(DE3) TF cells transformed with A3A were much smaller than those in the NEB Turbo cells, indicating high levels of deaminase activity. The catalytic mutants, A3AE72A, A3Bn-A3AE72A, and A3B, had medium, homogeneous-sized colonies for BL21(DE3) cells. This phenotype suggests that these three constructs either have no deaminase activity or that the activity of the low amount of protein expressed pre-induction was not high enough to be toxic to the E. coli. Lastly, when A3Bn-A3A was transformed into BL21(DE3) TF cells the bacteria do not grow at all, indicating that A3Bn-A3A was extremely active.

Figure 2B:
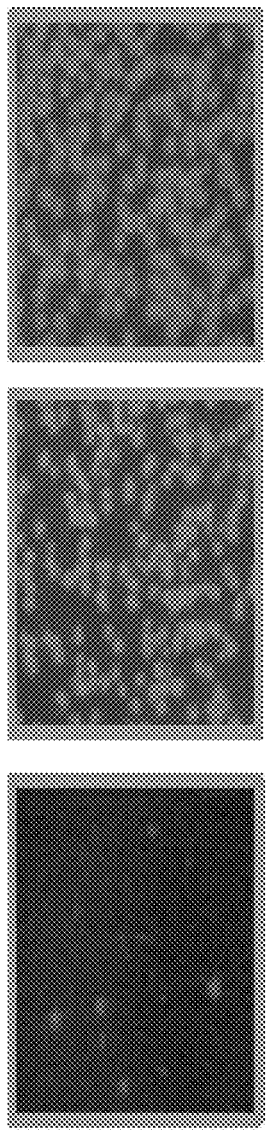
FIGS. 2B-2D illustrate APOBEC constructs in pET41 vectors were transformed into BL21(DE3) TF $E.\ coli$ and grown overnight on Kanamycin/Chloramphenicol LB Agar plates overnight at 37° C.

The observed differences in toxicity—especially between A3B, A3A, and A3Bn-A3A—prompted questioning of the importance of A3B's domains in deaminase activity, as the NTD was previously predicted to be responsible for decreasing deaminase activity. To isolate the levels of toxicity of A3B's domains, constructs that encoded A3Bn and A3Bc were also transformed into BL21(DE3) TF cells (FIG. 2B). Comparing the colony sizes between the BL21(DE3) TF cells transformed with all of these constructs allowed comparison of the levels of toxicity to the BL21(DE3) TF cells. The comparative toxicity then allowed for a qualitative comparison of deaminase activity. Specifically examining the constructs shown in FIG. 2B, A3Bn-A3A was the most toxic with no colony growth, followed by A3A with its small colonies. A3Bn and A3Bc both had colony sizes comparable to A3B, A3AE72A, and A3Bn-A3AE72A, which suggested that these two constructs were not as toxic as A3Bn-A3A or A3A and thus either had no activity or activity similar to that of A3B.

Figure 2C:
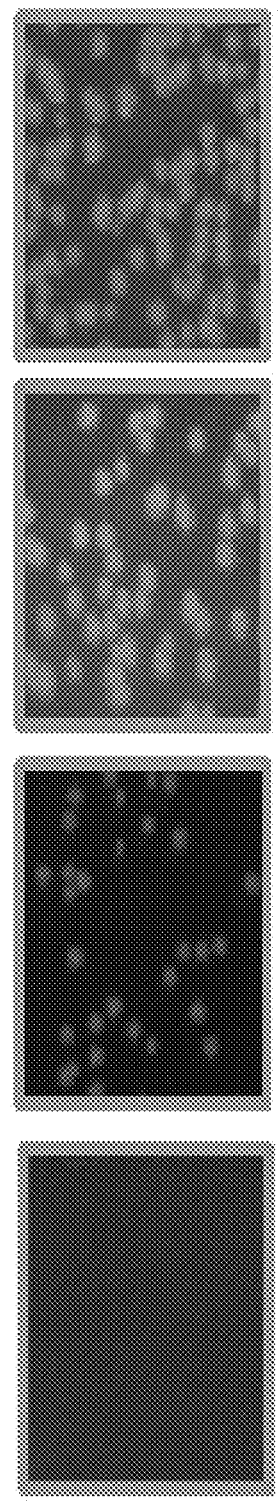

These observations further led to the examination of why A3A was much more toxic than A3Bc, given their high sequence identity. In order to probe this question, two "half constructs" of the catalytic domains of A3A and A3B were cloned, A3Bc/A3Ac and A3Ac/A3Bc. Since A3B's NTD seemed to be enhancing deaminase activity, the difference in catalytic activity between A3A and A3B were hypothesized to be a result of the differences in the catalytic domains of A3B and A3A. These differences were clustered mainly on either ends of the catalytic domain, with the middle region, containing all the important catalytic residues, largely conserved. Thus, the two catalytic half constructs tested the effect on deaminase activity of either the first cluster of differences or the last cluster of differences. Transforming the two catalytic half constructs into BL21(DE3) TF cells, however, didn't reveal a difference in phenotype between each other (FIG. 2C). Thus, no conclusions could be drawn about the difference in activity between the two catalytic half-constructs. Although, both yielded colonies similar in size to A3B and A3Bc, predicting levels of deaminase activity on the same order as both proteins.

Figure 3A:
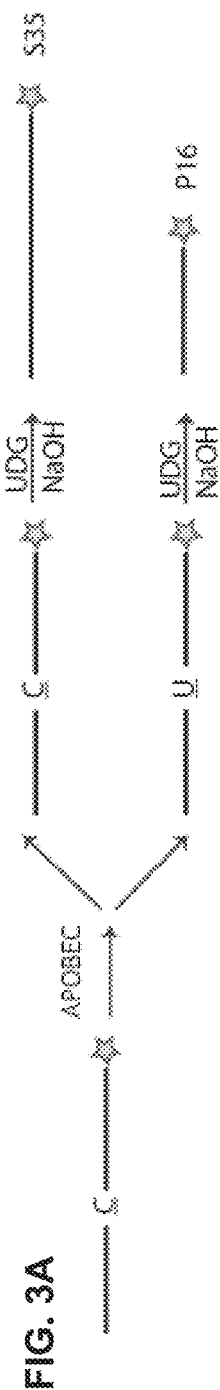
FIG. 3A is a schematic of a Uracil DNA Glycosylase (UDG)-based assay.
Figure 3B:
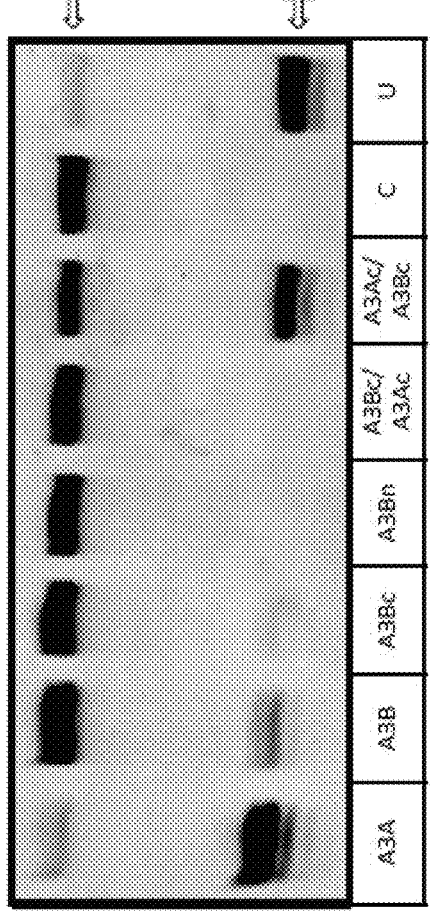
FIG. 3B depicts results from a UDG assay wherein 400 nM of protein was used and the reactions were incubated for 3.5 hours at 37° C.

While this E. coli screen allowed for an assessment of relative activity based on the observed toxicity of the constructs to the bacteria, it was neither quantitative nor a direct test of deaminase activity. Thus, to more quantitatively determine the deaminase activity of these constructs, the constructs that did grow in the BL21(DE3) TF expression cell lines were expressed and purified. A Uracil DNA Glycosylase (UDG)-based assay was then conducted with these constructs on a single-stranded DNA substrate with a single cytosine in the middle (FIG. 3A). After treatment with UDG and alkali conditions, if the cytosine was deaminated by the construct, the DNA strand would be cleaved, allowing for size separation of substrate versus product by gel electrophoresis. Thus, an untreated cytosine substrate runs higher than an untreated uracil substrate, which would be the size of the product band for treated substrates if there was deaminase activity (FIG. 3B, lanes 7 and 8). Examining the ratio of the product to substrate bands allows for a determination of the amount of activity of each construct when compared to the uracil control substrate (FIG. 3B, lane 8). The UDG assay was conducted by treating the substrate with two different enzyme concentrations for the same amount of time. Lower enzyme concentrations were used in the experiment illustrated in FIG. 3B compared to the experiment illustrated in FIG. 3C for all constructs, except A3A in which 400 nM of protein was used in both experiments.

Figure 3C:
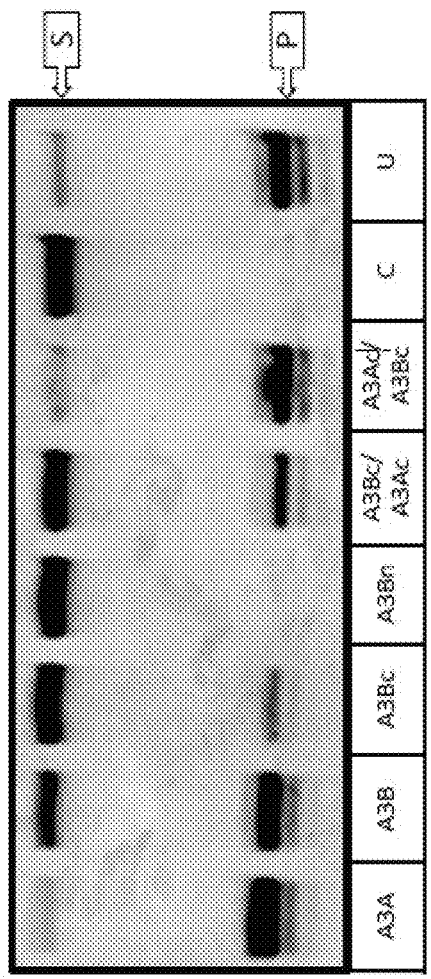
FIG. 3C depicts results from a UDG assay wherein 400 nM of A3A was used and 5 µM of the rest of the constructs were used. The reactions were incubated for 3.5 hrs. C and U substrates, untreated with protein, were used as size controls for the substrate and product, respectively.
Figure 5A:
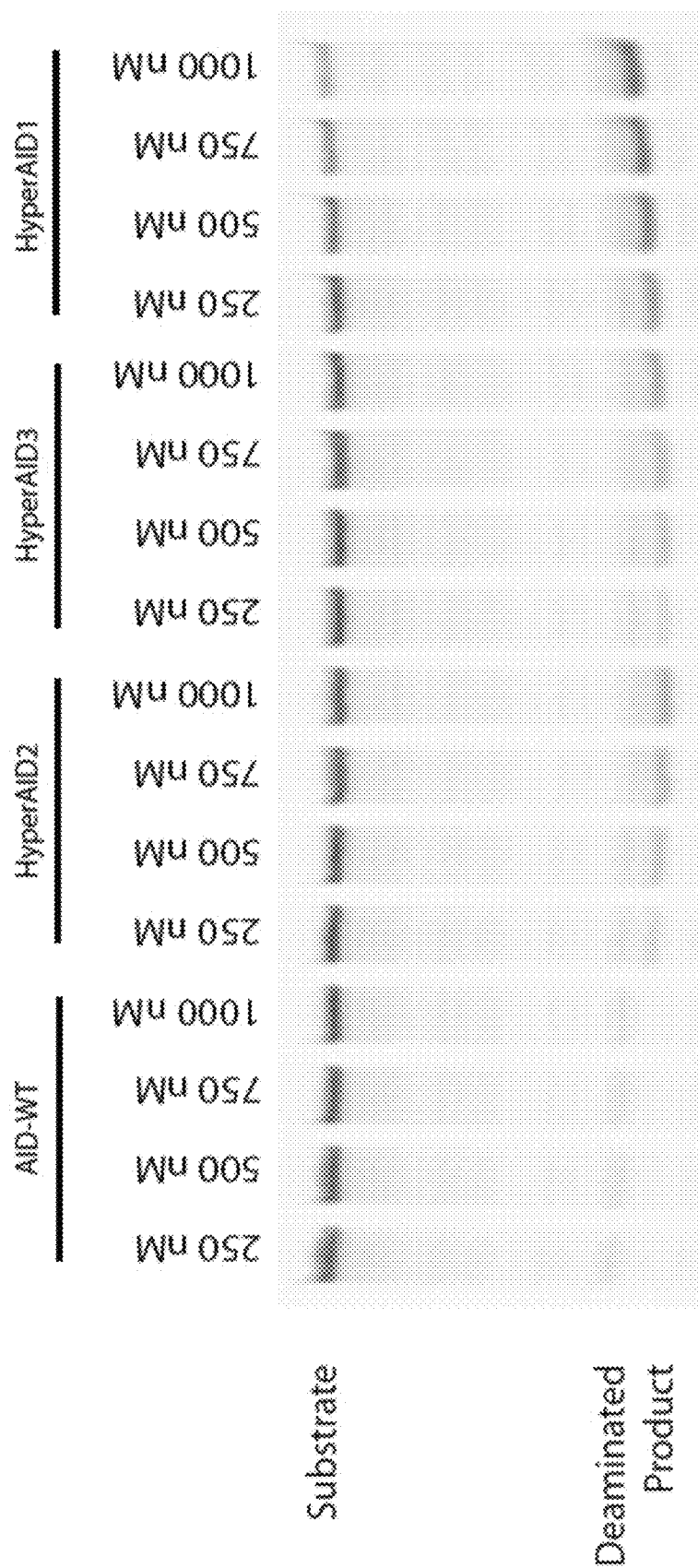
FIGS. 5A-5B are a set of images illustrating activity of hyperactive AIDs.
Figure 5B:
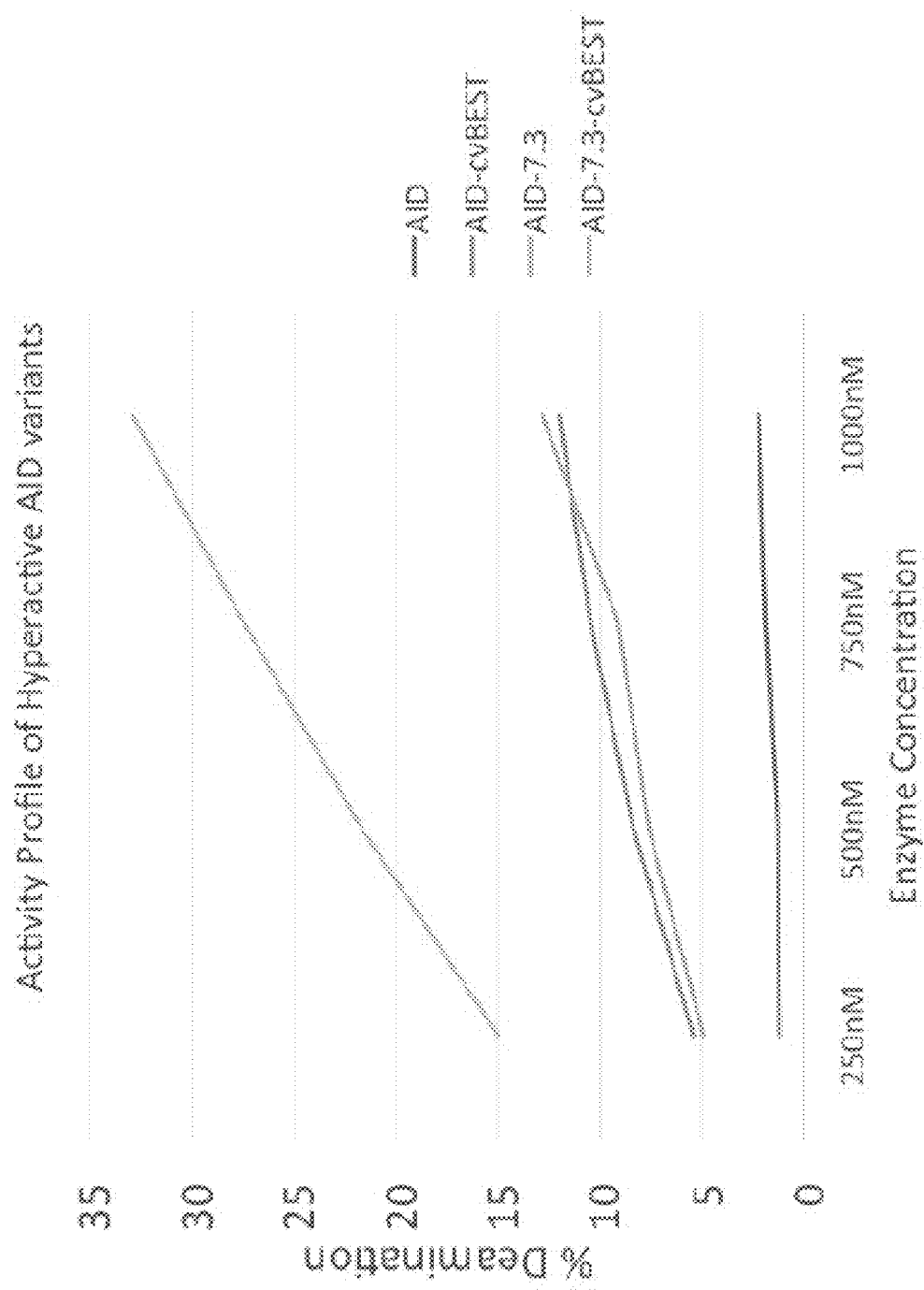

Judging by the sizable product band in comparison to the U control, A3A converted almost all of the substrate to product (FIGS. 3B-3C, lane 1). A3B also showed deaminase activity due to the product band present in both low and high enzyme concentration conditions (FIGS. 3B-3C, lane 2). To definitively observe A3Bc's activity, larger enzyme concentrations were necessary. This is evidenced by the only slightly detectable product band at low enzyme conditions (FIG. 3B, lane 3) and the much darker product band at higher enzyme concentrations (FIG. 3C, lane 3). Predictably, no product band was detectable for the A3Bn-treated substrate at either low or high enzyme concentrations, confirming its lack of deaminase activity (FIGS. 3B-3C, lane 4). Interestingly, no product band was detectable for the A3Bc/A3Ac treated substrate at low enzyme concentrations, but was visible for high enzyme concentrations at levels comparable to, if not more than, A3Bc (FIG. 3C, lane 5). A3Ac/A3Bc did show visible product bands at both low and high concentrations (FIGS. 3B-3C, lane 6). However, comparing the substrate:product band ratio at the higher enzyme concentration condition with that of the U control suggests that A3Ac/A3Bc was able to fully convert substrate to product (FIG. 3C, lane 6).

Analyzing these gels not only confirms the level of deaminase activity seen in the E. coli screen, but also allows for a more careful comparison between deaminase potency between the different constructs. As seen in the E. coli screen, A3A is the most active of all the colony-forming constructs. This is followed by A3Ac/A3Bc, which is more active than A3B, A3Bc, and A3Bc/A3Ac as evidenced by its more than 50% conversion of substrate to product in FIG. 3B, lane 6 and FIG. 4 and almost 100% conversion in FIG. 3C, lane 6. While, the activity of A3Ac/A3Bc was indiscernible from that of many other constructs through the E. coli screen, the A3Bn-A3Ac/A3Bc construct, much like A3Bn-A3A, grew no colonies, suggesting that A3Ac/A3Bc was much more active than A3Bc/A3Ac. A3B was the next most active, followed by both A3Bc/A3A and A3Bc. Attempting to compare A3Bc/A3A and A3Bc activity with these two gels and without repeated experiments was difficult because A3Bc shows about 10% conversion of substrate at lower enzyme conditions whereas A3Bc/A3Ac had 0% conversion; however, at higher enzyme conditions, A3Bc/A3Ac showed 48% conversion of substrate to product, while A3Bc had about 39% conversion of substrate to product. From these data, however, it was clear that A3Bn does not have any direct deaminase, catalytic activity.

Figure 2D:
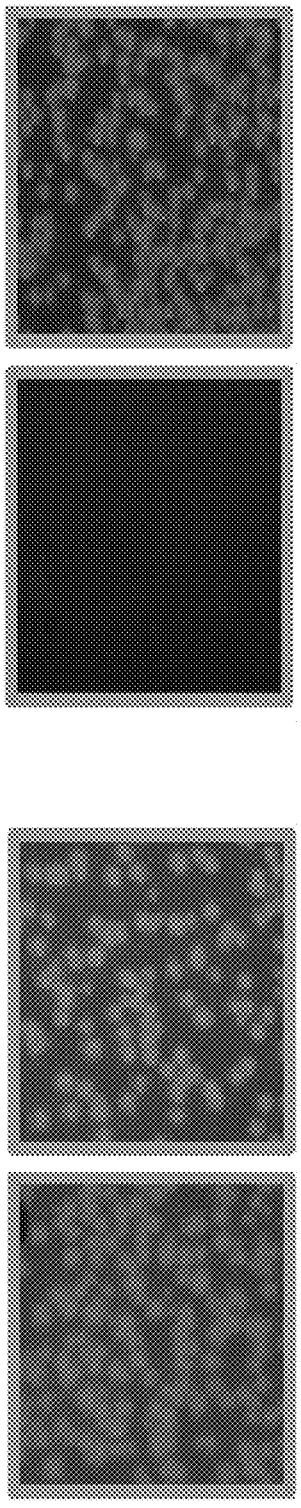

While the UDG activity assay characterization and comparison in deaminase potency was useful to understand the activities of the constructs, intrigue still surrounded the biochemical characteristics of A3Bn-A3A due to its toxicity to expression cell line E. coli. This led to further investigations of the NTD's role in enhancing catalytic activity, which involved fusing the two catalytic half constructs to the C-terminal end of A3Bn. Transforming these two half constructs into BL21(DE3) TF led to observable differences in phenotypes in the E. coli screen. The cells transformed with A3Bn-A3Ac/A3Bc did not grow, whereas A3Bn-A3Bc/A3Ac cells did grow with colony sizes comparable to the other "half constructs" and A3B (FIG. 2D). This result wasn't entirely surprising given the UDG activity assay data, which showed A3Ac/A3Bc was more active than A3Bc/A3Ac; however, it was surprising that the addition of the NTD rendered A3Ac/A3Bc toxic to the E. coli. This observation of toxicity is more closely explored in experiments described in Example 3.

Figure 6A:
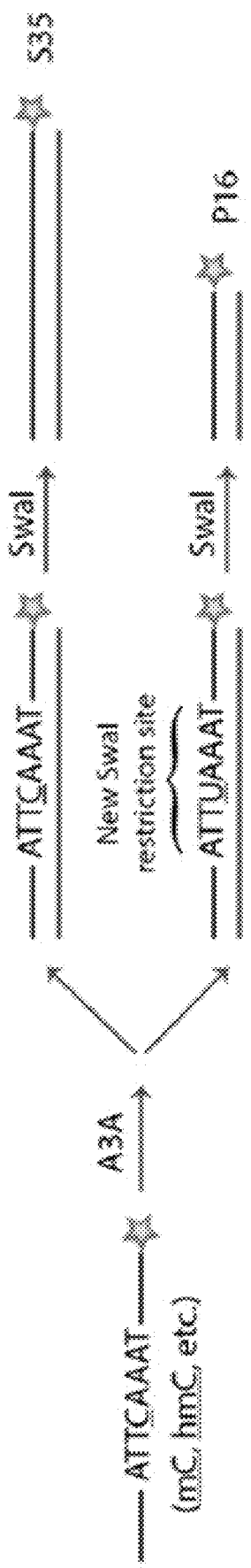
FIGS. 6A-6B are a set of images illustrating activity of APOBEC constructs on 5mC.
Figure 6B:
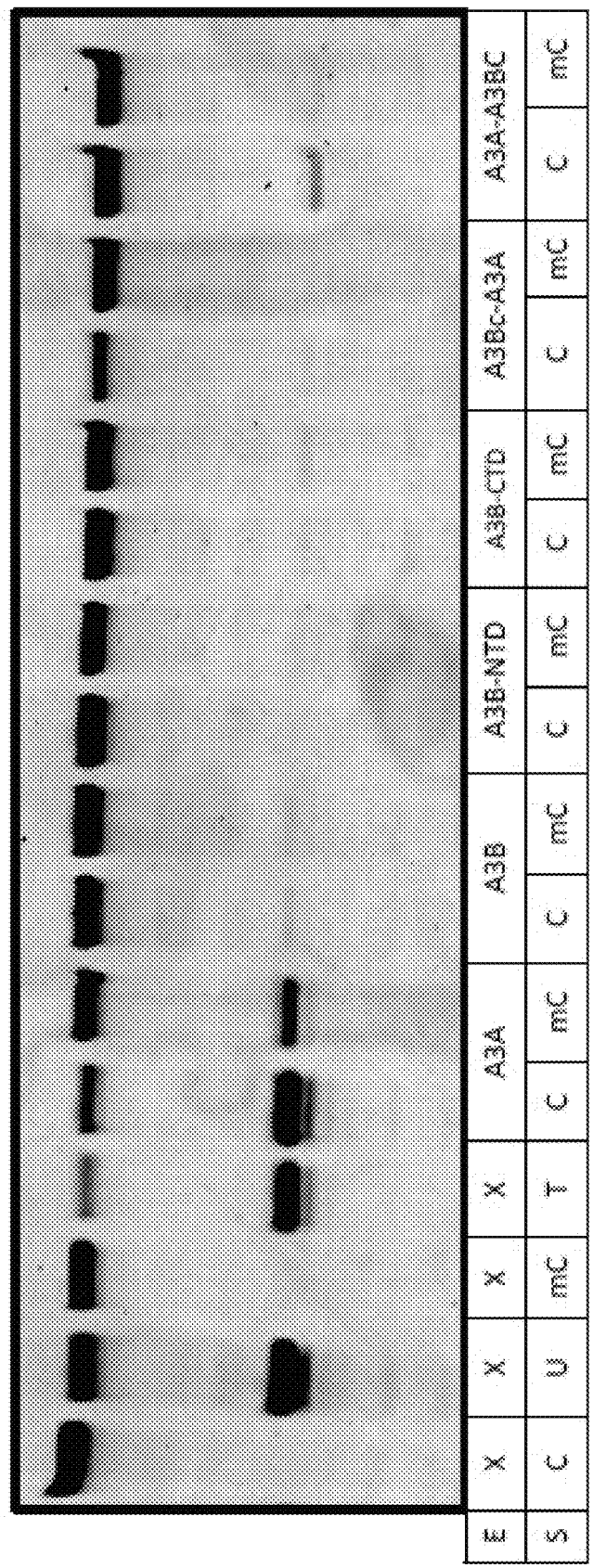

The last biochemical characterization of A3B attempted to assess its activity on 5-methylcytosines (5mCs). The regulation of 5mC on genomic DNA is of interest because 5mC is an important epigenetic marker that represses transcription of certain genes. APOBECs has been implicated in demethylation pathway by potentially deaminating 5mC to thymine, leading to T-G mismatches that would activate the base excision repair (BER) pathway, replacing the T with unmethylated cytosine. Previous studies with mouse APOBEC1, APOBEC2, APOBEC3, and AID had shown that biochemically, this is highly unlikely (Nabel et al., *Nat. Chem. Biol.*, 2012); however, studies have shown that A3A and A3B do have some activity on 5mC (Fu, *Biochem. J.*, 2015). Thus, to examine the deaminase activity of our constructs and confirm previous findings, the SwaI activity assay for modified cytosine deamination was conducted with A3A, A3B, A3Bn, A3Bc, A3Bc-A3Ac, and A3Ac-A3Bc. This assay utilizes a restriction site created upon deamination of C to U or 5mC to T that can then be cleaved with SwaI restriction endonuclease (FIG. 6A). The reactions were run on a DNA-PAGE gel to separate uncleaved substrate from cleaved product bands, analogous to the readout from the UDG assay previously described herein (FIG. 6B). However, the results were hard to interpret due to the inefficient activity SwaI on substrate as indicated by the U and T controls (FIG. 6B, lanes 2 and 4). Despite this, the gel confirmed that A3A activity on mC was lower than its activity on C (FIG. 6B, lanes 5 and 6).

1.2 Expression of A3Bn-A3A (HYPER-A3B-1)

From the *E. coli* screen, the A3Bn-A3A fusion construct was shown to be highly toxic to bacterial cells (FIG. 2A), necessitating an alternative expression system and cell line in order to express and purify it for further biochemical characterization. The expression system used previously placed the A3Bn-A3A gene in a pET41 plasmid that places the transcriptional control under a T7 bacteriophage RNA polymerase (RNAP) promoter. Thus, the production of the protein encoded in a pET41 plasmid should only occur if T7 RNAP is produced within E. coll. In BL21(DE3) cells, the cell lines used in FIGS. 2A-2D, RNAP production is under the control of the lac promoter and is induced upon addition of isopropyl b-D-1-thiogalactopyranoside (IPTG). While transcription of pET41 is only theoretically initiated upon induction with IPTG, some copies of A3Bn-A3A were likely translated before induction, due to "leaky" expression of T7 RNAP, thus leading to cell death and no colonies.

Figure 7:
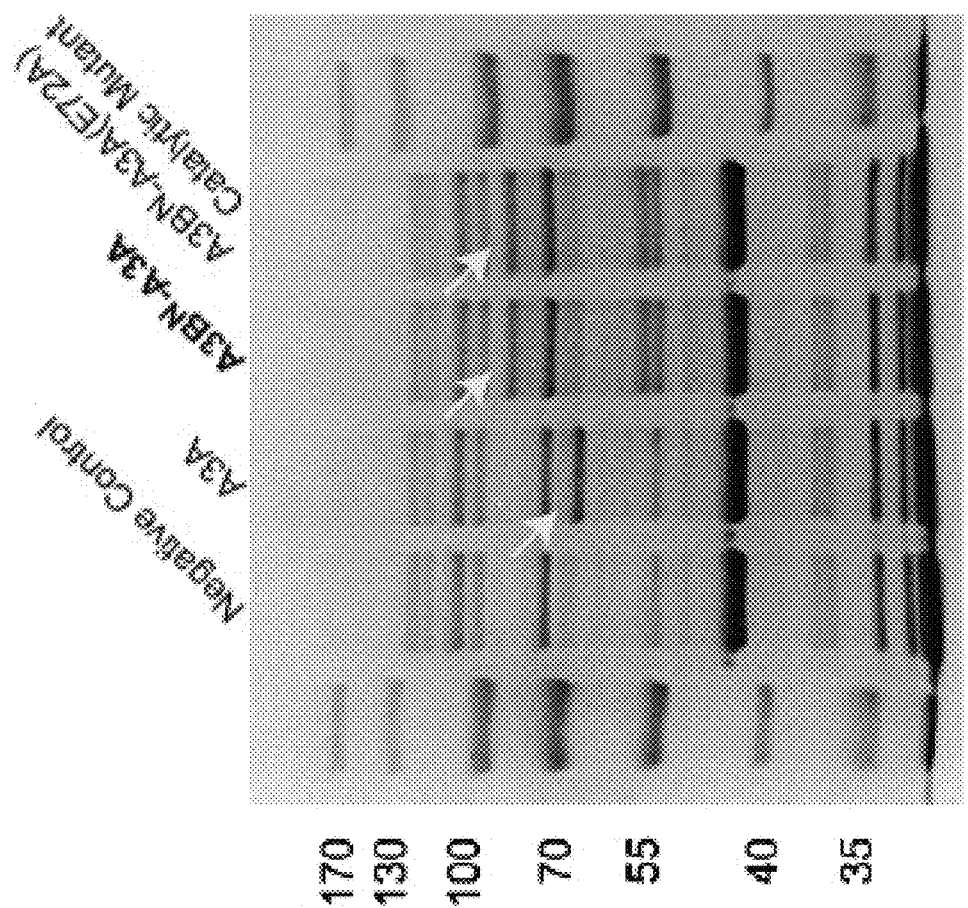
FIG. 7 is an image illustrating in vitro protein synthesis of HYPER-A3B-1: A3A, HYPER-A3B-1, and a catalytically inactive mutant of HYPER-A3B-1. Bands at the appropriate sizes of these proteins were visualized on an SDS-PAGE gel stained with Coomassie dye (denoted by yellow arrows).
Figure 8:
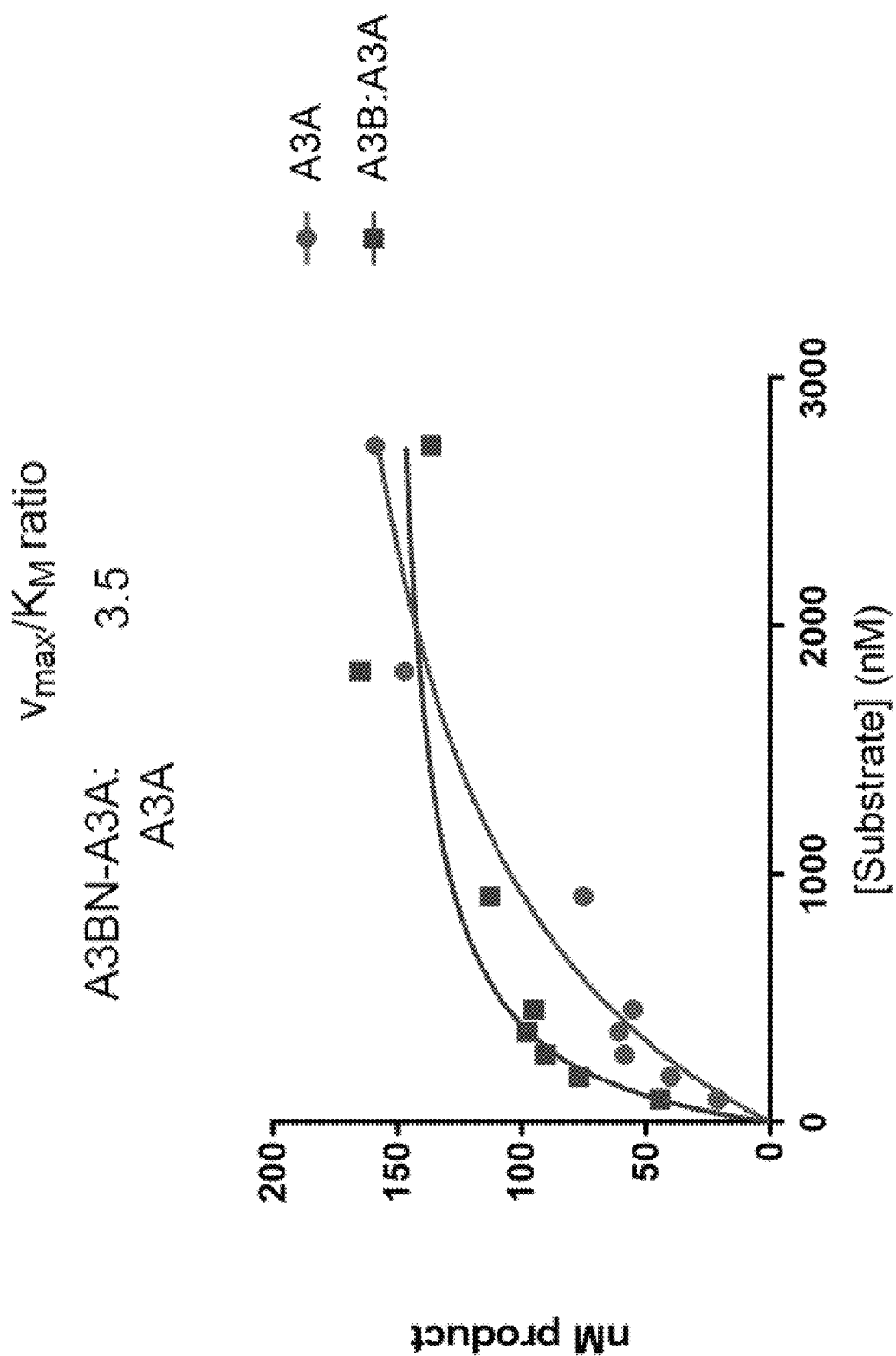
FIG. 8 is a plot illustrating activity of HYPER-A3B-1: Partially-purified A3A (red) and HYPER-A3B-1 (blue) were utilized in the UDG activity assay described herein. Substrate concentration was varied up to 2750 nM and initial reaction rates were measured based on the amount of product formed as quantified on DNA PAGE gels. The vmax/KM ratio is shown above the graph.

After attempting the use of multiple different bacterial expression systems to little avail (as the toxicity of the construct still prevented adequate growth of bacteria), a cell-free expression system was pursued. Expressing HYPER-A3B-1 using the NEB PureExpress In Vitro Protein Synthesis Kit yielded discernible protein levels via Coomassie stain (FIG. 7). Utilizing the MBP tag at the N terminus, small scale purification over amylose resin was used to partially purify HYPER-A3B-1 away from other components of the in vitro transcription/translation reaction mix. A UDG activity assay was then performed with the partially-purified A3A and HYPER-A3B-1 proteins in which the substrate concentration was titrated and the initial rates of reaction were measured (FIG. 8). This assay confirmed that HYPER-A3B-1 has high activity (in this preliminary assay, on par with A3A in terms of maximal velocity). This observation supported the prior hypothesis that the high activity and therefore toxicity of HYPER-A3B-1 prevented its expression in traditional bacterial systems. In comparing the activity curves of A3A and HYPER-A3B-1, a small shift in KM value was observed, calculated as the substrate concentration where the enzyme has half maximal velocity. HYPER-A3B-1 exhibited a ~5-fold lower KM value, which suggested that HYPER-A3B-1 could bind substrate more tightly or possibly exhibit processivity, either of which could cause the increase in toxicity seen in the bacterial assays.

1.3 Library Construction

Differences in the catalytic domains between A3B and A3A were explored more specifically. A3A and A3B's catalytic domains differ by 15 amino acid residues and one insert in A3B, which is absent in A3A. The half constructs created and tested revealed that the residues in the first half of A3A's catalytic domain are likely responsible for the increased activity of A3A over A3B; however, there is no clear residue or set of residues that could account for the difference in activity between A3A and A3Bc or even A3Ac/A3Bc and A3Bc (FIGS. 3A-3C). Thus, it was hypothesized that the difference in activity between A3 A and A3B is not due to a single residue, but due to a combination of residues that collectively enhance the deaminase ability of the protein. Furthermore, the N-terminal domain has been shown to enhance deaminase activity, while not being catalytically active.

To explore the combinations of residues that could account for the differences in activity between the two proteins and further investigate the role of A3B's NTD, a strategy was devised that would allow for the creation of $2^{16}$ (or 65,536) constructs that permute between the differences in the two proteins. These permutations were accessed by ordering oligos that incorporated a 1:1 mixture of two bases at certain positions that would lead to the codon that encodes either the A3A or A3B amino acid at that position. To access all of the differences across the catalytic domain, five different oligos were ordered from Integrated DNA Technologies that had overlapping regions. Through a series of polymerase chain reactions (PCRs), these oligos were annealed together and extended. Incorporation of a mixed population of bases at the desired positions was verified qualitatively through Sanger sequencing after each round of annealing.

All but two amino acid differences were accessed through incorporating mixed bases. This complication led to the necessity for four pools of oligos that were synthesized separately, accounting for the four permutations that could occur with those two inaccessible amino acids. Thus, each of those pools had a population of $2^{13}$ (or 8,192) different constructs. These four pools were then split in half and an oligo either encoding for the insert in A3B or the A3A sequence at that position was incorporated by PCR.

Thus, in total, 8 pools of oligos were synthesized that were either 585 or 594 bases long depending on whether or not it had the A3B insert, respectively. The same process was repeated for the catalytically inactive mutant, as a control for future experiment.

The eight pools are now being ligated, through classical ligation, into a pET41 vector that already encodes for the N-terminal MBP tag, the NTD of A3B, and the C-terminal His tag. After an overnight cycling ligation that would ligate the oligos to the C-terminus end of A3B's NTD and before the His Tag, the library of plasmids is electroporated into *E. coli*. In order to get efficient transformation of all 2" different plasmids, Turbo Electrocompetent *E. coli* (New England-BioLabs) were used. A portion of the electroporated cells are plated to assess library size and the rest are grown up overnight. The plasmids from the overnight culture are then extracted and should, at this point, account for an eight of the library. These can then be pooled in an equivalent ratio to account for the entire library.

Example 2: AID Hyperactive Mutants

The materials and methods employed in the experiments of Example 2 are now described.

Hyperactive AID mutant proteins were generated herein (SEQ ID NOs. 16-20). Nucleic acid sequences of the AID mutants are also disclosed herein (SEQ ID NOs. 40-44).

Wild Type AID (Genbank Accession No. NP_065712)(SEQ ID NO: 15):
MDSLLMNRRKFLYQFKNVRWAKGRRETYLCYVVKRRDSATSFSLDFGYLRNKNGC

HVELLFLRYISDWDLDPGRCYRVTWFTSWSPCYDCARHVADFLRGNPNLSLRIFTAR

LYFCEDRKAEPEGLRRLHRAGVQIAIMTFKDYFYCWNTFVENHERTFKAWEGLHEN

SVRLSRQLRRILLPLYEVDDLRDAFRTLGL*

HyperAID-1 (AID-7.3-cvBEST-1-181)(SEQ ID NO: 16):
MDSLLMNRREFLYQFKNVRWAKGRRETYLCYVVKRRDSATSFSLDFGYLRNKNGC

HVELLFLRYISDWDLDPGRCYRVTWFISWSPCYDCARHVADFLRGNPNLSLRIFTAR

LYFCEAGRREPEGLRRLHRAGVQIAIMTFKDYFYCWNTFVENHGRTFKAWEGLHEN

SVRLSRQLRRILL*
Mutations compared to wild-type AID: K10E, T82I, D118A, R119G, K120R, A121R, E156G, P182*

HyperAID-2 (AID-7.3-cvBEST)(SEQ ID NO: 17):
MDSLLMNRREFLYPFKNVRWAKGRRETYLCYVVKRRDSATSFSLDFGYLRNKNGC

HVELLFLRYISDWDLDPGRCYRVTWFISWSPCYDCARHVADFLRGNPNLSLRIFTAR

LYFCEAGRREPEGLRRLHRAGVQIAIMTFKDYFYCWNTFVENHGRTFKAWEGLHEN

SVRLSRQLRRILLPLYEVDDLRDAFRTLGL*
Mutations: K10E, T82I, D118A, R119G, K120R, A121R, E156G HyperAID-3 (AID-cvBEST)(SEQ ID NO: 18):
MDSLLMNRRKFLYPFKNVRWAKGRRETYLCYVVKRRDSATSFSLDFGYLRNKNGC

HVELLFLRYISDWDLDPGRCYRVTWFTSWSPCYDCARHVADFLRGNPNLSLRIFTAR

LYFCEAGRREPEGLRRLHRAGVQIAIMTFKDYFYCWNTFVENHERTFKAWEGLHEN

SVRLSRQLRRILL*
Mutations: D118A, R119G, K120R, A121R, P182*

HyperAID-4 (AID-7.3-R119G-1-181)(SEQ ID NO: 19):
MDSLLMNRREFLYQFKNVRWAKGRRETYLCYVVKRRDSATSFSLDFGYLRNKNGC

HVELLFLRYISDWDLDPGRCYRVTWFISWSPCYDCARHVADFLRGNPNLSLRIFTAR

LYFCEDGKAEPEGLRRLHRAGVQIAIMTFKDYFYCWNTFVENHGRTFKAWEGLHEN

SVRLSRQLRRILL*
Mutations: K10E, T82I, R119G, E156G, P182*

HyperAID-5 (AID-7.3-cvBEST-CS-1-181) aka AID123* (SEQ ID NO: 20)
MDSLLMNRREFLYQFKNVRWAKGRRETYLCYVVKRRDSATSESLDFGYLRNKNGC

HVELLFLRYISDWDLDPGRCYRVTWFISWSPCYDCARHVADFLRGNPNLSLRIFTAR

LYFCEAGRREPEGLRRLAEAGVQIAIMTYKDYEYCWNTFVENHGRTFKAWEGLHEN

SVRLSRQLRRILLPLYEVDDLRDAFRTLGL*
Mutations: K10E, F42E, T82I, D118A, R119G, K120R, A121R, H130A, R131E, F141Y, F145E, E156G Wild Type AID (Genbank Accession No. NP_065712)(SEQ ID NO: 39):
atggatagcctgctgatgaaccgtcgtaaatttctgtatcagtttaaaaacgtgcgttgggcgaaaggccgtcgt gaaacctatctgtgctatgtggtgaaacgtcgtgatagcgcgaccagctttagcctggattttggctatctgcgt aacaaaaacggctgccatgtggaactgctgtttctgcgttatattagcgattgggatctggatccgggccgttgc tatcgtgtgacctggtttaccagctggagcccgtgctatgattgcgcgcgtcatgtggcggattttctgcgtggc aacccgaacctgagcctgcgtatttttaccgcgcgtctgtattttgcgaagatcgtaaagcggaaccggaaggc ctgcgtcgtctgcatcgtgcgggcgtgcagattgcgattatgacctttaaagattatttttattgctggaacacc tttgtggaaaaccatgaacgtacctttaaagcgtgggaaggcctgcatgaaaacagcgtgcgtctgagccgtcag ctgcgtcgtattctgctgccgctgtatgaagtggatgatctgcgtgatgcgtttcgtaccctgggcctgtag HyperAID-1(AID-7.3-cvBEST-1-181)(SEQ ID NO: 40):
atggatagcctgctgatgaaccgtcgtgaatttctgtatcagtttaaaaacgtgcgttgggcgaaaggccgtcgt -continued gaaacctatctgtgctatgtggtgaaacgtcgtgatagcgcgaccagctttagcctggattttggctatctgcgt aacaaaaacggctgccatgtggaactgctgtttctgcgttatattagcgattgggatctggatccgggccgttgc tatcgtgtgacctggtttatcagctggagcccgtgctatgattgcgcgcgtcatgtggcggattttctgcgtggc aacccgaacctgagcctgcgtattttttaccgcgcgtctgtattttttgcgaagccggcaggcgtgaaccggaaggc ctgcgtcgtctgcatcgtgcgggcgtgcagattgcgattatgacctttaaagattattttttattgctggaacacc tttgtggaaaaccatggacgtacctttaaagcgtgggaaggcctgcatgaaaacagcgtgcgtctgagccgtcag ctgcgtcgtattctgctgtag
Mutations compared to wild-type AID: K10E, T82I, D118A, R119G, K120R, A121R, E156G, P182*

HyperAID-2 (AID-7.3-cvBEST)(SEQ ID NO: 41):
atggatagcctgctgatgaaccgtcgtgaatttctgtatcagtttaaaaacgtgcgttgggcgaaaggccgtcgt gaaacctatctgtgctatgtggtgaaacgtcgtgatagcgcgaccagctttagcctggattttggctatctgcgt aacaaaaacggctgccatgtggaactgctgtttctgcgttatattagcgattgggatctggatccgggccgttgc tatcgtgtgacctggtttatcagctggagcccgtgctatgattgcgcgcgtcatgtggcggattttctgcgtggc aacccgaacctgagcctgcgtattttttaccgcgcgtctgtattttttgcgaagccggcaggcgtgaaccggaaggc ctgcgtcgtctgcatcgtgcgggcgtgcagattgcgattatgacctttaaagattattttttattgctggaacacc tttgtggaaaaccatggacgtacctttaaagcgtgggaaggcctgcatgaaaacagcgtgcgtctgagccgtcag ctgcgtcgtattctgctgccgctgtatgaagtggatgatctgcgtgatgcgtttcgtacccctgggcctgtag
Mutations: K10E, T82I, D118A, R119G, K120R, A121R, E156G Hyper AID-3 (AID-cvBEST)(SEQ ID NO: 42):
atggatagcctgctgatgaaccgtcgtaaatttctgtatcagtttaaaaacgtgcgttgggcgaaaggccgtcgt gaaacctatctgtgctatgtggtgaaacgtcgtgatagcgcgaccagctttagcctggattttggctatctgcgt aacaaaaacggctgccatgtggaactgctgtttctgcgttatattagcgattgggatctggatccgggccgttgc tatcgtgtgacctggtttaccagctggagcccgtgctatgattgcgcgcgtcatgtggcggattttctgcgtggc aacccgaacctgagcctgcgtattttttaccgcgcgtctgtattttttgcgaagccggcaggcgtgaaccggaaggc ctgcgtcgtctgcatcgtgcgggcgtgcagattgcgattatgacctttaaagattattttttattgctggaacacc tttgtggaaaaccatgaacgtacctttaaagcgtgggaaggcctgcatgaaaacagcgtgcgtctgagccgtcag ctgcgtcgtattctgctgtag
Mutations: K10E, T82I, D118A, R119G, K120R, A121R, E156G, P182*

HyperAID-4 (AID-7.3-R119G-1-181)(SEQ ID NO: 43):
atggatagcctgctgatgaaccgtcgtgaatttctgtatcagtttaaaaacgtgcgttgggcgaaaggccgtcgt gaaacctatctgtgctatgtggtgaaacgtcgtgatagcgcgaccagctttagcctggattttggctatctgcgt aacaaaaacggctgccatgtggaactgctgtttctgcgttatattagcgattgggatctggatccgggccgttgc tatcgtgtgacctggtttatcagctggagcccgtgctatgattgcgcgcgtcatgtggcggattttctgcgtggc aacccgaacctgagcctgcgtattttttaccgcgcgtctgtattttttgcgaagatggcaaagcggaaccggaaggc ctgcgtcgtctgcatcgtgcgggcgtgcagattgcgattatgacctttaaagattattttttattgctggaacacc tttgtggaaaaccatggacgtacctttaaagcgtgggaaggcctgcatgaaaacagcgtgcgtctgagccgtcag ctgcgtcgtattctgctgtag
Mutations: K10E, T82I, R119G, E156G, P182*

HyperAID-5 (AID-7.3-cvBEST-CS-1-181) aka AID123* (SEQ ID NO: 44):
atggatagcctgctgatgaaccgtcgtgaatttctgtatcagtttaaaaacgtgcgttgggcgaaaggccgtcgt gaaacctatctgtgctatgtggtgaaacgtcgtgatagcgcgaccagcgaaagcctggattttggctatctgcgt aacaaaaacggctgccatgtggaactgctgtttctgcgttatattagcgattgggatctggatccgggccgttgc tatcgtgtgacctggtttatcagctggagcccgtgctatgattgcgcgcgtcatgtggcggattttctgcgtggc aacccgaacctgagcctgcgtattttttaccgcgcgtctgtattttttgcgaagccggcaggcgtgaaccggaaggc -continued

```
ctgcgtcgtctggcggaagcgggcgtgcagattgcgattatgacctataaagattatgaatattgctggaacacc tttgtggaaaaccatggacgtacctttaaagcgtgggaaggcctgcatgaaaacagcgtgcgtctgagccgtcag ctgcgtcgtattctgctgccgctgtatgaagtggatgatctgcgtgatgcgtttcgtaccctgggcctgtag
Mutations: K10E, F42E, T82I, D118A, R119G, K120R, A121R, H130A, R131E, F141Y,
F145E, E156G
```

Cloning, expression and purification of human AID: Synthetic oligonucleotides for cloning and assays were purchased from Integrated DNA Technologies. Alanine scanning loop variants were generated by overlap extension polymerase chain reaction (PCR) as previously described (Kohli et al. (2009) *J. Biol. Chem.*, 284, 22898-22904). Inserts were cloned into the EcoRI-XhoI region of AID-expressing pET41b vector (Novagen) also containing an N-terminal maltose binding protein, with the human AID gene codon optimized for expression in *Escherichia coli* as previously described (Kohli et al. (2009) *J. Biol. Chem.*, 284, 22898-22904). Plasmids were co-transformed with the chaperone trigger factor for heterologous expression in *E. coli* BL21 (DE3) pLysS (Novagen). Enzyme expression and purification were carried out as previously described (Nabel et al. (2013) *Proc. Natl. Acad. Sci. U.S.A.*, 110, 14225-14230).

Deamination assays and sequence preference profiles: Similar to previously described protocols (Kohli et al. (2009) *J. Biol. Chem.*, 284, 22898-22904), the substrate was a 27-mer oligonucleotide containing a single C within an AGC context. For fluorescence-based assays, 1 µM substrate containing a 3'-fluorescein was incubated with 1 µM enzyme, 1 unit uracil DNA glycosylase (UDG; NEB) and 1 µg RNaseA(Fermentas) in 20 mM Tris-Cl (pH 8), 1 mM dithiothreitol (DTT), 1 mM ethylenediaminetetraacetic acid (EDTA) for 3 hours at 30° C. followed by heating to 95° C. for 20 min. For kinetic assays, the substrate was 32P end-labeled by standard methods, gel purified and quantified using liquid scintillation counting. An end-labeled 40-mer was also generated as an internal standard. In the assay, 50-300 nM radioactive substrate was incubated with 15 nM standard oligonucleotide under reaction conditions described above for 1 hour at 30° C. (within linear product formation range). Abasic sites formed in the substrates were cleaved by adding NaOH (100 mM final), an equal volume of formamide and heating to 95° C. for 20 min. Samples were then separated on 20% Tris/Borate/EDTA (TBE), 7 M Urea polyacrylamide gels (45-50° C.). For assays with fluorescent substrate, gels were imaged using a Typhoon imager (GE healthcare) and the products quantified using QuantityOne (Biorad). For kinetic assays, gels were imaged via storage phosphor screen on the Typhoon imager, quantified using custom MATLAB software, and the total amount of deamination was calculated using the known concentration of the standard oligonucleotide as the reference. Data were fit to the Michaelis-Menten equation using least squares fitting with PRISM (Graphpad) software.

Sequence preference profiles were calculated as previously described (MacMillan et al. (2013) *J. Virol.*, 87, 4808-4817). Briefly, purified AID-WT, R119G or cvBEST were assayed against an array of 16 substrates containing cytosine in an XXC sequence context, where X=A, 5-methylcytosine, G or T. A total of 150 nM of each substrate was incubated with a fixed amount of enzyme as detailed. Product formation was averaged across substrates sharing the same nucleotide at the −1 or −2 position and the relative reactivity for different nucleotides was used to derive the sequence preference.

Rifampicin mutagenesis assays were carried out as previously described (Kohli et al. (2009) *J. Biol. Chem.*, 284, 22898-22904). Briefly, *E. coli* BL21 (DE3) pLysS were transformed with the AID expression plasmid and a pET-coco2 (Novagen) plasmid expressing uracil DNA glycosylase inhibitor (UGI), hereafter called the selection strain. Overnight cultures grown from single colonies were diluted to an A600 of 0.3 and grown for 1 hour at 37° C. before inducing them with 1 mM isopropyl-D-1-thiogalactopyranoside (IPTG). After 4 hours of additional growth, aliquots of cultures were separately plated on Luria Bertani (LB) agar plates containing Rifampicin (100 µg/ml) and plasmid-selective antibiotics. The mutation frequencies were then calculated by the ratio of rifampicin resistant colonies to total population.

Saturation mutagenesis, selection and sequencing (Sat-Sel-Seq): The parent vector for generation of the saturation mutant libraries was made to contain AscI and AatII restriction sites flanking the region of interest and a stop codon for added negative selection. For each mutant, a ds-DNA oligonucleotide cassette was generated using oligonucleotides which contained 5' overhangs of MluI (AscI compatible) and AatII sites, the NNS degenerate codon and a silent mutation (positional barcode) immediately 3' to the NNS codon. The oligonucleotides were 5'-phosphorylated, annealed and ligated into the AscI/AatII digested parent vector. Ligations were transformed into high-efficiency competent cells (NEB 10(3), after which 1/10th volume of cells were plated to determine the library size, while the rest were used to inoculate 25 ml of LB/Kanamycin and grown at 37° C. prior to plasmid extraction, resulting in the G0 library at each position. The library sizes were all >100-fold represented and the presence of the degenerate NNS codon in the library was verified by Sanger sequencing.

The plasmid libraries were transformed into the selection strain and 1/10 of the culture was plated to verify the library size. The remaining liquid culture was grown overnight and diluted into 10 independent cultures at A600 of 0.3. Cultures were grown for 1 hour at 37° C., induced with 1 mMIPTG and after 3 hours of additional growth 1 ml of each culture was plated on LB agar with rifampin (100 µg/ml). The rifampin resistant colonies on each plate were washed with 5 ml media and the pooled 50 ml culture with LB Kanamycin was grown overnight. Selection across generations always maintained at least 10-fold overrepresentation of the library. The extracted plasmid encoded the next-generation library, which could be transformed into a naïve selection strain to restart the selection cycle.

The region in AID spanning nucleotides 211-507 was PCR amplified using one of four primer sets that distinguished G0, G1, G2 and G3. From the 5'-direction forward, PCR primers contained a leader sequence for 454 sequencing, an 8 bp DNA barcode (different for each generation) and the touchdown sequence for AID amplification. The PCR products were gel purified and the 48 samples (12 positions×4 generations) were pooled in equal amounts. A total of 2.5 µg of DNA was subjected to high-throughput sequencing on a Roche 454 GS FLX sequencer. The aligned sequence reads were filtered to remove sequence lacking either the generational barcode or a single positional barcode and then each codon identity from each read at the variable position was tabulated.

Selection by covariation of loop residues was performed by constructing eight different sublibraries using oligonucleotides as shown in Gajula et al. (2014) Nucleic Acids Res. These were pooled in the ratio of 2:2:2:2:1:1:1:1, respectively, to generate the starting library that contained equal amount of each of the 384-library family members. The library was then subjected to several rounds of rifampicin selection as described in Sat-Sel-Seq method above.

The results of the experiments from Example 2 are now described.

Figure 10:
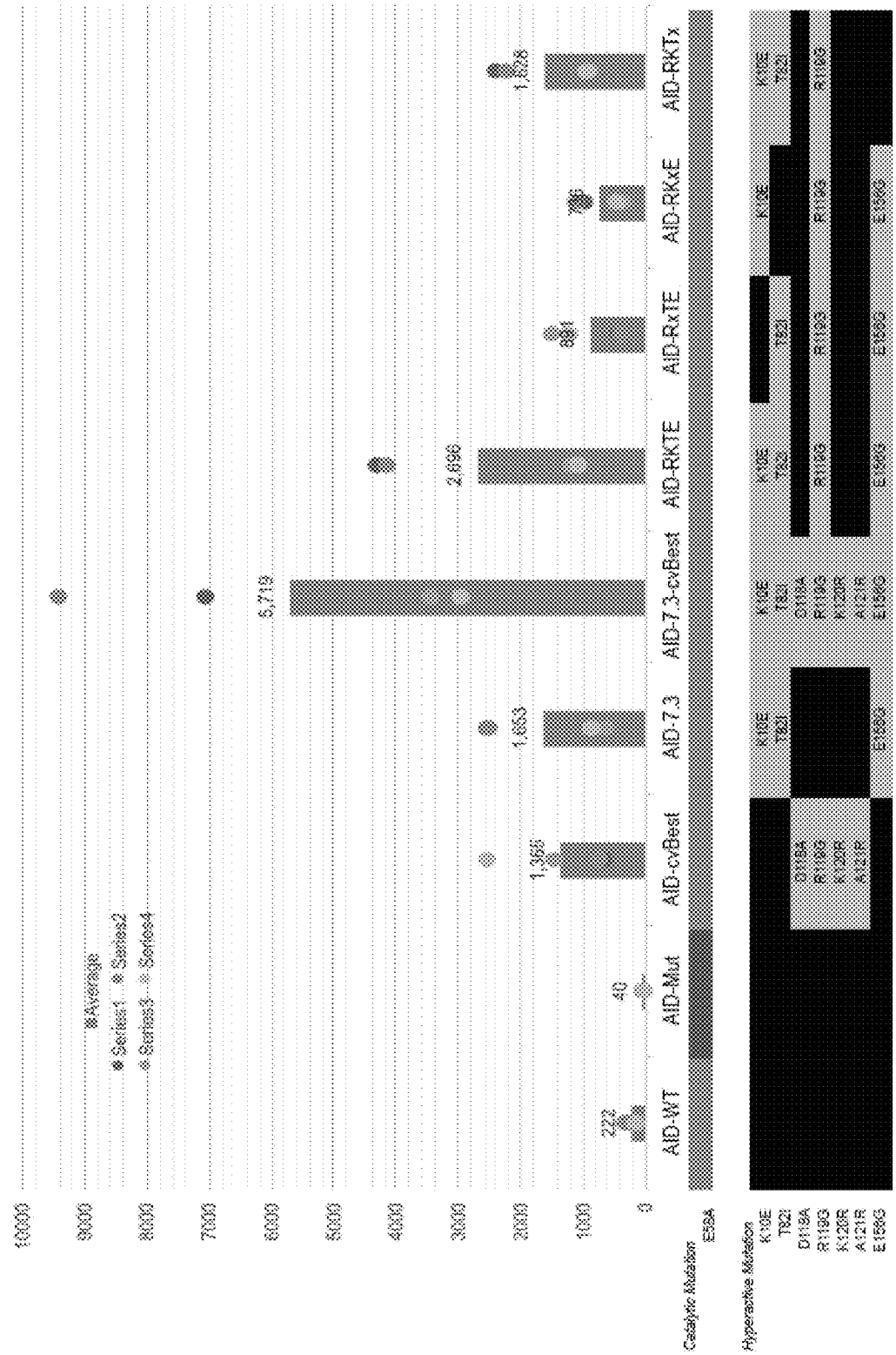
FIG. 10 is a graph and table illustrating activity of hyperactive AID mutants in an assay measuring mutational frequency. Each dot represents the data from an individual experiment and blue bars represent the average of four experiments. Mutations encoded in these mutant constructs are illustrated in the table below the graph.

Hyperactive AID mutants were expressed and demonstration enhanced activity in a UDG assay (FIG. 9). Hyperactive AID mutants were also tested for mutation frequency (FIG. 10). In this experiment the various combination of mutations were assessed by looking at mutation frequency when the enzymes are expressed in E. coli. The deaminases cause mutations in the rpoB gene which encodes for RNA polymerase. If a mutations confers resistance to the antibiotic rifampin it "scores" as a mutant. In this assay, the WT enzyme mutates at a rate of 222 per $10^9$ cells. The mutation rate in the most hyperactive construct is 5719 per $10^9$, showing a dramatic increase in deaminase activity.

Figure 28:
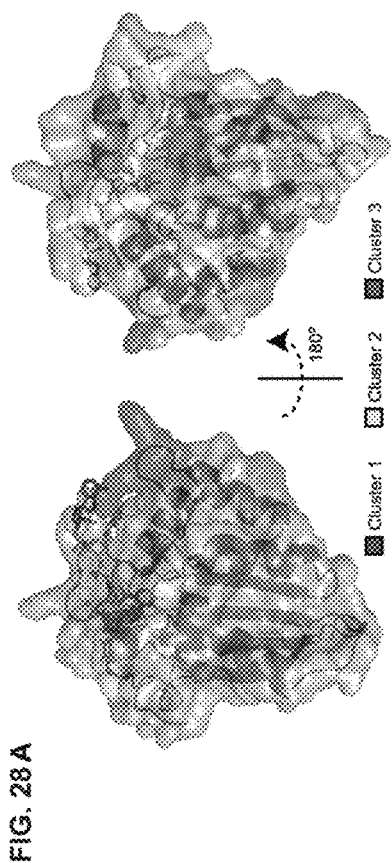
FIGS. 28A-28C are a set of images depicting hyperactive AID.
Figure 28:
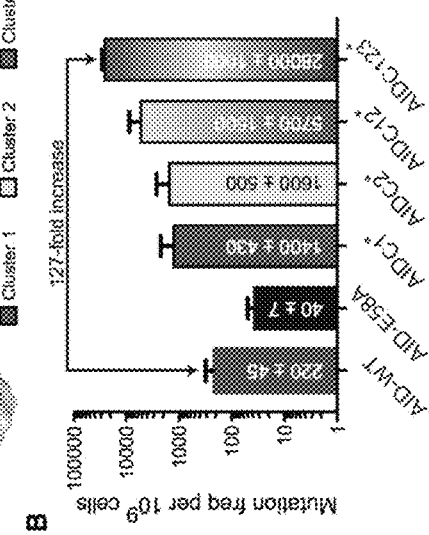
Figure 28:
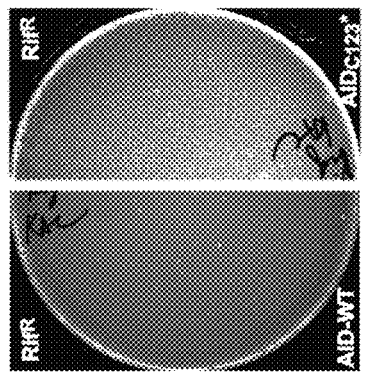

In addition, a structural model of AID bound to ssDNA, as described by Gajula et al. (2014) Nucleic Acids Res., overlaid with three clusters of residues where mutations have been independently shown to confer hyperactivity was generated and is shown in FIG. 28A. A modified fluctuation analysis approach used to analyze and quantify deamination efficiency. Results of those studies are shown in FIG. 28B. Combining mutational clusters results in significant AID hyperactivation. AID-E58A, inactive mutant. In addition, cells expressing AID-WT and the AIDC123* variant were plated under rifampin selection. Results shown in FIG. 28C, demonstrate the increase in mutagenesis with variant expression.

Example 3: hmC-Dominant TET Mutants

The materials and methods employed in the experiments of Example 3 are now described.

Wild type TET2 sequences are providing as SEQ ID NOs: 21-22. SEQ ID NO: 22 (TET2-CD) provides the entire human TET2 catalytic domain whereas SEQ ID NO: 21 is a variant which has a large linker removed. Mutants generated from TET2 are described herein including SEQ ID NOs: 23-24 and 45-48.

```
Wild Type Human TET2-CS
                                                              (SEQ ID NO: 21)
mdykddddkhmggsDFPSCRCVEQIIEKDEGPFYTHLGAGPNVAAIREIMEERFGQKGKAI

RIERVIYTGKEGKSSQGCPIAKWVVRRSSSEEKLLCLVRERAGHTCEAAVIVILILVW

EGIPLSLADKLYSELTETLRKYGTLTNRRCALNEERTCACQGLDPETCGASFSFGCSW

SMYYNGCKFARSKIPRKFKLLGDDPKEEEKLESHLQNLSTLMAPTYKKLAPDAYNN

QIEYEHRAPECRLGLKEGRPFSGVTACLDFCAHAHRDLHNMQNGSTLVCTLTREDN

REFGGKPEDEPLHVLPLYKVSDVDEFGSVEAQEEKKRSGAIPVLSSFRRKVRMLAEP

VKTCRQRKLEAKKAAAEKLSggggsggggsggggsDEVWSDSEQSFLDPDIGGVAVAPTH

GSILIECAKRELHATTPLKNPNRNHPTRISLVFYQHKSMNEPKHGLALWEAKMAEKA

REKEEECEKYG*

Wild Type Human TET2-CD
                                                              (SEQ ID NO: 22)
MGGSDFPSCRCVEQIIEKDEGPFYTHLGAGPNVAAIREIMEERFGQKGKAIRIERVIYT

GKEGKSSQGCPIAKWVVRRSSSEEKLLCLVRERAGHTCEAAVIVILILVWEGIPLSLA

DKLYSELTETLRKYGTLTNRRCALNEERTCACQGLDPETCGASFSFGCSWSMYYNG

CKFARSKIPRKFKLLGDDPKEEEKLESHLQNLSTLMAPTYKKLAPDAYNNQIEYEHR

APECRLGLKEGRPFSGVTACLDFCAHAHRDLHNMQNGSTLVCTLTREDNREFGGKP

EDEQLHVLPLYKVSDVDEFGSVEAQEEKKRSGAIQVLSSFRRKVRMLAEPVKTCRQ

RKLEAKKAAAEKLSSLENSSNKNEKEKSAPSRTKQTENASQAKQLAELLRLSGPVM

QQSQQPQPLQKQPPQPQQQQRPQQQQPHHPQTESVNSYSASGSTNPYMRRPNPVSPY

PNSSHTSDIYGSTSPMNFYSTSSQAAGSYLNSSNPMNPYPGLLNQNTQYPSYQCNGN

LSVDNCSPYLGSYSPQSQPMDLYRYPSQDPLSKLSLPPIHTLYQPRFGNSQSFTSKYL

GYGNQNMQGDGFSSCTIRPNVHHVGKLPPYPTHEMDGHFMGATSRLPPNLSNPNM

DYKNGEHHSPSHIIHNYSAAPGMFNSSLHALHLQNKENDMLSHTANGLSKMLPALN

HDRTACVQGGLHKLSDANGQEKQPLALVQGVASGAEDNDEVWSDSEPSFLDPDIG

GVAVAPTHGSILIECAKRELHATTPLKNPNRNHPTRISLVFYQHKSMNEPKHGLALW
```

```
EAKMAEKAREKEEECEKYGPDYVPQKSHGKKVKREPAEPHETSEPTYLRFIKSLAER

TMSVTTDSTVTTSPYAFTRVTGPYNRYI* hTET2-CS-T1372E                                              (SEQ ID NO: 23)
mdykddddkhmggsDFPSCRCVEQIIEKDEGPFYTHLGAGPNVAAIREIMEERFGQKGKAI

RIERVIYTGKEGKSSQGCPIAKWVVRRSSSEEKLLCLVRERAGHTCEAAVIVILILVW

EGIPLSLADKLYSELTETLRKYGTLTNRRCALNEERTCACQGLDPETCGASFSFGCSW

SMYYNGCKFARSKIPRKFKLLGDDPKEEEKLESHLQNLSTLMAPTYKKLAPDAYNN

QIEYEHRAPECRLGLKEGRPFSGVEACLDFCAHAHRDLHNMQNGSTLVCTLTREDN

REFGGKPEDEQLHVLPLYKVSDVDEFGSVEAQEEKKRSGAIQVLSSFRRKVRMLAEP

VKTCRQRKLEAKKAAAEKLSggggsggggsggggsDEVWSDSEQSFLDPDIGGVAVAPTH

GSILIECAKRELHATTPLKNPNRNHPTRISLVFYQHKSMNEPKHGLALWEAKMAEKA

REKEEECEKYG* hTET2-CD-T1372E                                              (SEQ ID NO: 24)
MGGSDFPSCRCVEQIIEKDEGPFYTHLGAGPNVAAIREIMEERFGQKGKAIRIERVIYT

GKEGKSSQGCPIAKWVVRRSSSEEKLLCLVRERAGHTCEAAVIVILILVWEGIPLSLA

DKLYSELTETLRKYGTLTNRRCALNEERTCACQGLDPETCGASFSFGCSWSMYYNG

CKFARSKIPRKFKLLGDDPKEEEKLESHLQNLSTLMAPTYKKLAPDAYNNQIEYEHR

APECRLGLKEGRPFSGVEACLDFCAHAHRDLHNMQNGSTLVCTLTREDNREFGGKP

EDEQLHVLPLYKVSDVDEFGSVEAQEEKKRSGAIQVLSSFRRKVRMLAEPVKTCRQ

RKLEAKKAAAEKLSSLENSSNKNEKEKSAPSRTKQTENASQAKQLAELLRLSGPVM

QQSQQPQPLQKQPPQPQQQQRPQQQQPHHPQTESVNSYSASGSTNPYMRRPNPVSPY

PNSSHTSDIYGSTSPMNFYSTSSQAAGSYLNSSNPMNPYPGLLNQNTQYPSYQCNGN

LSVDNCSPYLGSYSPQSQPMDLYRYPSQDPLSKLSLPPIHTLYQPRFGNSQSFTSKYL

GYGNQNMQGDGFSSCTIRPNVHHVGKLPPYPTHEMDGHFMGATSRLPPNLSNPNM

DYKNGEHHSPSHIIHNYSAAPGMFNSSLHALHLQNKENDMLSHTANGLSKMLPALN

HDRTACVQGGLHKLSDANGQEKQPLALVQGVASGAEDNDEVWSDSEQSFLDPDIG

GVAVAPTHGSILIECAKRELHATTPLKNPNRNHPTRISLVFYQHKSMNEPKHGLALW

EAKMAEKAREKEEECEKYGPDYVPQKSHGKKVKREPAEPHETSEPTYLRFIKSLAER

TMSVTTDSTVTTSPYAFTRVTGPYNRYI

Wild Type Human TET2-CS                                      (SEQ ID NO: 45)
atggacttccccagctgcaggtgcgtggagcagatcatcgagaaggacgagggcccttctacacccacctgggc gccggccccaacgtggccgccatcagggagatcatggaggagaggttcggccagaagggcaaggccatcaggatc gagagggtgatctacaccggcaaggagggcaagagcagccagggctgccccatcgccaagtgggtggtgaggagg agcagcagcgaggagaagctgctgtgcctggtgagggagagggcaggccacacctgcgaggccgccgtgatcgtg atcctgatcctggtgtgggagggcatcccctgtccctggccgacaagctgtacagcgagctgaccgagaccctg aggaagtacggcaccctgaccaacaggaggtgcgccctgaacgaggagagaacctgcgcctgccagggcctggac cccgagacctgcggcgccagcttcagcttcggctgcagctggagcatgtactacaacggctgcaagttcgccagg agcaagatccccaggaagttcaagctgctgggcgacgaccccaaggaggaggagaagctggagagccacctgcag aacctgtccaccctgatggcccccacctacaagaagctggccccgacgcctacaacaaccagatcgagtacgag cacagggcccccgagtgccgcctaggcctgaaggagggccggcccttcagcggggtgaccgcctgcctggacttc
```

-continued tgcgcccacgcacaccgtgacctgcacaacatgcagaacggatccaccctggtgtgcaccctgaccagggaggac aacagggagttcggcggcaagcccgaggacgagcagctgacgtgctgcccctgtacaaggtgagcgacgtggac gagttcggcagcgtggaggcccaggaggagaagaagaggagcggcgccatccaggtgctgagcagcttcaggagg aaggtgaggatgctggccgagcccgtgaagacctgcaggcagaggaagctggaggccaagaaggccgcagccgag aagctgagcggcggaggcggaagcggcggaggaggcagcggcggaggcggaagcgacgaggtgtggagcgacagc gagcagagcttcctggaccccgacatcggcggcgtggccgtggcccccacccacggcagcatcctgatcgagtgc gccaagagggagctgcacgccaccacccccttaagaaccccaacaggaaccaccccacgcgtatcagcctggtg ttctaccagcacaagagcatgaacgagcctaagcacgggctagccctgtgggaggccaagatggccgagaaggcc agggagaaggaggaggagtgcgagaagtacggctga Wild Type Human TET2-CD (SEQ ID NO: 46)

atggacttccccagctgcaggtgcgtggagcagatcatcgagaaggacgagggcccttctacacccacctgggc gccggccccaacgtggccgccatcagggagatcatggaggagaggttcggccagaagggcaaggccatcaggatc gagagggtgatctacaccggcaaggagggcaagagcagccagggctgccccatcgccaagtgggtggtgaggagg agcagcagcgaggagaagctgctgtgcctggtgagggagagggcaggccacacctgcgaggccgccgtgatcgtg atcctgatcctggtgtgggagggcatcccctgtccctggccgacaagctgtacagcgagctgaccgagaccctg aggaagtacggcaccctgaccaacaggaggtgcgccctgaacgaggagagaacctgcgcctgccagggcctggac cccgagacctgcggcgccagcttcagcttcggctgcagctggagcatgtactacaacggctgcaagttcgccagg agcaagatccccaggaagttcaagctgctgggcgacgaccccaaggaggaggagaagctggagagccacctgcag aacctgtccaccctgatggcccccacctacaagaagctggccccgacgcctacaacaaccagatcgagtacgag cacagggcccccgagtgccgcctaggcctgaaggagggccggcccttcagcggggtgaccgcctgcctggacttc tgcgcccacgcacaccgtgacctgcacaacatgcagaacggatccaccctggtgtgcaccctgaccagggaggac aacagggagttcggcggcaagcccgaggacgagcagctgcacgtgctgcccctgtacaaggtgagcgacgtggac gagttcggcagcgtggaggcccaggaggagaagaagaggagcggcgccatccaggtgctgagcagcttcaggagg aaggtgaggatgctggccgagcccgtgaagacctgcaggcaaaggaaactggaagccaagaaagctgccgctgag aagctctcttcactggagaactcaagcaataagaatgagaaggagaagagtgcaccctccagaacgaaacagact gaaaacgcatcccaggcgaaacagctggctgagctgctgcgcctctctggaccagtgatgcaacagagccagcag cctcaacccctgcagaaacaaccccccacagccccaacagcaacaacgcccacagcagcagcaaccccatcatcct cagacggaatctgtcaactcatacagcgcatccggttctacgaatccgtatatgcgaagacctaatcctgtctca ccctatcccaattccagccatacatccgacatctacggcagcacgtccctatgaacttttacagtacaagctcc caggctgccggatcatacctcaattcatctaaccccatgaaccctacccagggctgcttaaccaaaacactcag tacccttcatatcaatgtaacggcaatttgagcgttgataactgtagtccctatctgggttcctattcaccgcag agccagccgatggacctgtaccgatatccctcccaggaccctctgtccaagctcagtctgcctcccattcacaca ctttaccagcccgctttggcaacagtcagtcatttactagcaaataccttggctacgggaatcagaacatgcag ggcgacgggttctcttcttgcaccattcgcccgaatgtacatcacgtggggaagctcccccctatcctacacac gagatggatgggcattttatgggcgcgacttctcggcttcctcccaaccttagtaacctaacatggactacaag aatggcgaacaccatagtccctcacacattattcataactactccgccgcacccggaatgtttaactcttccctg cacgctctgcacctgcaaaacaaagagaatgatatgttgagtcataccgccaacggcctgtccaagatgctcccc gctcttaaccacgatagaaccgcctgtgtccaggaggtcttcacaaattgagcgatgctaatggccaggagaag cagccactggccttggtgcaggggggtggcatccggggcagaggacaatgatgaagtgtggtctgactctgagcaa tccttcctggaccccgacatcggcggggtagcagtggctcctacccacggctctatcttgattgagtgcgccaaa agagagctgcacgctactaccccacttaagaaccccaacaggaaccaccccacgcgtatcagcctggtgttctac -continued cagcacaagagcatgaacgagcctaagcacgggctagctctgtgggaggccaaaatggcagagaaagctcgggaa aaagaagaggaatgtgagaaatacggaccagattatgtgccgcagaaatctcatggaaaaaaagtgaaacgggaa cctgcagaaccccatgagaccagtgagcccacttacctgaggtttatcaagtccctcgccgaacgaaccatgtca gtgacgaccgatagcaccgttactaccagtccttacgctttcacccgggttactggcccctacaatcgatatata tga hTET2-CS-T1372E (SEQ ID NO: 47)

atggacttccccagctgcaggtgcgtggagcagatcatcgagaaggacgagggccccttctacacccacctgggc gccggccccaacgtggccgccatcagggagatcatggaggagaggttcggccagaagggcaaggccatcaggatc gagagggtgatctacaccggcaaggagggcaagagcagccagggctgccccatcgccaagtgggtggtgaggagg agcagcagcgaggagaagctgctgtgcctggtgagggagagggcaggccacacctgcgaggccgccgtgatcgtg atcctgatcctggtgtgggagggcatccccctgtccctggccgacaagctgtacagcgagctgaccgagaccctg aggaagtacggcaccctgaccaacaggaggtgcgccctgaacgaggagagaacctgcgcctgccagggcctggac cccgagacctgcggcgccagcttcagcttcggctgcagctggagcatgtactacaacggctgcaagttcgccagg agcaagatccccaggaagttcaagctgctgggcgacgaccccaaggaggaggagaagctggagagccacctgcag aacctgtccaccctgatggcccccacctacaagaagctggcccccgacgcctacaacaaccagatcgagtacgag cacagggccccgagtgccgcctaggcctgaaggagggtcgacccttcagcggggtggaggcctgcctggacttc tgcgcccacgcacaccgtgacctgcacaacatgcagaacggatccaccctggtgtgcaccctgaccaggaggac aacagggagttcggcggcaagcccgaggacgagcagctgcacgtgctgccccctgtacaaggtgagcgacgtggac gagttcggcagcgtggaggcccaggaggagaagaagaggagcggcgccatccaggtgctgagcagcttcaggagg aaggtgaggatgctggccgagcccgtgaagacctgcaggcagaggaagctggaggccaagaaggccgcagccgag aagctgagcggcggaggcggaagcggcggaggaggcagcggcggaggcggaagcgacgaggtgtggagcgacagc gagcagagcttcctggaccccgacatcggcggcgtggccgtggccccacccacggcagcatcctgatcgagtgc gccaagagggagctgcacgccaccaccccccttaagaacccaacaggaaccaccccacgcgtatcagcctggtg ttctaccagcacaagagcatgaacgagcctaagcacgggctagccctgtgggaggccaagatggccgagaaggcc agggagaaggaggaggagtgcgagaagtacggctga hTET2-CD-T1372E (SEQ ID NO: 48)

atggacttccccagctgcaggtgcgtggagcagatcatcgagaaggacgagggccccttctacacccacctgggc gccggccccaacgtggccgccatcagggagatcatggaggagaggttcggccagaagggcaaggccatcaggatc gagagggtgatctacaccggcaaggagggcaagagcagccagggctgccccatcgccaagtgggtggtgaggagg agcagcagcgaggagaagctgctgtgcctggtgagggagagggcaggccacacctgcgaggccgccgtgatcgtg atcctgatcctggtgtgggagggcatccccctgtccctggccgacaagctgtacagcgagctgaccgagaccctg aggaagtacggcaccctgaccaacaggaggtgcgccctgaacgaggagagaacctgcgcctgccagggcctggac cccgagacctgcggcgccagcttcagcttcggctgcagctggagcatgtactacaacggctgcaagttcgccagg agcaagatccccaggaagttcaagctgctgggcgacgaccccaaggaggaggagaagctggagagccacctgcag aacctgtccaccctgatggcccccacctacaagaagctggcccccgacgcctacaacaaccagatcgagtacgag cacagggccccgagtgccgcctaggcctgaaggagggtcgacccttcagcggggtggaggcctgcctggacttc tgcgcccacgcacaccgtgacctgcacaacatgcagaacggatccaccctggtgtgcaccctgaccaggaggac aacagggagttcggcggcaagcccgaggacgagcagctgcacgtgctgccccctgtacaaggtgagcgacgtggac gagttcggcagcgtggaggcccaggaggagaagaagaggagcggcgccatccaggtgctgagcagcttcaggagg aaggtgaggatgctggccgagcccgtgaagacctgcaggcaaaggaaactggaagccaagaaagctgccgctgag -continued
```
aagctctcttcactggagaactcaagcaataagaatgagaaggagaagagtgcaccctccagaacgaaacagact gaaaacgcatcccaggcgaaacagctggctgagctgctgcgcctctctggaccagtgatgcaacagagccagcag cctcaaccctgcagaaacaaccccacagccccaacagcaacaacgccacagcagcagcaaccccatcatcct cagacggaatctgtcaactcatacagcgcatccggttctacgaatccgtatatgcgaagacctaatcctgtctca ccctatcccaattccagccatacatccgacatctacggcagcacgtccctatgaactttacagtacaagctcc caggctgccggatcatacctcaattcatctaacccatgaaccctacccagggctgcttaaccaaaacactcag taccttcatatcaatgtaacggcaatttgagcgttgataactgtagtccctatctgggttcctattcaccgcag agccagccgatggacctgtaccgatatccctcccaggaccctctgtccaagctcagtctgcctcccattcacaca ctttaccagcccgctttggcaacagtcagtcatttactagcaaataccttggctacgggaatcagaacatgcag ggcgacgggttctcttcttgcaccattcgcccgaatgtacatcacgtggggaagctccccccctatcctacacac gagatggatgggcattttatgggcgcgacttctcggcttcctcccaaccttagtaaccctaacatggactacaag aatggcgaacaccatagtccctcacacattattcataactactccgccgcacccggaatgtttaactcttccctg cacgctctgcacctgcaaaacaaagagaatgatatgttgagtcataccgccaacggcctgtccaagatgctcccc gctcttaaccacgatagaaccgcctgtgtccagggaggtcttcacaaattgagcgatgctaatggccaggagaag cagccactggccttggtgcaggggtggcatccggggcagaggacaatgatgaagtgtggtctgactctgagcaa tccttcctggaccccgacatcggcggggtagcagtggctcctacccacggctctatcttgattgagtgcgccaaa agagagctgcacgctactaccccacttaagaaccccaacaggaaccaccccacgcgtatcagcctggtgttctac cagcacaagagcatgaacgagcctaagcacgggctagctctgtgggaggccaaaatggcagagaaagctcgggaa aaagaagaggaatgtgagaaatacggaccagattatgtgccgcagaaatctcatggaaaaaaagtgaaacgggaa cctgcagaacccatgagaccagtgagcccacttacctgaggtttatcaagtccctcgccgaacgaaccatgtca gtgacgaccgatagcaccgttactaccagtccttacgctttcacccgggttactggcccctacaatcgatatata tga
```

Saturation cassette mutagenesis: A codon-optimized hTET2-CS construct (residues 1129-1936 A1481-1843) was designed with an N-terminal FLAG tag and unique restriction sites flanking the Thr1372 and Val1900 codons, purchased as a gene block from Integrated DNA Technologies (IDT), and cloned into a pLEXm vector for mammalian expression. Thirty-eight pairs of complementary oligos encoding all amino acid substitutions at both positions (as well as the Y1902F mutation) were ordered, annealed, and cloned by cassette mutagenesis in place of the WT sequence (FIGS. 27A-27C). Mutations were confirmed by gene sequencing and/or digestion at a unique restriction site within the oligo.

TET2 overexpression in HEK293T cells: HEK293T cells (mycoplasma tested and verified by ATCC) were cultured in DMEM with GlutaMAX (Thermo Fisher Scientific) and 10% FBS (Sigma). Cells were transfected with WT or mutant hTET2-CS or an empty vector control using Lipofectamine 2000 (Thermo) according to the manufacturer's protocol. Media was changed 24 hours after transfection, cells were harvested by trypsinization 48 hours after transfection and resuspended in PBS, and genomic DNA (gDNA) was purified from four fifths of the collected cells using the DNeasy Blood & Tissue Kit (Qiagen).

Western blot for FLAG-tagged hTET2-CS: One-fifth portion of the transfected cells was lysed using CytoBuster Protein Extraction Reagent (EMD Millipore). The clarified lysates were diluted 50-fold into CytoBuster and run on two 8% SDS-PAGE gels, with WT sample as a standard on each gel. To further standardize the blots, the gels were cut at the 70-kDa marker, so that the upper half contained the Hsp90 control band and the bottom half hTET2-CS. The Hsp90 halves of both gels were transferred together onto a single PVDF membrane, and the two TET halves were transferred onto another membrane using an iBlot Gel Transfer Device (Thermo). Membranes were blocked for 2 hours at room temperature with 5% (w/v) milk in Tris-buffered saline with 0.1% (v/v) Tween-20 (TBST), washed 3× with TBST, blotted with primary 1:10,000 anti-FLAG M2 (Sigma; cat. no. F1804) or 1:1,000 anti-Hsp90a/p (Santa Cruz Biotechnology; cat. no. sc-13119) antibodies at 4° C. overnight, washed, blotted with secondary 1:5,000 goat anti-mouse-HRP (Santa Cruz Biotechnology; cat. no. sc-2005) for 2 h, washed, and imaged with Immobilon Western Chemiluminescent HRP Substrate (Millipore) on a Fujifilm LAS-1000 imager with 30-s exposures.

Dot blot for cytosine modifications in gDNA: Purified gDNA from HEK293T cells was diluted to 10 ng/µl in Tris-EDTA (TE) buffer, pH 8.0. To this was added V volume of 2 M NaOH-50 mM EDTA. The DNA was denatured for 10 minutes at 95° C. and transferred quickly to ice, followed by addition of 1:1 ice cold 2 M ammonium acetate. Sequi-Blot PVDF membranes (Bio-Rad) were cut to size, wet with MeOH and equilibrated in TE buffer, then assembled into a 96-well Bio-Dot microfiltration apparatus (Bio-Rad). Each well was washed with 400 µl TE drawn through with gentle vacuum, and 400 ng of gDNA was loaded, followed by another TE wash. Membranes were blocked for 2 hours in 5% milk-TBST, washed 3× with TB ST, and blotted at 4° C. overnight with primary antibodies against each modified cytosine (Active Motif)-1:5,000 mouse anti-mC (cat. no. 39649); 1:10,000 rabbit anti-hmC (cat. no. 39769); 1:5,000 rabbit anti-fC (cat. no. 61223); 1:5,000 rabbit anti-caC (cat. no. 61225). Blots were then washed, incubated with secondary 1:2,000 goat anti-mouse-HRP or 1:5,000 goat anti-rabbit-HRP (Santa Cruz Biotechnology, cat. no. sc-2004) for 2 hours, washed, and imaged as described above.

Figure 18A:
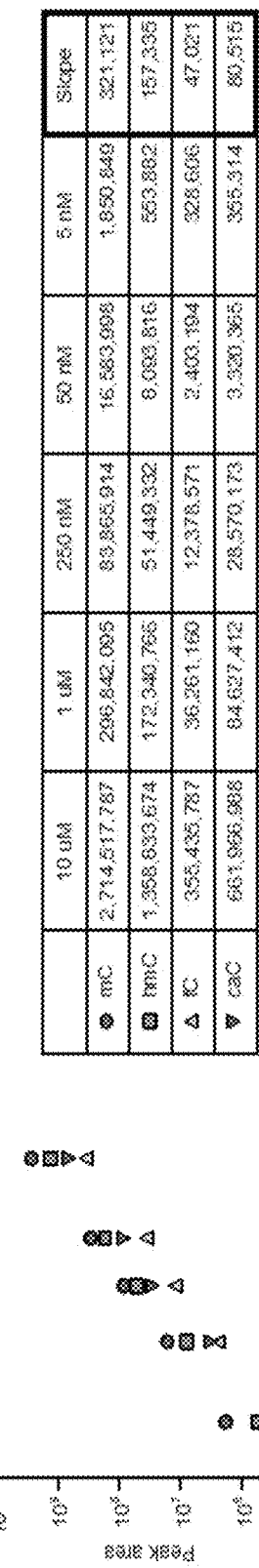
FIGS. 18A-18B are a series of plots and images illustrating LC-MS/MS analysis of modified cytosine nucleosides.
Figure 18B:
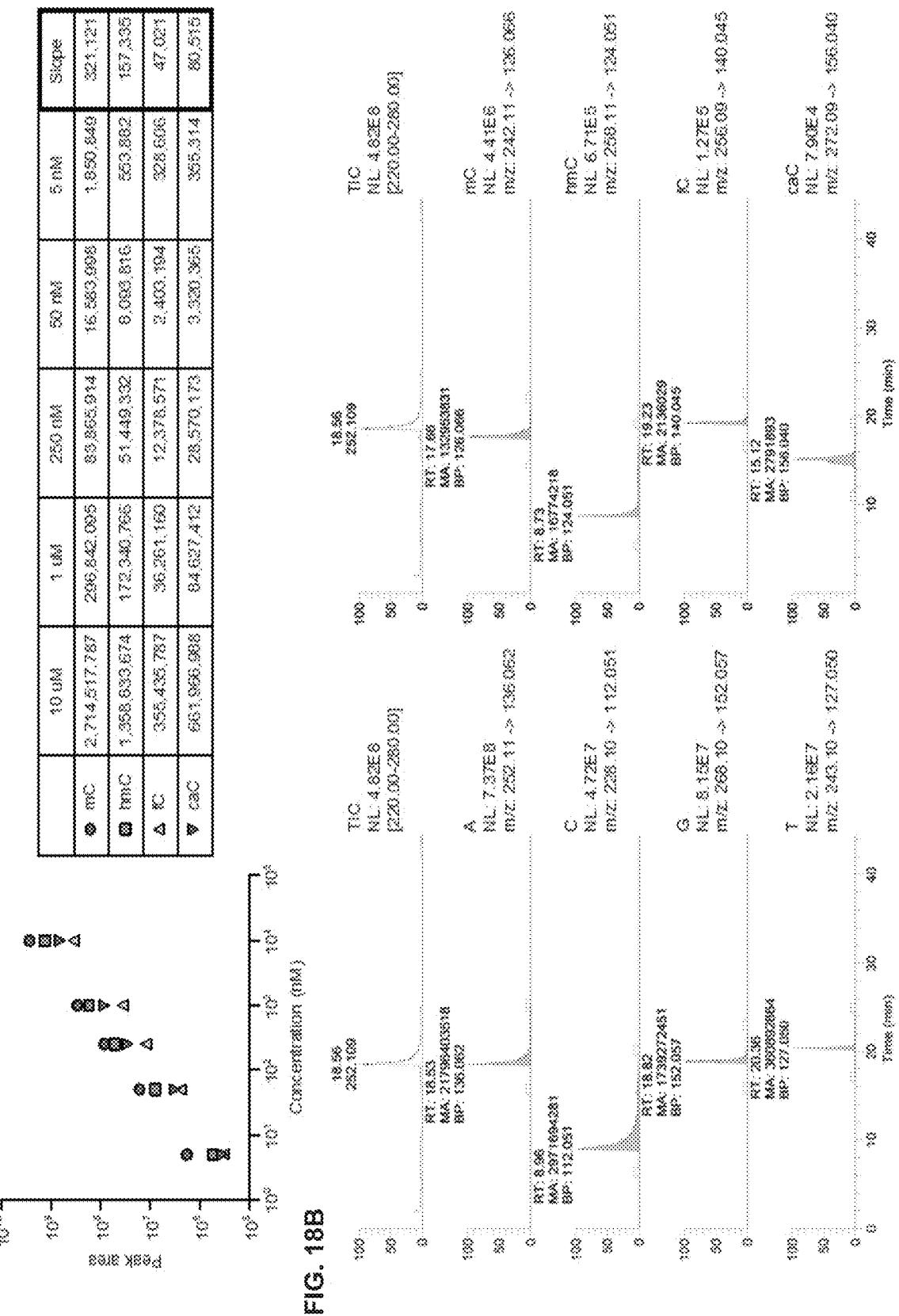

Nano LC-MS/MS analysis of gDNA: Based on published protocols (Liu et al. (2016) Methods Enzymol. 573, 365-385), LC-MS/MS methods were adapted and optimized. To quantify genomic levels of cytosine modifications in HEK293T cells, 20 μg of purified gDNA was concentrated by ethanol precipitation and degraded to component nucleosides with 20 U DNA Degradase Plus (Zymo) in 20 μl at 37° C. overnight. A 150 μm×17 cm pre-column and 100 μm×26 cm analytical reverse phase column were made from fused-silica tubing (New Objective) with a Kasil frit: The column was dipped into a 1:3 formamide:Kasil 1624 potassium silicate solution (PQ Corporation), polymerized at 100° C. overnight and trimmed to ~3 mm. Using a pressure injection cell, the columns were packed with Supelcosil LC-18-S resin (Sigma). Using this column setup equilibrated in Buffer A1 (0.1% formic acid in $H_2O$), the nucleoside mixture was diluted ten-fold into 0.1% formic acid, and 1 μl was injected onto an EASY-nLC 1000 (Thermo) nano LC. The sample was desalted for 5 minutes over the pre-column, nucleosides resolved using a gradient of 0-30% of Buffer B1 (0.1% formic acid in acetonitrile) over 30 minutes at a flow rate of 600 nL/min, and tandem MS/MS performed by positive ion mode electrospray ionization on a Q Exactive Hybrid Quadrupole-Orbitrap mass spectrometer (Thermo), with a spray voltage of 2.9 kV, capillary temperature of 275° C., and normalized collision energy of 30%. Mass transitions were mC 242.11→126.066 m/z; hmC 258.11→124.051; fC 256.09→140.046; caC 272.09→156.041; and T 243.10→127.050. Standard curves were generated from standard nucleosides (Berry & Associates) ranging from 10 to 5 nM (10 pmol to 5 fmol total) (FIGS. 18A-18B). The sample peak areas were fit to the standard curve to determine amounts of each modified cytosine in the gDNA sample and expressed as the percent of total cytosine modifications in each sample.

Molecular dynamics simulations: Forty-four molecular dynamics (MD) simulations were carried out on WT and all experimentally tested mutants (T1372S/C/A/E/Q/N/D/V, Y1902F, T1372A/Y1902F) with all four cytosine derivatives (mC, hmC, fC, caC), α-KG, and Fe(ii)/Mg(ii) (FIGS. 21A-25G). All structures were modeled based on WT hTET2-CS bound to mC-containing DNA (PDB 4NM6) (Hu et al. (2013) Cell 155, 1545-1555). Initially, the PDB structure was evaluated with MOLPROBITY to check all possible rotamers, followed by hydrogen atom addition to every system with the Leap program using the ff99SB parameter set and solvation in a truncated octahedral box of TIP3P water. In addition, protonation states of titratable residues were tested with $PropK_a3.0$, which confirmed that the default ionization at pH 7 was correct for all residues. Both coordinated histidines are protonated on ND1. All systems were explicitly neutralized with potassium counterions, which were added to the system using the Leap program. The final system size was 60,000 total atoms with 17-21 counterions. All structures were minimized with 3,000 steps of conjugate gradient, followed by gradual warm-up to 300 K using Langevin dynamics with a collision frequency of 1.0 $ps^{-1}$ in the NVT (particle number, volume, and temperature; canonical) ensemble for 100 ps. All simulations were performed with the GPU version of the pmemd program in AMBER12 (Case et al. (2005) J. Comput. Chem. 26, 1668-1688). The iron cation was approximated by using Mg(ii) parameters based on the precedent established by previous studies on AlkB (Fang et al (2013) J. Phys. Chem. B 117, 6410-6420; Fang et al (2014) J. Chem. Theory Comput. 10, 5136-5148) this approximation was also validated again for the systems used herein (FIGS. 23A-23F).

Once the systems achieved the target temperature, production MD simulations were performed using Langevin dynamics with a collision frequency of 1.0 $ps^{-1}$ in the NPT (particle number, pressure, and temperature; isothermal-isobaric) ensemble with the Berendsen barostat using a 2-ps relaxation time at 300 K. The production length for each of the simulations was 50 ns, and snapshots were saved every 10 ps; all snapshots were subjected to subsequent analysis (see below). Values reported are generally a time average over calculations from all snapshots. The most relevant simulations were performed 2-5 times for 50 ns each, with the results averaged across all simulations. All systems were simulated using the Amberff99SB force field with a 1-fs step size and a 9-Å cutoff for non-bonded interactions. SHAKE was used for all the simulations, and the smooth particle mesh Ewald (PME) method was employed to treat long-range Coulomb interactions. Hydrogen bond, root mean square deviation (r.m.s. deviation), and distance analysis on trajectories were carried out using the CPPTRAJ module available in the AMBER 12 suite, and the trajectories were visualized with the VMD program. Hydrogen bond analysis criteria were (1) angles over 120 degrees and (2) O—H distances less than 3 Å (default cpptraj settings). r.m.s. deviation and distance analysis are presented in FIGS. 23A-23F and 24A-24C.

Additional analyses to investigate intermolecular interactions in the active site were carried out by non-covalent interaction analysis (NCi) and energy decomposition analysis (EDA). NCi is a visualization tool to identify non-covalent interactions between molecules. The results obtained from the NCI analysis consist of surfaces between the interacting molecules. These surfaces are assigned specific colors to denote the strength and characteristic of the interactions: green surfaces denote weak interactions (for example, van der Waals (VdW)), blue surfaces strong attractive interactions (for example, hydrogen bonds), and red surfaces strong repulsive interactions. The NCI calculations were performed with the NCI-Plot program. Focus was on the hmC systems, and a representative snapshot from every system was subjected to NCI analysis. In all cases, the hmC substrate was considered as a ligand interacting with a spherical region of 10 Å around the binding site. All calculations were obtained with a step size of 0.2 Å for the cube and a cutoff of 5 Å for the calculation of the interactions between the nucleotides and the active site. The NCI analysis for a selected snapshot of WT and all mutants in the presence of hmC are presented in FIGS. 21A-21I. The WT and T1372A/E/V mutants were further examined in the presence of mC and fC; these NCI analyses are presented in FIGS. 22A-22H. The snapshots for NCI plots have been selected to highlight the most frequent interactions relevant to the underlying mechanism.

All EDA calculations were carried out with an in-house FORTRAN90 program to determine the non-bonded interactions (Coulomb and VdW interactions) for all the residues. The average non-bonded interaction between a particular cytosine derivative and every other residue, $AE^i$, is approximated by $AE_{int}^i=<AE_i>$, where i represents an individual residue, $AE_i$ represents the nonbonded interaction (Coulomb or VdW) between residue i and the particular cytosine derivative, and the broken brackets represent averages over the complete production ensemble obtained from the MD simulations. This analysis has been previously employed for quantum mechanics/molecular mechanics (QM/MM) and MD simulations to study a number of protein systems. As noted, the above-described analyses were performed on each individual snapshot over each individual simulation, and the reported data consist of the averages over all the simulations for each system.

Purification of hTET2 variants from Sf9 insect cells: WT and select hTET2-CS mutants were subcloned into a pFast-Bacl vector for expression in Sf9 insect cells. WT and T1372E were also generated in the full catalytic domain (hTET2-FCD, residues 1129-2002). Proteins were expressed for 24 h, and the cell pellet from a 500-ml culture was resuspended in lysis buffer (50 mM HEPES, pH 7.5, 300 mM NaCl, 0.2% (v/v) NP-40) with cOmplete, EDTA-free Protease Inhibitor Cocktail (Roche, 1 tablet/10 ml) and 10 U/ml of Benzonase Nuclease (Millipore). Cells were lysed by one freeze-thaw cycle followed by passage through a 20-gauge and then a 25-gauge needle. The lysate was cleared by centrifugation at 20,000 g for 30 minutes, and the supernatant was passed through a 0.2-µm syringe filter. A 250-µl column of anti-FLAG M2 affinity gel (Sigma) was prepared per manufacturer instructions and equilibrated in lysis buffer. The filtered lysate was applied twice to the column under gravity flow, and bound protein was washed with 10 ml then 2×5 ml of wash buffer (50 mM HEPES, pH 7.5, 150 mM NaCl, 15% (v/v) glycerol). Elutions of 250 µl were collected in wash buffer containing 100 µg/ml 3×FLAG peptide (Sigma), with each elution incubated on the column for 5 minutes before collection, until no protein was detected by Bio-Rad Protein Assay and SDS-PAGE. Fractions were pooled, DTT added to 1 mM, and aliquots flash frozen in liquid nitrogen and stored at −80° C.

TET reactions in vitro: For reactions under 'driving' conditions, purified TET2 enzymes were reacted with fluorescein (FAM)-labeled, 27-bp oligonucleotides containing a central reactive site (5'-GTA TCT AGT TCA ATC XGG TTC ATA GCA FAM-3', X=mC, hmC, or fC), duplexed with a complementary strand containing an unmodified CpG. Protein concentrations were measured by the Bio-Rad Protein Assay and standardized by diluting in elution buffer. A mixture of 20-25 nM duplexed DNA, 50 mM HEPES, pH 6.5, 100 mM NaCl, 1 mM a-ketoglutarate, 1 mM DTT, and 2 mM sodium ascorbate was pre-warmed to 37° C. Immediately before the reaction, fresh ammonium iron(II) sulfate (Sigma) was added to 75 µM, and at time t=0, TET2 was added to a final concentration of 30 jig/ml (maximally 0.57 jaM of hTET2-CS and 0.30 jaM of hTET2-FCD). Reaction volumes were typically 200-350 µl. After incubation at 37° C. for 30 minutes (or at designated time points), the reactions were quenched by addition of 8 volumes of 100% ethanol with 2 volumes of Oligo Binding Buffer (Zymo). Reaction products were purified using the Zymo Oligo Clean & Concentrator kit, eluted in LC-MS grade H2O, and analyzed by LC-MS/MS and/or enzyme-coupled assays.

For enzyme titration experiments, substrates were generated by PCR using 5-methyl- or 5-hydroxymethyl-dCTP and standard protocols for Taq polymerase. Each 745-bp amplicon contained a total of 391 modified cytosines (280 in CpG context) and was purified by gel extraction. Reaction conditions were the same as above, except for using 80 ng of PCR substrates and 1.856-72.5 µg/ml of enzyme in a 25-µl reaction. Following randomized analysis by LC-MS/MS, the percentage of total oxidation products (i.e., substrate consumed) was converted to nanomoles based on the known composition of the substrate. Plots were generated of total oxidation products versus enzyme concentration (FIG. 20A-20B), and the slopes from linear regression were compiled in FIG. 16.

Chemoenzymatic assays of TET activity: Three chemoenzymatic assays were designed to probe for specific cytosine modifications. Concentrated, purified reaction products representing 50 µl of the TET reaction (up to 1.25 pmol) were used for each assay. To distinguish mC-containing oligos, the restriction enzyme MspI (NEB) was used, which normally cleaves CCGG sites containing C, mC, or hmC, with partial activity on fC and no activity on caC[6]. A combination of aldehyde reactive probe (ARP) (Thermo) and T4 p-glucosyltransferase (pGT) (NEB) were used to protect fC and hmC, respectively, from MspI cleavage, leaving only mC susceptible. The reaction products, along with controls, were treated first with 4.4 µM ARP in 6 mM HEPES, pH 5.0 (10 µl total volume), incubated at 37° C. overnight, then diluted into 20 µl with 1× CutSmart Buffer (NEB), 2 mM uridine diphosphoglucose (UDP-Glc) and 1:25 volume of pGT for 30 minutes at 37° C. To this mixture was added 50 U MspI in 1× CutSmart Buffer and digestion carried out at 37° C. for >2 h.

To visualize the extent of higher-order oxidation to fC and caC, the reaction products were treated with 25-fold molar excess of thymine DNA glycosylase (TDG) purified as described herein, in TDG buffer (20 mM HEPES, pH 7.5, 100 mM NaCl, 0.2 mM EDTA, 2.5 mM MgCy for 2-4 hours at 37° C. After the reaction, 1:1 volume of 0.3 M NaOH/0.03 M EDTA was added and the mixture incubated at 85° C. for 15 minutes to cleave oligos at abasic sites. The TDG mutant N191A, which was previously found to excise fC and not caC, was also purified and used in the same manner to identify fC specifically.

As the final step of all three chemoenzymatic processes, the samples were mixed 1:1 with formamide containing bromophenol blue loading dye, loaded onto a 7 M urea/20% acrylamide/1×TBE gel pre-warmed to 50° C., and imaged for FAM fluorescence on a Typhoon 9200 variable mode imager.

LC-MS/MS analysis of reaction products: Concentrated, purified reaction products representing 200 µl of the TET reaction (up to 5 pmol) were degraded to component nucleosides with 1 U DNA Degradase Plus (Zymo) in 10 µl at 37° C. overnight. The nucleoside mixture was diluted ten-fold into 0.1% formic acid, and 20 µl was injected onto an Agilent 1200 Series HPLC with a 5 µm, 2.1×250 mm Supelcosil LC-18-S analytical column (Sigma) equilibrated to 50° C. in Buffer A2 (5 mM ammonium formate, pH 4.0). The nucleosides were separated in a gradient of 0-10% Buffer B2 (4 mM ammonium formate, pH 4.0, 20% (v/v) methanol) over 7 minutes at a flow rate of 0.5 ml/min. Tandem MS/MS was performed by positive ion mode ESI on an Agilent 6460 triple-quadrupole mass spectrometer, with gas temperature of 175° C., gas flow of 10 l/min, nebulizer at 35 psi, sheath gas temperature of 300° C., sheath gas flow of 11 L/min, capillary voltage of 2,000 V, fragmentor voltage of 70 V, and delta EMV of +1,000 V. Collision energies were optimized to 10 V for mC, fC, and T; 15 V for caC; and 25 V for hmC. MRM mass transitions and data analysis were as described above.

Purification of hTDG from E. coli: WT and N191A TDG were expressed and purified from BL21(DE3) cells. 1 L cultures were grown to OD ~0.6, cooled gradually to 16° C., induced with 0.25 mM IPTG at OD ~0.8, and grown for another 4 hours. Cells were collected by centrifugation, resuspended in 20 ml TDG lysis buffer (50 mM NaPhos, pH 8.0, 300 mM NaCl, 25 mM imidazole) with protease inhibitors, and lysed by four passes on a microfluidizer. The lysate was cleared by centrifugation at 20,000 g for 20 minutes, then passed through a 0.22-μm syringe filter. A 1-ml column of HisPur cobalt resin (Thermo) was equilibrated in TDG lysis buffer, and the lysate bound by two applications to the column under gravity flow. The column was washed three times with 5 ml of TDG lysis buffer containing 1 M NaCl, then three times with 5 ml of regular TDG lysis buffer. Elutions of 1 ml each were collected in TDG lysis buffer containing increasing concentrations of imidazole: 50, 100, 150, 200, 250, and 500 mM imidazole. Elutions were evaluated by SDS-PAGE and dialyzed overnight at 4° C. into TDG storage buffer (20 mM HEPES, pH 7.5, 100 mM NaCl, 1 mM DTT, 0.5 mM EDTA, 1% (v/v) glycerol). Final protein concentrations were measured with the Bio-Rad Protein Assay and aliquots stored at −80° C.

The results of the experiments from Example 3 are now described.

3.1 Saturation Mutagenesis at Thr1372

The active site of human TET2 was interrogated by performing saturation mutagenesis, which can comprehensively capture structure-function relationships at a particular residue. Using the hTET2-CS construct, plasmids encoding all 20 natural amino acids at either the Thr1372 or Val1900 positions were generated. The plasmids were transiently transfected into HEK293T cells, and genomic DNA (gDNA) was purified from the cells after 48 h. Using dot blotting to assess the qualitative pattern of genomic cytosine modifications, it was discovered that the Val1900 position was fairly tolerant of mutation, with a variety of mutants showing WT-like stepwise oxidation or reduced overall activity, while bulky and charged residues largely inactivated the enzyme (FIGS. 17A-17C).

Figure 12A:
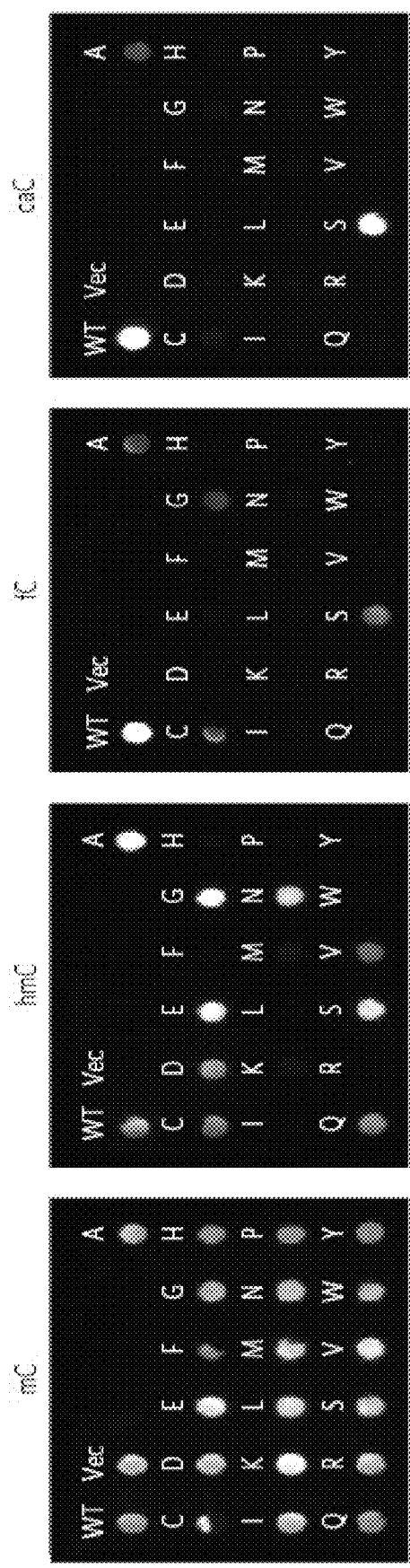
FIGS. 12A-12B are a series of plots and images illustrating the screening for Tet mutant activity.

Thus, attention was focused on the Thr1372 mutants. TET2 over-expression was confirmed to be uniform by western blotting of cell lysates, with only T1372P having slightly reduced expression (FIG. 17B). Dot blotting showed that, more so than at Val1900, mutations at Thr1372 produced distinctive patterns of cytosine oxidation, which clustered based on the biochemical properties of the side chain (FIG. 12A). Replacing Thr1372 with a proline, positively charged (H, K, R), or bulkier hydrophobic residue (I, F, L, M, W, Y) rendered TET2 inactive. Only the T1372S mutant, which preserved the side chain hydroxyl group, exhibited a WT-like activity. Smaller residues (A, C, G) were proficient at oxidation to fC and caC, but at reduced levels compared to WT. Most remarkably, the acidic or related polar residues (D, E, N, Q) and the nearly isosteric valine permit WT-like formation of hmC but no fC or caC, as detected by dot blot. Given this stalling of oxidation at hmC, Thr1372 appeared to play a unique role in stepwise oxidation.

3.2 Nucleoside LC-MS/MS Quantifies Range of Mutant Activity

Figure 12B:
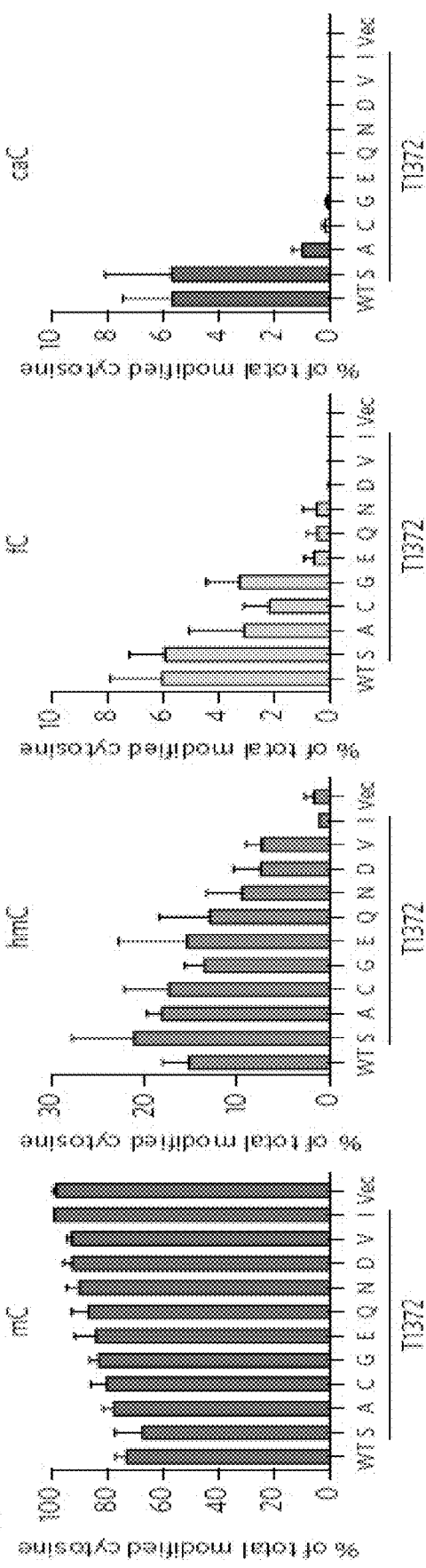

The cellular activity was quantified for all Thr1372 mutants capable of oxidizing at least to hmC. The gDNA was degraded to component nucleosides and analyzed by liquid chromatography-tandem mass spectrometry (LC-MS/MS) (FIGS. 18A-18B). In 0.1 μg of HEK293T gDNA, limits of detection in the low femtomole range enabled reliable quantification of 1 in $10^3$-$10^4$ of all cytosines. While the total abundance of modified cytosine bases (mC+ox-mCs) was similar across all conditions, the distribution of specific modifications differed significantly. In vector-transfected cells, ox-mC products were minimal: 1.6±1.0% of total cytosine modifications are hmC, with no fC or caC detected (FIG. 12B). Cells overexpressing WT hTET2-CS contained 15.2±2.8% hmC, 6.0±1.9% fC, and 5.7±1.8% caC, demonstrating robust TET-dependent oxidation at a genomic level.

The mutants exhibited a gradient of activity reflected in the fraction of genomic ox-mC bases (FIG. 12B). T1372S was the only mutant with WT-like levels of fC and caC, and hmC levels are slightly higher than WT. T1372A/C/G mutants generate WT-like levels of hmC but only one-third to one-half as much fC and barely detectable caC. Further down the activity gradient, the E/Q/N/D/V mutants produce hmC at levels at least half of that of WT, but fC and caC are near or below detection limits, consistent with the dot blotting results. Among this group, T1372E had the highest activity with WT-like hmC levels and <1% fC, while T1372V had the lowest, generating half as much hmC but no fC. Finally, the slightly bulkier T1372I mutant resembled the vector control, underscoring the steric constraints at this position. Thus, the LC-MS/MS results more clearly elucidated the patterns seen on dot blot, showing a spectrum of activity among the Thr1372 mutants correlating with the side chain properties, with E/Q/N/D/V mutants stalling oxidation at hmC.

3.3 Computational Modeling Reveals Thr1372-Tyr1902 Scaffold

To probe potential mechanisms behind the mutants' effects, classical molecular dynamics (MD) simulations of all the active Thr1372 variants were performed. WT hTET2-CS and the Thr1372 mutants bound to each of the four cytosine derivatives were modeled (FIGS. 21A-25G). Simulations were based on the crystal structure of TET2 in complex with DNA containing mC (PDB 4NM6) (Hu et al. (2013) *Cell* 155, 1545-1555), using α-KG and an Fe(n) surrogate (Mg(ii)). WT models with hmC and fC proved consistent with the more recently published structures of TET2 with these bases; all the key interactions between the enzyme, α-KG, active site metal ion, and DNA substrate for varying durations were observed across our simulations. Furthermore, energy decomposition analysis (EDA) and the root-mean-square (r.m.s.) deviation comparing the simulations to the reference crystal structure showed that the cytosine bases stably occupy the active site across time in all the models.

The hmC models in particular revealed distinct patterns of active site interactions in WT, A/C/G, and E/Q/N/D/V mutants, consistent with hmC being the fulcrum of the observed stalling effect. These patterns helped us to define a key structural scaffold in the WT enzyme that is required for efficient stepwise oxidation. This WT active site scaffold consists of a Thr1372-Tyr1902 hydrogen bond that critically supports optimal non-bonded interactions between Tyr1902 and the substrate cytosine base (FIG. 13A). The Thr1372-Tyr1902 hydrogen bond is observed in 65% of the simulation time (average over five runs of 50 ns each), and the total non-bonded interaction energy between these residues is −3.37 kcal/mol (FIG. 13B). Tyr1902, thus oriented by Thr1372, shows significant non-bonded interaction with the hmC base (−6.10 kcal/mol). This core scaffold is present across all WT models bound to mC, hmC, fC, and caC and remains fully intact in the T1372S mutant, consistent with this mutant's WT-like activity in cells.

All the other mutants eliminate the Thr1372-Tyr1902 hydrogen bond, perturbing the interaction between Y1902 and the substrate base, with a corresponding loss of enzymatic activity. For the A/C/G mutants, loss of the Thr1372-Tyr1902 scaffold appears to weaken interactions between misaligned active site components, as exemplified by T1372A (FIGS. 13A-13B). Combined with the gDNA results, the A/C/G phenotype was termed 'low efficiency, since these mutants permitted higher-order oxidation but at reduced levels compared to WT.

In the modeling, the E/Q/N/D/V mutants went a step further; they not only eliminated the Thr1372-Tyr1902 scaffold but also elicited new hydrogen bonds specifically with hmC. These new interactions, not present in WT models, positioned hmC in a different orientation relative to Tyr1902 (FIGS. 13A-13B). For instance, in T1372E, the Glu1372 hydrogen bonded directly with the 5-hydroxymethyl group for 88% of the simulation time (average over two runs of 50 ns each). Direct hydrogen bonding to hmC was also observed in T1372D and T1372Q, whereas in T1372N and T1372V, the new hydrogen bond was between hmC and other nearby residues (FIGS. 21A-21I). For example, T1372V elicited an hmC-Asp1384 hydrogen bond (38% of simulation time, average over two runs of 50 ns each). The loss of the Thr1372-Tyr1902 scaffold, together with new interactions specific to hmC, could contribute to the unique stalling phenotype of T1372E/Q/N/D/V mutants, termed herein as 'hmC-dominant'.

3.4 Biochemical Characterization of TET2 Variants

Figure 19B:
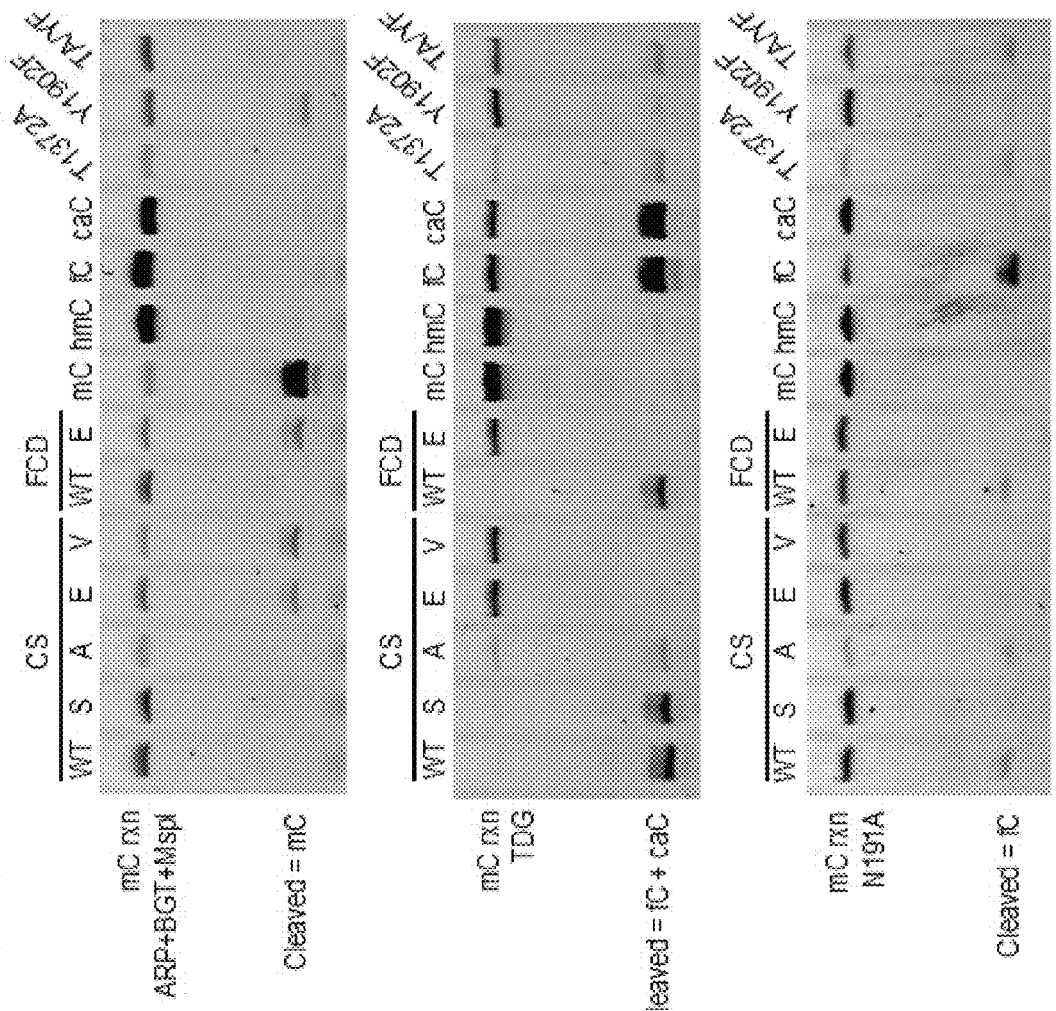
FIGS. 19A-19D are a series of plots and images illustrating biochemical characterization of select TET2 mutants.
Figure 19A:
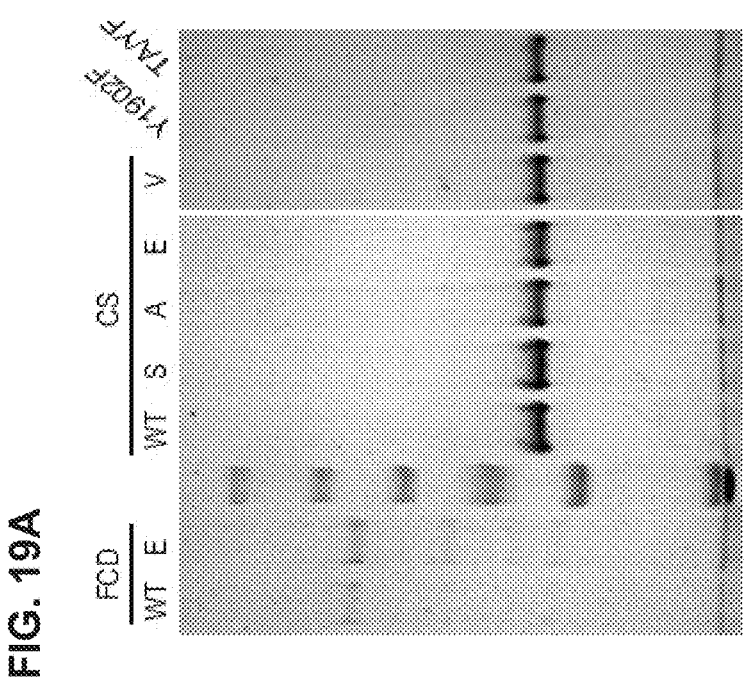
Figure 19D:
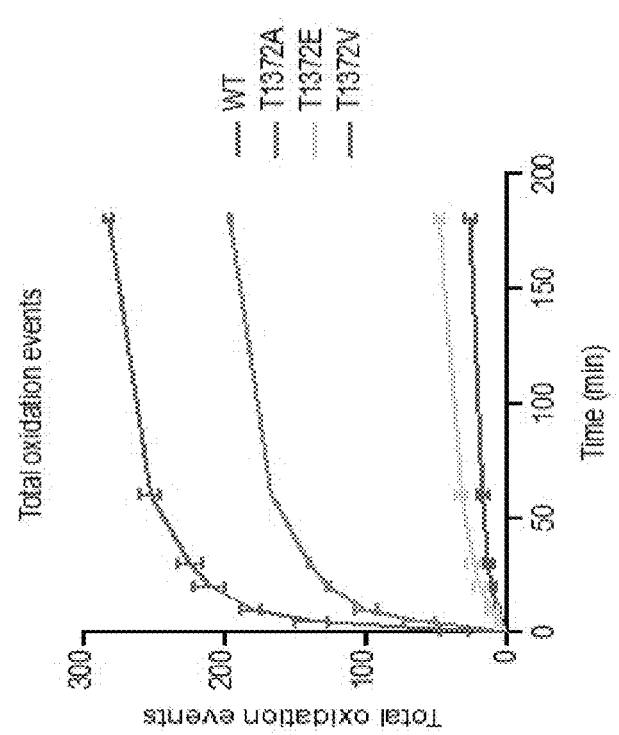
Figure 19C:
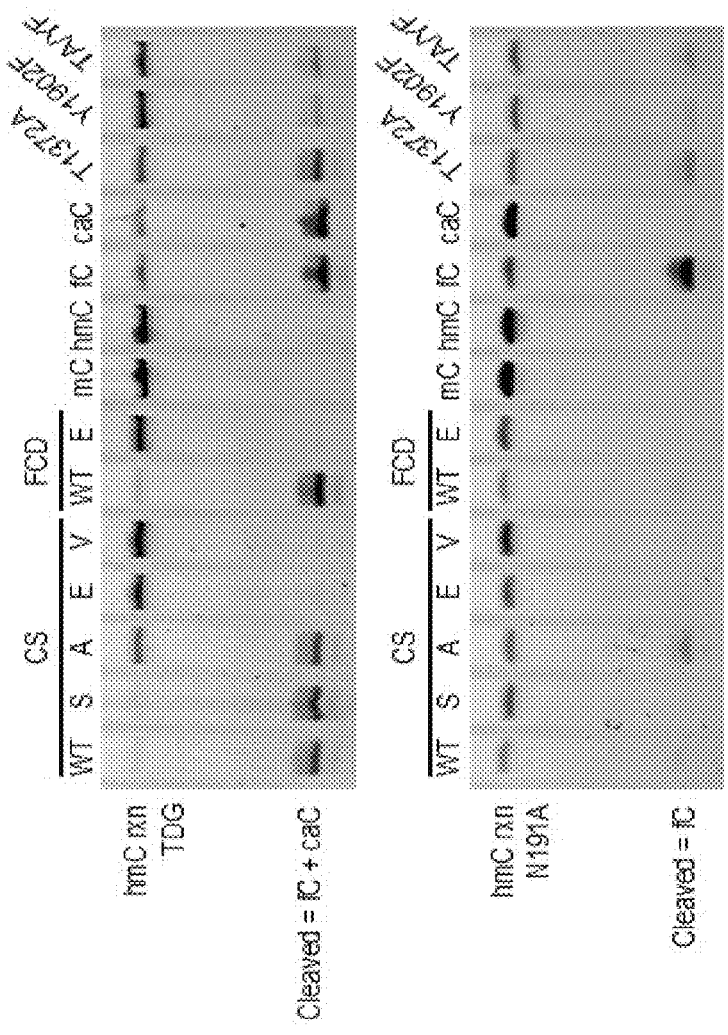

With results from cells and MD showing that side chain properties defined WT, low-efficiency, and hmC-dominant phenotypes, the TET variants were subjected to rigorous comparison in vitro. Driving conditions were used to compare the maximum extent of the variants' activity and then limiting conditions were used to compare the reactivity on mC versus hmC. Representative hTET2-CS variants—WT and T1372S, T1372A, T1372E, and T1372V—were expressed and purified from Sf9 insect cells (FIG. 19A). To drive oxidation forward, excess enzyme was reacted with limiting substrate: 27-bp oligonucleotides containing a single reactive mC, hmC, or fC duplexed to an unmodified complementary strand. The reaction products were quantified by LC-MS/MS and the results corroborated by three complementary, chemoenzymatic assays (FIGS. 19B-19C).

In reactions with 20 nM mC-containing duplexes, 30 µg/ml (maximally 0.57 µM) of WT, T1372S, or T1372A converted nearly all substrate to oxidized products in 30 minutes (FIG. 14A). However, while WT and T1372S advanced efficiently through stepwise oxidation, turning over ~93% of substrate to fC and caC, T1372A lagged behind, formed predominantly hmC (30%) and fC (54%), and only 13% caC. This aligned with the gDNA and modeling results, indicating that low-efficiency mutants were capable of oxidation to caC but at reduced levels compared to WT.

The hmC-dominant T1372E and T1372V mutants showed noticeably reduced activity on mC (54% and 76% of mC substrate remaining, respectively), and oxidation products were strongly restricted to hmC, with 4% and 1% conversion to fC, respectively (FIG. 14A).

Compared to the gDNA results, where the levels of hmC produced by the E/V mutants were within two-fold of WT (FIG. 12B), this indicated that other factors could likely tune the activity of TET2 and/or the levels of hmC in cells. Importantly, the patterns of oxidation and hmC stalling held true in cells and in vitro. T1372E was observed to be slightly more active than T1372V, consistent with the gDNA results, which suggests a trade-off between more hmC production and better stringency of stalling. Time-course analysis further demonstrated that overall reactivity on mC decreases from WT to the low-efficiency T1372A, and the hmC-dominant E/V mutants failed to produce significant fC even after 3 hours (FIG. 14B, FIG. 19D). To validate that the hmC-dominant phenotype was not restricted to the truncated CS form of the protein, the T1372E mutation was also generated in the full catalytic domain of TET2 (hTET2-FCD, residues 1129-2002) and similar results were noted (FIG. 14A).

When all available substrate was hmC, WT and T1372S again converted >93% of substrate to fC and caC. T1372A produced 65% fC and caC, while T1372E and T1372V were able to produce only 8% and 3% fC, respectively. When starting with fC substrate under the same conditions, WT enzymes converted about half of fC to caC, corroborating that the final step of oxidation is the least efficient. T1372A generated 19% caC, ~⅓ of the WT level, while E/V mutants made <3% caC, near or below the detection limits of the assays. These results strongly supported our model that the Thr1372-Tyr1902 scaffold was required for WT TET2 activity. Loss of the active site scaffold decreased the activity of low-efficiency mutants and had a more severe effect on hmC-dominant mutants, which did not make significant fC or caC even under driving reaction conditions.

Since TET2 is known to prefer mC over hmC, enzyme-limiting conditions were examined to distinguish whether the decrease in overall activity alone was sufficient to explain the restriction of oxidation products to hmC. The reactivity of WT, T1372A, and T1372E mutants on mC were compared to hmC by titrating enzyme against 745-bp substrates fully modified with mC or hmC. Kinetic analysis was simplified to measure total oxidation products (i.e., substrate consumed), since iterative oxidation links the kinetics of each oxidation step in ways not easily dissected.

Figure 20A:
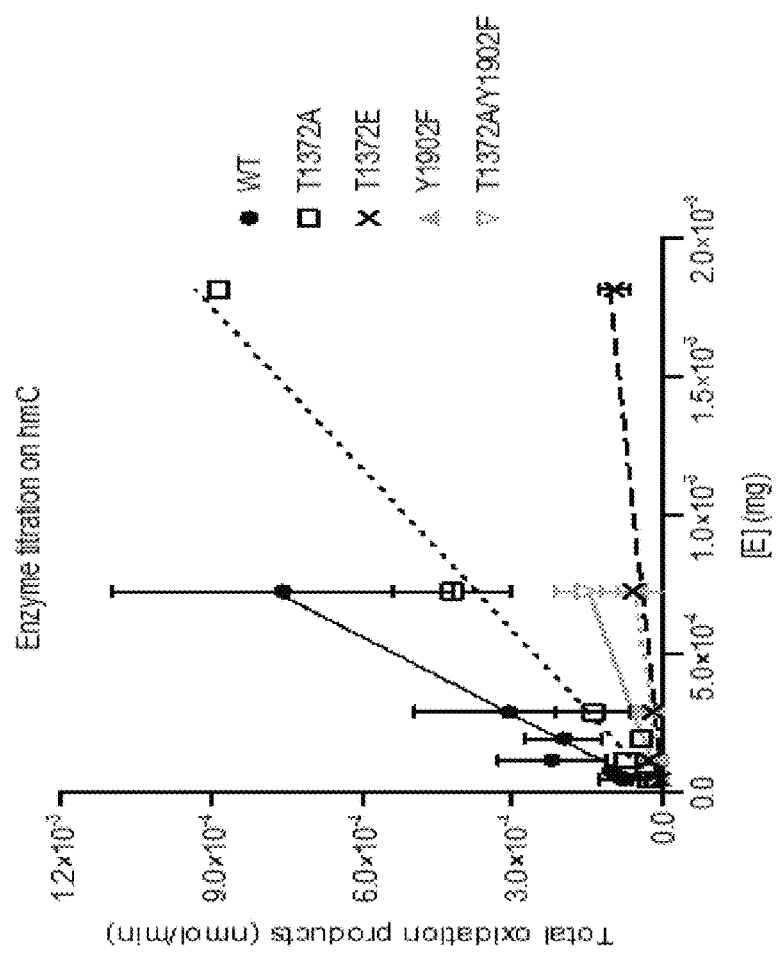
FIGS. 20A-20B are a set of plots illustrating enzyme titrations to compare reactivity of select TET variants on (FIG. 20A) mC and (FIG. 20B) hmC substrates. PCR amplicons fully modified with mC or hmC were reacted with varying concentrations of enzyme for 30 min, and total oxidation products were quantified by LC-MS/MS. For the mC reaction, total oxidation products are hmC+fC+caC; for the hmC reaction, total oxidation products are fC+caC. Linear dependence of activity with enzyme concentration suggests that the assays are reporting on steady-state consumption of mC or hmC substrate. Under all conditions shown, for determination of the specific activity, <50% of the substrate is consumed. Shown are the mean±s.d. from three independent experiments. The slopes of the linear regression lines are given in FIG. 16.
Figure 20B:
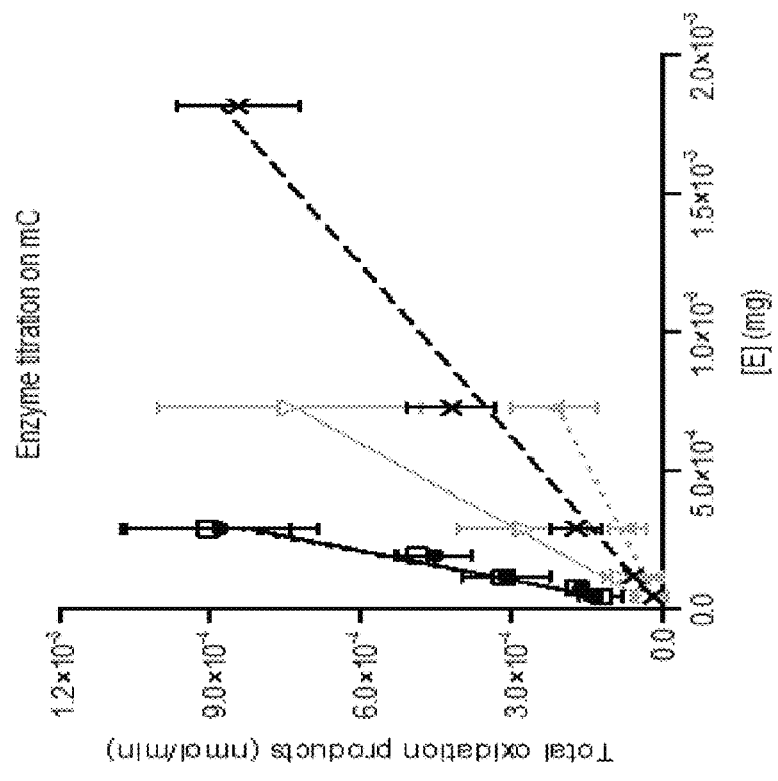
Figure 26A:
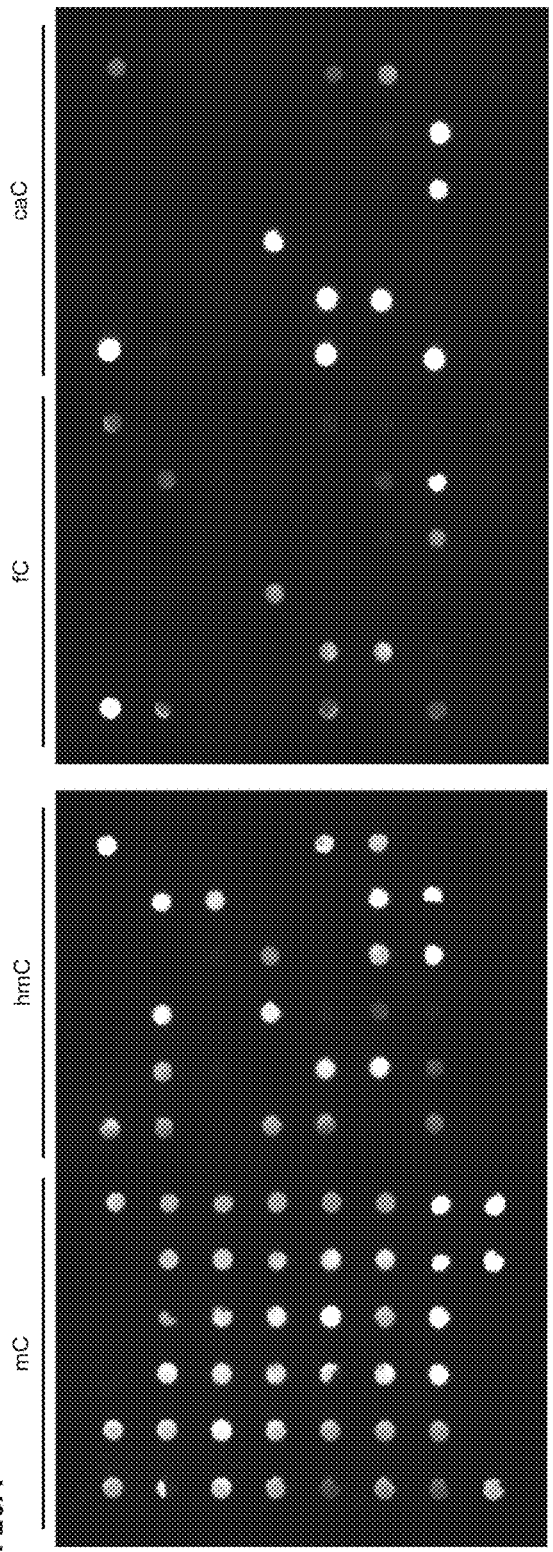
FIGS. 26A-26B are a series of images illustrating uncropped versions of images used in previous figures.
Figure 26B:
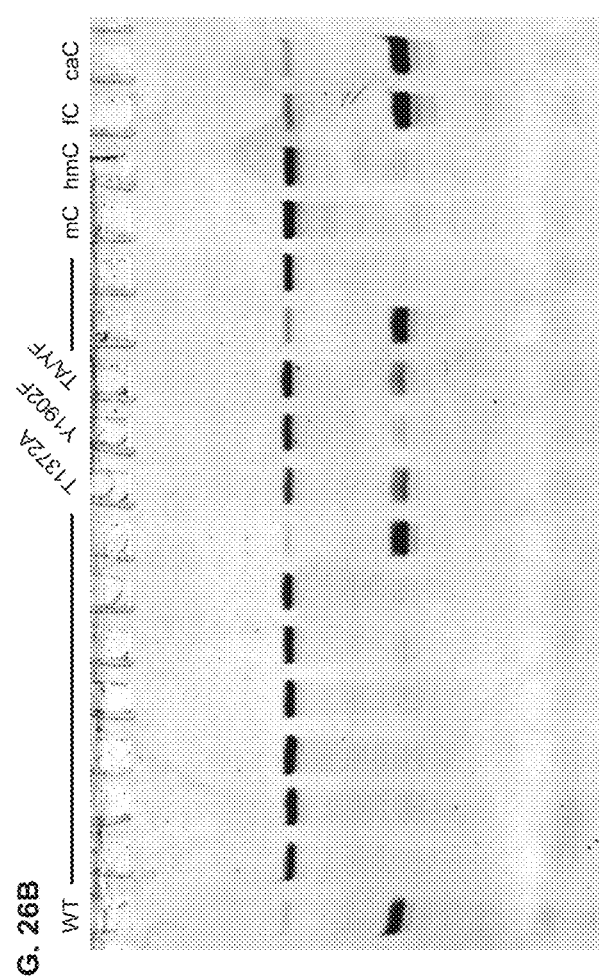

By this analysis, WT TET2 consumed 2.9±0.2 nmol of mC substrate per milligram enzyme per minute, while activity on hmC decreased 2.6-fold to 1.1±0.1 nmol/mg/min (FIG. 16; FIGS. 20A-20B). The T1372A mutant displayed similar activity on mC and is only 5.5-fold slower in hmC-to-fC conversion, in line with this mutant's capacity for less efficient higher-order oxidation. By contrast, relative to the most proficient WT reaction, the T1372E mutant was 5.9-fold slower in mC-to-hmC conversion but 48-fold slower in hmC-to-fC conversion. Thus, the hmC-dominant mutant exhibited decreased activity overall, but the usual mild preference for mC substrate was not sufficient to explain the larger loss of activity on hmC, which underlies the stalling effect.

3.5 Tyr1902 Mutagenesis Strongly Supports the Model

MD simulations suggested that active site scaffold mutations could introduce aberrant interactions that contributed to hmC stalling. Keeping in mind the challenges of modeling new interactions with classical MD, the model was subjected to an independent test: mutating the other scaffold residue, Tyr1902, to phenylalanine. Modeling predicted that Y1902F would liberate Thr1372 to form a hydrogen bond directly with hmC (18% of simulation time, average over two runs of 50 ns each), potentially favoring an hmC-dominant phenotype (FIG. 15A). Taking the hypothesis one step further, by adding a T1372A mutation to Y1902F, the modeling predicted that the T1372A/Y1902F double mutant could rescue activity by alleviating the aberrant hydrogen bonding interaction.

To test these predictions, the activities of purified T1372A, Y1902F, and T1372A/Y1902F enzymes were compared in vitro. The results strikingly confirmed the predictions. Compared to the WT mC-to-hmC reaction, the Y1902F single mutant was 9.9-fold slower at mC-to-hmC conversion and 36-fold slower at hmC-to-fC conversion (FIG. 16; FIGS. 20A-20B). Addition of the second T1372A mutation partially restored activity so that the double mutant was only 2.8-fold slower at mC-to-hmC conversion and 14-fold slower at hmC-to-fC conversion. Under driving conditions, the Y1902F mutant left 38% of mC substrate unreacted, with products consisting of 49% hmC, 13% fC, and no caC (FIG. 15B)—similar to T1372E/V but with less stringent stalling at hmC. The introduction of a second mutation in the T1372A/Y1902F double mutant rescued activity, such that 97% of mC substrate was consumed, like in the T1372A single mutant.

To complement these LC-MS/MS results, rather than digesting the reaction products to nucleosides, the intact oligonucleotides were treated with purified TDG followed by DNA gel electrophoresis to differentiate strands containing mC or hmC from strands containing fC or caC (FIG. 15C). While Y1902F showed only trace generation of fC and caC, the addition of the second mutation in T1372A/Y1902F restored stepwise oxidation and mirrored the results for T1372A. Thus, structural modeling correctly predicted the biochemical behavior of the Y1902F and T1372A/Y1902F mutants, strongly supporting both the requirement of the Thr1372-Tyr1902 scaffold for WT stepwise oxidation and the contribution of aberrant active site interactions to the hmC-dominant phenotype.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A fusion protein comprising deamination activity comprising a first domain and a second domain, wherein the first domain comprises an apolipoprotein B editing complex (APOBEC) 3B (A3B) domain and the second domain comprises an APOBEC3A (A3A) catalytic domain, said fusion protein comprising SEQ ID NO: 8 and exhibiting deamination activity that is greater than that of either A3B or A3A alone.

2. A mutant A3B protein of SEQ ID NO: 3, wherein the mutant A3B sequence mutations in SEQ ID NO: 3 consist of D196H, T197I, Delta(206-210), Ins(206)GIG, R212H Q213K, W228S 1230K, M235R, C239H, E241Q, E342K, Y343H, Y350D, R351H, and E363D, wherein the mutant A3B protein displays deamination activity that is greater than A3B.

* * * * *